(12) United States Patent
Baum et al.

(10) Patent No.: US 10,494,408 B2
(45) Date of Patent: Dec. 3, 2019

(54) CHIMERIC INSECTICIDAL PROTEINS TOXIC OR INHIBITORY TO LEPIDOPTERAN PESTS

(71) Applicant: Monsanto Technology LLC, St. Louis, MO (US)

(72) Inventors: James A. Baum, Webster Groves, MO (US); Thomas A. Cerruti, Newton, MA (US); Crystal L. Dart, Norton, MA (US); Leigh H. English, Chesterfield, MO (US); Stanislaw Flasinski, Chesterfield, MO (US); Xiaoran Fu, Belmont, MA (US); Victor M. Guzov, Cambridge, MA (US); Arlene R. Howe, Chesterfield, MO (US); Jay P. Morgenstern, Boston, MA (US); James K. Roberts, Chesterfield, MO (US); Sara A. Salvador, Wildwood, MO (US); Jinling Wang, Belmont, MA (US)

(73) Assignee: Monsanto Technology LLC, St. Louis, MO (US)

( * ) Notice: Subject to any disclaimer, the term of this patent is extended or adjusted under 35 U.S.C. 154(b) by 69 days.

(21) Appl. No.: 15/848,837

(22) Filed: Dec. 20, 2017

(65) Prior Publication Data

US 2018/0127772 A1 May 10, 2018

Related U.S. Application Data

(63) Continuation of application No. 14/884,469, filed on Oct. 15, 2015, now Pat. No. 10,233,217.

(60) Provisional application No. 62/064,989, filed on Oct. 16, 2014.

(51) Int. Cl.
*C07K 14/325* (2006.01)
*C12N 15/82* (2006.01)
*A01N 63/02* (2006.01)
*C12N 15/62* (2006.01)

(52) U.S. Cl.
CPC ............ *C07K 14/325* (2013.01); *A01N 63/02* (2013.01); *C12N 15/8286* (2013.01); *C07K 2319/00* (2013.01); *C12N 15/62* (2013.01); *Y02A 40/162* (2018.01)

(58) Field of Classification Search
None
See application file for complete search history.

(56) References Cited

U.S. PATENT DOCUMENTS

| | | |
|---|---|---|
| 5,188,642 A | 2/1993 | Shah et al. |
| 5,312,910 A | 5/1994 | Kishore et al. |
| 5,500,365 A | 3/1996 | Fischhoff et al. |
| 5,510,471 A | 4/1996 | Lebrun et al. |
| 5,627,061 A | 5/1997 | Barry et al. |
| 5,633,435 A | 5/1997 | Barry et al. |
| 5,633,448 A | 5/1997 | Lebrun et al. |
| 5,728,925 A | 3/1998 | Herrera-Estrella et al. |
| 5,880,275 A | 3/1999 | Fischhoff et al. |
| 6,017,534 A * | 1/2000 | Malvar ............... C07K 14/325 424/185.1 |
| 6,033,874 A | 3/2000 | Baum et al. |
| 6,204,246 B1 | 3/2001 | Bosch et al. |
| 6,218,188 B1 * | 4/2001 | Cardineau ........... C07K 14/325 435/468 |
| 6,501,009 B1 | 12/2002 | Romano |
| 6,713,063 B1 | 3/2004 | Malvar et al. |
| 6,962,705 B2 | 11/2005 | Malvar et al. |
| 7,064,249 B2 | 6/2006 | Corbin et al. |
| 7,070,982 B2 | 7/2006 | Malvar et al. |
| 7,193,133 B2 | 3/2007 | Lassner et al. |
| 7,510,878 B2 | 3/2009 | Abad et al. |
| 7,772,465 B2 | 8/2010 | Abad et al. |
| 7,812,129 B1 | 10/2010 | Abad et al. |
| 8,344,207 B2 | 1/2013 | Bogdanova et al. |
| 8,609,936 B2 | 12/2013 | Baum et al. |
| 2003/0119158 A1 * | 6/2003 | Malvar ............... C07K 14/325 435/184 |
| 2006/0021087 A1 | 1/2006 | Baum et al. |
| 2006/0112447 A1 | 5/2006 | Bogdanova et al. |
| 2008/0172762 A1 | 7/2008 | Cerf et al. |
| 2008/0256667 A1 | 10/2008 | Dersch et al. |
| 2008/0280361 A1 | 11/2008 | Calabotta et al. |
| 2008/0282432 A1 | 11/2008 | Duncan et al. |
| 2009/0138985 A1 | 5/2009 | Martinell et al. |
| 2009/0142837 A1 | 6/2009 | Adams, Jr. et al. |
| 2009/0313721 A1 | 12/2009 | Abad et al. |

(Continued)

FOREIGN PATENT DOCUMENTS

| | | |
|---|---|---|
| EP | 0189707 A2 | 8/1986 |
| EP | 0508909 A1 | 10/1992 |

(Continued)

OTHER PUBLICATIONS

Pardo Lopez et al, Peptides (2009) 30:589-595.*

(Continued)

*Primary Examiner* — Mykola V. Kovalenko
(74) *Attorney, Agent, or Firm* — Timothy K. Ball; Carine M. Doyle; Arnold & Porter Kaye Scholer LLP

(57) ABSTRACT

Nucleotide sequences are disclosed that encode novel chimeric insecticidal proteins exhibiting Lepidopteran inhibitory activity. Particular embodiments provide compositions and transformed plants, plant parts, and seeds containing the recombinant nucleic acid molecules encoding one or more of the chimeric insecticidal proteins.

19 Claims, No Drawings

Specification includes a Sequence Listing.

(56) References Cited

U.S. PATENT DOCUMENTS

| | | |
|---|---|---|
| 2010/0004176 A1 | 1/2010 | Sampson et al. |
| 2010/0017914 A1 | 1/2010 | Hart et al. |
| 2010/0077507 A1 | 3/2010 | Abad et al. |
| 2010/0077508 A1 | 3/2010 | Abad et al. |
| 2010/0137216 A1 | 6/2010 | Carozzi et al. |
| 2010/0160231 A1 | 6/2010 | Sampson et al. |
| 2010/0192256 A1 | 6/2010 | Abad et al. |
| 2010/0197592 A1 | 8/2010 | Heinrichs |
| 2010/0269221 A1 | 10/2010 | Abad et al. |
| 2010/0317569 A1 | 12/2010 | Lira et al. |
| 2010/0319092 A1 | 12/2010 | Lira et al. |
| 2010/0319093 A1 | 12/2010 | Lira et al. |
| 2011/0030096 A1 | 2/2011 | Lira et al. |
| 2011/0055968 A1 | 3/2011 | Cerf et al. |
| 2011/0112013 A1 | 5/2011 | Abad et al. |
| 2011/0154536 A1 | 6/2011 | Abad et al. |
| 2012/0047606 A1 | 2/2012 | Abad et al. |
| 2012/0117690 A1 | 5/2012 | Cerf et al. |
| 2012/0167259 A1 | 6/2012 | Liu et al. |
| 2012/0192310 A1 | 7/2012 | Abad et al. |
| 2012/0210462 A1 | 8/2012 | Bermudez et al. |
| 2012/0233726 A1 | 9/2012 | Abad et al. |
| 2012/0317681 A1 | 12/2012 | Meade et al. |
| 2013/0055469 A1 | 2/2013 | Sampson et al. |
| 2013/0097735 A1 | 4/2013 | Bowen et al. |
| 2013/0104259 A1 | 4/2013 | Sampson et al. |
| 2013/0117884 A1 | 5/2013 | Hargiss et al. |
| 2013/0167264 A1 | 6/2013 | Sampson et al. |
| 2013/0219570 A1 | 8/2013 | Lira et al. |
| 2013/0269060 A1 | 10/2013 | Baum et al. |
| 2013/0303440 A1 | 11/2013 | Sampson et al. |
| 2013/0310543 A1 | 11/2013 | Sampson et al. |
| 2014/0007292 A1 | 1/2014 | Cerf et al. |
| 2014/0033361 A1 | 1/2014 | Altier et al. |
| 2014/0033363 A1 | 1/2014 | Sampson |
| 2014/0196175 A1 | 7/2014 | Sampson et al. |
| 2014/0223599 A1 | 8/2014 | Sampson et al. |
| 2014/0245491 A1 | 8/2014 | Sampson et al. |
| 2014/0298538 A1 | 10/2014 | Heinrichs et al. |
| 2014/0366227 A1 | 12/2014 | Gatehouse et al. |
| 2014/0373195 A1 | 12/2014 | Sampson et al. |

FOREIGN PATENT DOCUMENTS

| | | |
|---|---|---|
| EP | 0218571 B1 | 2/1993 |
| EP | 0924299 A1 | 6/1999 |
| JP | 2009-505679 A | 2/2009 |
| JP | 2013-514769 A | 5/2013 |
| WO | WO 90/10076 | 9/1990 |
| WO | WO 99/24581 A2 | 5/1999 |
| WO | WO 01/14562 A1 | 3/2001 |
| WO | WO 01/19859 A2 | 3/2001 |
| WO | WO 02/14517 A1 | 2/2002 |
| WO | WO 2004/020636 A1 | 3/2004 |
| WO | WO 2007027777 A1 | 3/2007 |
| WO | WO 2011/075588 A1 | 6/2011 |
| WO | WO 2011075588 A1 | 6/2011 |
| WO | WO 2014/008054 A2 | 1/2014 |
| WO | WO 2014/055881 A1 | 4/2014 |

OTHER PUBLICATIONS

Aronson et al, FEMS Microbiol. Lett. (2001) 195:1-8.*
Herrero et al., Biochem. J. (2004) 384, 507-513.*
Abdul-Rauf et al, Curr. Microbiol. (1999) 39, 94-98.*
Abdul-Rauf et al., "Mutations of Loop 2 and Loop 3 Residues in Domain II of *Bacillus thuringiensis* Cry1C δ-Endotoxin Affect Insecticidal Specificity and Initial Binding to *Spodoptera littoralis* and *Aedes aegypti* Midgut Membranes," *Current Microbiology*, 39:94-98 (1999).

Aronson et al., "Why *Bacillus thuringiensis* insecticidal toxins are so effective: unique features of their mode of action," *FEMS Microbiology Letters*, 195:1-8 (2001).
Baig et al., "cry Genes profiling and the toxicity of isolates of *Bacillus thuringiensis* from soil samples against American bollworm, *Helicoverpa armigera*," *Journal of Applied Microbiology*, 109:1967-1978 (2010).
Bravo et al., "Mode of action of *Bacillus thuringiensis* Cry and Cyt toxins and their potential for insect control," *Toxins*, 49:423-435 (2007).
Database UniProt, Database accession No. D9U3MO (2010).
De Maagd et al., "*Bacillus thuringiensis* delta-endotoxin Cry1C domain III Can Function as a Specificity Determinant for *Spodoptera exigua* in Different, but Not All, Cry1-Cry1C Hybrids," *Applied and Environmental Microbiology*, 66(4):1559-1563 (2000).
Della-Cioppa et al., "Translocation of the precursor of 5-enolpyruvylshikimate-3-phosphate synthase into chloroplasts of higher plants in vitro," *Proc. Natl. Acad. Sci. USA*, 83:6873-6877, (1986).
Forgoux-Nicol et al., "Isolation of repeseed genes expressed early and specifically during development of the male gametophyte," *Plant Molecular Biology*, 40:857-872 (1999).
Herrero et al., "Mutations in the *Bacillus thuringiensis* Cry1Ca toxin demonstrate the role of domains II and III in specificity towards *Spodoptera exigua* larvae," *Biochem J.*, 384:507-513 (2004).
International Search Report dated Jun. 6, 2016, in International Patent Application No. PCT US2015/055800.
IUPAC-IUB Joint Commission on Biochemical Nomenclature, "Nomenclature and Symbolism for Amino Acids and Peptides," *Eur. J. Biochem.* 138:9-37(1984).
Klee et al., "Cloning of an *Arabidopsis thaliana* gene encoding 5-enolpyruvylshikimate-3-phosphate synthase: sequence analysis and manipulation to obtain glyphosate-tolerant plants," *Mol Gen Genet*, 210:437-442 (1987).
Knight et al., "A Strategy for Shuffling Numerous *Bacillus thuringiensis* Crystal Protein Domains," *Journal of Economic Entomology*, 97:1805-1813 (2004).
James, "Global Status of Commercialized Biotech/GM Crops: 2012," *ISAAA*, Brief No. 44 (2012).
Lucena et al., "Molecular Approaches to Improve the Insecticidal Activity of Bacillus thuringiensis Cry toxins," *Toxins*, 6(8):2393-2423 (2014).
Pardo-Lopez et al., "Strategies to improve the insecticidal activity of Cry toxins from Bacillus thuringiensis," *Peptides*, 30:589-595 (2009).
Pardo-Lopez et al., "*Bacillus thuringiensis* insecticidal three-domain Cry toxins: mode of action, insect resistance and consequences for crop protection," *FEMS Microbiology Reviews*, 37:3-22 (2013).
Thompson et al., "Clustal W: improving the sensitivity of progressive multiple sequence alignment through sequence weighting, position-specific gap penalties and weight matrix choice," *Nucleic Acids Research*, 22:4673-4680 (1994).
Bravo et al., "Evolution of *Bacillus thuringiencis* Cry toxins insecticidal activity," *Microbial Biotechnology*, 6:17-26 (2012).
Gen Bank Database, Apr. 25, 1994, Accession No. AAA 22344.1.
GenBank Database, Aug. 24, 1998, Accession No. AAC 32850.1.
GenBank Database, Apr. 18, 2005, Accession No. CAA 31951.1.
GenBank Database, Dec. 31, 2013, Accession No. AEH 31431.1.
GenBank Database, Apr. 26, 1993, Accession No. AAA 22561.1.
Gen Bank Database, Apr. 26, 1993, Accession No. AAA 22331.1.
GenBank Database, Nov. 18, 2005, Accession No. ABB 766664.1.
Maagd R. A. et al., "*Bacillus thuringiencis* Delta-Endotoxin Cry 1C Domain III Can Function as a Specificity Determinant for *Spodoptera exigua* in Different, but Not All, Cry 1-Cry 1C Hybrids," *Applied and Environmental Microbiology*, 66(4):1559-1563 (2000).
Office Action in corresponding Application No. JP 2017-0520352, dated Feb. 5, 2019.
Perlak et al., Insect Resistant Cotton Plants, *FEMS Microbiology Reviews*, 37:3-22 (2013).

* cited by examiner

SEQUENCE LISTING

```
<160> NUMBER OF SEQ ID NOS: 53

<210> SEQ ID NO 1
<211> LENGTH: 3570
<212> TYPE: DNA
<213> ORGANISM: Artificial
<220> FEATURE:
<223> OTHER INFORMATION: Recombinant nucleotide sequence used for
      expression in a bacterial cell encoding TIC1100.

<400> SEQUENCE: 1
atggagatag tgaataatca gaatcaatgc gtgccttata attgtttgaa taatcccgaa       60
atcgaaatat tagaaggcgg aagaatatca gttggtaata ccccaattga tatttctctt      120
tcgcttactc agtttctttt gagtgaattt gtcccaggtg cggggtttgt attaggatta      180
```

| | |
|---|---|
| attgatttaa tatggggatt tgtaggtcct tcccaatggg acgcatttct tgctcaagtg | 240 |
| gaacagttaa ttaaccaaag aatagcagaa gctgtaagaa atacagcaat tcaggaatta | 300 |
| gagggaatgg cacgggttta tagaacctat gctactgctt ttgctgagtg ggaaaaagct | 360 |
| cctgatgacc cagagctaag agaagcacta cgtacacaat ttacagcaac tgagacttat | 420 |
| ataagtggaa gaatatccgt tttaaaaatt caaacttttg aagtacagct gttatcagtg | 480 |
| tttgcccaag ctgcaaattt acatttatct ttattaagag acgttgtgtt ttttgggcaa | 540 |
| agatggggtt tttcaacgac aaccgtaaat aattactaca atgatttaac agaagggatt | 600 |
| agtacctata cagattatgc tgtacgctgg tacaatacgg gattagaacg tgtatgggga | 660 |
| ccggattcta gagattgggt aaggtataat caatttagaa gagaattaac actaactgta | 720 |
| ttagatatcg ttgctctgtt cccgaattat gatagtagaa gatatccaat tcgaacagtt | 780 |
| tcccaattaa caagagaaat ttatacaaac ccagtattag aaaattttga tggtagtttt | 840 |
| cgaggctcgg ctcagggcat agaaagaagt attaggagtc cacatttgat ggatatactt | 900 |
| aacagtataa ccatctatac ggatgctcat agggggttatt attattggtc agggcatcaa | 960 |
| ataatggctt ctcctgtcgg ttttttcgggg ccagaattca cgtttccgct atatggaacc | 1020 |
| atgggaaatg cagctccaca acaacgtatt gttgctcaac taggtcaggg cgtgtataga | 1080 |
| acattatcgt ccactttata tagaagacct tttaatatag ggataaataa tcaacaacta | 1140 |
| tctgttcttg acgggacaga atttgctat ggaacctcct caaatttgcc atccgctgta | 1200 |
| tacagaaaaa gcggaacggt agattcgctg gatgaaatac cgccacagaa taacaacgtg | 1260 |
| ccacctaggc aaggatttag tcatcgatta agccatgttt caatgtttcg ttcaggcttt | 1320 |
| agtaatagta gtgtaagtat aataagagct cctatgttct cttggataca tcgtagtgct | 1380 |
| gaatttaata atataattgc atcggatagt attaatcaaa tacctttagt gaaaggattt | 1440 |
| agagtttggg ggggcaccctc tgtcattaca ggaccaggat ttacaggagg ggatatcctt | 1500 |
| cgaagaaata cctttggtga ttttgtatct ctacaagtca atattaattc accaattacc | 1560 |
| caaagatacc gtttaagatt tcgttacgct tccagtaggg atgcacgagt tatagtatta | 1620 |
| acaggagcgg catccacagg agtgggaggc caagttagtg taaatatgcc tcttcagaaa | 1680 |
| actatggaaa tagggagaa cttaacatct agaacattta gatataccga ttttagtaat | 1740 |
| cctttttcat ttagagctaa tccagatata attgggataa gtgaacaacc tctatttggt | 1800 |
| gcaggttcta ttagtagcgg tgaactttat atagataaaa ttgaaattat tctagcagat | 1860 |
| gcaacatttg aagcagaatc tgatttagaa agagcgcaga aggcggtgaa tgcgctgttt | 1920 |
| acgtctacaa accaactagg gctaaaaaca aatgtaacgg attatcatat tgatcaagtg | 1980 |
| tccaattag ttacgtattt atcggatgaa ttttgtctgg atgaaaagcg agaattgtcc | 2040 |
| gagaaagtca aacatgcgaa gcgactcagt gatgaacgca atttactcca agattcaaat | 2100 |
| ttcaaagaca ttaataggca accagaacgt gggtggggcg gaagtacagg gattaccatc | 2160 |
| caaggagggg atgacgtatt taagaaaat tacgtcacac tatcaggtac ctttgatgag | 2220 |
| tgctatccaa catatttgta tcaaaaaatc gatgaatcaa aattaaaagc ctttacccgt | 2280 |
| tatcaattaa gagggtatat cgaagatagt caagacttag aaatctattt aattcgctac | 2340 |
| aatgcaaaac atgaaacagt aaatgtgcca ggtacgggtt ccttatggcc gctttcagcc | 2400 |
| caaagtccaa tcggaaagtg tggagagccg aatcgatgcg cgccacacct tgaatggaat | 2460 |
| cctgacttag attgttcgtg tagggatgga gaaaagtgtg cccatcattc gcatcatttc | 2520 |
| tccttagaca ttgatgtagg atgtacagac ttaaatgagg acctaggtgt atgggtgatc | 2580 |

```
tttaagatta agacgcaaga tgggcacgca agactaggga atctagagtt tctcgaagag    2640
aaaccattag taggagaagc gctagctcgt gtgaaaagag cggagaaaaa atggagagac    2700
aaacgtgaaa aattggaatg ggaaacaaat atcgtttata agaggcaaa  agaatctgta    2760 gatgctttat ttgtaaactc tcaatatgat caattacaag cggatacgaa tattgccatg    2820
attcatgcgg cagataaacg tgttcatagc attcgagaag cttatctgcc tgagctgtct    2880
gtgattccgg gtgtcaatgc ggctattttt gaagaattag aagggcgtat tttcactgca    2940
ttctccctat atgatgcgag aaatgtcatt aaaaatggtg attttaataa tggcttatcc    3000
tgctggaacg tgaaagggca tgtagatgta gaagaacaaa acaaccaacg ttcggtcctt    3060
gttgttccgg aatgggaagc agaagtgtca caagaagttc gtgtctgtcc gggtcgtggc    3120
tatatccttc gtgtcacagc gtacaaggag ggatatggaa aggttgcgt  aaccattcat    3180 gagatcgaga acaatacaga cgaactgaag tttagcaact gcgtagaaga ggaaatctat    3240
ccaaataaca cggtaacgtg taatgattat actgtaaatc aagaagaata cggaggtgcg    3300
tacacttctc gtaatcgagg atataacgaa gctccttccg taccagctga ttatgcgtca    3360
gtctatgaag aaaaatcgta tacagatgga cgaagagaga atccttgtga atttaacaga    3420
gggtataggg attacacgcc actaccagtt ggttatgtga caaaagaatt agaatacttc    3480
ccagaaaccg ataaggtatg gattgagatt ggagaaacgg aaggaacatt tatcgtggac    3540
agcgtggaat tactccttat ggaggaatga                                    3570
```

<210> SEQ ID NO 2
<211> LENGTH: 3570
<212> TYPE: DNA
<213> ORGANISM: Artificial
<220> FEATURE:
<223> OTHER INFORMATION: Synthetic nucleotide sequence designed for
      expression in a plant cell encoding TIC1100.

<400> SEQUENCE: 2

```
atggagattg tgaacaacca gaaccagtgc gttccttaca actgcttgaa caaccctgag     60
attgagattc ttgagggtgg tagaatttct gttggcaaca ctcctattga catctctttg    120
agtttgactc aattcttgtt gagtgagttc gttcctggtg ctggtttcgt cttgggtttg    180
attgatttga tttggggttt cgttggtcct agtcaatggg atgctttctt ggctcaagtt    240
gagcaattga ttaaccagag gatcgctgag gctgtgagga cactgctat  tcaagagttg    300 gagggtatgg ctagagtttta cagaacttac gctactgctt tcgctgagtg ggagaaggct    360
cctgatgacc ctgagttgag ggaggctttg agaactcaat tcactgctac tgagacttac    420
atcagtggta gaatcagtgt cttgaagatt caaacttttcg aggttcaatt gctttctgtg    480
ttcgctcaag ctgcaaactt gcacttgtct tgcttagag  atgttgtgtt ctttggtcaa    540
agatggggtt tctccactac tacgtgaac  aattactaca acgatttgac tgagggtatt    600
tctacttaca ctgattacgc tgttagatgg tacaacactg tgttggagag agtttggggt    660
ccagattcca gagattgggt cagatacaac cagttcagaa gggagttgac tttgactgtc    720
ttggacattg ttgctctctt ccctaactac gatagtcgtc gttacccctat agaactgtt    780 tctcaactta ctagggaaat ctacactaac cctgttcttg agaacttcga tggtagtttc    840
cgtggtagtg ctcaagggat tgagcgttct attcgttctc ctcatcttat ggacattctt    900
aactctatta ctatctacac tgatgctcat cgtggttact attactggtc tggtcatcaa    960
attatggcta gtcctgttgg tttcagtggt cctgagttca cttttccctct ttacggtact   1020
```

```
atgggcaacg ctgcacctca acagaggatc gttgctcaac ttggtcaagg tgtttacagg    1080
actctttctt caacccttta caggcgtcct ttcaacattg ggatcaacaa ccagcagctt    1140
tctgttcttg atggaaccga gttcgcttac ggaacctctt caaaccttcc tagtgctgtt    1200
tacaggaagt ctggaaccgt tgacagtctt gatgagattc accgcagaa caataacgtt     1260 ccacccaggc aaggcttcag tcataggctt tctcatgttt ctatgttccg ctctggattc    1320
agcaactctt cagtttctat tatcagggct ccaatgttct cgtggattca taggtctgcc    1380
gagttcaaca acattatcgc ttccgatagc attaaccaga ttccacttgt taagggattc    1440
cgtgtttggg gaggcacctc tgttattacc ggaccaggct tcaccggagg cgacattctt    1500
cgtcgtaaca ccttcggaga tttcgtttca cttcaagtga acattaactc accaatcacc    1560
cagcgctaca ggcttcgctt ccgctacgca tcatccaggg atgcaagggt gatcgtgctt    1620
accggagcag cctcaaccgg agtgggaggc caagtgagcg tgaacatgcc acttcagaag    1680
acgatggaga tcggcgagaa ccttacctca agaacctttc gttacaccga tttcagcaac    1740
ccattcagct ttcgtgcaaa cccagacatc atagggatct cagagcagcc actgtttgga    1800
gctggatcaa tctcatccgg agagctttac atcgacaaga tcgagatcat actcgcagat    1860
gcaaccttcg aggctgagag cgatctggag cgtgcacaga aggcagtgaa cgcactcttt    1920
acctctacca accagctcgg actcaagacc aacgtgaccg attaccacat cgaccaagtg    1980
agcaacctcg tgacctacct ctcagatgag ttctgcttgg atgagaaacg cgaactcagc    2040
gagaaggtga agcacgcaaa gcgtctctca gatgagcgta acctcctcca ggatagcaat    2100
ttcaaggaca tcaatcgtca gccagagcgt ggatgcggag gctcaaccgg aatcaccatc    2160
cagggaggcg atgatgtgtt taaggagaat tacgtgacac tctccggaac attcgatgag    2220
tgctacccaa catacctcta tcagaagatc gacgagtcca agctcaaggc gttcacccgt    2280
tatcagctcc gtggctacat cgaggatagt caagacctgg aaatctacct catccgctac    2340
aatgcaaagc acgagacagt gaatgtgcca ggaacaggct ccctctggcc actctccgca    2400
cagtctccaa tcggcaagtg cggcgagcca atcgctgcg cgccacacct ggagtggaat     2460
cccgacctgg actgctcctg ccgcgacggc gagaagtgcc cccaccactc ccaccacttt    2520
agcctggaca tcgacgtggg ctgtacagac ctgaatgagg atctggcgt gtgggtgatc     2580 tttaagatca agacacagga cggccacgcc cgcctgggca atctggagtt ctgaggag      2640 aagcctctgg tgggcaagc cctggcccgc gtgaagcgcg ccgagaagaa atggcgcgac     2700
aaacgcgaga aactggaatg ggaaacaaac atcgtgtaca agaagccaa agaatccgtg     2760 gacgccctat ttgtgaactc ccagtatgac cagctacagg ccgacacaaa catcgcgatg    2820
atccacgctg cggacaagcg cgtgcactcc atacgcgaag cctatctacc gaactatcc    2880 gtgatacccg gcgtcaatgc cgcgatcttt gaagaattgg aaggccgcat cttcacagcc    2940
tttagcctct atgacgcccg aaatgtcatc aagaatggcg actttaacaa tgggctatcc    3000
tgttggaatg tcaaagggca cgtggacgtc gaagagcaga acaatcagcg atccgtctta    3060
gtcgtacccg aatgggaagc cgaagtctcc caggaagtcc gagtctgtcc tggtagaggt    3120
tacatcttga gagtgactgc ttacaaggag ggttacggtg agggatgcgt gactattcac    3180
gagattgaga caacactga tgagttgaag ttcagtaact gcgtggagga ggaaatctac     3240
cccaacaaca ctgtgacttg taacgattac accgtgaacc aggaggaata cggaggcgct    3300
tacacctcca gaaaccgtgg atacaatgag gctccctcgg tccccgctga ttatgcctcc    3360
```

```
gtctatgagg agaagtccta caccgatgga aggcgcgaga atccctgcga gttcaatcgc    3420
ggctatcgag actacactcc gctacccgtt ggctatgtca caaaggaact ggaatacttc    3480
ccggaaacag acaaagtctg gatcgaaatc ggcgaaacag aagggacgtt catagtcgat    3540
agcgtagaac ttctccttat ggaagaatga                                    3570

<210> SEQ ID NO 3
<211> LENGTH: 3570
<212> TYPE: DNA
<213> ORGANISM: Artificial
<220> FEATURE:
<223> OTHER INFORMATION: Synthetic nucleotide sequence designed for
      expression in a plant cell encoding TIC1100.

<400> SEQUENCE: 3
atggagattg tgaacaacca gaaccagtgc gttccttaca actgcttgaa caaccctgag      60
attgagattc ttgagggtgg tagaatttct gttggcaaca ctcctattga catctctttg     120
agtttgactc aattcttgtt gagtgagttc gttcctggtg ctggtttcgt cttgggtttg     180
attgatttga tttggggttt cgttggtcct agtcaatggg atgctttctt ggctcaagtt     240
gagcaattga ttaaccagag gatcgctgag gctgtgagga cactgctat tcaagagttg      300 gagggtatgg ctagagttta cagaacttac gctactgctt cgctgagtg ggagaaggct      360 cctgatgacc tgagttgag ggaggctttg agaactcaat tcactgctac tgagacttac     420
atcagtggta gaatcagtgt cttgaagatt caaactttcg aggttcaatt gctttctgtg     480
ttcgctcaag ctgcaaactt gcacttgtct ttgcttagag atgttgtgtt ctttggtcaa      540
agatggggtt tctccactac taccgtgaac aattactaca acgatttgac tgagggtatt      600
tctacttaca ctgattacgc tgttagatgg tacaacactg gtttggagag agtttggggt      660
ccagattcca gagattgggt cagatacaac cagttcagaa gggagttgac tttgactgtc      720
ttggacattg ttgctctctt ccctaactac gatagtcgtc gttacccata tagaactgtt     780
tctcaactta ctagggaaat ctacactaac cctgttcttg agaacttcga tggtagtttc      840
cgtggtagtg ctcaagggat tgagcgttct attcgttctc ctcatcttat ggacattctt      900
aactctatta ctatctacac tgatgctcat cgtggtact attactggtc tggtcatcaa      960
attatggcta gtcctgttgg tttcagtggt cctgagttca ctttccctct ttacggtact    1020
atgggcaacg ctgcacctca acagaggatc gttgctcaac ttggtcaagg tgtttacagg    1080
actctttctt caacccttta caggcgtcct ttcaacattg ggatcaacaa ccagcagctt    1140
tctgttcttg atggaaccga gttcgcttac ggaacctctt caaaccttcc tagtgctgtt    1200
tacaggaagt ctggaaccgt tgacagtctt gatgagattc caccgcagaa caataacgtt    1260
ccacccaggc aaggcttcag tcataggctt tctcatgttt ctatgttccg ctctggattc    1320
agcaactctt cagtttctat tatcagggct ccaatgttct cgtggattca taggtctgcc    1380
gagttcaaca acattatcgc ttccgatagc attaaccaga ttccacttgt aagggattc    1440 cgtgtttggg gaggcacctc tgttattacc ggaccaggct tcaccggagg cgacattctt    1500
cgtcgtaaca ccttcggaga tttcgtttca cttcaagtga acattaactc accaatcacc    1560
cagcgctaca ggcttcgctt ccgctacgca tcatccaggg atgcaagggt gatcgtgctt    1620
accggagcag cctcaaccgg agtgggaggc caagtgagcg tgaacatgcc acttcagaag    1680
acgatggaga tcggcgagaa ccttacctca agaaccttc gttacaccga tttcagcaac    1740
ccattcagct ttcgtgcaaa cccagacatc ataggatct cagagcagcc actgtttgga    1800
```

| | |
|---|---|
| gctggatcaa tctcatccgg agagctttac atcgacaaga tcgagatcat actcgcagat | 1860 |
| gcaaccttcg aggctgagag cgatctggag cgtgcacaga aggcagtgaa cgcactcttt | 1920 |
| acctctacca accagctcgg actcaagacc aacgtgaccg attaccacat cgaccaagtg | 1980 |
| agcaacctcg tgacctacct ctcagatgag ttctgcttgg atgagaaacg cgaactcagc | 2040 |
| gagaaggtga agcacgcaaa gcgtctctca gatgagcgta acctcctcca ggatagcaat | 2100 |
| ttcaaggaca tcaatcgtca gccagagcgt ggatggggag gctcaaccgg aatcaccatc | 2160 |
| cagggaggcg atgatgtgtt taaggagaat tacgtgacac tctccggaac attcgatgag | 2220 |
| tgctacccaa catacctcta tcagaagatc gacgagtcca agctcaaggc gttcacccgt | 2280 |
| tatcagctcc gtggctacat cgaggatagt caagacctgg aaatctacct catccgctac | 2340 |
| aatgcaaagc acgagacagt gaatgtacca ggaacaggct ccctctggcc actctccgca | 2400 |
| cagtctccaa tcggcaagtg cggcgagcca atcgctgcg cgccacacct ggagtggaat | 2460 |
| cccgacctgg actgctcctg ccgcgacggc gagaagtgcg cccaccactc ccaccacttt | 2520 |
| agcctggaca tcgacgtggg ctgtacagac ctgaatgagg atctgggcgt gtgggtgatc | 2580 |
| tttaagatca agacacagga cggccacgcc cgcctgggca atctggagtt tctggaggag | 2640 |
| aagcctctgg tgggcgaagc cctggcccgc gtgaagcgcg ccgagaagaa atggcgcgac | 2700 |
| aaacgcgaga aactggaatg ggaaacaaac atcgtgtaca agaagccaa agaatccgtg | 2760 |
| gacgccctat ttgtgaactc ccagtatgac cagctacagg ccgacacaaa catcgcgatg | 2820 |
| atccacgctg cggacaagcg cgtgcactcc atacgcgaag cctatctacc cgaactatcc | 2880 |
| gtgatacccg cgtcaatgc cgcgatcttt gaagaattgg aaggccgcat cttcacagcc | 2940 |
| tttagcctct atgacgcccg aaatgtcatc aagaatggcg actttaacaa tgggctatcc | 3000 |
| tgttggaatg tcaaagggca cgtggacgtc gaagagcaga acaatcagcg atccgtctta | 3060 |
| gtcgtacccg aatgggaagc cgaagtctcc caggaagtcc gagtctgtcc tggtagaggt | 3120 |
| tacatcttga gagtgactgc ttacaaggag ggttacggtg agggatgcgt gactattcac | 3180 |
| gagattgaga acaacactga tgagttgaag ttcagtaact gcgtggagga ggaaatctac | 3240 |
| cccaacaaca ctgtgacttg taacgattac accgtgaacc aggaggaata cggaggcgct | 3300 |
| tacacctcca gaaaccgtgg atacaatgag gctccctcgg tccccgctga ttatgcctcc | 3360 |
| gtctatgagg agaagtccta caccgatgga aggcgcgaga tccctgcga gttcaatcgc | 3420 |
| ggctatcgag actacactcc gctacccgtt ggctatgtca caaggaact ggaatacttc | 3480 |
| ccggaaacag acaaagtctg gatcgaaatc ggcgaaacag aagggacgtt catagtcgat | 3540 |
| agcgtagaac ttctccttat ggaagaatga | 3570 |

<210> SEQ ID NO 4
<211> LENGTH: 1189
<212> TYPE: PRT
<213> ORGANISM: Artificial
<220> FEATURE:
<223> OTHER INFORMATION: Amino acid sequence of the chimeric protein
      TIC1100.

<400> SEQUENCE: 4

Met Glu Ile Val Asn Asn Gln Asn Gln Cys Val Pro Tyr Asn Cys Leu
1               5                   10                  15

Asn Asn Pro Glu Ile Glu Ile Leu Glu Gly Gly Arg Ile Ser Val Gly
            20                  25                  30

Asn Thr Pro Ile Asp Ile Ser Leu Ser Leu Thr Gln Phe Leu Leu Ser
        35                  40                  45

-continued

```
Glu Phe Val Pro Gly Ala Gly Phe Val Leu Gly Leu Ile Asp Leu Ile
 50                  55                  60

Trp Gly Phe Val Gly Pro Ser Gln Trp Asp Ala Phe Leu Ala Gln Val
 65                  70                  75                  80

Glu Gln Leu Ile Asn Gln Arg Ile Ala Glu Ala Val Arg Asn Thr Ala
                 85                  90                  95

Ile Gln Glu Leu Glu Gly Met Ala Arg Val Tyr Arg Thr Tyr Ala Thr
            100                 105                 110

Ala Phe Ala Glu Trp Glu Lys Ala Pro Asp Asp Pro Glu Leu Arg Glu
        115                 120                 125

Ala Leu Arg Thr Gln Phe Thr Ala Thr Glu Thr Tyr Ile Ser Gly Arg
    130                 135                 140

Ile Ser Val Leu Lys Ile Gln Thr Phe Glu Val Gln Leu Leu Ser Val
145                 150                 155                 160

Phe Ala Gln Ala Ala Asn Leu His Leu Ser Leu Leu Arg Asp Val Val
                165                 170                 175

Phe Phe Gly Gln Arg Trp Gly Phe Ser Thr Thr Thr Val Asn Asn Tyr
            180                 185                 190

Tyr Asn Asp Leu Thr Glu Gly Ile Ser Thr Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460
```

```
Ile Ile Ala Ser Asp Ser Ile Asn Gln Ile Pro Leu Val Lys Gly Phe
465                 470                 475                 480

Arg Val Trp Gly Gly Thr Ser Val Ile Thr Gly Pro Gly Phe Thr Gly
            485                 490                 495

Gly Asp Ile Leu Arg Arg Asn Thr Phe Gly Asp Phe Val Ser Leu Gln
                500                 505                 510

Val Asn Ile Asn Ser Pro Ile Thr Gln Arg Tyr Arg Leu Arg Phe Arg
                515                 520                 525

Tyr Ala Ser Ser Arg Asp Ala Arg Val Ile Val Leu Thr Gly Ala Ala
530                 535                 540

Ser Thr Gly Val Gly Gly Gln Val Ser Val Asn Met Pro Leu Gln Lys
545                 550                 555                 560

Thr Met Glu Ile Gly Glu Asn Leu Thr Ser Arg Thr Phe Arg Tyr Thr
                565                 570                 575

Asp Phe Ser Asn Pro Phe Ser Phe Arg Ala Asn Pro Asp Ile Ile Gly
                580                 585                 590

Ile Ser Glu Gln Pro Leu Phe Gly Ala Gly Ser Ile Ser Ser Gly Glu
        595                 600                 605

Leu Tyr Ile Asp Lys Ile Glu Ile Ile Leu Ala Asp Ala Thr Phe Glu
        610                 615                 620

Ala Glu Ser Asp Leu Glu Arg Ala Gln Lys Ala Val Asn Ala Leu Phe
625                 630                 635                 640

Thr Ser Thr Asn Gln Leu Gly Leu Lys Thr Asn Val Thr Asp Tyr His
                645                 650                 655

Ile Asp Gln Val Ser Asn Leu Val Thr Tyr Leu Ser Asp Glu Phe Cys
                660                 665                 670

Leu Asp Glu Lys Arg Glu Leu Ser Glu Lys Val Lys His Ala Lys Arg
            675                 680                 685

Leu Ser Asp Glu Arg Asn Leu Leu Gln Asp Ser Asn Phe Lys Asp Ile
            690                 695                 700

Asn Arg Gln Pro Glu Arg Gly Trp Gly Gly Ser Thr Gly Ile Thr Ile
705                 710                 715                 720

Gln Gly Gly Asp Asp Val Phe Lys Glu Asn Tyr Val Thr Leu Ser Gly
                725                 730                 735

Thr Phe Asp Glu Cys Tyr Pro Thr Tyr Leu Tyr Gln Lys Ile Asp Glu
                740                 745                 750

Ser Lys Leu Lys Ala Phe Thr Arg Tyr Gln Leu Arg Gly Tyr Ile Glu
        755                 760                 765

Asp Ser Gln Asp Leu Glu Ile Tyr Leu Ile Arg Tyr Asn Ala Lys His
770                 775                 780

Glu Thr Val Asn Val Pro Gly Thr Gly Ser Leu Trp Pro Leu Ser Ala
785                 790                 795                 800

Gln Ser Pro Ile Gly Lys Cys Gly Glu Pro Asn Arg Cys Ala Pro His
                805                 810                 815

Leu Glu Trp Asn Pro Asp Leu Asp Cys Ser Cys Arg Asp Gly Glu Lys
                820                 825                 830

Cys Ala His His Ser His His Phe Ser Leu Asp Ile Asp Val Gly Cys
835                 840                 845

Thr Asp Leu Asn Glu Asp Leu Gly Val Trp Val Ile Phe Lys Ile Lys
            850                 855                 860

Thr Gln Asp Gly His Ala Arg Leu Gly Asn Leu Glu Phe Leu Glu Glu
865                 870                 875                 880

Lys Pro Leu Val Gly Glu Ala Leu Ala Arg Val Lys Arg Ala Glu Lys
```

|   |   |   |   | 885 |   |   |   | 890 |   |   |   | 895 |   |
|---|---|---|---|---|---|---|---|---|---|---|---|---|---|

Lys Trp Arg Asp Lys Arg Glu Lys Leu Glu Trp Glu Thr Asn Ile Val
            900            905            910

Tyr Lys Glu Ala Lys Glu Ser Val Asp Ala Leu Phe Val Asn Ser Gln
    915            920            925

Tyr Asp Gln Leu Gln Ala Asp Thr Asn Ile Ala Met Ile His Ala Ala
  930            935            940

Asp Lys Arg Val His Ser Ile Arg Glu Ala Tyr Leu Pro Glu Leu Ser
945            950            955            960

Val Ile Pro Gly Val Asn Ala Ala Ile Phe Glu Glu Leu Glu Gly Arg
            965            970            975

Ile Phe Thr Ala Phe Ser Leu Tyr Asp Ala Arg Asn Val Ile Lys Asn
    980            985            990

Gly Asp Phe Asn Asn Gly Leu Ser Cys Trp Asn Val Lys Gly His Val
  995           1000         1005

Asp Val Glu Glu Gln Asn Asn Gln Arg Ser Val Leu Val Val Pro
1010         1015         1020

Glu Trp Glu Ala Glu Val Ser Gln Glu Val Arg Val Cys Pro Gly
1025         1030         1035

Arg Gly Tyr Ile Leu Arg Val Thr Ala Tyr Lys Glu Gly Tyr Gly
1040         1045         1050

Glu Gly Cys Val Thr Ile His Glu Ile Glu Asn Asn Thr Asp Glu
1055         1060         1065

Leu Lys Phe Ser Asn Cys Val Glu Glu Ile Tyr Pro Asn Asn
1070         1075         1080

Thr Val Thr Cys Asn Asp Tyr Thr Val Asn Gln Glu Glu Tyr Gly
1085         1090         1095

Gly Ala Tyr Thr Ser Arg Asn Arg Gly Tyr Asn Glu Ala Pro Ser
1100         1105         1110

Val Pro Ala Asp Tyr Ala Ser Val Tyr Glu Glu Lys Ser Tyr Thr
1115         1120         1125

Asp Gly Arg Arg Glu Asn Pro Cys Glu Phe Asn Arg Gly Tyr Arg
1130         1135         1140

Asp Tyr Thr Pro Leu Pro Val Gly Tyr Val Thr Lys Glu Leu Glu
1145         1150         1155

Tyr Phe Pro Glu Thr Asp Lys Val Trp Ile Glu Ile Gly Glu Thr
1160         1165         1170

Glu Gly Thr Phe Ile Val Asp Ser Val Glu Leu Leu Leu Met Glu
1175         1180         1185

Glu

<210> SEQ ID NO 5
<211> LENGTH: 3672
<212> TYPE: DNA
<213> ORGANISM: Artificial
<220> FEATURE:
<223> OTHER INFORMATION: Recombinant nucleotide sequence used for
    expression in a bacterial cell encoding TIC860.

<400> SEQUENCE: 5

| atgacttcaa | ataggaaaaa | tgagaatgaa | attataaatg | ctttatcgat | tccaacggta | 60 |
|---|---|---|---|---|---|---|
| tcgaatcctt | ccacgcaaat | gaatctatca | ccagatgctc | gtattgaaga | tagcttgtgt | 120 |
| gtagccgagg | tgaacaatat | tgatccattt | gttagcgcat | caacagtcca | aacgggtata | 180 |
| aacatagctg | gtagaatatt | gggcgtatta | ggtgtgccgt | ttgctggaca | actagctagt | 240 |

```
ttttatagtt ttcttgttgg ggaattatgg cctagtggca gagatccatg ggaaattttc      300
ctggaacatg tagaacaact tataagacaa caagtaacag aaaatactag gaatacggct      360
attgctcgat tagaaggtct aggaagaggc tatagatctt accagcaggc tcttgaaact      420
tggttagata accgaaatga tgcaagatca agaagcatta ttcttgagcg ctatgttgct      480
ttagaacttg acattactac tgctataccg cttttcagaa tacgaaatga agaagttcca      540
ttattaatgg tatatgctca agctgcaaat ttacacctat tattattgag agacgcatcc      600 cttttggta gtgaatgggg gatggcatct tccgatgtta accaatatta ccaagaacaa       660
atcagatata cagaggaata ttctaaccat tgcgtacaat ggtataatac agggctaaat      720
aacttaagag ggacaaatgc tgaaagttgg ttgcggtata tcaattccg tagagaccta       780 acgttagggg tattagattt agtagcccta ttcccaagct atgatactcg cacttatcca      840
atcaatacga gtgctcagtt aacaagagaa atttatacag atccaattgg gagaacaaat      900
gcaccttcag gatttgcaag tacgaattgg tttaataata atgcaccatc gttttctgcc      960
atagaggctg ccattttcag gcctccgcat ctacttgatt ttccagaaca acttacaatt     1020
tacagtgcat caagccgttg gagtagcact caacatatga attattgggt gggacatagg     1080
cttaacttcc gcccaatagg agggacatta aatacctcaa cacaaggact tactaataat     1140
acttcaatta atcctgtaac attacagttt acgtctcgag acgttatag aacagaatca      1200 aatgcaggga caaatatact atttactact cctgtgaatg gagtaccttg ggctagattt     1260
aattttataa accctcagaa tatttatgaa agaggcgcca ctacctacag tcaaccgtat     1320
cagggagttg ggattcaatt atttgattca gaaactgaat taccaccaga aacaacagaa     1380
cgaccaaatt atgaatcata tagtcataga ttatctcata taggactaat cataggaaac     1440
actttgagag caccagtcta ttcttggacg catcgtagtg cagatcgtac gaatacgatt     1500
ggaccaaata gaattaatca aatacctta gtgaaaggat ttagagtttg ggggggcacc      1560
tctgtcatta caggaccagg atttacagga ggggatatcc ttcgaagaaa taccttggt     1620 gattttgtat ctctacaagt caatattaat tcaccaatta cccaaagata ccgtttaaga     1680
tttcgttacg cttccagtag ggatgcacga gttatagtat taacaggagc ggcatccaca     1740
ggagtgggag gccaagttag tgtaaatatg cctcttcaga aaactatgga aataggggag     1800
aacttaacat ctagaacatt tagatatacc gattttgta atccttttc atttagagct       1860 aatccagata taattgggat aagtgaacaa cctctatttg gtgcaggttc tattagtagc     1920
ggtgaacttt atatagataa aattgaaatt attctagcag atgcaacatt tgaagcagaa     1980
tctgatttag aaagagcgca gaaggcggtg aatgcgctgt ttacgtctac aaaccaacta     2040
gggctaaaaa caaatgtaac ggattatcat attgatcaag tgtccaattt agttacgtat     2100
ttatcggatg aattttgtct ggatgaaaag cgagaattgt ccgagaaagt caaacatgcg     2160
aagcgactca gtgatgaacg caatttactc caagattcaa atttcaaaga cattaatagg     2220
caaccagaac gtgggtgggg cggaagtaca gggattacca tccaaggagg ggatgacgta     2280
tttaaagaaa attacgtcac actatcaggt acctttgatg agtgctatcc aacatatttg     2340
tatcaaaaaa tcgatgaatc aaaattaaaa gcctttaccc gttatcaatt aagagggtat     2400
atcgaagata gtcaagactt agaaatctat ttaattcgct acaatgcaaa acatgaaaca     2460
gtaaatgtgc caggtacggg ttccttatgg ccgctttcag cccaaagtcc aatcggaaag     2520
tgtggagagc cgaatcgatg cgcgccacac cttgaatgga atcctgactt agattgttcg     2580
```

| | |
|---|---:|
| tgtagggatg gagaaaagtg tgcccatcat tcgcatcatt tctccttaga cattgatgta | 2640 |
| ggatgtacag acttaaatga ggacctaggt gtatgggtga tctttaagat taagacgcaa | 2700 |
| gatgggcacg caagactagg gaatctagag tttctcgaag agaaaccatt agtaggagaa | 2760 |
| gcgctagctc gtgtgaaaag agcggagaaa aaatggagag acaaacgtga aaaattggaa | 2820 |
| tgggaaacaa atatcgttta taagaggca aaagaatctg tagatgcttt atttgtaaac | 2880 |
| tctcaatatg atcaattaca agcggatacg aatattgcca tgattcatgc ggcagataaa | 2940 |
| cgtgttcata gcattcgaga agcttatctg cctgagctgt ctgtgattcc gggtgtcaat | 3000 |
| gcggctattt ttgaagaatt agaagggcgt attttcactg cattctccct atatgatgcg | 3060 |
| agaaatgtca ttaaaaatgg tgattttaat aatggcttat cctgctggaa cgtgaaaggg | 3120 |
| catgtagatg tagaagaaca aaacaaccaa cgttcggtcc ttgttgttcc ggaatgggaa | 3180 |
| gcagaagtgt cacaagaagt tcgtgtctgt ccgggtcgtg gctatatcct tcgtgtcaca | 3240 |
| gcgtacaagg agggatatgg agaaggttgc gtaaccattc atgagatcga aacaataca | 3300 |
| gacgaactga agtttagcaa ctgcgtagaa gaggaaatct atccaaataa cacggtaacg | 3360 |
| tgtaatgatt atactgtaaa tcaagaagaa tacggaggtg cgtacacttc tcgtaatcga | 3420 |
| ggatataacg aagctccttc cgtaccagct gattatgcgt cagtctatga agaaaaatcg | 3480 |
| tatacagatg gacgaagaga gaatccttgt gaatttaaca gagggtatag ggattacacg | 3540 |
| ccactaccag ttggttatgt gacaaaagaa ttagaatact tcccagaaac cgataaggta | 3600 |
| tggattgaga ttggagaaac ggaaggaaca tttatcgtgg acagcgtgga attactcctt | 3660 |
| atggaggaat ag | 3672 |

<210> SEQ ID NO 6
<211> LENGTH: 3672
<212> TYPE: DNA
<213> ORGANISM: Artificial
<220> FEATURE:
<223> OTHER INFORMATION: Synthetic nucleotide sequence designed for
      expression in a plant cell encoding TIC860.

<400> SEQUENCE: 6

| | |
|---|---:|
| atgaccagca accggaagaa cgagaacgag atcatcaacg ccctgagcat cccgaccgtg | 60 |
| agcaaccta gcacccagat gaacctgagc cctgacgctc gcatcgagga ctccctctgc | 120 |
| gtggctgagg tgaacaacat cgacccgttc gtgtccgcct ccaccgtgca gaccggcatc | 180 |
| aacatcgcgg ccgcatcct cggcgtgctc ggcgtgccct tgcgggcca gctcgcctcc | 240 |
| ttctactcct tcctcgtggg agagctgtgg ccctccggcc gcgacccgtg ggagatcttc | 300 |
| ctggagcacg tggagcagct catccgccag caagtcaccg agaacacccg caacaccgcc | 360 |
| atcgcccgcc tggagggcct gggccgtggc taccgctcct accagcaagc cctggagacc | 420 |
| tggctcgaca accgcaacga cgcccgctcc cgctccatca tcctggagcg ctacgtcgcc | 480 |
| ctggaactgg acatcaccac tgccatccca ctcttccgca tcaggaacga ggaggtgcct | 540 |
| ctgctgatgg tgtacgccca ggctgcgaac ctgcacctgc tgctgctgcg cgacgcaagc | 600 |
| ctgtttggct ccgagtgggg tatggcaagc tccgacgtca accagtacta ccaggagcag | 660 |
| atccgctaca ccgaggagta cagcaaccac tgcgtccagt ggtacaacac cggtctgaac | 720 |
| aatctcagag ggaccaacgc tgagagctgg ctgcgctaca accagttccg gcgggatctg | 780 |
| accctaggtg tcctggatct ggtcgctctg ttccgagct acgataccag gacgtacct | 840 |
| atcaacacct ctgctcagct taccagggag atctacactg atcctatcgg taggactaac | 900 |

```
gctcctagtg gtttcgccag cactaactgg ttcaacaaca acgcgcctag tttctctgcc    960
atcgaggcgg cgatcttccg gcctcctcac ctcctcgact tcccggagca gcttactatc   1020
tactctgcgt cttcgcggtg gtcttcgact cagcacatga actactgggt tggtcaccgg   1080
cttaacttcc gcccgattgg aggaactctt aacaccagta cgcaaggtct tacgaacaac   1140
acttccatca acccggttac gttgcagttc acgtctcggg acgtttaccg gacggagtcg   1200
aatgctggga cgaacatcct gttcacgaca ccggtgaatg gtgttccgtg ggcacgtttc   1260
aacttcatca acccgcagaa catctacgag cgtggagcaa cgacatactc gcaaccatac   1320
caaggcgttg gcatccaact gtttgactcg gagacggaac tgccaccaga gacgacagaa   1380
cgtccgaatt acgagtcata ctcacacaga ctatcacaca ttggactcat tatcggaaac   1440
acactgagag caccagtgta ctcatggaca catcggtcag cagatcgtac gaacaccatc   1500
ggacccaatc ggatcaacca gatcccgctc gtgaagggct ccgcgtgtg gggcggcacc   1560
tccgtcatca ccggtccggg cttcaccggc ggcgacatcc tccgccgcaa caccttcggc   1620
gacttcgtgt cactccaagt gaacatcaac agcccgatca cccagcgcta tcgcctccgc   1680
ttccgctacg cctcctcccg cgacgctaga gtgatcgtgc tcaccggagc ggcgtccaca   1740
ggcgtaggcg gccaagtgtc tgtgaacatg ccgctccaga agactatgga gattggtgag   1800
aacctcacct ctcgcacctt ccgctacacc gacttctcca atccgttctc cttcagagcc   1860
aacccagaca tcatcggcat ctccgagcag cctctctttg gcgctggctc catctcctcc   1920
ggcgagctgt acatcgacaa gattgagatc atccttgccg acgccacctt cgaagctgag   1980
tccgatctcg agcgcgccca gaaggccgtg aacgccctct tcactagcac taaccagctc   2040
ggcctcaaga ctaacgtgac cgactaccac attgaccaag tgagcaacct agtgacctac   2100
cttagcgacg agttctgcct tgacgagaag cgtgagctga gcgagaaggt gaagcacgcc   2160
aagcgcctct ccgacgagcg caacctcctc caggactcca acttcaagga catcaaccgc   2220
cagcccgagc gcggctgggg cggtagcacc ggcatcacca tccagggcgg tgacgatgtg   2280
ttcaaggaga actacgtgac cctctccggc accttcgacg agtgctaccc gacctacctc   2340
taccagaaga tcgacgagtc caagctcaag gcgttcaccc gctaccagct tcgcggctac   2400
atcgaggact cccaggatct ggagatctac ctcatccgct acaacgccaa gcacgagacc   2460
gtgaacgtgc ccggcaccgg ctccctctgg ccgctctccg cccagagccc tatcggcaag   2520
tgcggcgagc ccaaccgctg cgcgcctcac ctggagtgga accctgacct cgactgctcc   2580
tgccgcgacg gcgagaagtg cgcccaccat agccaccact tctctctcga catcgacgtg   2640
ggctgcaccg acctcaacga ggatctgggc gtgtgggtga tcttcaagat caagacccag   2700
gacgccacg ccaggctggg caacctggag ttcctggagg agaagcctct ggtgggtgag   2760
gccctggcca gggtcaagag ggctgagaag aaatggaggg acaagaggga gaagctggag   2820
tgggagacca acatcgtgta caaggaggct aaggagtccg tggacgctct gttcgtcaac   2880
tctcagtacg atcagctcca ggctgacacc aacatcgcta tgatccacgc tgcggataag   2940
agggtccact ctatcaggga ggcttacctg cctgagcttt ctgtcatccc tggtgtcaac   3000
gcggcaatct tcgaggaact tgagggccgc atcttcactg cgttctcgct ttacgatgcg   3060
cggaacgtca ttaagaacgg tgacttcaac aatggtcttt cgtgctggaa cgtcaagggt   3120
catgtcgatg tcgaggaaca gaacaaccag cggtcggtcc ttgtcgttcc cgagtgggag   3180
gccgaggtct cgcaagaggt ccgggtctgc cctgggcgcg gtacattct  tcgtgtcact   3240
gcgtacaagg agggctacgg cgagggctgc gttactattc atgagattga gaacaatacg   3300
```

-continued

```
gatgagctta agtttagtaa ctgtgttgag gaggagatct acccgaacaa tacggttacg    3360
tgcaatgatt acacggtgaa ccaggaggaa tacggcggag catacacctc acgtaataga    3420
gggtacaatg aggcaccgtc agttccggca gattatgcct cagtttatga ggagaagtcc    3480
tacacggatg gaagacgcga gaatccatgt gagtttaata gaggataccg agactacaca    3540
ccactcccag ttggatacgt tacaaaggag ttggaatact tcccagaaac agataaagtt    3600
tggatagaga tcggagaaac agaaggaacc ttcatcgtgg acagtgtaga actgctgctg    3660
atggaagaat ga                                                        3672
```

<210> SEQ ID NO 7
<211> LENGTH: 1223
<212> TYPE: PRT
<213> ORGANISM: Artificial
<220> FEATURE:
<223> OTHER INFORMATION: Amino acid sequence of the chimeric protein TIC860.

<400> SEQUENCE: 7

```
Met Thr Ser Asn Arg Lys Asn Glu Asn Glu Ile Ile Asn Ala Leu Ser
1               5                   10                  15

Ile Pro Thr Val Ser Asn Pro Ser Thr Gln Met Asn Leu Ser Pro Asp
            20                  25                  30

Ala Arg Ile Glu Asp Ser Leu Cys Val Ala Glu Val Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asn Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Glu Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ala Ser Ser Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285
```

```
Arg Glu Ile Tyr Thr Asp Pro Ile Gly Arg Thr Asn Ala Pro Ser Gly
        290                 295                 300

Phe Ala Ser Thr Asn Trp Phe Asn Asn Ala Pro Ser Phe Ser Ala
305                 310                 315                 320

Ile Glu Ala Ala Ile Phe Arg Pro Pro His Leu Leu Asp Phe Pro Glu
            325                 330                 335

Gln Leu Thr Ile Tyr Ser Ala Ser Ser Arg Trp Ser Ser Thr Gln His
        340                 345                 350

Met Asn Tyr Trp Val Gly His Arg Leu Asn Phe Arg Pro Ile Gly Gly
            355                 360                 365

Thr Leu Asn Thr Ser Thr Gln Gly Leu Thr Asn Asn Thr Ser Ile Asn
        370                 375                 380

Pro Val Thr Leu Gln Phe Thr Ser Arg Asp Val Tyr Arg Thr Glu Ser
385                 390                 395                 400

Asn Ala Gly Thr Asn Ile Leu Phe Thr Thr Pro Val Asn Gly Val Pro
            405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
        435                 440                 445

Asp Ser Glu Thr Glu Leu Pro Pro Glu Thr Thr Glu Arg Pro Asn Tyr
450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
            485                 490                 495

Thr Asn Thr Ile Gly Pro Asn Arg Ile Asn Gln Ile Pro Leu Val Lys
        500                 505                 510

Gly Phe Arg Val Trp Gly Gly Thr Ser Val Ile Thr Gly Pro Gly Phe
        515                 520                 525

Thr Gly Gly Asp Ile Leu Arg Arg Asn Thr Phe Gly Asp Phe Val Ser
        530                 535                 540

Leu Gln Val Asn Ile Asn Ser Pro Ile Thr Gln Arg Tyr Arg Leu Arg
545                 550                 555                 560

Phe Arg Tyr Ala Ser Ser Arg Asp Ala Arg Val Ile Val Leu Thr Gly
            565                 570                 575

Ala Ala Ser Thr Gly Val Gly Gly Gln Val Ser Val Asn Met Pro Leu
            580                 585                 590

Gln Lys Thr Met Glu Ile Gly Glu Asn Leu Thr Ser Arg Thr Phe Arg
        595                 600                 605

Tyr Thr Asp Phe Ser Asn Pro Phe Ser Phe Arg Ala Asn Pro Asp Ile
610                 615                 620

Ile Gly Ile Ser Glu Gln Pro Leu Phe Gly Ala Gly Ser Ile Ser Ser
625                 630                 635                 640

Gly Glu Leu Tyr Ile Asp Lys Ile Glu Ile Ile Leu Ala Asp Ala Thr
            645                 650                 655

Phe Glu Ala Glu Ser Asp Leu Glu Arg Ala Gln Lys Ala Val Asn Ala
            660                 665                 670

Leu Phe Thr Ser Thr Asn Gln Leu Gly Leu Lys Thr Asn Val Thr Asp
        675                 680                 685

Tyr His Ile Asp Gln Val Ser Asn Leu Val Thr Tyr Leu Ser Asp Glu
        690                 695                 700
```

-continued

Phe Cys Leu Asp Glu Lys Arg Glu Leu Ser Glu Lys Val Lys His Ala
705                 710                 715                 720

Lys Arg Leu Ser Asp Glu Arg Asn Leu Leu Gln Asp Ser Asn Phe Lys
            725                 730                 735

Asp Ile Asn Arg Gln Pro Glu Arg Gly Trp Gly Gly Ser Thr Gly Ile
        740                 745                 750

Thr Ile Gln Gly Gly Asp Val Phe Lys Glu Asn Tyr Val Thr Leu
    755                 760                 765

Ser Gly Thr Phe Asp Glu Cys Tyr Pro Thr Tyr Leu Tyr Gln Lys Ile
770                 775                 780

Asp Glu Ser Lys Leu Lys Ala Phe Thr Arg Tyr Gln Leu Arg Gly Tyr
785                 790                 795                 800

Ile Glu Asp Ser Gln Asp Leu Glu Ile Tyr Leu Ile Arg Tyr Asn Ala
                805                 810                 815

Lys His Glu Thr Val Asn Val Pro Gly Thr Gly Ser Leu Trp Pro Leu
            820                 825                 830

Ser Ala Gln Ser Pro Ile Gly Lys Cys Gly Glu Pro Asn Arg Cys Ala
        835                 840                 845

Pro His Leu Glu Trp Asn Pro Asp Leu Asp Cys Ser Cys Arg Asp Gly
850                 855                 860

Glu Lys Cys Ala His His Ser His His Phe Ser Leu Asp Ile Asp Val
865                 870                 875                 880

Gly Cys Thr Asp Leu Asn Glu Asp Leu Gly Val Trp Val Ile Phe Lys
                885                 890                 895

Ile Lys Thr Gln Asp Gly His Ala Arg Leu Gly Asn Leu Glu Phe Leu
            900                 905                 910

Glu Glu Lys Pro Leu Val Gly Glu Ala Leu Ala Arg Val Lys Arg Ala
        915                 920                 925

Glu Lys Lys Trp Arg Asp Lys Arg Glu Lys Leu Glu Trp Glu Thr Asn
930                 935                 940

Ile Val Tyr Lys Glu Ala Lys Glu Ser Val Asp Ala Leu Phe Val Asn
945                 950                 955                 960

Ser Gln Tyr Asp Gln Leu Gln Ala Asp Thr Asn Ile Ala Met Ile His
                965                 970                 975

Ala Ala Asp Lys Arg Val His Ser Ile Arg Glu Ala Tyr Leu Pro Glu
            980                 985                 990

Leu Ser Val Ile Pro Gly Val Asn Ala Ala Ile Phe Glu Glu Leu Glu
        995                 1000                1005

Gly Arg Ile Phe Thr Ala Phe Ser Leu Tyr Asp Ala Arg Asn Val
1010                1015                1020

Ile Lys Asn Gly Asp Phe Asn Asn Gly Leu Ser Cys Trp Asn Val
1025                1030                1035

Lys Gly His Val Asp Val Glu Glu Gln Asn Asn Gln Arg Ser Val
1040                1045                1050

Leu Val Val Pro Glu Trp Glu Ala Glu Val Ser Gln Glu Val Arg
1055                1060                1065

Val Cys Pro Gly Arg Gly Tyr Ile Leu Arg Val Thr Ala Tyr Lys
1070                1075                1080

Glu Gly Tyr Gly Glu Gly Cys Val Thr Ile His Glu Ile Glu Asn
1085                1090                1095

Asn Thr Asp Glu Leu Lys Phe Ser Asn Cys Val Glu Glu Ile
1100                1105                1110

Tyr Pro Asn Asn Thr Val Thr Cys Asn Asp Tyr Thr Val Asn Gln

Glu Glu Tyr Gly Gly Ala Tyr Thr Ser Arg Asn Arg Gly Tyr Asn
1130                1135                1140

Glu Ala Pro Ser Val Pro Ala Asp Tyr Ala Ser Val Tyr Glu Glu
1145                1150                1155

Lys Ser Tyr Thr Asp Gly Arg Arg Glu Asn Pro Cys Glu Phe Asn
1160                1165                1170

Arg Gly Tyr Arg Asp Tyr Thr Pro Leu Pro Val Gly Tyr Val Thr
1175                1180                1185

Lys Glu Leu Glu Tyr Phe Pro Glu Thr Asp Lys Val Trp Ile Glu
1190                1195                1200

Ile Gly Glu Thr Glu Gly Thr Phe Ile Val Asp Ser Val Glu Leu
1205                1210                1215

Leu Leu Met Glu Glu
1220

<210> SEQ ID NO 8
<211> LENGTH: 3564
<212> TYPE: DNA
<213> ORGANISM: Artificial
<220> FEATURE:
<223> OTHER INFORMATION: Recombinant nucleotide sequence used for
      expression in a bacterial cell encoding TIC867.

<400> SEQUENCE: 8

| | |
|---|---|
| atgacttcaa ataggaaaaa tgagaatgaa attataaatg ctttatcgat tccagctgta | 60 |
| tcgaatcatt ccgcacaaat gaatctatca accgatgctc gtattgagga tagcttgtgt | 120 |
| atagccgagg ggaacaatat cgatccattt gttagcgcat caacagtcca acgggtatt | 180 |
| aacatagctg gtagaatact aggtgtatta ggcgtaccgt ttgctggaca aatagctagt | 240 |
| ttttatagtt ttcttgttgg tgaattatgg ccccgcggca gagatccttg ggaaattttc | 300 |
| ctagaacatg tcgaacaact tataagacaa caagtaacag aaaatactag ggatacggct | 360 |
| cttgctcgat tacaaggttt aggaaattcc tttagagcct atcaacagtc acttgaagat | 420 |
| tggctagaaa accgtgatga tgcaagaacg agaagtgttc tttataccca atatatagcc | 480 |
| ttagaacttg attttcttaa tgcgatgccg cttttcgcaa ttagaaacca agaagttcca | 540 |
| ttattaatgg tatatgctca agctgcaaat ttacacctat tattattgag agatgcctct | 600 |
| cttttttggta gtgaatttgg gcttacatcc caagaaattc aacgttatta tgagcgccaa | 660 |
| gtggaaaaaa cgagagaata ttctgattat tgcgcaagat ggtataatac gggtttaaat | 720 |
| aatttgagag ggacaaatgc tgaaagttgg ttgcgatata tcaattccg tagagactta | 780 |
| acgctaggag tattagatct agtggcacta ttcccaagct atgacacgcg tgttatcca | 840 |
| atgaatacca gtgctcaatt aacaagagaa atttatacag atccaattgg agaacaaat | 900 |
| gcaccttcag gatttgcaag tacgaattgg tttaataata tgcaccatcg tttttctgcc | 960 |
| atagaggctg ccgttattag gcctccgcat ctacttgatt ttccagaaca gcttacaatt | 1020 |
| ttcagcgtat taagtcgatg gagtaatact caatatatga attactgggt gggacataga | 1080 |
| cttgaatcgc gaacaataag ggggtcatta agtacctcga cacacggaaa taccaatact | 1140 |
| tctattaatc ctgtaacatt acagttcaca tctcgagacg tttatagaac agaatcattt | 1200 |
| gcagggataa atatacttct aactactcct gtgaatggag taccttgggc tagatttaat | 1260 |
| tggagaaatc ccctgaattc tcttagaggt agccttctct atactatagg gtatactgga | 1320 |
| gtggggacac aactatttga ttcagaaact gaattaccac cagaaacaac agaacgacca | 1380 |

```
aattatgaat cttacagtca tagattatct aatataagac taatatcagg aaacactttg    1440
agagcaccag tatattcttg gacgcaccgt agtgcagatc gtacaaatac cattagttca    1500
gatagcatta cacaaatacc attggtaaag gcgcataccc tccaatcggg taccactgta    1560
gtaaaagggc cagggtttac aggaggggat atcctccgtc gaacaagtgg aggaccattt    1620
gcttttagta atgttaatct agattttaac ttgtcacaaa ggtatcgtgc tagaattcgt    1680
tatgcctcta ctactaacct aagaatttac gtaacggttg caggtgaacg aattttttgct   1740 ggtcaatttg acaaaactat ggatgctggt gccccattaa cattccaatc ttttagttac    1800
gcaactatta atacagcttt tacattccca gaaagatcga gcagcttgac tgtaggtgcc    1860
gatacgttta gttcaggtaa tgaagtttat gtagatagat ttgaattaat cccagttact    1920
gcaaccttcg aggcagaatc tgatttagaa agagcacaaa aggcggtgaa tgagctgttt    1980
acttcttcca atcaaatcgg gttaaaaaca gatgtgacgg attatcatat tgatcaagta    2040
tccaatttag ttgagtgttt atctgatgaa ttttgtctgg atgaaaaaaa agaattgtcc    2100
gagaaagtca aacatgcgaa gcgacttagt gatgagcgga atttacttca agatccaaac    2160
tttagaggga tcaatagaca actagaccgt ggctggagag aagtacggaa tattaccatc    2220
caaggaggcg atgacgtatt caaagagaat tacgttacgc tattgggtac ctttgatgag    2280
tgctatccaa cgtatttata tcaaaaaata gatgagtcga aattaaaagc ctatacccgt    2340
taccaattaa gagggtatat cgaagatagt caagacttag aaatctattt aattcgctac    2400
aatgccaaac acgaaacagt aaatgtgcca ggtacgggtt ccttatggcc gctttcagcc    2460
ccaagtccaa tcggaaaatg tgcccatcat tcccatcatt tctccttgga cattgatgtt    2520
ggatgtacag acttaaatga ggacttaggt gtatgggtga tattcaagat taagacgcaa    2580
gatggccatg caagactagg aaatctagaa tttctcgaag agaaaccatt agtaggagaa    2640
gcactagctc gtgtgaaaag agcggagaaa aaatggagag acaaacgtga aaaattggaa    2700
tgggaaacaa atattgttta taagaggca aaagaatctg tagatgcttt atttgtaaac     2760
tctcaatatg atagattaca agcggatacc aacatcgcga tgattcatgc ggcagataaa    2820
cgcgttcata gcattcgaga agcttatctg cctgagctgt ctgtgattcc gggtgtcaat    2880
gcggctattt ttgaagaatt agaagggcgt attttcactg cattctccct atatgatgcg    2940
agaaatgtca ttaaaaatgg tgattttaat aatggcttat cctgctggaa cgtgaaaggg    3000
catgtagatg tagaagaaca aaacaaccac cgttcggtcc ttgttgttcc ggaatgggaa    3060
gcagaagtgt cacaagaagt tcgtgtctgt ccgggtcgtg gctatatcct tcgtgtcaca    3120
gcgtacaagg agggatatgg agaaggttgc gtaaccattc atgagatcga gaacaataca    3180
gacgaactga agtttagcaa ctgtgtagaa gaggaagtat atccaaacaa cacggtaacg    3240
tgtaatgatt atactgcgac tcaagaagaa tatgagggta cgtacacttc tcgtaatcga    3300
ggatatgacg gagcctatga aagcaattct tctgtaccag ctgattatgc atcagcctat    3360
gaagaaaaag catatacaga tggacgaaga gacaatcctt gtgaatctaa cagaggatat    3420
ggggattaca caccactacc agctggctat gtgacaaaag aattagagta cttcccagaa    3480
accgataagg tatggattga gatcggagaa acggaaggaa cattcatcgt ggacagcgtg    3540
gaattacttc ttatggagga atag                                          3564

<210> SEQ ID NO 9
<211> LENGTH: 3564
<212> TYPE: DNA
```

<213> ORGANISM: Artificial
<220> FEATURE:
<223> OTHER INFORMATION: Synthetic nucleotide sequence designed for expression in a plant cell encoding TIC867.

<400> SEQUENCE: 9

```
atgaccagca accgaaagaa cgagaacgag atcatcaacg ccctgtccat accggccgtg    60
tcaaaccact ccgcccagat gaacctctcc accgacgcga ggatcgagga ctccctctgc   120
atcgccgagg caacaacat cgacccgttc gtgtctgcaa gcacggtcca gaccggcatc    180
aacatcgcgg gccgcatcct gggcgtgctc ggcgtgccct tcgcgggtca aatcgcctct   240
ttctactcat tcctcgtggg cgagctgtgg ccgcgcggac gtgacccgtg gaaatcttc    300
ctggagcacg ttgagcagct catccggcag caagtgaccg agaacaccag gacaccgca    360
ctggcacggc tccagggcct tggcaacagc ttccgcgcct accagcagtc gctggaggac   420
tggctggaga accgagacga cgccagaacc cgctcagttc tgtacacaca gtacatcgcc   480
ctagagctgg acttcctcaa cgctatgccg ctcttcgcca tccgtaacca ggaagtaccg   540
cttctgatgg tgtacgcaca agcagcgaac ctccatctgc tcctgctgcg agacgcatct   600
ctgttcggca gtgagttcgg gctgacgagc caggagatcc agcgctacta cgagcgccaa   660
gtggagaaga ctcgtgagta cagcgactac tgcgcgcgct ggtacaacac gggcttgaac   720
aaccttcgcg gacaaacgc cgaatcctgg cttcgctaca accagttccg ccgcgacctc   780
acgctgggtg tgctggacct ggtcgcgctc ttcccgtcct acgacacacg ggtgtaccca   840
atgaacacga gcgcacagct cacccgtgag atctacacag atcccatcgg ccgcaccaac   900
gctcccagtg gcttcgcaag cacgaattgg ttcaacaata cgctccttc tttctctgcc    960
atcgaggccg ctgtcatcag accgccgcac ttactcgatt cccggagca gctcactatc   1020
ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctagggacg tttacaggac agagtcgttc   1200
gctggcatta acattctgtt gaccactccg gtgaacggcg tcccttgggc ccgcttcaac   1260
tggaggaatc ctctgaactc actgcgcggc agccttctct acactatcgg ctacaccggc   1320
gttgggacgc aactcttcga ctcggagacc gagctgccgc ccgagaccac cgagcggcct   1380
aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
gtcaagggcc ctggcttcac cggcggcgac atcctgcgtc gcacatctgg cggacccttc   1620
gccttcagca acgtgaactt ggacttcaat ttgtcacagc ggtatcgtgc cagaatccgg   1680
tacgccagca ctacgaacct gcgaatctat gttactgtgg cgggcgagcg gatcttcgcc   1740
gggcaattcg acaagacgat ggacgcggga gcacctctga cattccagtc attctcttac   1800
gccacgatca acacggcatt cacgtttccg gagcgttcca gtagcctgac cgtgggcgct   1860
gataccttca gtagcgggaa cgaggtgtac gttgaccgtt tcgagctgat cccggtcacc   1920
gccaccttcg aagctgagtc ggacctggag cgtgcacaga aggcagtcaa cgagctgttc   1980
acctctagca accagatcgg cctcaagacc gacgtcacag actaccacat cgaccaagtg   2040
tccaacctgg tcgagtgcct tagcgacgag ttctgcctag acgagaagaa ggagctgtcg   2100
gagaaggtca aacacgccaa gcgtctgagc gatgagcgca acctgctcca agaccctaac   2160
```

```
ttccgtggca tcaacaggca gcttgaccgt ggctggcgcg gctcgacgga catcacgatc    2220
cagggtggcg acgacgtatt caaggagaat tacgtgacct tgcttgggac gtttgacgag    2280
tgctatccca cctacctcta ccagaagatt gatgaatcga aattgaaggc gtacacgaga    2340
taccagctcc gtggctacat cgaggacagc caggacttgg agatctacct catacgctac    2400
aacgctaaac atgagaccgt gaacgtccct gggacgggca gtctgtggcc actctctgct    2460
cctagcccta tcggcaagtg cgctcaccac tcgcaccact tcagccttga catcgacgtg    2520
ggatgtactg acctcaacga agacctgggc gtctgggtta tcttcaagat caagacccag    2580
gacggccacg cccgactcgg caacctggag ttcctggagg agaaaccact ggtgggcgag    2640
gcgctcgccc gcgtgaagcg tgccgagaag aagtggcggg acaagaggga gaagctagaa    2700
tgggagacga acatcgtgta caaggaggcc aaggaaagcg tcgatgccct gttcgtgaac    2760
tcacagtacg accgtctcca ggcggacacg aacatcgcca tgatccacgc ggctgacaag    2820
cgcgtccact ccatccgcga ggcgtactta ccggagctgt cggtgatccc aggcgtaaac    2880
gcggcgatct tcgaggagct agagggacgc atcttcacag cgttcagcct gtacgacgca    2940
cgcaacgtca tcaagaacgg cgatttcaac aacggactgt cctgctggaa cgtgaagggc    3000
cacgtcgatg tcgaggaaca gaacaaccac cgctctgtcc tggtggtccc agagtgggag    3060
gccgaggtct cccaggaggt ccgcgtgtgc cctgggcgtg gctacatcct ccgtgtgaca    3120
gcctacaagg agggctacgg tgagggctgc gtcaccattc acgagatcga gaacaacact    3180
gacgaactca agttctcgaa ttgcgtggag gaggaggtgt acccgaacaa tacggtgacg    3240
tgcaacgact acacggcaac ccaagaggag tacgagggca cctacaccag taggaaccgt    3300
ggctacgacg gtgcctacga gtcgaactcc agcgtccctg cggactacgc cagcgcgtac    3360
gaggagaagg cttacaccga cggacgccgg acaacccat gcgagagcaa ccgtggctac    3420
ggcgactaca ctcctctccc ggccggatac gtcacaaagg agctggagta tttcccagag    3480
acggacaagg tgtggatcga aatcggagag acagagggaa ccttcatcgt ggacagcgtg    3540
gagctgctcc tcatggagga gtga                                           3564
```

<210> SEQ ID NO 10
<211> LENGTH: 1187
<212> TYPE: PRT
<213> ORGANISM: Artificial
<220> FEATURE:
<223> OTHER INFORMATION: Amino acid sequence of the chimeric protein
      TIC867.

<400> SEQUENCE: 10

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
                100                 105                 110
```

```
Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
        515                 520                 525
```

```
Gly Asp Ile Leu Arg Arg Thr Ser Gly Gly Pro Phe Ala Phe Ser Asn
    530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
        595                 600                 605

Phe Pro Glu Arg Ser Ser Ser Leu Thr Val Gly Ala Asp Thr Phe Ser
    610                 615                 620

Ser Gly Asn Glu Val Tyr Val Asp Arg Phe Glu Leu Ile Pro Val Thr
625                 630                 635                 640

Ala Thr Phe Glu Ala Glu Ser Asp Leu Glu Arg Ala Gln Lys Ala Val
                645                 650                 655

Asn Glu Leu Phe Thr Ser Ser Asn Gln Ile Gly Leu Lys Thr Asp Val
            660                 665                 670

Thr Asp Tyr His Ile Asp Gln Val Ser Asn Leu Val Glu Cys Leu Ser
        675                 680                 685

Asp Glu Phe Cys Leu Asp Glu Lys Lys Glu Leu Ser Glu Lys Val Lys
    690                 695                 700

His Ala Lys Arg Leu Ser Asp Glu Arg Asn Leu Leu Gln Asp Pro Asn
705                 710                 715                 720

Phe Arg Gly Ile Asn Arg Gln Leu Asp Arg Gly Trp Arg Gly Ser Thr
                725                 730                 735

Asp Ile Thr Ile Gln Gly Gly Asp Asp Val Phe Lys Glu Asn Tyr Val
            740                 745                 750

Thr Leu Leu Gly Thr Phe Asp Glu Cys Tyr Pro Thr Tyr Leu Tyr Gln
        755                 760                 765

Lys Ile Asp Glu Ser Lys Leu Lys Ala Tyr Thr Arg Tyr Gln Leu Arg
    770                 775                 780

Gly Tyr Ile Glu Asp Ser Gln Asp Leu Glu Ile Tyr Leu Ile Arg Tyr
785                 790                 795                 800

Asn Ala Lys His Glu Thr Val Asn Val Pro Gly Thr Gly Ser Leu Trp
                805                 810                 815

Pro Leu Ser Ala Pro Ser Pro Ile Gly Lys Cys Ala His His Ser His
            820                 825                 830

His Phe Ser Leu Asp Ile Asp Val Gly Cys Thr Asp Leu Asn Glu Asp
        835                 840                 845

Leu Gly Val Trp Val Ile Phe Lys Ile Lys Thr Gln Asp Gly His Ala
    850                 855                 860

Arg Leu Gly Asn Leu Glu Phe Leu Glu Glu Lys Pro Leu Val Gly Glu
865                 870                 875                 880

Ala Leu Ala Arg Val Lys Arg Ala Glu Lys Lys Trp Arg Asp Lys Arg
                885                 890                 895

Glu Lys Leu Glu Trp Glu Thr Asn Ile Val Tyr Lys Glu Ala Lys Glu
            900                 905                 910

Ser Val Asp Ala Leu Phe Val Asn Ser Gln Tyr Asp Arg Leu Gln Ala
        915                 920                 925

Asp Thr Asn Ile Ala Met Ile His Ala Ala Asp Lys Arg Val His Ser
    930                 935                 940

Ile Arg Glu Ala Tyr Leu Pro Glu Leu Ser Val Ile Pro Gly Val Asn
```

```
                945                 950                 955                 960
Ala Ala Ile Phe Glu Glu Leu Glu Gly Arg Ile Phe Thr Ala Phe Ser
                    965                 970                 975
Leu Tyr Asp Ala Arg Asn Val Ile Lys Asn Gly Asp Phe Asn Asn Gly
                    980                 985                 990
Leu Ser Cys Trp Asn Val Lys Gly His Val Asp Val Glu Glu Gln Asn
                    995                1000                1005
Asn His Arg Ser Val Leu Val Val Pro Glu Trp Glu Ala Glu Val
            1010                1015                1020
Ser Gln Glu Val Arg Val Cys Pro Gly Arg Gly Tyr Ile Leu Arg
            1025                1030                1035
Val Thr Ala Tyr Lys Glu Gly Tyr Gly Glu Gly Cys Val Thr Ile
            1040                1045                1050
His Glu Ile Glu Asn Asn Thr Asp Glu Leu Lys Phe Ser Asn Cys
            1055                1060                1065
Val Glu Glu Val Tyr Pro Asn Asn Thr Val Thr Cys Asn Asp
            1070                1075                1080
Tyr Thr Ala Thr Gln Glu Glu Tyr Glu Gly Thr Tyr Thr Ser Arg
            1085                1090                1095
Asn Arg Gly Tyr Asp Gly Ala Tyr Glu Ser Asn Ser Ser Val Pro
            1100                1105                1110
Ala Asp Tyr Ala Ser Ala Tyr Glu Glu Lys Ala Tyr Thr Asp Gly
            1115                1120                1125
Arg Arg Asp Asn Pro Cys Glu Ser Asn Arg Gly Tyr Gly Asp Tyr
            1130                1135                1140
Thr Pro Leu Pro Ala Gly Tyr Val Thr Lys Glu Leu Glu Tyr Phe
            1145                1150                1155
Pro Glu Thr Asp Lys Val Trp Ile Glu Ile Gly Glu Thr Glu Gly
            1160                1165                1170
Thr Phe Ile Val Asp Ser Val Glu Leu Leu Leu Met Glu Glu
            1175                1180                1185

<210> SEQ ID NO 11
<211> LENGTH: 3642
<212> TYPE: DNA
<213> ORGANISM: Artificial
<220> FEATURE:
<223> OTHER INFORMATION: Recombinant nucleotide sequence used
      for expression in a bacterial cell encoding TIC867_20.

<400> SEQUENCE: 11
atgacttcaa ataggaaaaa tgagaatgaa attataaatg ctttatcgat tccagctgta    60
tcgaatcatt ccgcacaaat gaatctatca accgatgctc gtattgagga tagcttgtgt   120
atagccgagg ggaacaatat cgatccattt gttagcgcat caacagtcca aacgggtatt   180
aacatagctg gtagaatact aggtgtatta ggcgtaccgt ttgctggaca aatagctagt   240
ttttatagtt ttcttgttgg tgaattatgg ccccgcggca gagatccttg ggaaattttc   300
ctagaacatg tcgaacaact tataagacaa caagtaacag aaaatactag ggatacggct   360
cttgctcgat acaaggtttt aggaaattcc tttagagcct atcaacagtc acttgaagat   420
tggctagaaa accgtgatga tgcaagaacg agaagtgttc tttataccca atatatagcc   480
ttagaacttg atttttctta atgcgatgccg cttttcgcaa ttagaaacca agaagttcca   540
ttattaatgg tatatgctca agctgcaaat ttacacctat tattattgag agatgcctct   600 cttttggta gtgaatttgg gcttacatcc caagaaattc aacgttatta tgagcgccaa   660
```

```
gtggaaaaaa cgagagaata ttctgattat tgcgcaagat ggtataatac gggtttaaat    720
aatttgagag ggacaaatgc tgaaagttgg ttgcgatata atcaattccg tagagactta    780
acgctaggag tattagatct agtggcacta ttcccaagct atgacacgcg tgtttatcca    840
atgaatacca gtgctcaatt aacaagagaa atttatacag atccaattgg gagaacaaat    900
gcaccttcag gatttgcaag tacgaattgg tttaataata atgcaccatc gttttctgcc    960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta cacaaatacc attggtaaag gcgcataccc tccaatcggg taccactgta   1560 gtaaagggc cagggtttac aggaggggat atcctccgtc gaacaagtgg aggaccattt   1620
gcttttagta atgttaatct agattttaac ttgtcacaaa ggtatcgtgc tagaattcgt   1680
tatgcctcta ctactaacct aagaatttac gtaacggttg caggtgaacg aattttttgct  1740 ggtcaatttg acaaaactat ggatgctggt gccccattaa cattccaatc tttagttac   1800 gcaactatta atacagcttt tacattccca gaaagatcga gcagcttgac tgtaggtgcc   1860
gatacgttta gttcaggtaa tgaagtttat gtagatagat ttgaattaat cccagttact   1920
gcaacctttg aggcagaata tgattttagaa agagcgcaaa aggtggtgaa tgccctgttt   1980
acgtctacaa accaactagg gctaaaaaca gatgtgacgg attatcatat tgatcaggta   2040
tccaatctag ttgcgtgttt atcggatgaa ttttgtctgg atgaaaagag agaattgtcc   2100
gagaaagtta aacatgcaaa gcgactcagt gatgagcgga atttacttca agatccaaac   2160
ttcagaggga tcaataggca accagaccgt ggctggagag gaagtacgga tattactatc   2220
caaggaggag atgacgtatt caaagagaat tacgttacgc taccgggtac ctttgatgag   2280
tgctatccaa cgtatttata tcaaaaaata gatgagtcga aattaaaagc ctatacccgt   2340
tatcaattaa gagggtatat cgaagatagt caagacttag aaatctattt aattcgttac   2400
aatgcaaaac acgaaatagt aaatgtacca ggtacaggaa gtttatggcc tctttctgta   2460
gaaaatcaaa ttggaccttg tggagaaccg aatcgatgcg cgccacacct tgaatggaat   2520
cctgatttac actgttcctg cagagacggg gaaaaatgtg cacatcattc tcatcatttc   2580
tctttggaca ttgatgttgg atgtacagac ttaaatgagg acttaggtgt atgggtgata   2640
ttcaagatta agacgcaaga tggccacgca cgactaggga atctagagtt tctcgaagag   2700
aaaccattat taggagaagc actagctcgt gtgaaaagag cggagaaaaa atggagagac   2760
aaacgcgaaa cattacaatt ggaaacaact atcgtttata aagaggcaaa agaatctgta   2820
gatgctttat ttgtaaactc tcaatatgat agattacaag cggatacgaa catcgcgatg   2880
attcatgcgg cagataaacg cgttcataga attcgagaag cgtatctgcc ggagctgtct   2940
gtgattccgg gtgtcaatgc ggctattttt gaagaattag aagagcgtat tttcactgca   3000
```

```
tttccctat atgatgcgag aaatattatt aaaaatggcg atttcaataa tggcttatta    3060
tgctggaacg tgaaagggca tgtagaggta gaagaacaaa acaatcaccg ttcagtcctg    3120
gttatcccag aatgggaggc agaagtgtca caagaggttc gtgtctgtcc aggtcgtggc    3180
tatatccttc gtgttacagc gtacaaagag ggatatggag aaggttgcgt aacgatccat    3240
gagatcgaga acaatacaga cgaactgaaa ttcaacaact gtgtagaaga ggaagtatat    3300
ccaaacaaca cggtaacgtg tattaattat actgcgactc aagaagaata tgagggtacg    3360
tacacttctc gtaatcgagg atatgacgaa gcctatggta ataacccttc cgtaccagct    3420
gattatgcgt cagtctatga agaaaaatcg tatacagata gacgaagaga gaatccttgt    3480
gaatctaaca gaggatatgg agattacaca ccactaccag ctggttatgt aacaaaggaa    3540
ttagagtact ccagagac cgataaggta tggattgaga ttggagaaac agaaggaaca    3600
ttcatcgtgg acagcgtgga attactcctt atggaggaat ag                      3642
```

<210> SEQ ID NO 12
<211> LENGTH: 3642
<212> TYPE: DNA
<213> ORGANISM: Artificial
<220> FEATURE:
<223> OTHER INFORMATION: Synthetic nucleotide sequence designed for
      expression in a plant cell encoding TIC867_20.

<400> SEQUENCE: 12

```
atgaccagca accgaaagaa cgagaacgag atcatcaacg ccctgtccat accggccgtg     60
tcaaaccact ccgcccagat gaacctctcc accgacgcga ggatcgagga ctccctctgc    120
atcgccgagg gcaacaacat cgacccgttc gtgtctgcaa gcacggtcca gaccggcatc    180
aacatcgcgg gccgcatcct gggcgtgctc ggcgtgccct cgcgggtca aatcgcctct    240 ttctactcat tcctcgtggg cgagctgtgg ccgcgcggac gtgacccgtg ggaaatcttc    300
ctggagcacg ttgagcagct catccggcag caagtgaccg agaacaccag ggacaccgca    360
ctggcacggc tccagggcct tggcaacagc ttccgcgcct accagcagtc gctggaggac    420
tggctggaga accgagacga cgccagaacc cgctcagttc tgtacacaca gtacatcgcc    480
ctagagctgg acttcctcaa cgctatgccg ctcttcgcca tccgtaacca ggaagtaccg    540
cttctgatgg tgtacgcaca agcagcgaac ctccatctgc tcctgctgcg agacgcatct    600
ctgttcggca gtgagttcgg gctgacgagc caggagatcc agcgctacta cgagcgccaa    660
gtggagaaga ctcgtgagta cagcgactac tgcgcgcgct ggtacaacac gggcttgaac    720
aaccttcgcg gacaaacgc cgaatcctgg cttcgctaca accagttccg ccgcgacctc    780
acgctgggtg tgctggacct ggtcgcgctc ttccgtcct acgacacacg ggtgtaccca    840
atgaacacga gcgcacagct cacccgtgag atctacacag atcccatcgg ccgcaccaac    900
gctcccagtg gcttcgcaag cacgaattgg ttcaacaata cgctccttc tttctctgcc    960 atcgaggccg ctgtcatcag accgccgcac ttactcgatt tcccggagca gctcactatc   1020
ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctagggacg tttacaggac agagtcgttc   1200
gctggcatta acattctgtt gaccactccg gtgaacggcg tcccttgggc ccgcttcaac   1260
tggaggaatc ctctgaactc actgcgcggc agccttctct acactatcgg ctacaccggc   1320
gttgggacgc aactcttcga ctcggagacc gagctgccgc ccgagaccac cgagcggcct   1380
```

-continued

```
aactacgaga gttattcaca caggctctcc aacatccgct tgatttctgg gaacaccttg    1440
cgggctccgg tgtactcctg gacgcaccgc agcgccgaca gaactaatac catcagctcc    1500
gactcgatca cccagatccc gctggtgaag gctcacacgc ttcagtcggg caccacagtc    1560
gtcaagggcc ctggcttcac cggcggcgac atcctgcgtc gcacatctgg cggacccttc    1620
gccttcagca acgtgaactt ggacttcaat ttgtcacagc ggtatcgtgc cagaatccgg    1680
tacgccagca ctacgaacct gcgaatctat gttactgtgg cgggcgagcg gatcttcgcc    1740
gggcaattcg acaagacgat ggacgcggga gcacctctga cattccagtc attctcttac    1800
gccacgatca acacggcatt cacgtttccg gagcgttcca gtagcctgac cgtgggcgct    1860
gataccttca gtagcgggaa cgaggtgtac gttgaccgtt tcgagctgat cccggtcacc    1920
gccaccttcg aggccgagta cgaccttgag cgcgcccaga aggtggtgaa cgccctcttc    1980
actagcacta ccagctaggc ctgaagact  gacgtgaccg actaccacat cgaccaagtg    2040
agcaacctag tggcctgcct ctccgacgag ttctgcctcg acgagaagcg cgagctgtcc    2100
gagaaggtga agcacgccaa gcgcctctcc gacgagcgca acctgctcca ggaccccaac    2160
ttcaggggca tcaacaggca gcccgaccgc ggctggcgcg gctccaccga catcaccatc    2220
cagggcggtg acgacgtatt caaggagaac tacgttaccc tccccggcac cttcgacgag    2280
tgttaccca  cctacctcta ccagaagatc gacgagtcca agctgaaggc ctacacccgc    2340
taccagctcc gcggctacat cgaggactcc caggacctgg aaatctacct catccgctac    2400
aacgccaagc acgagatcgt gaacgtgcct ggcaccggca gcctctggcc tctcagcgtg    2460
gagaaccaga tcggcccttg cggcgagcct aaccgctgcg cccctcacct cgagtggaac    2520
cctgacctcc actgctcgtg cagggacggc gagaagtgcg cccaccatag ccaccacttc    2580
tctctggaca tcgacgtggg ctgcaccgac ctgaacgagg acctgggcgt gtgggttatc    2640
ttcaagatca agacccagga cggtcacgcc aggctgggta acctggagtt ccttgaggaa    2700
aagcctctgc tgggtgaggc cctggccagg gtcaagaggg ctgagaagaa atggagggat    2760
aagagggaga ccctgcagct ggagaccact atcgtctaca aggaggctaa ggagtctgtc    2820
gatgctctgt tcgtcaactc tcagtacgat agactgcaag ctgataccaa catcgctatg    2880
atccacgctg cggataagcg ggtccaccgg atccgggagg cttaccttcc ggagctttct    2940
gtcatcccgg tgtcaacgc  tgcgatcttc gaggaacttg aggaacggat cttcactgcg    3000
tttagtcttt acgatgcgcg gaacatcatc aagaacgggg acttcaacaa tggtctgctg    3060
tgctggaacg tcaagggtca tgtcgaggtc gaggaacaaa acaatcatcg tagtgtcctt    3120
gtcattcctg agtgggaggc ggaggtctct caagaggtcc gtgtttgccc ggggcgtggg    3180
tacattcttc gtgttactgc gtacaaggag gggtacgggg aggggtgcgt tactattcat    3240
gagattgaga acaatactga tgagcttaag ttcaacaatt gtgttgagga ggaggtttac    3300
ccgaacaata ctgttacgtg catcaactac acggcaacgc aagaggaata cgagggacg    3360
tacacctcgc gtaatagagg gtatgatgag gcgtacggaa caacccgtc  ggttccagca    3420
gattatgcct cggtttatga ggagaagtcg tacacggata gacgacgcga gaatccatgt    3480
gagtcaaatc gaggatacgg agattacaca ccattaccag caggatacgt tacaaaggag    3540
ttggaatact ccccggaaac agataaagtt tggattgaaa tcggagaaac agaaggaaca    3600
ttcatcgtcg actcagtaga attgttgttg atggaagaat ga                      3642
```

<210> SEQ ID NO 13
<211> LENGTH: 1213

<212> TYPE: PRT
<213> ORGANISM: Artificial
<220> FEATURE:
<223> OTHER INFORMATION: Amino acid sequence of the chimeric protein variant TIC867_20.

<400> SEQUENCE: 13

| | | | | | | | | | | | | | | | |
|---|---|---|---|---|---|---|---|---|---|---|---|---|---|---|---|
| Met | Thr | Ser | Asn | Arg | Lys | Asn | Glu | Asn | Glu | Ile | Ile | Asn | Ala | Leu | Ser |
| 1 | | | | 5 | | | | | 10 | | | | | 15 | |
| Ile | Pro | Ala | Val | Ser | Asn | His | Ser | Ala | Gln | Met | Asn | Leu | Ser | Thr | Asp |
| | | | 20 | | | | | 25 | | | | | 30 | | |
| Ala | Arg | Ile | Glu | Asp | Ser | Leu | Cys | Ile | Ala | Glu | Gly | Asn | Asn | Ile | Asp |
| | | 35 | | | | | 40 | | | | | 45 | | | |
| Pro | Phe | Val | Ser | Ala | Ser | Thr | Val | Gln | Thr | Gly | Ile | Asn | Ile | Ala | Gly |
| | 50 | | | | | 55 | | | | | 60 | | | | |
| Arg | Ile | Leu | Gly | Val | Leu | Gly | Val | Pro | Phe | Ala | Gly | Gln | Ile | Ala | Ser |
| 65 | | | | | 70 | | | | | 75 | | | | | 80 |
| Phe | Tyr | Ser | Phe | Leu | Val | Gly | Glu | Leu | Trp | Pro | Arg | Gly | Arg | Asp | Pro |
| | | | | 85 | | | | | 90 | | | | | 95 | |
| Trp | Glu | Ile | Phe | Leu | Glu | His | Val | Glu | Gln | Leu | Ile | Arg | Gln | Gln | Val |
| | | | 100 | | | | | 105 | | | | | 110 | | |
| Thr | Glu | Asn | Thr | Arg | Asp | Thr | Ala | Leu | Ala | Arg | Leu | Gln | Gly | Leu | Gly |
| | | 115 | | | | | 120 | | | | | 125 | | | |
| Asn | Ser | Phe | Arg | Ala | Tyr | Gln | Gln | Ser | Leu | Glu | Asp | Trp | Leu | Glu | Asn |
| | 130 | | | | | 135 | | | | | 140 | | | | |
| Arg | Asp | Asp | Ala | Arg | Thr | Arg | Ser | Val | Leu | Tyr | Thr | Gln | Tyr | Ile | Ala |
| 145 | | | | | 150 | | | | | 155 | | | | | 160 |
| Leu | Glu | Leu | Asp | Phe | Leu | Asn | Ala | Met | Pro | Leu | Phe | Ala | Ile | Arg | Asn |
| | | | | 165 | | | | | 170 | | | | | 175 | |
| Gln | Glu | Val | Pro | Leu | Leu | Met | Val | Tyr | Ala | Gln | Ala | Ala | Asn | Leu | His |
| | | | 180 | | | | | 185 | | | | | 190 | | |
| Leu | Leu | Leu | Leu | Arg | Asp | Ala | Ser | Leu | Phe | Gly | Ser | Glu | Phe | Gly | Leu |
| | | | 195 | | | | | 200 | | | | | 205 | | |
| Thr | Ser | Gln | Glu | Ile | Gln | Arg | Tyr | Tyr | Glu | Arg | Gln | Val | Glu | Lys | Thr |
| | 210 | | | | | 215 | | | | | 220 | | | | |
| Arg | Glu | Tyr | Ser | Asp | Tyr | Cys | Ala | Arg | Trp | Tyr | Asn | Thr | Gly | Leu | Asn |
| 225 | | | | | 230 | | | | | 235 | | | | | 240 |
| Asn | Leu | Arg | Gly | Thr | Asn | Ala | Glu | Ser | Trp | Leu | Arg | Tyr | Asn | Gln | Phe |
| | | | | 245 | | | | | 250 | | | | | 255 | |
| Arg | Arg | Asp | Leu | Thr | Leu | Gly | Val | Leu | Asp | Leu | Val | Ala | Leu | Phe | Pro |
| | | | 260 | | | | | 265 | | | | | 270 | | |
| Ser | Tyr | Asp | Thr | Arg | Val | Tyr | Pro | Met | Asn | Thr | Ser | Ala | Gln | Leu | Thr |
| | | 275 | | | | | 280 | | | | | 285 | | | |
| Arg | Glu | Ile | Tyr | Thr | Asp | Pro | Ile | Gly | Arg | Thr | Asn | Ala | Pro | Ser | Gly |
| | 290 | | | | | 295 | | | | | 300 | | | | |
| Phe | Ala | Ser | Thr | Asn | Trp | Phe | Asn | Asn | Asn | Ala | Pro | Ser | Phe | Ser | Ala |
| 305 | | | | | 310 | | | | | 315 | | | | | 320 |
| Ile | Glu | Ala | Ala | Val | Ile | Arg | Pro | Pro | His | Leu | Leu | Asp | Phe | Pro | Glu |
| | | | | 325 | | | | | 330 | | | | | 335 | |
| Gln | Leu | Thr | Ile | Phe | Ser | Val | Leu | Ser | Arg | Trp | Ser | Asn | Thr | Gln | Tyr |
| | | | 340 | | | | | 345 | | | | | 350 | | |
| Met | Asn | Tyr | Trp | Val | Gly | His | Arg | Leu | Glu | Ser | Arg | Thr | Ile | Arg | Gly |
| | | 355 | | | | | 360 | | | | | 365 | | | |
| Ser | Leu | Ser | Thr | Ser | Thr | His | Gly | Asn | Thr | Asn | Thr | Ser | Ile | Asn | Pro |
| | 370 | | | | | 375 | | | | | 380 | | | | |

```
Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
        515                 520                 525

Gly Asp Ile Leu Arg Arg Thr Ser Gly Gly Pro Phe Ala Phe Ser Asn
530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
        595                 600                 605

Phe Pro Glu Arg Ser Ser Ser Leu Thr Val Gly Ala Asp Thr Phe Ser
    610                 615                 620

Ser Gly Asn Glu Val Tyr Val Asp Arg Phe Glu Leu Ile Pro Val Thr
625                 630                 635                 640

Ala Thr Phe Glu Ala Glu Tyr Asp Leu Glu Arg Ala Gln Lys Val Val
                645                 650                 655

Asn Ala Leu Phe Thr Ser Thr Asn Gln Leu Gly Leu Lys Thr Asp Val
            660                 665                 670

Thr Asp Tyr His Ile Asp Gln Val Ser Asn Leu Val Ala Cys Leu Ser
        675                 680                 685

Asp Glu Phe Cys Leu Asp Glu Lys Arg Glu Leu Ser Glu Lys Val Lys
    690                 695                 700

His Ala Lys Arg Leu Ser Asp Glu Arg Asn Leu Leu Gln Asp Pro Asn
705                 710                 715                 720

Phe Arg Gly Ile Asn Arg Gln Pro Asp Arg Gly Trp Arg Gly Ser Thr
                725                 730                 735

Asp Ile Thr Ile Gln Gly Gly Asp Asp Val Phe Lys Glu Asn Tyr Val
            740                 745                 750

Thr Leu Pro Gly Thr Phe Asp Glu Cys Tyr Pro Thr Tyr Leu Tyr Gln
        755                 760                 765

Lys Ile Asp Glu Ser Lys Leu Lys Ala Tyr Thr Arg Tyr Gln Leu Arg
    770                 775                 780

Gly Tyr Ile Glu Asp Ser Gln Asp Leu Glu Ile Tyr Leu Ile Arg Tyr
785                 790                 795                 800
```

-continued

Asn Ala Lys His Glu Ile Val Asn Val Pro Gly Thr Gly Ser Leu Trp
            805                 810                 815

Pro Leu Ser Val Glu Asn Gln Ile Gly Pro Cys Gly Glu Pro Asn Arg
            820                 825                 830

Cys Ala Pro His Leu Glu Trp Asn Pro Asp Leu His Cys Ser Cys Arg
            835                 840                 845

Asp Gly Glu Lys Cys Ala His His Ser His His Phe Ser Leu Asp Ile
850                 855                 860

Asp Val Gly Cys Thr Asp Leu Asn Glu Asp Leu Gly Val Trp Val Ile
865                 870                 875                 880

Phe Lys Ile Lys Thr Gln Asp Gly His Ala Arg Leu Gly Asn Leu Glu
            885                 890                 895

Phe Leu Glu Glu Lys Pro Leu Leu Gly Glu Ala Leu Ala Arg Val Lys
            900                 905                 910

Arg Ala Glu Lys Lys Trp Arg Asp Lys Arg Glu Thr Leu Gln Leu Glu
            915                 920                 925

Thr Thr Ile Val Tyr Lys Glu Ala Lys Glu Ser Val Asp Ala Leu Phe
930                 935                 940

Val Asn Ser Gln Tyr Asp Arg Leu Gln Ala Asp Thr Asn Ile Ala Met
945                 950                 955                 960

Ile His Ala Ala Asp Lys Arg Val His Arg Ile Arg Glu Ala Tyr Leu
            965                 970                 975

Pro Glu Leu Ser Val Ile Pro Gly Val Asn Ala Ala Ile Phe Glu Glu
            980                 985                 990

Leu Glu Glu Arg Ile Phe Thr Ala Phe Ser Leu Tyr Asp Ala Arg Asn
            995                 1000                1005

Ile Ile Lys Asn Gly Asp Phe Asn Asn Gly Leu Leu Cys Trp Asn
        1010                1015                1020

Val Lys Gly His Val Glu Val Glu Glu Gln Asn Asn His Arg Ser
        1025                1030                1035

Val Leu Val Ile Pro Glu Trp Glu Ala Glu Val Ser Gln Glu Val
        1040                1045                1050

Arg Val Cys Pro Gly Arg Gly Tyr Ile Leu Arg Val Thr Ala Tyr
        1055                1060                1065

Lys Glu Gly Tyr Gly Glu Gly Cys Val Thr Ile His Glu Ile Glu
        1070                1075                1080

Asn Asn Thr Asp Glu Leu Lys Phe Asn Cys Val Glu Glu Glu
        1085                1090                1095

Val Tyr Pro Asn Asn Thr Val Thr Cys Ile Asn Tyr Thr Ala Thr
        1100                1105                1110

Gln Glu Glu Tyr Glu Gly Thr Tyr Thr Ser Arg Asn Arg Gly Tyr
        1115                1120                1125

Asp Glu Ala Tyr Gly Asn Asn Pro Ser Val Pro Ala Asp Tyr Ala
        1130                1135                1140

Ser Val Tyr Glu Glu Lys Ser Tyr Thr Asp Arg Arg Arg Glu Asn
        1145                1150                1155

Pro Cys Glu Ser Asn Arg Gly Tyr Gly Asp Tyr Thr Pro Leu Pro
        1160                1165                1170

Ala Gly Tyr Val Thr Lys Glu Leu Glu Tyr Phe Pro Glu Thr Asp
        1175                1180                1185

Lys Val Trp Ile Glu Ile Gly Glu Thr Glu Gly Thr Phe Ile Val
        1190                1195                1200

Asp Ser Val Glu Leu Leu Leu Met Glu Glu

<210> SEQ ID NO 14
<211> LENGTH: 3690
<212> TYPE: DNA
<213> ORGANISM: Artificial
<220> FEATURE:
<223> OTHER INFORMATION: Recombinant nucleotide sequence used
      for expression in a bacterial cell encoding TIC867_21.

<400> SEQUENCE: 14

```
atgacttcaa ataggaaaaa tgagaatgaa attataaatg ctttatcgat tccagctgta      60
tcgaatcatt ccgcacaaat gaatctatca accgatgctc gtattgagga tagcttgtgt     120
atagccgagg ggaacaatat cgatccattt gttagcgcat caacagtcca acgggtatt     180
aacatagctg gtagaatact aggtgtatta ggcgtaccgt ttgctggaca atagctagt     240
ttttatagtt ttcttgttgg tgaattatgg ccccgcggca gagatccttg ggaaattttc     300
ctagaacatg tcgaacaact tataagacaa caagtaacag aaaatactag ggatacggct     360
cttgctcgat tacaaggttt aggaaattcc tttagagcct atcaacagtc acttgaagat     420
tggctagaaa accgtgatga tgcaagaacg agaagtgttc tttataccca atatatagcc     480
ttagaacttg attttcttaa tgcgatgccg cttttcgcaa ttagaaacca agaagttcca     540
ttattaatgg tatatgctca agctgcaaat ttacacctat tattattgag agatgcctct     600
cttttggta gtgaatttgg gcttacatcc caagaaattc aacgttatta tgagcgccaa     660
gtggaaaaaa cgagagaata ttctgattat tgcgcaagat ggtataatac gggtttaaat     720
aatttgagag gacaaatgc tgaaagttgg ttgcgatata atcaattccg tagagactta     780
acgctaggag tattagatct agtggcacta ttcccaagct atgacacgcg tgtttatcca     840
atgaatacca gtgctcaatt aacaagagaa atttatacag atccaattgg gagaacaaat     900
gcaccttcag gatttgcaag tacgaattgg tttaataata atgcaccatc gtttctgcc     960
atagaggctg ccgttattag gcctccgcat ctacttgatt ttccagaaca gcttacaatt    1020
ttcagcgtat taagtcgatg gagtaatact caatatatga attactgggt gggacataga    1080
cttgaatcgc gaacaataag ggggtcatta agtacctcga cacacggaaa taccaatact    1140
tctattaatc ctgtaacatt acagttcaca tctcgagacg tttatagaac agaatcattt    1200
gcagggataa atacttct aactactcct gtgaatggag taccttgggc tagatttaat    1260
tggagaaatc ccctgaattc tcttagaggt agccttctct atactatagg gtatactgga    1320
gtggggacac aactatttga ttcagaaact gaattaccac cagaaacaac agaacgacca    1380
aattatgaat cttacagtca tagattatct aatataagac taatatcagg aaacactttg    1440
agagcaccag tatattcttg gacgcaccgt agtgcagatc gtacaaatac cattagttca    1500
gatagcatta cacaaatacc attggtaaag gcgcataccc tccaatcggg taccactgta    1560
gtaaaagggc cagggtttac aggaggggat atcctccgtc gaacaagtgg aggaccattt    1620
gcttttagta atgttaatct agattttaac ttgtcacaaa ggtatcgtgc tagaattcgt    1680
tatgcctcta ctactaacct aagaatttac gtaacggttg caggtgaacg aatttttgct    1740
ggtcaatttg acaaaactat ggatgctggt gccccattaa cattccaatc ttttagttac    1800
gcaactatta atacagcttt tacattccca gaaagatcga gcagcttgac tgtaggtgcc    1860
gatacgttta gttcaggtaa tgaagtttat gtagatagat ttgaattaat cccagttact    1920
gcaaccggaa cgacaacct atgagtatgaa gagaagcaga atctagaaaa agcgcagaaa    1980
```

```
gcgttgaacg ctttgtttac ggatggcacg aatggctatc tacaaatgga tgccactgat    2040
tatgatatca atcaaactgc aaacttaata gaatgtgtat cagatgaatt gtatgcaaaa    2100
gaaaagatag ttttattaga tgaagtcaaa tatgcgaagc ggcttagcat atcacgtaac    2160
ctacttttga acgatgattt agaattttca gatggatttg gagaaaacgg atggacgaca    2220
agtgataata tttcaatcca ggcggataat cccctttta agggaatta tttaaaaatg    2280 tttgggcaa gagatattga tggaacccta tttccaactt atctctatca aaaatagat    2340 gagtccaggt taaaaccata tacacgttat cgagtaagag ggtttgtggg aagtagtaaa    2400
aatctaaaat tagtggtaac acgctatgag aaagaaattg atgccattat gaatgttcca    2460
aatgatttgg cacatatgca gcttaaccct tcatgtggag attatcgctg tgaatcatcg    2520
tcccagtttt tggtgaacca agtgcatcct acaccaacag ctggatatgc tcttgatatg    2580
tatgcatgcc cgtcaagttc agataaaaaa catattatgt gtcacgatcg tcatccattt    2640
gattttcata ttgacaccgg agaattaaat ccaaacacaa acctgggtat tgatgtcttg    2700
tttaaaattt ctaatccaaa tggatacgct acattaggga atctagaagt cattgaagaa    2760
ggaccactaa cagatgaagc attggtacat gtaaaacaaa aggaaaagaa atggcgtcag    2820
cacatggaga aaaacgaat ggaaacacaa caagcctatg atccagcaaa acaagctgta    2880
gatgcattat ttacaaatga acaagagtta gactatcata ctactttaga tcatattcag    2940
aacgccgatc agctggtaca ggcgattccc tatgtacacc atgcttggtt accggatgct    3000
ccaggtatga actatgatgt atatcaaggg ttaaacgcac gtatcatgca ggcgtacaat    3060
ttatatgatg cacgaaatgt cataataaat ggtgacttta cacaaggact acaaggatgg    3120
cacgcaacag gaaaagcagc ggtacaacaa atagatggag cttcagtatt agttctatca    3180
aactggagtg ccgaggtatc tcagaatctg catgcccaag atcatcatgg atatatgtta    3240
cgtgtgattg ccaaaaaga aggtcctgga aaagggtatg taatgatgat ggattttaat    3300
ggaaagcagg aaacacttac gttcacttct tgtgaagaag gatatataac aaaaacaata    3360
gaggtattcc cggaaagtga tcgaatacga attgaaatgg gagaaacaga gggtacgttt    3420
tatgtagata gcatcgagtt gctttgtatg caaggatatg ctagcgataa taacccgcac    3480
acgggtaata tgtatgagca aagttataat ggaaattata atcaaaatac tagcgatgtg    3540
tatcaccaag gatatataaa caactataac caaaattcta gtagtatgta taatcaaaat    3600
tatattaaca atgatgacct gcattccggt tgcacatgta accaagggca taactctggc    3660
tgtacatgta atcaaggata taaccgttag                                     3690
```

<210> SEQ ID NO 15
<211> LENGTH: 3690
<212> TYPE: DNA
<213> ORGANISM: Artificial
<220> FEATURE:
<223> OTHER INFORMATION: Synthetic nucleotide sequence designed for
      expression in a plant cell encoding TIC867_21.

<400> SEQUENCE: 15

```
atgaccagca accgaaagaa cgagaacgag atcatcaacg ccctgtccat accggccgtg      60
tcaaaccact ccgcccagat gaacctctcc accgacgcga ggatcgagga ctccctctgc     120
atcgccgagg gcaacaacat cgacccgttc gtgtctgcaa gcacggtcca gaccggcatc     180
aacatcgcgg gccgcatcct gggcgtgctg ggcgtgccct tcgcgggtca atcgcctct     240 ttctactcat tcctcgtggg cgagctgtgg ccgcgcggac gtgacccgtg ggaaatcttc     300
```

```
ctggagcacg ttgagcagct catccggcag caagtgaccg agaacaccag ggacaccgca      360
ctggcacggc tccagggcct tggcaacagc ttccgcgcct accagcagtc gctggaggac      420
tggctggaga accgagacga cgccagaacc cgctcagttc tgtacacaca gtacatcgcc      480
ctagagctgg acttcctcaa cgctatgccg ctcttcgcca tccgtaacca ggaagtaccg      540
cttctgatgg tgtacgcaca agcagcgaac ctccatctgc tcctgctgcg agacgcatct      600
ctgttcggca gtgagttcgg gctgacgagc caggagatcc agcgctacta cgagcgccaa      660
gtggagaaga ctcgtgagta cagcgactac tgcgcgcgct ggtacaacac gggcttgaac      720
aaccttcgcg ggacaaacgc cgaatcctgg cttcgctaca accagttccg ccgcgacctc      780
acgctgggtg tgctggacct ggtcgcgctc ttcccgtcct acgacacacg ggtgtaccca      840
atgaacacga gcgcacagct cacccgtgag atctacacag atcccatcgg ccgcaccaac      900
gctcccagtg gcttcgcaag cacgaattgg ttcaacaata cgctccttc tttctctgcc       960 atcgaggccg ctgtcatcag accgccgcac ttactcgatt tcccggagca gctcactatc     1020
ttctctgtgt tgtcccggtg gtcgaacacg cagtacatga actactgggt gggccacagg     1080
ctagagagcc ggaccatccg tggcagtctc tcaacctcga cccacggcaa cacgaacacg     1140
agcatcaacc ctgtcactct ccagtttaca tctaggacg tttacaggac agagtcgttc      1200
gctggcatta acattctgtt gaccactccg gtgaacggcg tcccttgggc ccgcttcaac     1260
tggaggaatc ctctgaactc actgcgcggc agccttctct acactatcgg ctacaccggc     1320
gttgggacgc aactcttcga ctcggagacc gagctgccgc ccgagaccac cgagcggcct     1380
aactacgaga gttattcaca caggctctcc aacatccgct tgatttctgg gaacaccttg     1440
cgggctccgg tgtactcctg gacgcaccgc agcgccgaca gaactaatac catcagctcc     1500
gactcgatca cccagatccc gctggtgaag gctcacacgc ttcagtcggg caccacagtc     1560
gtcaagggcc ctggcttcac cggcggcgac atcctgcgtc gcacatctgg cggacccttc     1620
gccttcagca acgtgaactt ggacttcaat ttgtcacagc ggtatcgtgc cagaatccgg     1680
tacgccagca ctacgaacct gcgaatctat gttactgtgg cgggcgagcg gatcttcgcc     1740
gggcaattcg acaagacgat ggacgcggga gcacctctga cattccagtc attctcttac     1800
gccacgatca acacggcatt cacgtttccg gagcgttcca gtagcctgac cgtgggcgct     1860
gataccttca gtagcgggaa cgaggtgtac gttgaccgtt tcgagctgat cccggtcacc     1920
gccaccggga ctaccaccta cgagtacgag gagaagcaga atctcgagaa ggctcagaag     1980
gctctgaacg ctctgttcac tgacgggacc aacggctacc tccagatgga cgccactgac     2040
tacgacatca accagacagc taacctgatt gagtgtgtga gtgacgaact gtacgctaag     2100
gagaagatcg tactcctgga cgaggtgaag tacgctaagc gcctgagcat tagccgtaac     2160
ctgctgctga acgacgatct ggagttcagc gacggctttg gcgagaacgg ctggaccacc     2220
agcgacaaca tctccatcca ggccgacaat ccactcttca aggcaacta cctcaagatg     2280 ttcggagcca gggacatcga cggcaccctc tttccgacct acctctacca gaagatcgac     2340
gagtcccgcc tcaaacccta cacccgctac agggtgcgcg gcttcgtggg cagcagcaag     2400
aacctcaagc tcgtggtcac acggtatgag aaggagatcg acgccatcat gaacgtgccc     2460
aacgatctcg cccacatgca gctcaatcca tcctgcggcg actaccggtg cgagtccagc     2520
tcccagttcc tcgtgaacca ggtgcaccct actccgaccg ctggctatgc cctggacatg     2580
tacgcctgcc ctagttcctc cgacaagaag cacatcatgt gccacgaccg tcatccgttc     2640
gacttccaca tcgacaccgg cgaactgaac ccgaacacca acctgggcat cgacgtactg     2700
```

```
ttcaagattt ccaacccgaa cgggtacgcc accttgggca acctggaggt catcgaagaa    2760
ggcccgctga ccgacgaggc cctggtccac gtcaaacaga aggagaagaa gtggcggcag    2820
cacatggaga agaagcggat ggagactcaa caagcctacg acccggccaa gcaagctgtg    2880
gacgctctgt tcaccaacga gcaagagctt gactaccaca ctactcttga ccacatccag    2940
aatgctgacc agcttgtcca ggctattccg tacgtccacc acgcttggct accggacgct    3000
ccagggatga actacgatgt gtaccagggt ctgaacgcgc ggatcatgca agcgtacaac    3060
ctgtacgacg cgcgtaacgt catcatcaac ggtgacttca ctcagggtct tcaaggttgg    3120
cacgcgactg gcaaagcggc agtccagcag attgatggtg cgtctgttct tgtgttgagc    3180
aactggtctg cggaggtttc tcagaacctg cacgcacagg atcaccacgg ctacatgctg    3240
agggtgattg ctaagaagga gggccctggc aaaggctacg tcatgatgat ggacttcaac    3300
ggaaagcaag aaaccctgac cttcactagc tgtgaggagg ctacatcac taagaccatt    3360 gaggtctttc cggagtctga ccgcatccgg atcgagatgg gcgagaccga aggcacgttc    3420
tacgtggact ccatcgaact cctctgcatg caaggctacg cctccgacaa caacccacac    3480
acgggcaaca tgtacgagca gtcctacaac gggaactaca accagaacac ctccgatgtg    3540
taccatcagg gctacatcaa caactacaac cagaacagca gcagcatgta caaccagaac    3600
tacatcaaca cgatgactt gcactcgggt tgcacctgca accagggtca acagtgggg    3660 tgcacgtgca accagggata caaccgttga                                     3690

<210> SEQ ID NO 16
<211> LENGTH: 1229
<212> TYPE: PRT
<213> ORGANISM: Artificial
<220> FEATURE:
<223> OTHER INFORMATION: Amino acid sequence of the chimeric protein
      variant TIC867_21.

<400> SEQUENCE: 16

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175
```

```
Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
            275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
            515                 520                 525

Gly Asp Ile Leu Arg Arg Thr Ser Gly Gly Pro Phe Ala Phe Ser Asn
530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
```

```
              595                 600                 605
Phe Pro Glu Arg Ser Ser Leu Thr Val Gly Ala Asp Thr Phe Ser
    610                 615                 620

Ser Gly Asn Glu Val Tyr Val Asp Arg Phe Glu Leu Ile Pro Val Thr
625                 630                 635                 640

Ala Thr Gly Thr Thr Thr Tyr Glu Tyr Glu Lys Gln Asn Leu Glu
                    645                 650                 655

Lys Ala Gln Lys Ala Leu Asn Ala Leu Phe Thr Asp Gly Thr Asn Gly
            660                 665                 670

Tyr Leu Gln Met Asp Ala Thr Asp Tyr Ile Asn Gln Thr Ala Asn
                675                 680                 685

Leu Ile Glu Cys Val Ser Asp Glu Leu Tyr Ala Lys Glu Lys Ile Val
            690                 695                 700

Leu Leu Asp Glu Val Lys Tyr Ala Lys Arg Leu Ser Ile Ser Arg Asn
705                 710                 715                 720

Leu Leu Leu Asn Asp Asp Leu Glu Phe Ser Asp Gly Phe Gly Glu Asn
                725                 730                 735

Gly Trp Thr Thr Ser Asp Asn Ile Ser Ile Gln Ala Asp Asn Pro Leu
            740                 745                 750

Phe Lys Gly Asn Tyr Leu Lys Met Phe Gly Ala Arg Asp Ile Asp Gly
                755                 760                 765

Thr Leu Phe Pro Thr Tyr Leu Tyr Gln Lys Ile Asp Glu Ser Arg Leu
770                 775                 780

Lys Pro Tyr Thr Arg Tyr Arg Val Arg Gly Phe Val Gly Ser Ser Lys
785                 790                 795                 800

Asn Leu Lys Leu Val Val Thr Arg Tyr Glu Lys Glu Ile Asp Ala Ile
                805                 810                 815

Met Asn Val Pro Asn Asp Leu Ala His Met Gln Leu Asn Pro Ser Cys
                820                 825                 830

Gly Asp Tyr Arg Cys Glu Ser Ser Gln Phe Leu Val Asn Gln Val
                835                 840                 845

His Pro Thr Pro Thr Ala Gly Tyr Ala Leu Asp Met Tyr Ala Cys Pro
    850                 855                 860

Ser Ser Ser Asp Lys Lys His Ile Met Cys His Asp Arg His Pro Phe
865                 870                 875                 880

Asp Phe His Ile Asp Thr Gly Glu Leu Asn Pro Asn Thr Asn Leu Gly
                885                 890                 895

Ile Asp Val Leu Phe Lys Ile Ser Asn Pro Asn Gly Tyr Ala Thr Leu
            900                 905                 910

Gly Asn Leu Glu Val Ile Glu Glu Gly Pro Leu Thr Asp Glu Ala Leu
                915                 920                 925

Val His Val Lys Gln Lys Glu Lys Lys Trp Arg Gln His Met Glu Lys
                930                 935                 940

Lys Arg Met Glu Thr Gln Gln Ala Tyr Asp Pro Ala Lys Gln Ala Val
945                 950                 955                 960

Asp Ala Leu Phe Thr Asn Glu Gln Glu Leu Asp Tyr His Thr Thr Leu
                965                 970                 975

Asp His Ile Gln Asn Ala Asp Gln Leu Val Gln Ala Ile Pro Tyr Val
            980                 985                 990

His His Ala Trp Leu Pro Asp Ala Pro Gly Met Asn Tyr Asp Val Tyr
                995                 1000                1005

Gln Gly Leu Asn Ala Arg Ile Met Gln Ala Tyr Asn Leu Tyr Asp
    1010                1015                1020
```

| | | | | | | | | | | |
|---|---|---|---|---|---|---|---|---|---|---|
| Ala | Arg | Asn | Val | Ile | Ile | Asn | Gly | Asp | Phe | Thr | Gln | Gly | Leu | Gln |
| | 1025 | | | | 1030 | | | | 1035 | |

Ala Arg Asn Val Ile Ile Asn Gly Asp Phe Thr Gln Gly Leu Gln
       1025                       1030                    1035

Gly Trp His Ala Thr Gly Lys Ala Ala Val Gln Gln Ile Asp Gly
 1040                           1045                     1050

Ala Ser Val Leu Val Leu Ser Asn Trp Ser Ala Glu Val Ser Gln
 1055                           1060                     1065

Asn Leu His Ala Gln Asp His His Gly Tyr Met Leu Arg Val Ile
 1070                           1075                     1080

Ala Lys Lys Glu Gly Pro Gly Lys Gly Tyr Val Met Met Met Asp
 1085                           1090                     1095

Phe Asn Gly Lys Gln Glu Thr Leu Thr Phe Thr Ser Cys Glu Glu
 1100                           1105                     1110

Gly Tyr Ile Thr Lys Thr Ile Glu Val Phe Pro Glu Ser Asp Arg
 1115                           1120                     1125

Ile Arg Ile Glu Met Gly Glu Thr Glu Gly Thr Phe Tyr Val Asp
 1130                           1135                     1140

Ser Ile Glu Leu Leu Cys Met Gln Gly Tyr Ala Ser Asp Asn Asn
 1145                           1150                     1155

Pro His Thr Gly Asn Met Tyr Glu Gln Ser Tyr Asn Gly Asn Tyr
 1160                           1165                     1170

Asn Gln Asn Thr Ser Asp Val Tyr His Gln Gly Tyr Ile Asn Asn
 1175                           1180                     1185

Tyr Asn Gln Asn Ser Ser Ser Met Tyr Asn Gln Asn Tyr Ile Asn
 1190                           1195                     1200

Asn Asp Asp Leu His Ser Gly Cys Thr Cys Asn Gln Gly His Asn
 1205                           1210                     1215

Ser Gly Cys Thr Cys Asn Gln Gly Tyr Asn Arg
 1220                           1225

<210> SEQ ID NO 17
<211> LENGTH: 3432
<212> TYPE: DNA
<213> ORGANISM: Artificial
<220> FEATURE:
<223> OTHER INFORMATION: Recombinant nucleotide sequence used
     for expression in a bacterial cell encoding TIC867_22.

<400> SEQUENCE: 17

| | |
|---|---|
| atgacttcaa ataggaaaaa tgagaatgaa attataaatg ctttatcgat tccagctgta | 60 |
| tcgaatcatt ccgcacaaat gaatctatca accgatgctc gtattgagga tagcttgtgt | 120 |
| atagccgagg ggaacaatat cgatccattt gttagcgcat caacagtcca aacgggtatt | 180 |
| aacatagctg gtagaatact aggtgtatta ggcgtaccgt ttgctggaca atagctagt | 240 |
| ttttatagtt ttcttgttgg tgaattatgg ccccgcggca gagatccttg ggaaattttc | 300 |
| ctagaacatg tcgaacaact tataagacaa caagtaacag aaaatactag ggatacggct | 360 |
| cttgctcgat tacaaggttt aggaaattcc tttagagcct atcaacagtc acttgaagat | 420 |
| tggctagaaa accgtgatga tgcaagaacg agaagtgttc tttatacca atatatagcc | 480 |
| ttagaacttg atttcttaa tgcgatgccg cttttcgcaa ttagaaacca agaagttcca | 540 |
| ttattaatgg tatatgctca agctgcaaat ttacacctat tattattgag agatgcctct | 600 |
| ctttttggta gtgaatttgg gcttacatcc aagaaattc aacgttatta tgagcgccaa | 660 |
| gtggaaaaaa cgagagaata ttctgattat tgcgcaagat ggtataatac gggtttaaat | 720 |
| aatttgagag ggacaaatgc tgaaagttgg ttgcgatata atcaattccg tagagactta | 780 |

| | |
|---|---|
| acgctaggag tattagatct agtggcacta ttcccaagct atgacacgcg tgtttatcca | 840 |
| atgaatacca gtgctcaatt aacaagagaa atttatacag atccaattgg gagaacaaat | 900 |
| gcaccttcag gatttgcaag tacgaattgg tttaataata atgcaccatc gtttctgcc | 960 |
| atagaggctg ccgttattag gcctccgcat ctacttgatt ttccagaaca gcttacaatt | 1020 |
| ttcagcgtat taagtcgatg gagtaatact caatatatga attactgggt gggacataga | 1080 |
| cttgaatcgc gaacaataag ggggtcatta agtacctcga cacacggaaa taccaatact | 1140 |
| tctattaatc ctgtaacatt acagttcaca tctcgagacg tttatagaac agaatcattt | 1200 |
| gcagggataa atatacttct aactactcct gtgaatggag taccttgggc tagatttaat | 1260 |
| tggagaaatc ccctgaattc tcttagaggt agccttctct atactatagg gtatactgga | 1320 |
| gtggggacac aactatttga ttcagaaact gaattaccac cagaaacaac agaacgacca | 1380 |
| aattatgaat cttacagtca tagattatct aatataagac taatatcagg aaacactttg | 1440 |
| agagcaccag tatattcttg gacgcaccgt agtgcagatc gtacaaatac cattagttca | 1500 |
| gatagcatta cacaaatacc attggtaaag gcgcataccc tccaatcggg taccactgta | 1560 |
| gtaaaagggc cagggtttac aggagggat atcctccgtc gaacaagtgg aggaccattt | 1620 |
| gcttttagta atgttaatct agattttaac ttgtcacaaa ggtatcgtgc tagaattcgt | 1680 |
| tatgcctcta ctactaacct aagaatttac gtaacggttg caggtgaacg aattttttgct | 1740 |
| ggtcaatttg acaaaactat ggatgctggt gccccattaa cattccaatc ttttagttac | 1800 |
| gcaactatta atacagcttt tacattccca gaaagatcga gcagcttgac tgtaggtgcc | 1860 |
| gatacgttta gttcaggtaa tgaagtttat gtagatagat ttgaattaat cccagttact | 1920 |
| gcaaccaatc cgacgcgaga ggcggaagag gatctagaag cagcgaagaa agcggtggcg | 1980 |
| agcttgttta cacgtacaag ggacggatta caagtaaatg tgacagatta tcaagtcgat | 2040 |
| caagcggcaa atttagtgtc atgcttatca gatgaacaat atgggcatga caaaaagatg | 2100 |
| ttattggaag cggtaagagc ggcaaaacgc ctcagccgag aacgcaactt acttcaggat | 2160 |
| ccagattta atacaatcaa tagtacagaa gaaatggat ggaaagcaag taacggcgtt | 2220 |
| actattagcg agggcggtcc attctataaa ggccgtgcgc ttcagctagc aagcgcaaga | 2280 |
| gaaaattacc caacatacat ttatcaaaaa gtaaatgcat cagagttaaa gccgtataca | 2340 |
| cgttatagac tggatgggtt cgtgaagagt agtcaagatt tagaaattga tctcattcac | 2400 |
| catcataaag tccatctcgt gaaaaatgta ccagataatt tagtatccga tacttactcg | 2460 |
| gatggttctt gcagtggaat gaatcgatgt gaggaacaac agatggtaaa tgcgcaactg | 2520 |
| gaaacagaac atcatcatcc gatggattgc tgtgaagcgg ctcaaacaca tgagttttct | 2580 |
| tcctatatta atacaggcga tctaaattca agtgtagatc aaggcatttg ggttgtattg | 2640 |
| aaagttcgaa caaccgatgg ttatgcgacg ctaggaaatc ttgaattggt agaggtcgga | 2700 |
| ccgttatcgg gtgaatctct agaacgtgaa caaagggata tgcgaaatg gagtgcagag | 2760 |
| ctaggaagaa agcgtgcaga aacagatcgc gtgtatcaag atgccaaaca atccatcaat | 2820 |
| catttatttg tggattatca agatcaacaa ttaaatccag aaatagggat ggcagatatt | 2880 |
| attgacgctc aaaatcttgt cgcatcaatt tcagatgtgt atagcgatgc agtactgcaa | 2940 |
| atccctggaa ttaactatga gatttacaca gagctatcca atcgcttaca acaagcatcg | 3000 |
| tatctgtata cgtctcgaaa tgcggtgcaa aatgggact ttaacagcgg tctagatagt | 3060 |
| tggaatgcaa caggggggc tacggtacaa caggatggca atacgcattt cttagttctt | 3120 |

| | |
|---|---:|
| tctcattggg atgcacaagt ttctcaacaa tttagagtgc agccgaattg taaatatgta | 3180 |
| ttacgtgtaa cagcagagaa agtaggcggc ggagacggat acgtgacaat ccgggatggt | 3240 |
| gctcatcata cagaaaagct tacatttaat gcatgtgatt atgatataaa tggcacgtac | 3300 |
| gtgactgata atacgtatct aacaaaagaa gtggtattct attcacatac agaacacatg | 3360 |
| tgggtagagg taagtgaaac agaaggtgca tttcatatag atagtattga attcgttgaa | 3420 |
| acagaaaagt ag | 3432 |

```
<210> SEQ ID NO 18
<211> LENGTH: 3432
<212> TYPE: DNA
<213> ORGANISM: Artificial
<220> FEATURE:
<223> OTHER INFORMATION: Synthetic nucleotide sequence designed for
      expression in a plant cell encoding TIC867_22.

<400> SEQUENCE: 18
```

| | |
|---|---:|
| atgaccagca accgaaagaa cgagaacgag atcatcaacg ccctgtccat accggccgtg | 60 |
| tcaaaccact ccgcccagat gaacctctcc accgacgcga ggatcgagga ctccctctgc | 120 |
| atcgccgagg gcaacaacat cgacccgttc gtgtctgcaa gcacggtcca gaccggcatc | 180 |
| aacatcgcgg gccgcatcct gggcgtgctc ggcgtgccct cgcgggtca aatcgcctct | 240 |
| ttctactcat tcctcgtggg cgagctgtgg ccgcgcggac gtgacccgtg ggaaatcttc | 300 |
| ctggagcacg ttgagcagct catccggcag caagtgaccg agaacaccag ggacaccgca | 360 |
| ctggcacggc tccagggcct tggcaacagc ttccgcgcct accagcagtc gctggaggac | 420 |
| tggctggaga ccgagacga cgccagaacc cgctcagttc tgtacacaca gtacatcgcc | 480 |
| ctagagctgg acttcctcaa cgctatgccg ctcttcgcca tccgtaacca ggaagtaccg | 540 |
| cttctgatgg tgtacgcaca agcagcgaac ctccatctgc cctgctgcg agacgcatct | 600 |
| ctgttcggca gtgagttcgg gctgacgagc caggagatcc agcgctacta cgagcgccaa | 660 |
| gtggagaaga ctcgtgagta cagcgactac tgcgcgcgct ggtacaacac gggcttgaac | 720 |
| aaccttcgcg ggacaaacgc cgaatcctgg cttcgctaca accagttccg ccgcgacctc | 780 |
| acgctgggtg tgctggacct ggtcgcgctc ttcccgtcct acgacacacg ggtgtaccca | 840 |
| atgaacacga gcgcacagct cacccgtgag atctacacag atcccatcgg ccgcaccaac | 900 |
| gctcccagtg gcttcgcaag cacgaattgg ttcaacaata cgctccttc tttctctgcc | 960 |
| atcgaggccg ctgtcatcag accgccgcac ttactcgatt cccggagca gctcactatc | 1020 |
| ttctctgtgt tgtcccggtg gtcgaacacg cagtacatga actactgggt gggccacagg | 1080 |
| ctagagagcc ggaccatccg tggcagtctc tcaacctcga cccacggcaa cacgaacacg | 1140 |
| agcatcaacc ctgtcactct ccagtttaca tctaggacg tttacaggac agagtcgttc | 1200 |
| gctggcatta acattctgtt gaccactccg gtgaacggcg tcccttgggc ccgcttcaac | 1260 |
| tggaggaatc tctgaactc actgcgcggc agccttctct acactatcgg ctacaccggc | 1320 |
| gttgggacgc aactcttcga ctcggagacc gagctgccgc ccgagaccac cgagcggcct | 1380 |
| aactacgaga gttattcaca caggctctcc aacatccgct tgatttctgg gaacaccttg | 1440 |
| cgggctccgg tgtactcctg gacgcaccgc agcgccgaca gaactaatac catcagctcc | 1500 |
| gactcgatca cccagatccc gctggtgaag gctcacacgc ttcagtcggg caccacagtc | 1560 |
| gtcaagggcc ctggcttcac cggcggcgac atcctgcgtc gcacatctgg cggaccctcc | 1620 |
| gccttcagca acgtgaactt ggacttcaat ttgtcacagc ggtatcgtgc cagaatccgg | 1680 |

```
tacgccagca ctacgaacct gcgaatctat gttactgtgg cgggcgagcg gatcttcgcc    1740
gggcaattcg acaagacgat ggacgcggga gcacctctga cattccagtc attctcttac    1800
gccacgatca acacggcatt cacgtttccg gagcgttcca gtagcctgac cgtgggcgct    1860
gataccttca gtagcgggaa cgaggtgtac gttgaccgtt tcgagctgat cccggtcacc    1920
gccaccaacc cgacgcggga agctgaggaa gacttggaag ccgccaagaa agcggtcgcc    1980
agcctgttta ctcggacgcg ggacgggctc caagtgaatg tgacggacta tcaagtggat    2040
caggccgcta acctcgtgtc atgcctgagc gacgagcagt acggtcacga caagaaaatg    2100
ctgctggagg ccgtccgggc cgccaagcgg ctgtccaggg agcgtaacct gctacaagat    2160
cccgacttta acacgatcaa cagcacagag gagaatggct ggaaggccag caacggagtt    2220
acgataagcg agggcggtcc gttctacaag ggtcgtgccc tccagctcgc ctctgcaagg    2280
gagaactatc caacctacat ctatcagaag gtgaacgcat ccgagcttaa gccctacaca    2340
cgctaccgcc tggacgggtt cgttaagtcc agtcaagacc tagagataga cctcatccac    2400
caccacaaag tgcatctggt caagaacgtt cccgataatc tcgtgagcga tacctactca    2460
gacggctcat gctctggcat gaacagatgt gaggagcaac agatggttaa tgctcaactc    2520
gaaaccgagc atcatcatcc tatggattgc tgcgaggccg cgcagaccca tgagttcagc    2580
tcttacatca acaccggaga cctcaacagt agcgtggatc agggaatttg gtggtgctt    2640
aaagtgcgta caaccgacgg ctacgccacc ctcggcaacc ttgagcttgt cgaggtcgga    2700
ccacttagcg gcgagtccct ggaacgtgag cagcgggaca acgccaaatg gagcgcagag    2760
ctagggcgca aacgcgcgga gacggaccgg gtttatcagg acgcgaagca gtccatcaat    2820
cacctcttcg tggattatca ggaccagcag cttaatccag agatcggcat ggccgacatc    2880
atcgacgccc agaacctagt agcgtcgatt tccgatgtct attccgacgc cgtgcttcaa    2940
atacctggca tcaactacga gatctacaca gagttgtcca acaggctcca gcaagcgtca    3000
tacctctaca ccagccgcaa cgccgtccag aatggcgact tcaattccgg actagactcc    3060
tggaacgcca cgggcggagc tacggtgcaa caagacggca acccactt cctcgtactt    3120
agccactggg acgctcaagt gagtcagcaa ttccgggttc agccgaactg caagtacgtc    3180
ctgcgcgtaa cggccgagaa ggttggaggc ggagacggct acgttaccat ccgcgacggc    3240
gctcaccaca ccgagaaact gacgttcaac gcttgtgact acgacatcaa cggcacttac    3300
gtgacggaca acacctacct gacgaaggag gtggtgttct attctcacac cgagcacatg    3360
tgggttgagg tcagcgagac cgagggagcc ttccacattg acagcatcga gttcgtggag    3420
actgagaagt ga                                                        3432
```

<210> SEQ ID NO 19
<211> LENGTH: 1143
<212> TYPE: PRT
<213> ORGANISM: Artificial
<220> FEATURE:
<223> OTHER INFORMATION: Amino acid sequence of the chimeric protein
      variant TIC867_22.

<400> SEQUENCE: 19

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

```
Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Gln Leu Ile Arg Gln Gln Val
                100                 105                 110

Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
    195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
    275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
    355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
    435                 440                 445

Glu Thr Glu Leu Pro Pro Glu Thr Thr Glu Arg Pro Asn Tyr Glu Ser
    450                 455                 460
```

-continued

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
            485                 490                 495

Thr Ile Ser Ser Asp Ser Ile Thr Gln Ile Pro Leu Val Lys Ala His
        500                 505                 510

Thr Leu Gln Ser Gly Thr Thr Val Val Lys Gly Pro Gly Phe Thr Gly
    515                 520                 525

Gly Asp Ile Leu Arg Arg Thr Ser Gly Gly Pro Phe Ala Phe Ser Asn
530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
        595                 600                 605

Phe Pro Glu Arg Ser Ser Ser Leu Thr Val Gly Ala Asp Thr Phe Ser
610                 615                 620

Ser Gly Asn Glu Val Tyr Val Asp Arg Phe Glu Leu Ile Pro Val Thr
625                 630                 635                 640

Ala Thr Asn Pro Thr Arg Glu Ala Glu Glu Asp Leu Glu Ala Ala Lys
                645                 650                 655

Lys Ala Val Ala Ser Leu Phe Thr Arg Thr Arg Asp Gly Leu Gln Val
            660                 665                 670

Asn Val Thr Asp Tyr Gln Val Asp Gln Ala Ala Asn Leu Val Ser Cys
        675                 680                 685

Leu Ser Asp Glu Gln Tyr Gly His Asp Lys Lys Met Leu Leu Glu Ala
    690                 695                 700

Val Arg Ala Ala Lys Arg Leu Ser Arg Glu Arg Asn Leu Leu Gln Asp
705                 710                 715                 720

Pro Asp Phe Asn Thr Ile Asn Ser Thr Glu Glu Asn Gly Trp Lys Ala
                725                 730                 735

Ser Asn Gly Val Thr Ile Ser Glu Gly Gly Pro Phe Tyr Lys Gly Arg
            740                 745                 750

Ala Leu Gln Leu Ala Ser Ala Arg Glu Asn Tyr Pro Thr Tyr Ile Tyr
        755                 760                 765

Gln Lys Val Asn Ala Ser Glu Leu Lys Pro Tyr Thr Arg Tyr Arg Leu
    770                 775                 780

Asp Gly Phe Val Lys Ser Ser Gln Asp Leu Glu Ile Asp Leu Ile His
785                 790                 795                 800

His His Lys Val His Leu Val Lys Asn Val Pro Asp Asn Leu Val Ser
                805                 810                 815

Asp Thr Tyr Ser Asp Gly Ser Cys Ser Gly Met Asn Arg Cys Glu Glu
            820                 825                 830

Gln Gln Met Val Asn Ala Gln Leu Glu Thr Glu His His Pro Met
        835                 840                 845

Asp Cys Cys Glu Ala Ala Gln Thr His Glu Phe Ser Tyr Ile Asn
    850                 855                 860

Thr Gly Asp Leu Asn Ser Ser Val Asp Gln Gly Ile Trp Val Leu
865                 870                 875                 880

Lys Val Arg Thr Thr Asp Gly Tyr Ala Thr Leu Gly Asn Leu Glu Leu

```
                885                 890                 895
Val Glu Val Gly Pro Leu Ser Gly Glu Ser Leu Glu Arg Glu Gln Arg
            900                 905                 910
Asp Asn Ala Lys Trp Ser Ala Glu Leu Gly Arg Lys Arg Ala Glu Thr
            915                 920                 925
Asp Arg Val Tyr Gln Asp Ala Lys Gln Ser Ile Asn His Leu Phe Val
            930                 935                 940
Asp Tyr Gln Asp Gln Gln Leu Asn Pro Glu Ile Gly Met Ala Asp Ile
945                 950                 955                 960
Ile Asp Ala Gln Asn Leu Val Ala Ser Ile Ser Asp Val Tyr Ser Asp
            965                 970                 975
Ala Val Leu Gln Ile Pro Gly Ile Asn Tyr Glu Ile Tyr Thr Glu Leu
            980                 985                 990
Ser Asn Arg Leu Gln Gln Ala Ser  Tyr Leu Tyr Thr Ser  Arg Asn Ala
            995                 1000                1005
Val Gln  Asn Gly Asp Phe Asn  Ser Gly Leu Asp Ser  Trp Asn Ala
            1010                1015                1020
Thr Gly  Gly Ala Thr Val Gln  Gln Asp Gly Asn Thr  His Phe Leu
            1025                1030                1035
Val Leu  Ser His Trp Asp Ala  Gln Val Ser Gln Gln  Phe Arg Val
            1040                1045                1050
Gln Pro  Asn Cys Lys Tyr Val  Leu Arg Val Thr Ala  Glu Lys Val
            1055                1060                1065
Gly Gly  Gly Asp Gly Tyr Val  Thr Ile Arg Asp Gly  Ala His His
            1070                1075                1080
Thr Glu  Lys Leu Thr Phe Asn  Ala Cys Asp Tyr Asp  Ile Asn Gly
            1085                1090                1095
Thr Tyr  Val Thr Asp Asn Thr  Tyr Leu Thr Lys Glu  Val Val Phe
            1100                1105                1110
Tyr Ser  His Thr Glu His Met  Trp Val Glu Val Ser  Glu Thr Glu
            1115                1120                1125
Gly Ala  Phe His Ile Asp Ser  Ile Glu Phe Val Glu  Thr Glu Lys
            1130                1135                1140
```

<210> SEQ ID NO 20
<211> LENGTH: 3696
<212> TYPE: DNA
<213> ORGANISM: Artificial
<220> FEATURE:
<223> OTHER INFORMATION: Synthetic nucleotide sequence designed for
      expression in a plant cell encoding TIC867_23.

<400> SEQUENCE: 20

| | | |
|---|---|---|
| atgaccagca accgaaagaa cgagaacgag atcatcaacg ccctgtccat accggccgtg | 60 |
| tcaaaccact ccgcccagat gaacctctcc accgacgcga ggatcgagga ctccctctgc | 120 |
| atcgccgagg caacaacat cgacccgttc gtgtctgcaa gcacggtcca gaccggcatc | 180 |
| aacatcgcgg gccgcatcct gggcgtgctc ggcgtgccct cgcgggtca atcgcctct | 240 |
| ttctactcat tcctcgtggg cgagctgtgg ccgcgcggac gtgacccgtg ggaaatcttc | 300 |
| ctggagcacg ttgagcagct catccggcag caagtgaccg agaacaccag ggacaccgca | 360 |
| ctggcacggc tccagggcct tggcaacagc ttccgcgcct accagcagtc gctggaggac | 420 |
| tggctggaga accgagacga cgccagaacc cgctcagttc tgtacacaca gtacatcgcc | 480 |
| ctagagctgg acttcctcaa cgctatgccg ctcttcgcca tccgtaacca ggaagtaccg | 540 |

```
cttctgatgg tgtacgcaca agcagcgaac ctccatctgc tcctgctgcg agacgcatct   600
ctgttcggca gtgagttcgg gctgacgagc caggagatcc agcgctacta cgagcgccaa   660
gtggagaaga ctcgtgagta cagcgactac tgcgcgcgct ggtacaacac gggcttgaac   720
aaccttcgcg ggacaaacgc cgaatcctgg cttcgctaca accagttccg ccgcgacctc   780
acgctgggtg tgctggacct ggtcgcgctc ttcccgtcct acgacacacg ggtgtaccca   840
atgaacacga gcgcacagct cacccgtgag atctacacag atcccatcgg ccgcaccaac   900
gctcccagtg gcttcgcaag cacgaattgg ttcaacaata cgctccttc tttctctgcc    960
atcgaggccg ctgtcatcag accgccgcac ttactcgatt cccggagca gctcactatc   1020
ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctagggacg tttacaggac agagtcgttc   1200
gctggcatta acattctgtt gaccactccg gtgaacggcg tcccttgggc ccgcttcaac   1260
tggaggaatc ctctgaactc actgcgcggc agccttctct acactatcgg ctacaccggc   1320
gttgggacgc aactcttcga ctcggagacc gagctgccgc ccgagaccac cgagcggcct   1380
aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
gtcaagggcc ctggcttcac cggcggcgac atcctgcgtc gcacatctgg cggacccttc   1620
gccttcagca acgtgaactt ggacttcaat ttgtcacagc ggtatcgtgc cagaatccgg   1680
tacgccagca ctacgaacct gcgaatctat gttactgtgg cgggcgagcg gatcttcgcc   1740
gggcaattcg acaagacgat ggacgcggga gcacctctga cattccagtc attctcttac   1800
gccacgatca acacggcatt cacgtttccg gagcgttcca gtagcctgac cgtgggcgct   1860
gataccttca gtagcgggaa cgaggtgtac gttgaccgtt tcgagctgat cccggtcacc   1920
gccaccacgg cgaccttcga ggcggagtat gacttggagc gggctcagga ggccgtcaac   1980
gcgctgttca caaacaccaa tcctcgccgc ctcaagacgg tgtgactga ttaccacatt    2040
gacgaggtct ccaacttggt cgcgtgtctg tccgatgagt tctgcctgga cgagaagcgg   2100
gaactgctgg agaaggtcaa gtacgccaag cgcctctccg acgaaaggaa cctcctccaa   2160
gatcccaact ttacttccat taacaagcag ccggacttca tctccaccaa cgagcagtcc   2220
aacttcacct caatccacga gcagtcggag cacgggtggt ggggcagcga gaacatcacc   2280
atccaagagg gcaacgacgt cttcaaggag aactacgtga tcctgcccgg caccttcaac   2340
gagtgttacc cgacctatct ctaccagaag attggcgaag cggaactcaa ggcttacacc   2400
cgttaccaac tgagtggcta cattgaggac tcacaagacc tggaaatcta cctgatccgc   2460
tacaacgcca agcacgagac cctcgacgtg cctggcacgg agtccgtctg gcccttgagc   2520
gtggagtctc ctatcggtcg ttgcggcgag cccaatcgct gcgctccgca ctttgagtgg   2580
aatcctgatt tggattgctc ctgccgagac ggtgagaaat gcgcccacca ctcgcaccac   2640
ttcagcctag acatcgacgt gggctgcatc gacctgcacg agaacttggg cgtctgggtc   2700
gtgttcaaga tcaagacaca ggagggccat gctcggcttg gaacctggga gttcatcgag   2760
gagaagccac tgctgggtga agccttgtca cgggtgaaac gcgccgagaa gaagtggcgg   2820
gacaaacggg agaagctcca gttggagaca aagcgtgtgt acacagaggc caaggaggcc   2880
gtggatgcct tgttcgtgga cagtcagtac gacaggctgc aagcggacac caacatcggg   2940
```

```
atgatccacg cggctgataa gcttgttcac agaatccgcg aggcgtacct gtcagagctt    3000
agcgtgatcc caggcgtcaa cgccgaaatc ttcgaggaac tggagggccg cattatcacg    3060
gcaatctcac tttatgacgc gaggaatgtg gtcaagaacg gtgacttcaa caacggcttg    3120
gcgtgttgga acgttaaagg gcacgtggat gtacaacagt cacaccacag aagtgtcttg    3180
gtcatcccgg agtgggaggc ggaagtgagc caggccgtcc gggtctgccc tgggcgcggt    3240
tacatcctcc gcgtgacagc gtacaaggag ggctacggtg agggctgcgt gacgatccac    3300
gagattgaga caacacgga cgagcttaag ttcaagaact gcgaggagga ggaagtgtac    3360
ccgacagaca ccggcacctg caacgactac accgcccacc aagggaccgc cgcctgcaac    3420
agccgcaacg cgggctatga agatgcgtac gaggttgata ccaccgcctc agtgaactac    3480
aaaccgactt atgaggagga gacatacacg gacgtcaggc gcgacaacca ttgtgagtac    3540
gaccgtggct acgtgaacta tccgccggtg ccagcgggct acatgacgaa ggagctagaa    3600
tacttccctg agacggacaa ggtgtggatt gaaatcggcg agaccgaggg caagtttatc    3660
gtggattctg tcgagctgct gctaatggag gagtag                              3696
```

<210> SEQ ID NO 21
<211> LENGTH: 1231
<212> TYPE: PRT
<213> ORGANISM: Artificial
<220> FEATURE:
<223> OTHER INFORMATION: Amino acid sequence of the chimeric protein variant TIC867_23.

<400> SEQUENCE: 21

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220
```

-continued

```
Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
            245                 250                 255

Arg Arg Asp Leu Thr Leu Gly Val Leu Asp Leu Val Ala Leu Phe Pro
        260                 265                 270

Ser Tyr Asp Thr Arg Val Tyr Pro Met Asn Thr Ser Ala Gln Leu Thr
    275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Ala Pro Ser Phe Ser Ala
305                 310                 315                 320

Ile Glu Ala Ala Val Ile Arg Pro Pro His Leu Leu Asp Phe Pro Glu
            325                 330                 335

Gln Leu Thr Ile Phe Ser Val Leu Ser Arg Trp Ser Asn Thr Gln Tyr
        340                 345                 350

Met Asn Tyr Trp Val Gly His Arg Leu Glu Ser Arg Thr Ile Arg Gly
    355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
        420                 425                 430

Leu Tyr Thr Ile Gly Tyr Thr Gly Val Gly Thr Gln Leu Phe Asp Ser
    435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
            485                 490                 495

Thr Ile Ser Ser Asp Ser Ile Thr Gln Ile Pro Leu Val Lys Ala His
        500                 505                 510

Thr Leu Gln Ser Gly Thr Thr Val Val Lys Gly Pro Gly Phe Thr Gly
    515                 520                 525

Gly Asp Ile Leu Arg Arg Thr Ser Gly Gly Pro Phe Ala Phe Ser Asn
530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
            565                 570                 575

Arg Ile Phe Ala Gly Gln Phe Asp Lys Thr Met Asp Ala Gly Ala Pro
        580                 585                 590

Leu Thr Phe Gln Ser Phe Ser Tyr Ala Thr Ile Asn Thr Ala Phe Thr
    595                 600                 605

Phe Pro Glu Arg Ser Ser Leu Thr Val Gly Ala Asp Thr Phe Ser
610                 615                 620

Ser Gly Asn Glu Val Tyr Val Asp Arg Phe Glu Leu Ile Pro Val Thr
625                 630                 635                 640
```

-continued

```
Ala Thr Thr Ala Thr Phe Glu Ala Glu Tyr Asp Leu Glu Arg Ala Gln
                    645                 650                 655

Glu Ala Val Asn Ala Leu Phe Thr Asn Thr Asn Pro Arg Arg Leu Lys
            660                 665                 670

Thr Gly Val Thr Asp Tyr His Ile Asp Glu Val Ser Asn Leu Val Ala
        675                 680                 685

Cys Leu Ser Asp Glu Phe Cys Leu Asp Glu Lys Arg Glu Leu Leu Glu
    690                 695                 700

Lys Val Lys Tyr Ala Lys Arg Leu Ser Asp Glu Arg Asn Leu Leu Gln
705                 710                 715                 720

Asp Pro Asn Phe Thr Ser Ile Asn Lys Gln Pro Asp Phe Ile Ser Thr
                725                 730                 735

Asn Glu Gln Ser Asn Phe Thr Ser Ile His Glu Gln Ser Glu His Gly
            740                 745                 750

Trp Trp Gly Ser Glu Asn Ile Thr Ile Gln Glu Gly Asn Asp Val Phe
        755                 760                 765

Lys Glu Asn Tyr Val Ile Leu Pro Gly Thr Phe Asn Glu Cys Tyr Pro
    770                 775                 780

Thr Tyr Leu Tyr Gln Lys Ile Gly Glu Ala Glu Leu Lys Ala Tyr Thr
785                 790                 795                 800

Arg Tyr Gln Leu Ser Gly Tyr Ile Glu Asp Ser Gln Asp Leu Glu Ile
                805                 810                 815

Tyr Leu Ile Arg Tyr Asn Ala Lys His Glu Thr Leu Asp Val Pro Gly
            820                 825                 830

Thr Glu Ser Val Trp Pro Leu Ser Val Glu Ser Pro Ile Gly Arg Cys
        835                 840                 845

Gly Glu Pro Asn Arg Cys Ala Pro His Phe Glu Trp Asn Pro Asp Leu
    850                 855                 860

Asp Cys Ser Cys Arg Asp Gly Glu Lys Cys Ala His His Ser His His
865                 870                 875                 880

Phe Ser Leu Asp Ile Asp Val Gly Cys Ile Asp Leu His Glu Asn Leu
                885                 890                 895

Gly Val Trp Val Val Phe Lys Ile Lys Thr Gln Glu Gly His Ala Arg
            900                 905                 910

Leu Gly Asn Leu Glu Phe Ile Glu Glu Lys Pro Leu Leu Gly Glu Ala
        915                 920                 925

Leu Ser Arg Val Lys Arg Ala Glu Lys Lys Trp Arg Asp Lys Arg Glu
    930                 935                 940

Lys Leu Gln Leu Glu Thr Lys Arg Val Tyr Thr Glu Ala Lys Glu Ala
945                 950                 955                 960

Val Asp Ala Leu Phe Val Asp Ser Gln Tyr Asp Arg Leu Gln Ala Asp
                965                 970                 975

Thr Asn Ile Gly Met Ile His Ala Ala Asp Lys Leu Val His Arg Ile
            980                 985                 990

Arg Glu Ala Tyr Leu Ser Glu Leu  Ser Val Ile Pro Gly Val Asn Ala
        995                 1000                 1005

Glu Ile  Phe Glu Glu Leu Glu  Gly Arg Ile Ile Thr  Ala Ile Ser
    1010                 1015                 1020

Leu Tyr Asp Ala Arg Asn Val  Val Lys Asn Gly Asp  Phe Asn Asn
    1025                 1030                 1035

Gly Leu Ala Cys Trp Asn Val  Lys Gly His Val Asp  Val Gln Gln
    1040                 1045                 1050

Ser His His Arg Ser Val Leu  Val Ile Pro Glu Trp  Glu Ala Glu
```

| | | | | | | | | | |
|---|---|---|---|---|---|---|---|---|---|
| | | | | 1055 | | | | 1060 | | | | 1065 | | |
| Val | Ser | Gln | Ala | Val | Arg | Val | Cys | Pro | Gly | Arg | Gly | Tyr | Ile | Leu |
| | 1070 | | | | 1075 | | | | 1080 | | | | | |
| Arg | Val | Thr | Ala | Tyr | Lys | Glu | Gly | Tyr | Gly | Glu | Gly | Cys | Val | Thr |
| | 1085 | | | | 1090 | | | | 1095 | | | | | |
| Ile | His | Glu | Ile | Glu | Asn | Asn | Thr | Asp | Glu | Leu | Lys | Phe | Lys | Asn |
| | 1100 | | | | 1105 | | | | 1110 | | | | | |
| Cys | Glu | Glu | Glu | Val | Tyr | Pro | Thr | Asp | Thr | Gly | Thr | Cys | Asn | |
| | 1115 | | | | 1120 | | | | 1125 | | | | | |
| Asp | Tyr | Thr | Ala | His | Gln | Gly | Thr | Ala | Ala | Cys | Asn | Ser | Arg | Asn |
| | 1130 | | | | 1135 | | | | 1140 | | | | | |
| Ala | Gly | Tyr | Glu | Asp | Ala | Tyr | Glu | Val | Asp | Thr | Thr | Ala | Ser | Val |
| | 1145 | | | | 1150 | | | | 1155 | | | | | |
| Asn | Tyr | Lys | Pro | Thr | Tyr | Glu | Glu | Glu | Tyr | Thr | Asp | Val | Arg | |
| | 1160 | | | | 1165 | | | | 1170 | | | | | |
| Arg | Asp | Asn | His | Cys | Glu | Tyr | Asp | Arg | Gly | Tyr | Val | Asn | Tyr | Pro |
| | 1175 | | | | 1180 | | | | 1185 | | | | | |
| Pro | Val | Pro | Ala | Gly | Tyr | Met | Thr | Lys | Glu | Leu | Glu | Tyr | Phe | Pro |
| | 1190 | | | | 1195 | | | | 1200 | | | | | |
| Glu | Thr | Asp | Lys | Val | Trp | Ile | Glu | Ile | Gly | Glu | Thr | Glu | Gly | Lys |
| | 1205 | | | | 1210 | | | | 1215 | | | | | |
| Phe | Ile | Val | Asp | Ser | Val | Glu | Leu | Leu | Leu | Met | Glu | Glu | | |
| | 1220 | | | | 1225 | | | | 1230 | | | | | |

<210> SEQ ID NO 22
<211> LENGTH: 3666
<212> TYPE: DNA
<213> ORGANISM: Artificial
<220> FEATURE:
<223> OTHER INFORMATION: Synthetic nucleotide sequence designed for
      expression in a plant cell encoding TIC867_24.

<400> SEQUENCE: 22

| | |
|---|---|
| atgaccagca accgaaagaa cgagaacgag atcatcaacg ccctgtccat accggccgtg | 60 |
| tcaaaccact ccgcccagat gaacctctcc accgacgcga ggatcgagga ctccctctgc | 120 |
| atcgccgagg gcaacaacat cgacccgttc gtgtctgcaa gcacggtcca gaccggcatc | 180 |
| aacatcgcgg gccgcatcct gggcgtgctc ggcgtgccct cgcgggtca atcgcctct | 240 |
| ttctactcat tcctcgtggg cgagctgtgg ccgcgcggac gtgacccgtg ggaaatcttc | 300 |
| ctggagcacg ttgagcagct catccggcag caagtgaccg agaacaccag ggacaccgca | 360 |
| ctggcacggc tccagggcct tggcaacagc ttccgcgcct accagcagtc gctggaggac | 420 |
| tggctggaga ccgagacga cgccagaacc cgctcagttc tgtacacaca gtacatcgcc | 480 |
| ctagagctgg acttcctcaa cgctatgccg ctcttcgcca tccgtaacca ggaagtaccg | 540 |
| cttctgatgg tgtacgcaca agcagcgaac ctccatctgc tcctgctgcg agacgcatct | 600 |
| ctgttcggca gtgagttcgg gctgacgagc aggagatcc agcgctacta cgagcgccaa | 660 |
| gtggagaaga ctcgtgagta cagcgactac tgcgcgcgct ggtacaacac gggcttgaac | 720 |
| aaccttcgcg gacaaacgc cgaatcctgg cttcgctaca accagttccg ccgcgacctc | 780 |
| acgctgggtg tgctggacct ggtcgcgctc ttcccgtcct acgacacacg ggtgtaccca | 840 |
| atgaacacga gcgcacagct cacccgtgag atctacacag atcccatcgg ccgcaccaac | 900 |
| gctcccagtg gcttcgcaag cacgaattgg ttcaacaata acgctccttc tttctctgcc | 960 |
| atcgaggccg ctgtcatcag accgccgcac ttactcgatt tcccggagca gctcactatc | 1020 |

```
ttctctgtgt tgtcccggtg gtcgaacacg cagtacatga actactgggt gggccacagg    1080
ctagagagcc ggaccatccg tggcagtctc tcaacctcga cccacggcaa cacgaacacg    1140
agcatcaacc ctgtcactct ccagtttaca tctagggacg tttacaggac agagtcgttc    1200
gctggcatta acattctgtt gaccactccg gtgaacggcg tcccttgggc ccgcttcaac    1260
tggaggaatc ctctgaactc actgcgcggc agccttctct acactatcgg ctacaccggc    1320
gttgggacgc aactcttcga ctcggagacc gagctgccgc ccgagaccac cgagcggcct    1380
aactacgaga gttattcaca caggctctcc aacatccgct tgatttctgg gaacaccttg    1440
cgggctccgg tgtactcctg gacgcaccgc agcgccgaca gaactaatac catcagctcc    1500
gactcgatca cccagatccc gctggtgaag gctcacacgc ttcagtcggg caccacagtc    1560
gtcaagggcc ctggcttcac cggcggcgac atcctgcgtc gcacatctgg cggacccttc    1620
gccttcagca acgtgaactt ggacttcaat tgtcacagc ggtatcgtgc cagaatccgg    1680
tacgccagca ctacgaacct gcgaatctat gttactgtgg cgggcgagcg gatcttcgcc    1740
gggcaattcg acaagacgat ggacgcggga gcacctctga cattccagtc attctcttac    1800
gccacgatca acacggcatt cacgtttccg gagcgttcca gtagcctgac cgtgggcgct    1860
gataccttca gtagcgggaa cgaggtgtac gttgaccgtt tcgagctgat cccggtcacc    1920
gccaccaccg cgacgtttga agctgaatcc gacctcgagc gtgcgcgcaa ggcggtgaac    1980
gctctgttca cgagcaccaa ccctcgtggc ttgaagacgg atgtgacgga ctaccacatc    2040
gaccaagtct cgaacctcgt ggagtgcctg agcgacgagt tctgtcttga caagaagcgc    2100
gagctgctgg aggaggtgaa gtacgccaag cgcctctccg atgagcgcaa cctgctccaa    2160
gatcctacct tcacgtcgat ttccggccaa accgaccgtg gatggatcgg ctcgactggc    2220
atctccatcc agggcggcga cgacatcttc aaggagaact atgttcggct gccgggcacg    2280
gtggacgagt gttacccgac gtacctctac cagaagatag acgagagtca actcaagtcc    2340
tacacgcggt atcagttacg tggctacatt gaagactccc aggacttgga aatctatctc    2400
atacggtaca cgccaagca cgagacctta agcgtgccgg gaacggagtc gccctggcca    2460
agctctggcg tgtacccttc cggtaggtgc ggcgagccca accgctgtgc acctcgaatc    2520
gaatggaacc cggaccttga ctgctcttgc cggtacggcg agaagtgcgt ccatcattct    2580
caccacttca gcttggacat tgacgtcggc tgcaccgacc tcaatgaaga cctcggagtg    2640
tgggtcatct tcaagatcaa gacacaggac gggcacgcga aactaggaaa cctggagttc    2700
atcgaggaga agccactcct cggcaaggca ctttccaggg tcaagcgggc cgagaagaaa    2760
tggagggaca gtacgagaa actccagctc gaaacaaagc gggtgtacac ggaggcaaag    2820
gaatccgtgg acgccctgtt cgtggactct cagtacgaca agctccaggc gaacacaaac    2880
attggcatca tccacggtgc ggacaagcaa gtgcacagga tacgggagcc ttacctctcg    2940
gagctgccgt tgattccctc gatcaacgcg gcgatcttcg aggaactgga gggccacatc    3000
ttcaaggcgt attctctgta cgacgcgcgt aacgtcatca agaacggcga cttcaacaat    3060
gggctgtcct gctggaacgt taaaggccac gtcgatgtcc agcagaacca ccataggtca    3120
gtcctggtgc tgagcgagtg ggaggcggag gtgtcccaga aggtgcgcgt gtgcccggat    3180
cgcggctaca tcttgagggt gacagcctac aaggagggct acggcgaggg ctgtgtcacg    3240
atccatgagt tcgaggacaa cacgcgatgtc ctgaaattcc gtaacttcgt cgaggaggag    3300
gtctatccca acaacaccgt gacctgcaac gactacacga ccaatcagtc ggctgagggc    3360
```

-continued

```
agtaccgatg cctgcaacag ctacaaccgt ggttacgaag atggatacga gaaccgctac    3420
gagcccaatc cttcggctcc cgtgaattac actcccacgt acgaggaggg catgtacact    3480
gacactcagg gctacaacca ttgcgtcagc gaccgtggct accgcaacca cacgccgctc    3540
ccagcgggct acgtgacgct ggagctggaa tactttcccg agacagaaca agtgtggata    3600
gagatcggcg agaccgaggg cacattcatc gtgggctctg tggaattgct cctcatggag    3660
gagtaa                                                               3666
```

<210> SEQ ID NO 23
<211> LENGTH: 1221
<212> TYPE: PRT
<213> ORGANISM: Artificial
<220> FEATURE:
<223> OTHER INFORMATION: Amino acid sequence of the chimeric protein variant TIC867_24.

<400> SEQUENCE: 23

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300
```

-continued

```
Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
                355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
                435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
                500                 505                 510

Thr Leu Gln Ser Gly Thr Thr Val Val Lys Gly Pro Gly Phe Thr Gly
                515                 520                 525

Gly Asp Ile Leu Arg Arg Thr Ser Gly Gly Pro Phe Ala Phe Ser Asn
530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
                580                 585                 590

Leu Thr Phe Gln Ser Phe Ser Tyr Ala Thr Ile Asn Thr Ala Phe Thr
                595                 600                 605

Phe Pro Glu Arg Ser Ser Leu Thr Val Gly Ala Asp Thr Phe Ser
                610                 615                 620

Ser Gly Asn Glu Val Tyr Val Asp Arg Phe Glu Leu Ile Pro Val Thr
625                 630                 635                 640

Ala Thr Thr Ala Thr Phe Glu Ala Glu Ser Asp Leu Glu Arg Ala Arg
                645                 650                 655

Lys Ala Val Asn Ala Leu Phe Thr Ser Thr Asn Pro Arg Gly Leu Lys
                660                 665                 670

Thr Asp Val Thr Asp Tyr His Ile Asp Gln Val Ser Asn Leu Val Glu
                675                 680                 685

Cys Leu Ser Asp Glu Phe Cys Leu Asp Lys Lys Arg Glu Leu Leu Glu
                690                 695                 700

Glu Val Lys Tyr Ala Lys Arg Leu Ser Asp Glu Arg Asn Leu Leu Gln
705                 710                 715                 720
```

-continued

Asp Pro Thr Phe Thr Ser Ile Ser Gly Gln Thr Asp Arg Gly Trp Ile
                725                     730                     735

Gly Ser Thr Gly Ile Ser Ile Gln Gly Gly Asp Asp Ile Phe Lys Glu
            740                     745                 750

Asn Tyr Val Arg Leu Pro Gly Thr Val Asp Glu Cys Tyr Pro Thr Tyr
        755                     760                 765

Leu Tyr Gln Lys Ile Asp Glu Ser Gln Leu Lys Ser Tyr Thr Arg Tyr
    770                     775                 780

Gln Leu Arg Gly Tyr Ile Glu Asp Ser Gln Leu Glu Ile Tyr Leu
785                 790                 795                 800

Ile Arg Tyr Asn Ala Lys His Glu Thr Leu Ser Val Pro Gly Thr Glu
                805                     810                 815

Ser Pro Trp Pro Ser Ser Gly Val Tyr Pro Ser Gly Arg Cys Gly Glu
            820                     825                 830

Pro Asn Arg Cys Ala Pro Arg Ile Glu Trp Asn Pro Asp Leu Asp Cys
        835                     840                 845

Ser Cys Arg Tyr Gly Glu Lys Cys Val His Ser His His Phe Ser
    850                     855                 860

Leu Asp Ile Asp Val Gly Cys Thr Asp Leu Asn Glu Asp Leu Gly Val
865                 870                     875                 880

Trp Val Ile Phe Lys Ile Lys Thr Gln Asp Gly His Ala Lys Leu Gly
                885                     890                 895

Asn Leu Glu Phe Ile Glu Glu Lys Pro Leu Leu Gly Lys Ala Leu Ser
            900                     905                 910

Arg Val Lys Arg Ala Glu Lys Lys Trp Arg Asp Lys Tyr Glu Lys Leu
        915                     920                 925

Gln Leu Glu Thr Lys Arg Val Tyr Thr Glu Ala Lys Glu Ser Val Asp
    930                     935                 940

Ala Leu Phe Val Asp Ser Gln Tyr Asp Lys Leu Gln Ala Asn Thr Asn
945                 950                     955                 960

Ile Gly Ile Ile His Gly Ala Asp Lys Gln Val His Arg Ile Arg Glu
                965                     970                 975

Pro Tyr Leu Ser Glu Leu Pro Val Ile Pro Ser Ile Asn Ala Ala Ile
            980                     985                 990

Phe Glu Glu Leu Glu Gly His Ile Phe Lys Ala Tyr Ser Leu Tyr Asp
        995                     1000                1005

Ala Arg Asn Val Ile Lys Asn Gly Asp Phe Asn Asn Gly Leu Ser
        1010                1015                1020

Cys Trp Asn Val Lys Gly His Val Asp Val Gln Gln Asn His His
    1025                1030                1035

Arg Ser Val Leu Val Leu Ser Glu Trp Glu Ala Glu Val Ser Gln
    1040                1045                1050

Lys Val Arg Val Cys Pro Asp Arg Gly Tyr Ile Leu Arg Val Thr
    1055                1060                1065

Ala Tyr Lys Glu Gly Tyr Gly Glu Gly Cys Val Thr Ile His Glu
    1070                1075                1080

Phe Glu Asp Asn Thr Asp Val Leu Lys Phe Arg Asn Phe Val Glu
    1085                1090                1095

Glu Glu Val Tyr Pro Asn Asn Thr Val Thr Cys Asn Asp Tyr Thr
    1100                1105                1110

Thr Asn Gln Ser Ala Glu Gly Ser Thr Asp Ala Cys Asn Ser Tyr
    1115                1120                1125

Asn Arg Gly Tyr Glu Asp Gly Tyr Glu Asn Arg Tyr Glu Pro Asn

|      | 1130 |      |      | 1135 |      |      |      | 1140 |      |
|------|------|------|------|------|------|------|------|------|------|

Pro Ser Ala Pro Val Asn Tyr Thr Pro Thr Tyr Glu Glu Gly Met
    1145            1150                1155

Tyr Thr Asp Thr Gln Gly Tyr Asn His Cys Val Ser Asp Arg Gly
    1160            1165                1170

Tyr Arg Asn His Thr Pro Leu Pro Ala Gly Tyr Val Thr Leu Glu
    1175            1180                1185

Leu Glu Tyr Phe Pro Glu Thr Glu Gln Val Trp Ile Glu Ile Gly
    1190            1195                1200

Glu Thr Glu Gly Thr Phe Ile Val Gly Ser Val Glu Leu Leu Leu
    1205            1210                1215

Met Glu Glu
    1220

```
<210> SEQ ID NO 24
<211> LENGTH: 3651
<212> TYPE: DNA
<213> ORGANISM: Artificial
<220> FEATURE:
<223> OTHER INFORMATION: Synthetic nucleotide sequence designed for
      expression in a plant cell encoding TIC867_25.

<400> SEQUENCE: 24
atgaccagca accgaaagaa cgagaacgag atcatcaacg ccctgtccat accggccgtg      60
tcaaaccact ccgcccagat gaacctctcc accgacgcga ggatcgagga ctccctctgc    120
atcgccgagg caacaacat cgacccgttc gtgtctgcaa gcacggtcca gaccggcatc     180
aacatcgcgg ccgcatcct gggcgtgctc ggcgtgccct cgcgggtca atcgcctct      240 ttctactcat tcctcgtggg cgagctgtgg ccgcgcggac gtgacccgtg gaaatcttc    300 ctggagcacg ttgagcagct catccggcag caagtgaccg agaacaccag ggacaccgca    360
ctggcacggc tccagggcct ggcaacagc ttccgcgcct accagcagtc gctggaggac    420
tggctggaga accgagacga cgccagaacc cgctcagttc tgtacacaca gtacatcgcc    480
ctagagctgg acttcctcaa cgctatgccg ctcttcgcca tccgtaacca ggaagtaccg    540
cttctgatgg tgtacgcaca agcagcgaac ctccatctgc cctgctgcg agacgcatct    600 ctgttcggca gtgagttcgg gctgacgagc aggagatcc agcgctacta cgagcgccaa    660
gtggagaaga ctcgtgagta cagcgactac tgcgcgcgct ggtacaacac gggcttgaac    720
aaccttcgcg ggacaaacgc cgaatcctgg cttcgctaca accagttccg ccgcgaccctc   780 acgctgggtg tgctggacct ggtcgcgctc ttcccgtcct acgacacacg ggtgtaccca    840
atgaacacga gcgcacagct cacccgtgag atctacacag atcccatcgg ccgcaccaac    900
gctcccagtg cttcgcaag cacgaattgg ttcaacaata cgctccttc tttctctgcc      960 atcgaggccg ctgtcatcag accgccgcac ttactcgatt tcccggagca gctcactatc   1020
ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctagggacg tttacaggac agagtcgttc   1200
gctggcatta acattctgtt gaccactccg gtgaacggcg tccttgggc ccgcttcaac    1260 tggaggaatc ctctgaactc actgcgcggc agccttctct acactatcgg ctacaccggc   1320
gttgggacga actcttcgga ctcggagacc gagctgccgc ccgagaccac cgagcggcct   1380
aactacgaga gttattcaca caggctctcc aacatccgct tgatttctgg gaacaccttg   1440
```

```
cgggctccgg tgtactcctg gacgcaccgc agcgccgaca gaactaatac catcagctcc    1500
gactcgatca cccagatccc gctggtgaag gctcacacgc ttcagtcggg caccacagtc    1560
gtcaagggcc ctggcttcac cggcggcgac atcctgcgtc gcacatctgg cggacccttc    1620
gccttcagca acgtgaactt ggacttcaat ttgtcacagc ggtatcgtgc cagaatccgg    1680
tacgccagca ctacgaacct gcgaatctat gttactgtgg cgggcgagcg gatcttcgcc    1740
gggcaattcg acaagacgat ggacgcggga gcacctctga cattccagtc attctcttac    1800
gccacgatca acacggcatt cacgtttccg gagcgttcca gtagcctgac cgtgggcgct    1860
gataccttca gtagcgggaa cgaggtgtac gttgaccgtt tcgagctgat cccggtcacc    1920
gccaccgatg ctacctttga agcagagtcc gacttggaac gtgcacagaa ggcagtgaac    1980
gcactcttca cctcaagcaa ccagatcgga ttgaagacag atgtgacaga ttaccacatc    2040
gaccaagtga gcaacttggt ggattgcttg tcagatgagt tctgcttgga tgagaagcgt    2100
gaactctccg agaaggtgaa gcacgcaaag cgtctctcag atgaacgtaa tctccttcaa    2160
gaccctaact ttcgtggtat caatcgtcag ccagatcgtg gatggcgtgg atcaacagac    2220
atcaccatcc agggaggcga tgatgtgttc aaggagaact acgtgaccct cccaggaacc    2280
gtggatgaat gctacccaac ctacctctac agaagatcg acgagtcaaa gctcaaggct    2340
tacacccgtt atgaactccg tggctacatc gaagatagcc aggatctcga aatctatctc    2400
atccgttaca atgctaagca cgaaatcgtg aatgtgccag gaaccggctc actctggcca    2460
ctctcagcac agtcaccaat cggcaagtgc ggcgaaccca atcgctgcgc tcctcatctc    2520
gaatggaatc ccgatctcga ctgctcctgc cgagacggcg agaagtgtgc acatcactca    2580
caccacttca ccctcgacat cgacgtgggc tgcaccgacc tcaatgaaga cctgggcgtg    2640
tgggtgatct tcaagatcaa gacccaggac ggccacgcac gactgggcaa tctggagttt    2700
ctggaggaga agccactgct tggcgaggca ctggcacgag tgaaacgagc cgagaagaaa    2760
tggcgagaca aacgtgagaa gctgcaactg gagaccaaca tcgtgtacaa agaggccaaa    2820
gagtcagttg acgccctgtt tgtcaatagc cagtatgacc gactgcaagt tgacaccaac    2880
atcgccatga tccacgctgc ggacaagcgc gtccaccgca tccgcgaggc ttatctgccc    2940
gagctgagcg tcattcccgg cgtcaatgcc gcgatcttcg aggagttaga gggccgcatc    3000
ttcaccgcct acagcctcta tgacgcccgc aatgtcatta agaatggcga cttcaacaat    3060
ggcttactat gctggaatgt caaagggcac gttgacgtcg aggagcagaa caatcaccgc    3120
agcgtcttag tcatacccga gtgggaggcc gaagtcagcc aggaagtccg cgtctgtcca    3180
gggcgcgggt acatcctgcg ggtcaccgcc tacaaagagg gatacggcga gggttgtgtc    3240
accatacacg agatagagga caataccgac gaactcaagt tcagcaattg tgtcgaggag    3300
gaagtctatc ccaacaatac cgtaacctgc aacaactaca ccggaaccca ggaggagtat    3360
gaagggacgt acacctcgcg gaaccagggc tatgacgaag cctatgggaa caacccgtcg    3420
gtgcctgctg actatgcgtc ggtctatgag gagaaatcgt acacggacgg gcggcgggag    3480
aatccgtgtg agtcgaatcg cgggtatggt gactacacgc cgctaccggc gggctatgta    3540
acgaaagacc tggaatactt cccggagacg gacaaagtat ggatagagat aggcgagacg    3600
gagggaacgt tcatcgtgga ctcggtagag ctgctgctca tggaggagtg a    3651
```

<210> SEQ ID NO 25
<211> LENGTH: 1216
<212> TYPE: PRT
<213> ORGANISM: Artificial
<220> FEATURE:
<223> OTHER INFORMATION: Amino acid sequence of the chimeric protein variant TIC867_25.

<400> SEQUENCE: 25

| Met | Thr | Ser | Asn | Arg | Lys | Asn | Glu | Asn | Glu | Ile | Ile | Asn | Ala | Leu | Ser |
|---|---|---|---|---|---|---|---|---|---|---|---|---|---|---|---|
| 1 | | | | 5 | | | | | 10 | | | | | 15 | |

| Ile | Pro | Ala | Val | Ser | Asn | His | Ser | Ala | Gln | Met | Asn | Leu | Ser | Thr | Asp |
| | | | 20 | | | | | 25 | | | | | 30 | | |

| Ala | Arg | Ile | Glu | Asp | Ser | Leu | Cys | Ile | Ala | Glu | Gly | Asn | Asn | Ile | Asp |
| | | 35 | | | | | 40 | | | | | 45 | | | |

| Pro | Phe | Val | Ser | Ala | Ser | Thr | Val | Gln | Thr | Gly | Ile | Asn | Ile | Ala | Gly |
| | 50 | | | | | 55 | | | | | 60 | | | | |

| Arg | Ile | Leu | Gly | Val | Leu | Gly | Val | Pro | Phe | Ala | Gly | Gln | Ile | Ala | Ser |
| 65 | | | | | 70 | | | | | 75 | | | | | 80 |

| Phe | Tyr | Ser | Phe | Leu | Val | Gly | Glu | Leu | Trp | Pro | Arg | Gly | Arg | Asp | Pro |
| | | | | 85 | | | | | 90 | | | | | 95 | |

| Trp | Glu | Ile | Phe | Leu | Glu | His | Val | Glu | Gln | Leu | Ile | Arg | Gln | Gln | Val |
| | | | | 100 | | | | | 105 | | | | | 110 | |

| Thr | Glu | Asn | Thr | Arg | Asp | Thr | Ala | Leu | Ala | Arg | Leu | Gln | Gly | Leu | Gly |
| | | | 115 | | | | | 120 | | | | | 125 | | |

| Asn | Ser | Phe | Arg | Ala | Tyr | Gln | Gln | Ser | Leu | Glu | Asp | Trp | Leu | Glu | Asn |
| | 130 | | | | | 135 | | | | | 140 | | | | |

| Arg | Asp | Asp | Ala | Arg | Thr | Arg | Ser | Val | Leu | Tyr | Thr | Gln | Tyr | Ile | Ala |
| 145 | | | | | 150 | | | | | 155 | | | | | 160 |

| Leu | Glu | Leu | Asp | Phe | Leu | Asn | Ala | Met | Pro | Leu | Phe | Ala | Ile | Arg | Asn |
| | | | | 165 | | | | | 170 | | | | | 175 | |

| Gln | Glu | Val | Pro | Leu | Leu | Met | Val | Tyr | Ala | Gln | Ala | Ala | Asn | Leu | His |
| | | | 180 | | | | | 185 | | | | | 190 | | |

| Leu | Leu | Leu | Leu | Arg | Asp | Ala | Ser | Leu | Phe | Gly | Ser | Glu | Phe | Gly | Leu |
| | | | 195 | | | | | 200 | | | | | 205 | | |

| Thr | Ser | Gln | Glu | Ile | Gln | Arg | Tyr | Tyr | Glu | Arg | Gln | Val | Glu | Lys | Thr |
| | 210 | | | | | 215 | | | | | 220 | | | | |

| Arg | Glu | Tyr | Ser | Asp | Tyr | Cys | Ala | Arg | Trp | Tyr | Asn | Thr | Gly | Leu | Asn |
| 225 | | | | | 230 | | | | | 235 | | | | | 240 |

| Asn | Leu | Arg | Gly | Thr | Asn | Ala | Glu | Ser | Trp | Leu | Arg | Tyr | Asn | Gln | Phe |
| | | | | 245 | | | | | 250 | | | | | 255 | |

| Arg | Arg | Asp | Leu | Thr | Leu | Gly | Val | Leu | Asp | Leu | Val | Ala | Leu | Phe | Pro |
| | | | 260 | | | | | 265 | | | | | 270 | | |

| Ser | Tyr | Asp | Thr | Arg | Val | Tyr | Pro | Met | Asn | Thr | Ser | Ala | Gln | Leu | Thr |
| | 275 | | | | | 280 | | | | | 285 | | | | |

| Arg | Glu | Ile | Tyr | Thr | Asp | Pro | Ile | Gly | Arg | Thr | Asn | Ala | Pro | Ser | Gly |
| 290 | | | | | 295 | | | | | 300 | | | | | |

| Phe | Ala | Ser | Thr | Asn | Trp | Phe | Asn | Asn | Asn | Ala | Pro | Ser | Phe | Ser | Ala |
| 305 | | | | | 310 | | | | | 315 | | | | | 320 |

| Ile | Glu | Ala | Ala | Val | Ile | Arg | Pro | Pro | His | Leu | Leu | Asp | Phe | Pro | Glu |
| | | | | 325 | | | | | 330 | | | | | 335 | |

| Gln | Leu | Thr | Ile | Phe | Ser | Val | Leu | Ser | Arg | Trp | Ser | Asn | Thr | Gln | Tyr |
| | | | 340 | | | | | 345 | | | | | 350 | | |

| Met | Asn | Tyr | Trp | Val | Gly | His | Arg | Leu | Glu | Ser | Arg | Thr | Ile | Arg | Gly |
| | | 355 | | | | | 360 | | | | | 365 | | | |

| Ser | Leu | Ser | Thr | Ser | Thr | His | Gly | Asn | Thr | Asn | Thr | Ser | Ile | Asn | Pro |
| | 370 | | | | | 375 | | | | | 380 | | | | |

| Val | Thr | Leu | Gln | Phe | Thr | Ser | Arg | Asp | Val | Tyr | Arg | Thr | Glu | Ser | Phe |

-continued

```
                385                 390                 395                 400
Ala Gly Ile Asn Ile Leu Leu Thr Thr Pro Val Asn Gly Val Pro Trp
                    405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
        450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
                    500                 505                 510

Thr Leu Gln Ser Gly Thr Thr Val Val Lys Gly Pro Gly Phe Thr Gly
            515                 520                 525

Gly Asp Ile Leu Arg Arg Thr Ser Gly Gly Pro Phe Ala Phe Ser Asn
        530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
                    580                 585                 590

Leu Thr Phe Gln Ser Phe Ser Tyr Ala Thr Ile Asn Thr Ala Phe Thr
            595                 600                 605

Phe Pro Glu Arg Ser Ser Leu Thr Val Gly Ala Asp Thr Phe Ser
        610                 615                 620

Ser Gly Asn Glu Val Tyr Val Asp Arg Phe Glu Leu Ile Pro Val Thr
625                 630                 635                 640

Ala Thr Asp Ala Thr Phe Glu Ala Glu Ser Asp Leu Glu Arg Ala Gln
                645                 650                 655

Lys Ala Val Asn Ala Leu Phe Thr Ser Ser Asn Gln Ile Gly Leu Lys
                    660                 665                 670

Thr Asp Val Thr Asp Tyr His Ile Asp Gln Val Ser Asn Leu Val Asp
            675                 680                 685

Cys Leu Ser Asp Glu Phe Cys Leu Asp Glu Lys Arg Glu Leu Ser Glu
        690                 695                 700

Lys Val Lys His Ala Lys Arg Leu Ser Asp Glu Arg Asn Leu Leu Gln
705                 710                 715                 720

Asp Pro Asn Phe Arg Gly Ile Asn Arg Gln Pro Asp Arg Gly Trp Arg
                725                 730                 735

Gly Ser Thr Asp Ile Thr Ile Gln Gly Gly Asp Asp Val Phe Lys Glu
                    740                 745                 750

Asn Tyr Val Thr Leu Pro Gly Thr Val Asp Glu Cys Tyr Pro Thr Tyr
            755                 760                 765

Leu Tyr Gln Lys Ile Asp Glu Ser Lys Leu Lys Ala Tyr Thr Arg Tyr
        770                 775                 780

Glu Leu Arg Gly Tyr Ile Glu Asp Ser Gln Asp Leu Glu Ile Tyr Leu
785                 790                 795                 800

Ile Arg Tyr Asn Ala Lys His Glu Ile Val Asn Val Pro Gly Thr Gly
                805                 810                 815
```

```
Ser Leu Trp Pro Leu Ser Ala Gln Ser Pro Ile Gly Lys Cys Gly Glu
            820                 825                 830

Pro Asn Arg Cys Ala Pro His Leu Glu Trp Asn Pro Asp Leu Asp Cys
            835                 840                 845

Ser Cys Arg Asp Gly Glu Lys Cys Ala His His Ser His His Phe Thr
850                 855                 860

Leu Asp Ile Asp Val Gly Cys Thr Asp Leu Asn Glu Asp Leu Gly Val
865                 870                 875                 880

Trp Val Ile Phe Lys Ile Lys Thr Gln Asp Gly His Ala Arg Leu Gly
                885                 890                 895

Asn Leu Glu Phe Leu Glu Glu Lys Pro Leu Leu Gly Glu Ala Leu Ala
            900                 905                 910

Arg Val Lys Arg Ala Glu Lys Lys Trp Arg Asp Lys Arg Glu Lys Leu
            915                 920                 925

Gln Leu Glu Thr Asn Ile Val Tyr Lys Glu Ala Lys Glu Ser Val Asp
            930                 935                 940

Ala Leu Phe Val Asn Ser Gln Tyr Asp Arg Leu Gln Val Asp Thr Asn
945                 950                 955                 960

Ile Ala Met Ile His Ala Ala Asp Lys Arg Val His Arg Ile Arg Glu
            965                 970                 975

Ala Tyr Leu Pro Glu Leu Ser Val Ile Pro Gly Val Asn Ala Ala Ile
            980                 985                 990

Phe Glu Glu Leu Glu Gly Arg Ile Phe Thr Ala Tyr Ser Leu Tyr Asp
        995                 1000                1005

Ala Arg  Asn Val Ile Lys Asn  Gly Asp Phe Asn Asn  Gly Leu Leu
    1010                1015                1020

Cys Trp  Asn Val Lys Gly His  Val Asp Val Glu Glu  Gln Asn Asn
    1025                1030                1035

His Arg  Ser Val Leu Val Ile  Pro Glu Trp Glu Ala  Glu Val Ser
    1040                1045                1050

Gln Glu  Val Arg Val Cys Pro  Gly Arg Gly Tyr Ile  Leu Arg Val
    1055                1060                1065

Thr Ala  Tyr Lys Glu Gly Tyr  Gly Glu Gly Cys Val  Thr Ile His
    1070                1075                1080

Glu Ile  Glu Asp Asn Thr Asp  Glu Leu Lys Phe Ser  Asn Cys Val
    1085                1090                1095

Glu Glu  Glu Val Tyr Pro Asn  Asn Thr Val Thr Cys  Asn Asn Tyr
    1100                1105                1110

Thr Gly  Thr Gln Glu Glu Tyr  Glu Gly Thr Tyr Thr  Ser Arg Asn
    1115                1120                1125

Gln Gly  Tyr Asp Glu Ala Tyr  Gly Asn Asn Pro Ser  Val Pro Ala
    1130                1135                1140

Asp Tyr  Ala Ser Val Tyr Glu  Glu Lys Ser Tyr Thr  Asp Gly Arg
    1145                1150                1155

Arg Glu  Asn Pro Cys Glu Ser  Asn Arg Gly Tyr Gly  Asp Tyr Thr
    1160                1165                1170

Pro Leu  Pro Ala Gly Tyr Val  Thr Lys Asp Leu Glu  Tyr Phe Pro
    1175                1180                1185

Glu Thr  Asp Lys Val Trp Ile  Glu Ile Gly Glu Thr  Glu Gly Thr
    1190                1195                1200

Phe Ile  Val Asp Ser Val Glu  Leu Leu Leu Met Glu  Glu
    1205                1210                1215
```

<210> SEQ ID NO 26
<211> LENGTH: 3600
<212> TYPE: DNA
<213> ORGANISM: Artificial
<220> FEATURE:
<223> OTHER INFORMATION: Recombinant nucleotide sequence used
 for expression in a bacterial cell encoding TIC868.

<400> SEQUENCE: 26

| | |
|---|---|
| atgacttcaa ataggaaaaa tgagaatgaa attataaatg ctttatcgat tccagctgta | 60 |
| tcgaatcatt ccgcacaaat gaatctatca accgatgctc gtattgagga tagcttgtgt | 120 |
| atagccgagg ggaacaatat cgatccattt gttagcgcat caacagtcca aacgggtatt | 180 |
| aacatagctg gtagaatact aggtgtatta ggcgtaccgt tgctggaca aatagctagt | 240 |
| ttttatagtt ttcttgttgg tgaattatgg ccccgcggca gagatccttg ggaaattttc | 300 |
| ctagaacatg tcgaacaact tataagacaa caagtaacag aaaatactag ggatacggct | 360 |
| cttgctcgat tacaaggttt aggaaaattcc tttagagcct atcaacagtc acttgaagat | 420 |
| tggctagaaa accgtgatga tgcaagaacg agaagtgttc tttataccca atatatagcc | 480 |
| ttagaacttg attttcttaa tgcgatgccg ctttttcgcaa ttagaaacca agaagttcca | 540 |
| ttattaatgg tatatgctca agctgcaaat ttacacctat tattattgag agatgcctct | 600 |
| cttttttggta gtgaatttgg gcttacatcc caagaaattc aacgttatta tgagcgccaa | 660 |
| gtggaaaaaa cgagagaata ttctgattat tgcgcaagat ggtataatac gggttaaat | 720 |
| aatttgagag ggacaaatgc tgaaagttgg ttgcgatata atcaattccg tagagactta | 780 |
| acgctaggag tattagatct agtggcacta ttcccaagct atgacacgcg tgtttatcca | 840 |
| atgaatacca gtgctcaatt aacaagagaa atttatacag atccaattgg gagaacaaat | 900 |
| gcaccttcag gatttgcaag tacgaattgg tttaataata tgcaccatc gttttctgcc | 960 |
| atagaggctg ccgttattag gcctccgcat ctacttgatt ttccagaaca gcttacaatt | 1020 |
| ttcagcgtat taagtcgatg gagtaatact caatatatga attactgggt gggacataga | 1080 |
| cttgaatcgc gaacaataag ggggtcatta agtacctcga cacacggaaa taccaatact | 1140 |
| tctattaatc ctgtaacatt acagttcaca tctcgagacg tttatagaac agaatcattt | 1200 |
| gcagggataa atatacttct aactactcct gtgaatggag taccttgggc tagatttaat | 1260 |
| tggagaaatc ccctgaattc tcttagaggt agccttctct atactatagg gtatactgga | 1320 |
| gtggggacac aactatttga ttcagaaact gaattaccac cagaaacaac agaacgacca | 1380 |
| aattatgaat cttacagtca tagattatct aatataagac taatatcagg aaacactttg | 1440 |
| agagcaccag tatattcttg gacgcaccgt agtgcagatc gtacaaatac cattagttca | 1500 |
| gatagcatta tcaaatacc tttagtgaaa ggatttagag tttggggggg cacctctgtc | 1560 |
| attacaggac caggatttac aggaggggat atccttcgaa gaaataccctt tggtgatttt | 1620 |
| gtatctctac aagtcaatat taattccacca attcccaaaa gataccgttt aagatttcgt | 1680 |
| tacgcttcca gtagggatgc acgagttata gtattaacag gagcggcatc cacaggagtg | 1740 |
| ggaggccaag ttagtgtaaa tatgcctctt cagaaaacta tggaaatagg ggagaactta | 1800 |
| acatctagaa catttagata taccgatttt agtaatcctt tttcatttag agctaatcca | 1860 |
| gatataattg ggataagtga acaacctcta tttggtgcag gttctattag tagcggtgaa | 1920 |
| ctttatatag ataaaattga aattattcta gcagatgcaa catttgaagc agaatctgat | 1980 |
| ttagaaagag cacaaaaggc ggtgaatgag ctgtttactt cttccaatca aatcgggtta | 2040 |

```
aaaacagatg tgacggatta tcatattgat caagtatcca atttagttga gtgtttatct    2100
gatgaatttt gtctggatga aaaaaaagaa ttgtccgaga agtcaaaca tgcgaagcga     2160 cttagtgatg agcggaattt acttcaagat ccaaacttta gagggatcaa tagacaacta   2220
gaccgtggct ggagaggaag tacggatatt accatccaag gaggcgatga cgtattcaaa   2280
gagaattacg ttacgctatt gggtaccttt gatgagtgct atccaacgta tttatatcaa   2340
aaaatagatg agtcgaaatt aaaagcctat acccgttacc aattaagagg gtatatcgaa   2400
gatagtcaag acttagaaat ctatttaatt cgctacaatg ccaaacacga aacagtaaat   2460
gtgccaggta cgggttcctt atggccgctt tcagccccaa gtccaatcgg aaaatgtgcc   2520
catcattccc atcatttctc cttggacatt gatgttggat gtacagactt aaatgaggac   2580
ttaggtgtat gggtgatatt caagattaag acgcaagatg ccatgcaag actaggaaat    2640 ctagaatttc tcgaagagaa accattagta ggagaagcac tagctcgtgt gaaaagagcg   2700
gagaaaaaat ggagagacaa acgtgaaaaa ttggaatggg aaacaaatat tgtttataaa   2760
gaggcaaaag aatctgtaga tgctttattt gtaaactctc aatatgatag attacaagcg   2820
gataccaaca tcgcgatgat tcatgcggca gataaacgcg ttcatagcat tcgagaagct   2880
tatctgcctg agctgtctgt gattccgggt gtcaatgcgg ctattttga agaattagaa    2940 gggcgtattt tcactgcatt ctccctatat gatgcgagaa atgtcattaa aaatggtgat   3000
tttaataatg gcttatcctg ctggaacgtg aaagggcatg tagatgtaga agaacaaaac   3060
aaccaccgtt cggtccttgt tgttccggaa tgggaagcag aagtgtcaca gaagttcgt    3120 gtctgtccgg gtcgtggcta tatccttcgt gtcacagcgt acaaggaggg atatggaaga   3180
ggttgcgtaa ccattcatga gatcgagaac aatacagacg aactgaagtt tagcaactgt   3240
gtagaagagg aagtatatcc aaacaacacg gtaacgtgta atgattatac tgcgactcaa   3300
gaagaatatg agggtacgta cacttctcgt aatcgaggat atgacggagc ctatgaaagc   3360
aattcttctg taccagctga ttatgcatca gcctatgaag aaaaagcata tacagatgga   3420
cgaagagaca atccttgtga atctaacaga ggatatgggg attacacacc actaccagct   3480
ggctatgtga caaaagaatt agagtacttc ccagaaaccg ataaggtatg gattgagatc   3540
ggagaaacgg aaggaacatt catcgtggac agcgtggaat tacttcttat ggaggaatag   3600
```

<210> SEQ ID NO 27
<211> LENGTH: 3600
<212> TYPE: DNA
<213> ORGANISM: Artificial
<220> FEATURE:
<223> OTHER INFORMATION: Synthetic nucleotide sequence designed for
      expression in a plant cell encoding TIC868.

<400> SEQUENCE: 27

```
atgacgagca accggaagaa cgagaacgag atcatcaacg ccctctcgat ccctgctgtt     60
tcaaaccact ccgcgcagat gaacctgtcc accgacgcgc gcatcgagga ctccctctgc    120
atagccgagg gcaacaacat cgacccattc gtgtcggcca gcacggttca gaccggcatc    180
aacatcgcgg gccgtatcct cggcgtcctc ggtgtcccat cgccggtca gatcgcgtcc     240 ttctactcgt tccttgtggg cgagctgtgg cctcgcggtc gtgacccgtg ggagatcttc    300
ctggagcatg tggagcagtt gatccggcag caagtcacgg agaacacccg cgatactgct    360
ctggccaggc tacagggcct gggaaactcc tttcgggcat accagcagtc actggaggac   420
tggttggaga acagggatga cgcgcgaaca cgctcggtac tctacaccca gtacatcgct    480
```

```
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag acccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc    1020
ttctccgtgc tctcacgctg gtccaacaca cagtacatga actactgggt cgggcaccga    1080
ttggagagta ggacgatccg tggcagcttg agcaccagta cccacggcaa caccaacacc    1140
tccatcaacc cagttacgct acagttcacg agccgcgacg tttaccggac tgagtcgttc    1200
gcgggcatta acatccttct gacaacgccc gtcaacggcg tcccgtgggc ccggttcaac    1260
tggcgtaacc cgttgaactc cctgcgcggg tcattgctct acaccatcgg gtacacgggc    1320
gtcggcaccc agctcttcga cagtgaaact gagctgccgc ccgagaccac ggaacgcccg    1380
aactacgagt cctacagcca ccgcctgtcc aacatccggc tcatctctgg caacacgctg    1440
cgtgcgccgg tgtactcctg gacacaccgc agcgccgacc ggaccaacac gatctcttcc    1500
gactccatta accagatccc gctcgtgaag ggcttccgtg tgtggggtgg cacgagcgtc    1560
atcaccggtc cgggcttcac cggtggagac atactgcggc gcaacacttt cggcgacttc    1620
gtttcgttgc aagtgaacat caactcgccg atcacccagc gttaccgtct gaggttccgc    1680
tacgcttcaa gccgcgacgc gagggtcatt gtcctgaccg gagccgcgtc cacaggcgtg    1740
ggaggccaag tctcagtcaa catgcctctc cagaagacga tggagatagg cgagaacttg    1800
actagccgaa cctccggta cactgatttc tcgaacccct tctcattcag agcgaaccct     1860
gacatcattg ggatctccga gcaaccgctg ttcggtgctg gctccatcag ctctggcgaa    1920
ctgtacatcg acaagattga gatcatcctg gcggatgcga cgttcgaggc cgagtctgac    1980
ctggagcggg ctcagaaggc tgtcaacgaa ctgttcacca gcagcaacca gattgggctc    2040
aagaccgacg tcacggacta tcacattgac caagtgtcca accttgtgga gtgcctgtcc    2100
gacgagttct gcctcgacga gaagaaggag ctgtccgaga aggtcaaaca cgcgaagcgt    2160
ctgagtgacg agcggaattt gctccaggac ccgaacttcc gtggcatcaa ccgccagctc    2220
gaccgtggtt ggcgcgggag tacagacatc accatccagg gaggcgacga tgtgttcaag    2280
gagaactatg tgacgctgct cgggactttc gacgaatgct acccgacgta tctctaccag    2340
aagatagacg agagtaaatt gaaggcgtac acccgctacc agcttcgcgg gtacatcgag    2400
gatagtcagg acctggaaat ctacctgatc cgatacaacg ccaagcacga gacagtgaac    2460
gtgccaggca cgggctcact ttggccattg agcgctccct ctccaatcgg aaagtgcgct    2520
caccactcgc accacttctc tctggacatc gacgtgggct gcaccgacct caacgaggac    2580
ctgggtgtct gggttatctt caagattaag acccaggacg gacatgcccg cctcggcaac    2640
ctggagttcc ttgaggagaa gcctctcgtg ggcgaggccc tcgctcgtgt gaagcgcgcc    2700
gagaagaaat ggcgagacaa gcgggagaag ctggagtggg agaccaacat cgtgtacaag    2760
gaggccaagg agtcagtgga cgcactcttc gtcaacagcc agtacgaccg cctccaggct    2820
gacaccaaca tcgccatgat ccacgcggct gacaagcggg tccacagcat ccgtgaggcg    2880
```

```
tacctgcccg agctgtcagt gatccctggt gtgaacgcgg cgatcttcga ggaactggag    2940
ggccgcatct tcacagcatt cagcctgtac gatgccagga atgttattaa gaacggtgac    3000
ttcaacaacg ggctgagttg ctggaacgtc aagggccatg tggacgtcga ggagcagaac    3060
aaccaccggt ccgtgctggt cgtgccggag tgggaggcag aggtgagcca ggaggtccgc    3120
gtctgccctg gtcgcggcta catcctccgt gtgactgcgt acaaggaagg ctacggtgaa    3180
ggctgcgtga ctatccacga gatcgagaac aacaccgacg agctcaagtt ctcgaactgt    3240
gtggaggagg aggtgtaccc gaacaacacc gttacttgca acgactacac tgccacgcaa    3300
gaggagtacg agggcactta cacttcccgg aatcgcggct atgatggcgc gtacgagtcc    3360
aacagcagcg tgcctgcgga ttatgcgtcc gcttacgagg agaaggcgta caccgacgga    3420
cggagggaca accttgcga gtccaaccgt ggctacggtg actacactcc gctgcccgcc    3480
gggtacgtca ccaaggagct ggagtacttc ccggagaccg acaaagtctg gatcgagatc    3540
ggcgagacgg agggcacttt catcgtggac tcggtcgagc tgctactgat ggaggagtga    3600
```

<210> SEQ ID NO 28
<211> LENGTH: 1199
<212> TYPE: PRT
<213> ORGANISM: Artificial
<220> FEATURE:
<223> OTHER INFORMATION: Amino acid sequence of the chimeric protein
      TIC868.

<400> SEQUENCE: 28

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn

```
            225                 230                 235                 240
Asn Leu Arg Gly Thr Asn Ala Glu Ser Trp Leu Arg Tyr Asn Gln Phe
                245                 250                 255
Arg Arg Asp Leu Thr Leu Gly Val Leu Asp Leu Val Ala Leu Phe Pro
                260                 265                 270
Ser Tyr Asp Thr Arg Val Tyr Pro Met Asn Thr Ser Ala Gln Leu Thr
                275                 280                 285
Arg Glu Ile Tyr Thr Asp Pro Ile Gly Arg Thr Asn Ala Pro Ser Gly
                290                 295                 300
Phe Ala Ser Thr Asn Trp Phe Asn Asn Asn Ala Pro Ser Phe Ser Ala
305                 310                 315                 320
Ile Glu Ala Ala Val Ile Arg Pro Pro His Leu Leu Asp Phe Pro Glu
                325                 330                 335
Gln Leu Thr Ile Phe Ser Val Leu Ser Arg Trp Ser Asn Thr Gln Tyr
                340                 345                 350
Met Asn Tyr Trp Val Gly His Arg Leu Glu Ser Arg Thr Ile Arg Gly
                355                 360                 365
Ser Leu Ser Thr Ser Thr His Gly Asn Thr Asn Thr Ser Ile Asn Pro
                370                 375                 380
Val Thr Leu Gln Phe Thr Ser Arg Asp Val Tyr Arg Thr Glu Ser Phe
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
                420                 425                 430
Leu Tyr Thr Ile Gly Tyr Thr Gly Val Gly Thr Gln Leu Phe Asp Ser
                435                 440                 445
Glu Thr Glu Leu Pro Pro Glu Thr Thr Glu Arg Pro Asn Tyr Glu Ser
                450                 455                 460
Tyr Ser His Arg Leu Ser Asn Ile Arg Leu Ile Ser Gly Asn Thr Leu
465                 470                 475                 480
Arg Ala Pro Val Tyr Ser Trp Thr His Arg Ser Ala Asp Arg Thr Asn
                485                 490                 495
Thr Ile Ser Ser Asp Ser Ile Asn Gln Ile Pro Leu Val Lys Gly Phe
                500                 505                 510
Arg Val Trp Gly Gly Thr Ser Val Ile Thr Gly Pro Gly Phe Thr Gly
                515                 520                 525
Gly Asp Ile Leu Arg Arg Asn Thr Phe Gly Asp Phe Val Ser Leu Gln
530                 535                 540
Val Asn Ile Asn Ser Pro Ile Thr Gln Arg Tyr Arg Leu Arg Phe Arg
545                 550                 555                 560
Tyr Ala Ser Ser Arg Asp Ala Arg Val Ile Val Leu Thr Gly Ala Ala
                565                 570                 575
Ser Thr Gly Val Gly Gly Gln Val Ser Val Asn Met Pro Leu Gln Lys
                580                 585                 590
Thr Met Glu Ile Gly Glu Asn Leu Thr Ser Arg Thr Phe Arg Tyr Thr
                595                 600                 605
Asp Phe Ser Asn Pro Phe Ser Phe Arg Ala Asn Pro Asp Ile Ile Gly
                610                 615                 620
Ile Ser Glu Gln Pro Leu Phe Gly Ala Gly Ser Ile Ser Ser Gly Glu
625                 630                 635                 640
Leu Tyr Ile Asp Lys Ile Glu Ile Ile Leu Ala Asp Ala Thr Phe Glu
                645                 650                 655
```

-continued

Ala Glu Ser Asp Leu Glu Arg Ala Gln Lys Ala Val Asn Glu Leu Phe
         660                 665                 670

Thr Ser Ser Asn Gln Ile Gly Leu Lys Thr Asp Val Thr Asp Tyr His
         675                 680                 685

Ile Asp Gln Val Ser Asn Leu Val Glu Cys Leu Ser Asp Glu Phe Cys
690                 695                 700

Leu Asp Glu Lys Lys Glu Leu Ser Glu Lys Val Lys His Ala Lys Arg
705                 710                 715                 720

Leu Ser Asp Glu Arg Asn Leu Leu Gln Asp Pro Asn Phe Arg Gly Ile
             725                 730                 735

Asn Arg Gln Leu Asp Arg Gly Trp Arg Gly Ser Thr Asp Ile Thr Ile
             740                 745                 750

Gln Gly Gly Asp Asp Val Phe Lys Glu Asn Tyr Val Thr Leu Leu Gly
             755                 760                 765

Thr Phe Asp Glu Cys Tyr Pro Thr Tyr Leu Tyr Gln Lys Ile Asp Glu
         770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
             805                 810                 815

Glu Thr Val Asn Val Pro Gly Thr Gly Ser Leu Trp Pro Leu Ser Ala
         820                 825                 830

Pro Ser Pro Ile Gly Lys Cys Ala His His Ser His Phe Ser Leu
         835                 840                 845

Asp Ile Asp Val Gly Cys Thr Asp Leu Asn Glu Asp Leu Gly Val Trp
         850                 855                 860

Val Ile Phe Lys Ile Lys Thr Gln Asp Gly His Ala Arg Leu Gly Asn
865                 870                 875                 880

Leu Glu Phe Leu Glu Glu Lys Pro Leu Val Gly Glu Ala Leu Ala Arg
             885                 890                 895

Val Lys Arg Ala Glu Lys Lys Trp Arg Asp Lys Arg Glu Lys Leu Glu
             900                 905                 910

Trp Glu Thr Asn Ile Val Tyr Lys Glu Ala Lys Glu Ser Val Asp Ala
         915                 920                 925

Leu Phe Val Asn Ser Gln Tyr Asp Arg Leu Gln Ala Asp Thr Asn Ile
         930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
             965                 970                 975

Glu Glu Leu Glu Gly Arg Ile Phe Thr Ala Phe Ser Leu Tyr Asp Ala
             980                 985                 990

Arg Asn Val Ile Lys Asn Gly Asp Phe Asn Asn Gly Leu Ser Cys Trp
         995                 1000                1005

Asn Val Lys Gly His Val Asp Val Glu Glu Gln Asn Asn His Arg
    1010                1015                1020

Ser Val Leu Val Val Pro Glu Trp Glu Ala Glu Val Ser Gln Glu
    1025                1030                1035

Val Arg Val Cys Pro Gly Arg Gly Tyr Ile Leu Arg Val Thr Ala
    1040                1045                1050

Tyr Lys Glu Gly Tyr Gly Glu Gly Cys Val Thr Ile His Glu Ile
    1055                1060                1065

```
Glu Asn Asn Thr Asp Glu Leu Lys Phe Ser Asn Cys Val Glu Glu
    1070                1075                1080

Glu Val Tyr Pro Asn Asn Thr Val Thr Cys Asn Asp Tyr Thr Ala
    1085                1090                1095

Thr Gln Glu Glu Tyr Glu Gly Thr Tyr Thr Ser Arg Asn Arg Gly
    1100                1105                1110

Tyr Asp Gly Ala Tyr Glu Ser Asn Ser Ser Val Pro Ala Asp Tyr
    1115                1120                1125

Ala Ser Ala Tyr Glu Glu Lys Ala Tyr Thr Asp Gly Arg Arg Asp
    1130                1135                1140

Asn Pro Cys Glu Ser Asn Arg Gly Tyr Gly Asp Tyr Thr Pro Leu
    1145                1150                1155

Pro Ala Gly Tyr Val Thr Lys Glu Leu Glu Tyr Phe Pro Glu Thr
    1160                1165                1170

Asp Lys Val Trp Ile Glu Ile Gly Glu Thr Glu Gly Thr Phe Ile
    1175                1180                1185

Val Asp Ser Val Glu Leu Leu Leu Met Glu Glu
    1190                1195
```

<210> SEQ ID NO 29
<211> LENGTH: 3600
<212> TYPE: DNA
<213> ORGANISM: Artificial
<220> FEATURE:
<223> OTHER INFORMATION: Synthetic nucleotide sequence designed for
      expression in a plant cell encoding TIC868_9.

<400> SEQUENCE: 29

```
atgacgagca accggaagaa cgagaacgag atcatcaacg ccctctcgat ccctgctgtt      60
tcaaaccact ccgcgcagat gaacctgtcc accgacgcgc gcatcgagga ctccctctgc     120
atagccgagg caacaacat cgacccattc gtgtcggcca gcacggttca gaccggcatc      180
aacatcgcgg gccgtatcct cggcgtcctc ggtgtcccat cgccggtca gatcgcgtcc      240 ttctactcgt tccttgtggg cgagctgtgg cctcgcggtc gtgacccgtg ggagatcttc     300
ctggagcatg tggagcagtt gatccggcag caagtcacgg agaacacccg cgatactgct     360
ctggccaggc tacagggcct gggaaactcc tttcgggcat accagcagtc actggaggac     420
tggttggaga cagggatga cgcgcgaaca cgctcggtac tctacaccca gtacatcgct      480
ctcgaactcg acttcctgaa cgctatgccg ctgttcgcca tcaggaacca ggaagttcca     540
ctccttatgg tgtacgccca ggccgccaac ttacatctgc cctgctgcg ggacgccagc      600 ctgttcggct ccgagttcgg actcacatct caagaaatcc agcgttacta cgagcgccaa     660
gtggagaaga cccgtgagta cagtgactac tgcgctcgat ggtacaacac agggctcaac     720
agcctgcgcg gcaccaacgc tgagtcatgg ctccgttaca accagttccg ccgcgacttg     780
actttgggtg tcctagacct ggtggcgcta ttcccgtctt acgacacacg ggtgtaccca     840
atgaacacta gcgcgcaact cacgcgggag atctacacag acccaatcgg ccggacgaac     900
gcaccctccg gtttcgcatc cacgaattgg ttcaacaaca cgcaccctc cttctcggca     960 atcgaggccg ccgtcatccg ccctcctcac ctgctcgact ttcccgagca gctcacgatc    1020
ttctccgtgc tctcacgctg gtccaacaca cagtacatga actactgggt cgggcaccga   1080
ttggagagta ggacgatccg tggcagcttg agccacagta cccacggcaa caccaacacc   1140
tccatcaacc cagttacgct acagttcacg agccgcgacg tttaccggac tgagtcgcag   1200
gcgggcatta acatccttat gacaacgccc gtcaacggcg tcccgtgggc ccggttcaac    1260
```

```
tggcgtaacc cgaagaactc cctgcgcggg tcattgctct acaccatcgg gtacacgggc    1320
gtcggcaccc agctcttcga cagtgaaact gagctgccgc ccgagaccac ggaacgcccg    1380
aactacgagt cctacagcca ccgcctgtcc aacatccggc tcatctctgg caacacgctg    1440
cgtgcgccgg tgtactcctg gacacaccgc agcgccgacc ggaccaacac gatctcttcc    1500
gactccatta accagatccc gctcgtgaag ggcttccgtg tgtggggtgg cacgagcgtc    1560
atcaccggtc cgggcttcac cggtggagac atactgcggc gcaacacttt cggcgacttc    1620
gtttcgttgc aagtgaacat caactcgccg atcacccagc gttaccgtct gaggttccgc    1680
tacgcttcaa gccgcgacgc gagggtcatt gtcctgaccg gagccgcgtc cacaggcgtg    1740
ggaggccaag tctcagtcaa catgcctctc cagaagacga tggagatagg cgagaacttg    1800
actagccgaa ccttccggta cactgatttc tcgaacccct tctcattcag agcgaaccct    1860
gacatcattg ggatctccga gcaaccgctg ttcggtgctg gctccatcag ctctggcgaa    1920
ctgtacatcg acaagattga gatcatcctg gcggatgcga cgttcgaggc cgagtctgac    1980
ctggagcggg ctcagaaggc tgtcaacgaa ctgttcacca gcagcaacca gattgggctc    2040
aagaccgacg tcacggacta tcacattgac caagtgtcca accttgtgga gtgcctgtcc    2100
gacgagttct gcctcgacga aagaaggag ctgtccgaga aggtcaaaca cgcgaagcgt    2160
ctgagtgacg agcggaattt gctccaggac ccgaacttcc gtggcatcaa ccgccagctc    2220
gaccgtggtt ggcgcgggag tacagacatc accatccagg gaggcgacga tgtgttcaag    2280
gagaactatg tgacgctgct cgggactttc gacgaatgct acccgacgta tctctaccag    2340
aagatagacg agagtaaatt gaaggcgtac acccgctacc agcttcgcgg gtacatcgag    2400
gatagtcagg acctggaaat ctacctgatc cgatacaacg ccaagcacga gacagtgaac    2460
gtgccaggca cgggctcact ttggccattg agcgctccct ctccaatcgg aaagtgcgct    2520
caccactcgc accacttctc tctggacatc gacgtgggct gcaccgacct caacgaggac    2580
ctgggtgtct gggttatctt caagattaag acccaggacg gacatgcccg cctcggcaac    2640
ctggagttcc ttgaggagaa gcctctcgtg ggcgaggccc tcgctcgtgt gaagcgcgcc    2700
gagaagaaat ggcgagacaa gcgggagaag ctggagtggg agaccaacat cgtgtacaag    2760
gaggccaagg agtcagtgga cgcactcttc gtcaacagcc agtacgaccg cctccaggct    2820
gacaccaaca tcgccatgat ccacgcggct gacaagcggg tccacagcat ccgtgaggcg    2880
tacctgcccg agctgtcagt gatccctggt gtgaacgcgg cgatcttcga ggaactggag    2940
ggccgcatct tcacagcatt cagcctgtac gatgccagga atgttattaa gaacggtgac    3000
ttcaacaacg ggctgagttg ctggaacgtc aagggccatg tggacgtcga ggagcagaac    3060
aaccaccggt ccgtgctggt cgtgccgag tgggaggcag aggtgagcca ggaggtccgc    3120
gtctgccctg gtcgcggcta catcctccgt gtgactgcgt acaaggaagg ctacggtgaa    3180
ggctgcgtga ctatccacga gatcgagaac aacaccgacg agctcaagtt ctcgaactgt    3240
gtggaggagg aggtgtaccc gaacaacacc gttacttgca acgactacac tgccacgcaa    3300
gaggagtacg agggcactta cacttcccgg aatcgcggct atgatggcgc gtacgagtcc    3360
aacagcagcg tgcctgcgga ttatgcgtcc gcttacgagg agaaggcgta caccgacgga    3420
cggagggaca accttgcga gtccaaccgt ggctacggtg actacactcc gctgcccgcc    3480
gggtacgtca ccaaggagct ggagtacttc ccggagaccg acaaagtctg gatcgagatc    3540
ggcgagacgg agggcacttt catcgtggac tcggtcgagc tgctactgat ggaggagtga    3600
```

<210> SEQ ID NO 30
<211> LENGTH: 1199
<212> TYPE: PRT
<213> ORGANISM: Artificial
<220> FEATURE:
<223> OTHER INFORMATION: Amino acid sequence of the chimeric protein variant TIC868_9.

<400> SEQUENCE: 30

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Ser Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365
```

```
Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Gln
385                 390                 395                 400

Ala Gly Ile Asn Ile Leu Met Thr Thr Pro Val Asn Gly Val Pro Trp
                405                 410                 415

Ala Arg Phe Asn Trp Arg Asn Pro Lys Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Phe Glu
                645                 650                 655

Ala Glu Ser Asp Leu Glu Arg Ala Gln Lys Ala Val Asn Glu Leu Phe
            660                 665                 670

Thr Ser Ser Asn Gln Ile Gly Leu Lys Thr Asp Val Thr Asp Tyr His
        675                 680                 685

Ile Asp Gln Val Ser Asn Leu Val Glu Cys Leu Ser Asp Glu Phe Cys
    690                 695                 700

Leu Asp Glu Lys Lys Glu Leu Ser Glu Lys Val Lys His Ala Lys Arg
705                 710                 715                 720

Leu Ser Asp Glu Arg Asn Leu Leu Gln Asp Pro Asn Phe Arg Gly Ile
                725                 730                 735

Asn Arg Gln Leu Asp Arg Gly Trp Arg Gly Ser Thr Asp Ile Thr Ile
            740                 745                 750

Gln Gly Gly Asp Asp Val Phe Lys Glu Asn Tyr Val Thr Leu Leu Gly
        755                 760                 765

Thr Phe Asp Glu Cys Tyr Pro Thr Tyr Leu Tyr Gln Lys Ile Asp Glu
    770                 775                 780
```

```
Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
            805                 810                 815

Glu Thr Val Asn Val Pro Gly Thr Gly Ser Leu Trp Pro Leu Ser Ala
            820                 825                 830

Pro Ser Pro Ile Gly Lys Cys Ala His His Ser His His Phe Ser Leu
            835                 840                 845

Asp Ile Asp Val Gly Cys Thr Asp Leu Asn Glu Asp Leu Gly Val Trp
850                 855                 860

Val Ile Phe Lys Ile Lys Thr Gln Asp Gly His Ala Arg Leu Gly Asn
865                 870                 875                 880

Leu Glu Phe Leu Glu Glu Lys Pro Leu Val Gly Glu Ala Leu Ala Arg
                885                 890                 895

Val Lys Arg Ala Glu Lys Lys Trp Arg Asp Lys Arg Glu Lys Leu Glu
            900                 905                 910

Trp Glu Thr Asn Ile Val Tyr Lys Glu Ala Lys Glu Ser Val Asp Ala
            915                 920                 925

Leu Phe Val Asn Ser Gln Tyr Asp Arg Leu Gln Ala Asp Thr Asn Ile
930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
                965                 970                 975

Glu Glu Leu Glu Gly Arg Ile Phe Thr Ala Phe Ser Leu Tyr Asp Ala
            980                 985                 990

Arg Asn Val Ile Lys Asn Gly Asp  Phe Asn Asn Gly Leu  Ser Cys Trp
                995                 1000                1005

Asn Val Lys Gly His Val Asp  Val Glu Glu Gln Asn  Asn His Arg
    1010            1015                1020

Ser Val Leu Val Val Pro Glu  Trp Glu Ala Glu Val  Ser Gln Glu
    1025            1030                1035

Val Arg Val Cys Pro Gly Arg  Gly Tyr Ile Leu Arg  Val Thr Ala
    1040            1045                1050

Tyr Lys Glu Gly Tyr Gly Glu  Gly Cys Val Thr Ile  His Glu Ile
    1055            1060                1065

Glu Asn Asn Thr Asp Glu Leu  Lys Phe Ser Asn Cys  Val Glu Glu
    1070            1075                1080

Glu Val Tyr Pro Asn Asn Thr  Val Thr Cys Asn Asp  Tyr Thr Ala
    1085            1090                1095

Thr Gln Glu Glu Tyr Glu Gly  Thr Tyr Thr Ser Arg  Asn Arg Gly
    1100            1105                1110

Tyr Asp Gly Ala Tyr Glu Ser  Asn Ser Ser Val Pro  Ala Asp Tyr
    1115            1120                1125

Ala Ser Ala Tyr Glu Glu Lys  Ala Tyr Thr Asp Gly  Arg Arg Asp
    1130            1135                1140

Asn Pro Cys Glu Ser Asn Arg  Gly Tyr Gly Asp Tyr  Thr Pro Leu
    1145            1150                1155

Pro Ala Gly Tyr Val Thr Lys  Glu Leu Glu Tyr Phe  Pro Glu Thr
    1160            1165                1170

Asp Lys Val Trp Ile Glu Ile  Gly Glu Thr Glu Gly  Thr Phe Ile
    1175            1180                1185

Val Asp Ser Val Glu Leu Leu  Leu Met Glu Glu
```

<210> SEQ ID NO 31
<211> LENGTH: 3678
<212> TYPE: DNA
<213> ORGANISM: Artificial
<220> FEATURE:
<223> OTHER INFORMATION: Recombinant nucleotide sequence used
      for expression in a bacterial cell encoding TIC868_10.

<400> SEQUENCE: 31

```
atgacttcaa ataggaaaaa tgagaatgaa attataaatg ctttatcgat tccagctgta      60
tcgaatcatt ccgcacaaat gaatctatca accgatgctc gtattgagga tagcttgtgt     120
atagccgagg ggaacaatat cgatccattt gttagcgcat caacagtcca acgggtatt     180
aacatagctg gtagaatact aggtgtatta ggcgtaccgt tgctggaca aatagctagt     240
ttttatagtt ttcttgttgg tgaattatgg ccccgcggca gagatccttg ggaaattttc     300
ctagaacatg tcgaacaact tataagacaa caagtaacag aaaatactag ggatacggct     360
cttgctcgat tacaaggttt aggaaattcc tttagagcct atcaacagtc acttgaagat     420
tggctagaaa accgtgatga tgcaagaacg agaagtgttc tttatacca atatatagcc     480
ttagaacttg attttcttaa tgcgatgccg cttttcgcaa ttagaaacca agaagttcca     540
ttattaatgg tatatgctca agctgcaaat ttacacctat tattattgag agatgcctct     600
cttttttggta gtgaatttgg gcttacatcc caagaaattc aacgttatta tgagcgccaa     660
gtggaaaaaa cgagagaata ttctgattat tgcgcaagat ggtataatac gggtttaaat     720
aatttgagag ggacaaatgc tgaaagttgg ttgcgatata atcaattccg tagagactta     780
acgctaggag tattagatct agtggcacta ttcccaagct atgacacgcg tgtttatcca     840
atgaatacca gtgctcaatt aacaagagaa atttatacag atccaattgg gagaacaaat     900
gcaccttcag gatttgcaag tacgaattgg tttaataata tgcaccatc gttttctgcc     960
atagaggctg ccgttattag gcctccgcat ctacttgatt ttccagaaca gcttacaatt    1020
ttcagcgtat taagtcgatg gagtaatact caatatatga attactgggt gggacataga    1080
cttgaatcgc gaacaataag ggggtcatta agtacctcga cacacggaaa taccaatact    1140
tctattaatc ctgtaacatt acagttcaca tctcgagacg tttatagaac agaatcattt    1200
gcagggataa atatacttct aactactcct gtgaatggag taccttgggc tagatttaat    1260
tggagaaatc ccctgaattc tcttagaggt agccttctct atactatagg gtatactgga    1320
gtggggacac aactatttga ttcagaaact gaattaccac cagaaacaac agaacgacca    1380
aattatgaat cttacagtca tagattatct aatataagac taatatcagg aaacactttg    1440
agagcaccag tatattcttg gacgcaccgt agtgcagatc gtacaaatac cattagttca    1500
gatagcatta tcaaatacc tttagtgaaa ggatttagag tttgggggggg cacctctgtc    1560
attacaggac caggatttac aggagggat atccttcgaa gaaataccttt ggtgattttt    1620
gtatctctac aagtcaatat taattcacca attacccaaa gataccgttt aagatttcgt    1680
tacgcttcca gtagggatgc acgagttata gtattaacag gagcggcatc cacaggagtg    1740
ggaggccaag ttagtgtaaa tatgcctctt cagaaaacta tggaaatagg ggagaactta    1800
acatctagaa catttagata taccgatttt agtaatcctt tttcatttag agctaatcca    1860
gatataattg ggataagtga acaacctcta tttggtgcag gttctattag tagcggtgaa    1920
ctttatatag ataaaattga aattattcta gcagatgcaa catttgaggc agaatatgat    1980
```

| | | | | |
|---|---|---|---|---|
| ttagaaagag | cgcaaaaggt | ggtgaatgcc | ctgtttacgt | ctacaaacca actagggcta | 2040 |
| aaaacagatg | tgacggatta | tcatattgat | caggtatcca | atctagttgc gtgtttatcg | 2100 |
| gatgaatttt | gtctggatga | aaagagagaa | ttgtccgaga | aagttaaaca tgcaaagcga | 2160 |
| ctcagtgatg | agcggaattt | acttcaagat | ccaaacttca | gagggatcaa taggcaacca | 2220 |
| gaccgtggct | ggagaggaag | tacggatatt | actatccaag | gaggagatga cgtattcaaa | 2280 |
| gagaattacg | ttacgctacc | gggtaccttt | gatgagtgct | atccaacgta tttatatcaa | 2340 |
| aaaatagatg | agtcgaaatt | aaaagcctat | acccgttatc | aattaagagg gtatatcgaa | 2400 |
| gatagtcaag | acttagaaat | ctatttaatt | cgttacaatg | caaaacacga aatagtaaat | 2460 |
| gtaccaggta | caggaagttt | atggcctctt | tctgtagaaa | atcaaattgg accttgtgga | 2520 |
| gaaccgaatc | gatgcgcgcc | acaccttgaa | tggaatcctg | atttacactg ttcctgcaga | 2580 |
| gacggggaaa | atgtgcaca | tcattctcat | catttctctt | tggacattga tgttggatgt | 2640 |
| acagacttaa | atgaggactt | aggtgtatgg | gtgatattca | agattaagac gcaagatggc | 2700 |
| cacgcacgac | tagggaatct | agagtttctc | gaagagaaac | cattattagg agaagcacta | 2760 |
| gctcgtgtga | aaagagcgga | gaaaaaatgg | agagacaaac | gcgaaacatt acaattggaa | 2820 |
| acaactatcg | tttataaaga | ggcaaaagaa | tctgtagatg | cttttatttgt aaactctcaa | 2880 |
| tatgatagat | acaagcggaa | tacgaacatc | gcgatgattc | atgcggcaga taaacgcgtt | 2940 |
| catagaattc | gagaagcgta | tctgccggag | ctgtctgtga | ttccgggtgt caatgcggct | 3000 |
| attttgaag | aattagaaga | gcgtattttc | actgcatttt | ccctatatga tgcgagaaat | 3060 |
| attattaaaa | atggcgattt | caataatggc | ttattatgct | ggaacgtgaa agggcatgta | 3120 |
| gaggtagaag | aacaaaacaa | tcaccgttca | gtcctggtta | tcccagaatg ggaggcagaa | 3180 |
| gtgtcacaag | aggttcgtgt | ctgtccaggt | cgtggctata | tccttcgtgt tacagcgtac | 3240 |
| aaagagggat | atggagaagg | ttgcgtaacg | atccatgaga | tcgagaacaa tacagacgaa | 3300 |
| ctgaaattca | acaactgtgt | agaagaggaa | gtatatccaa | acaacacggt aacgtgtatt | 3360 |
| aattatactg | cgactcaaga | agaatatgag | ggtacgtaca | cttctcgtaa tcgaggatat | 3420 |
| gacgaagcct | atggtaataa | cccttccgta | ccagctgatt | atgcgtcagt ctatgaagaa | 3480 |
| aaatcgtata | cagatagacg | aagagagaat | ccttgtgaat | ctaacagagg atatggagat | 3540 |
| tacacaccac | taccagctgg | ttatgtaaca | aaggaattag | agtacttccc agagaccgat | 3600 |
| aaggtatgga | ttgagattgg | agaaacagaa | ggaacattca | tcgtggacag cgtggaatta | 3660 |
| ctccttatgg | aggaatag | | | | 3678 |

<210> SEQ ID NO 32
<211> LENGTH: 3678
<212> TYPE: DNA
<213> ORGANISM: Artificial
<220> FEATURE:
<223> OTHER INFORMATION: Synthetic nucleotide sequence designed for
      expression in a plant cell encoding TIC868_10.

<400> SEQUENCE: 32

| | | | | |
|---|---|---|---|---|
| atgacgagca | accggaagaa | cgagaacgag | atcatcaacg | ccctctcgat ccctgctgtt | 60 |
| tcaaaccact | ccgcgcagat | gaacctgtcc | accgacgcgc | gcatcgagga ctcccctctgc | 120 |
| atagccgagg | gcaacaacat | cgacccattc | gtgtcggcca | gcacggttca gaccggcatc | 180 |
| aacatcgcgg | gccgtatcct | cggcgtcctc | ggtgtcccat | cgccggtca gatcgcgtcc | 240 |
| ttctactcgt | tccttgtggg | cgagctgtgg | cctcgcggtc | gtgacccgtg ggagatcttc | 300 |

```
ctggagcatg tggagcagtt gatccggcag caagtcacgg agaacacccg cgatactgct    360
ctggccaggc tacagggcct gggaaactcc tttcgggcat accagcagtc actggaggac    420
tggttggaga acagggatga cgcgcgaaca cgctcggtac tctacaccca gtacatcgct    480
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag cccaatcgg ccggacgaac    900
gcaccctccg gtttcgcatc cacgaattgg ttcaacaaca cgcaccctc cttctcggca    960
atcgaggccg ccgtcatccg ccctcctcac ctgctcgact ttcccgagca gctcacgatc   1020
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaacccct tctcattcag agcgaaccct   1860
gacatcattg gatctccga gcaaccgctg ttcggtgctg gctccatcag ctctggcgaa   1920
ctgtacatcg acaagattga gatcatcctg gcggatgcga cgttcgaggc cgagtacgac   1980
cttgagcgcg cccagaaggt ggtgaacgcc ctcttcacta gcactaacca gctaggcctg   2040
aagactgacg tgaccgacta ccacatcgac caagtgagca acctagtggc ctgcctctcc   2100
gacgagttct gcctcgacga gaagcgcgag ctgtccgaga aggtgaagca cgccaagcgc   2160
ctctccgacg agcgcaacct gctccaggac cccaacttca ggggcatcaa caggcagccc   2220
gaccgcggct ggcgcggctc caccgacatc accatccagg gcggtgacga cgtattcaag   2280
gagaactacg ttaccctccc cggcaccttc gacgagtgtt accccaccta cctctaccag   2340
aagatcgacg agtccaagct gaaggcctac acccgctacc agctccgcgg ctacatcgag   2400
gactcccagg acctggaaat ctacctcatc cgctacaacg ccaagcacga gatcgtgaac   2460
gtgcctggca ccggcagcct ctggcctctc agcgtggaga accagatcgg cccttgcggc   2520
gagcctaacc gctgcgcccc tcacctcgag tggaaccctg acctccactg ctcgtgcagg   2580
gacggcgaga agtgcgccca ccatagccac cacttctctc tggacatcga cgtgggctgc   2640
accgacctga acgaggacct gggcgtgtgg gttatcttca agatcaagac ccaggacggt   2700
```

```
cacgccaggc tgggtaacct ggagttcctt gaggaaaagc ctctgctggg tgaggccctg   2760
gccagggtca agagggctga gaagaaatgg agggataaga gggagaccct gcagctggag   2820
accactatcg tctacaagga ggctaaggag tctgtcgatg ctctgttcgt caactctcag   2880
tacgatagac tgcaagctga taccaacatc gctatgatcc acgctgcgga taagcgggtc   2940
caccggatcc gggaggctta ccttccggag ctttctgtca tcccgggtgt caacgctgcg   3000
atcttcgagg aacttgagga acggatcttc actgcgttta gtctttacga tgcgcggaac   3060
atcatcaaga acggggactt caacaatggt ctgctgtgct ggaacgtcaa gggtcatgtc   3120
gaggtcgagg aacaaaacaa tcatcgtagt gtccttgtca ttcctgagtg ggaggcggag   3180
gtctctcaag aggtccgtgt ttgcccgggg cgtgggtaca ttcttcgtgt tactgcgtac   3240
aaggaggggt acggggaggg gtgcgttact attcatgaga ttgagaacaa tactgatgag   3300
cttaagttca acaattgtgt tgaggaggag gtttacccga caatactgt tacgtgcatc   3360 aactacacgg caacgcaaga ggaatacgag gggacgtaca cctcgcgtaa tagagggtat   3420
gatgaggcgt acggaaacaa cccgtcggtt ccagcagatt atgcctcggt ttatgaggag   3480
aagtcgtaca cggatagacg acgcgagaat ccatgtgagt caaatcgagg atacggagat   3540
tacacaccat taccagcagg atacgttaca aaggagttgg aatacttccc ggaaacagat   3600
aaagtttgga ttgaaatcgg agaaacagaa ggaacattca tcgtcgactc agtagaattg   3660
ttgttgatgg aagaatga                                                 3678
```

<210> SEQ ID NO 33
<211> LENGTH: 1225
<212> TYPE: PRT
<213> ORGANISM: Artificial
<220> FEATURE:
<223> OTHER INFORMATION: Amino acid sequence of the chimeric protein
      variant TIC868_10.

<400> SEQUENCE: 33

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175
```

```
Gln Glu Val Pro Leu Leu Met Val Tyr Ala Gln Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
```

```
                595                 600                 605
Asp Phe Ser Asn Pro Phe Ser Phe Arg Ala Asn Pro Asp Ile Ile Gly
610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Phe Glu
                645                 650                 655

Ala Glu Tyr Asp Leu Glu Arg Ala Gln Lys Val Val Asn Ala Leu Phe
                660                 665                 670

Thr Ser Thr Asn Gln Leu Gly Leu Lys Thr Asp Val Thr Asp Tyr His
                675                 680                 685

Ile Asp Gln Val Ser Asn Leu Val Ala Cys Leu Ser Asp Glu Phe Cys
690                 695                 700

Leu Asp Glu Lys Arg Glu Leu Ser Glu Lys Val Lys His Ala Lys Arg
705                 710                 715                 720

Leu Ser Asp Glu Arg Asn Leu Leu Gln Asp Pro Asn Phe Arg Gly Ile
                725                 730                 735

Asn Arg Gln Pro Asp Arg Gly Trp Arg Gly Ser Thr Asp Ile Thr Ile
                740                 745                 750

Gln Gly Gly Asp Asp Val Phe Lys Glu Asn Tyr Val Thr Leu Pro Gly
                755                 760                 765

Thr Phe Asp Glu Cys Tyr Pro Thr Tyr Leu Tyr Gln Lys Ile Asp Glu
770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
                805                 810                 815

Glu Ile Val Asn Val Pro Gly Thr Gly Ser Leu Trp Pro Leu Ser Val
                820                 825                 830

Glu Asn Gln Ile Gly Pro Cys Gly Glu Pro Asn Arg Cys Ala Pro His
                835                 840                 845

Leu Glu Trp Asn Pro Asp Leu His Cys Ser Cys Arg Asp Gly Glu Lys
                850                 855                 860

Cys Ala His His Ser His His Phe Ser Leu Asp Ile Asp Val Gly Cys
865                 870                 875                 880

Thr Asp Leu Asn Glu Asp Leu Gly Val Trp Val Ile Phe Lys Ile Lys
                885                 890                 895

Thr Gln Asp Gly His Ala Arg Leu Gly Asn Leu Glu Phe Leu Glu Glu
                900                 905                 910

Lys Pro Leu Leu Gly Glu Ala Leu Ala Arg Val Lys Arg Ala Glu Lys
                915                 920                 925

Lys Trp Arg Asp Lys Arg Glu Thr Leu Gln Leu Glu Thr Thr Ile Val
                930                 935                 940

Tyr Lys Glu Ala Lys Glu Ser Val Asp Ala Leu Phe Val Asn Ser Gln
945                 950                 955                 960

Tyr Asp Arg Leu Gln Ala Asp Thr Asn Ile Ala Met Ile His Ala Ala
                965                 970                 975

Asp Lys Arg Val His Arg Ile Arg Glu Ala Tyr Leu Pro Glu Leu Ser
                980                 985                 990

Val Ile Pro Gly Val Asn Ala Ala  Ile Phe Glu Glu Leu  Glu Glu Arg
                995                 1000                1005

Ile Phe  Thr Ala Phe Ser Leu  Tyr Asp Ala Arg Asn  Ile Ile Lys
1010                1015                1020
```

```
Asn Gly Asp Phe Asn Asn Gly Leu Leu Cys Trp Asn Val Lys Gly
    1025            1030                1035

His Val Glu Val Glu Glu Gln Asn Asn His Arg Ser Val Leu Val
    1040            1045                1050

Ile Pro Glu Trp Glu Ala Glu Val Ser Gln Glu Val Arg Val Cys
    1055            1060                1065

Pro Gly Arg Gly Tyr Ile Leu Arg Val Thr Ala Tyr Lys Glu Gly
    1070            1075                1080

Tyr Gly Glu Gly Cys Val Thr Ile His Glu Ile Glu Asn Asn Thr
    1085            1090                1095

Asp Glu Leu Lys Phe Asn Asn Cys Val Glu Glu Val Tyr Pro
    1100            1105                1110

Asn Asn Thr Val Thr Cys Ile Asn Tyr Thr Ala Thr Gln Glu Glu
    1115            1120                1125

Tyr Glu Gly Thr Tyr Thr Ser Arg Asn Arg Gly Tyr Asp Glu Ala
    1130            1135                1140

Tyr Gly Asn Asn Pro Ser Val Pro Ala Asp Tyr Ala Ser Val Tyr
    1145            1150                1155

Glu Glu Lys Ser Tyr Thr Asp Arg Arg Arg Glu Asn Pro Cys Glu
    1160            1165                1170

Ser Asn Arg Gly Tyr Gly Asp Tyr Thr Pro Leu Pro Ala Gly Tyr
    1175            1180                1185

Val Thr Lys Glu Leu Glu Tyr Phe Pro Glu Thr Asp Lys Val Trp
    1190            1195                1200

Ile Glu Ile Gly Glu Thr Glu Gly Thr Phe Ile Val Asp Ser Val
    1205            1210                1215

Glu Leu Leu Leu Met Glu Glu
    1220            1225

<210> SEQ ID NO 34
<211> LENGTH: 3726
<212> TYPE: DNA
<213> ORGANISM: Artificial
<220> FEATURE:
<223> OTHER INFORMATION: Recombinant nucleotide sequence used
      for expression in a bacterial cell encoding TIC868_11.

<400> SEQUENCE: 34
atgacttcaa ataggaaaaa tgagaatgaa attataaatg ctttatcgat tccagctgta    60
tcgaatcatt ccgcacaaat gaatctatca accgatgctc gtattgagga tagcttgtgt   120
atagccgagg ggaacaatat cgatccattt gttagcgcat caacagtcca aacgggtatt   180
aacatagctg gtagaatact aggtgtatta ggcgtaccgt ttgctggaca atagctagt    240 ttttatagtt ttcttgttgg tgaattatgg ccccgcggca gagatccttg ggaaattttc   300
ctagaacatg tcgaacaact tataagacaa caagtaacag aaaatactag ggatacggct   360
cttgctcgat tacaaggttt aggaaaattcc tttagagcct atcaacagtc acttgaagat   420
tggctagaaa accgtgatga tgcaagaacg agaagtgttc tttatacccc atatatagcc   480
ttagaacttg attttcttaa tcgatgccg cttttcgcaa ttagaaacca agaagttcca   540
ttattaatgg tatatgctca agctgcaaat ttacacctat tattattgag agatgcctct   600 cttttttggta gtgaatttgg gcttacatcc caagaaattc aacgttatta tgagcgccaa   660
gtggaaaaaa cgagagaata ttctgattat tgcgcaagat ggtataatac gggtttaaat   720
aatttgagag ggacaaatgc tgaaagttgg ttgcgatata atcaattccg tagagactta   780
```

```
acgctaggag tattagatct agtggcacta ttcccaagct atgacacgcg tgtttatcca    840
atgaatacca gtgctcaatt aacaagagaa atttatacag atccaattgg gagaacaaat    900
gcaccttcag gatttgcaag tacgaattgg tttaataata atgcaccatc gttttctgcc    960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggcaca aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta atcaaatacc tttagtgaaa ggatttagag tttgggggg cacctctgtc    1560
attacaggac caggatttac aggagggat atccttcgaa gaaataccctt tggtgatttt    1620
gtatctctac aagtcaatat taattcacca attacccaaa gataccgttt aagatttcgt   1680
tacgcttcca gtagggatgc acgagttata gtattaacag gagcggcatc cacaggagtg   1740
ggaggccaag ttagtgtaaa tatgcctctt cagaaaacta tggaaatagg ggagaactta   1800
acatctagaa catttagata taccgatttt agtaatcctt tttcatttag agctaatcca   1860
gatataattg ggataagtga acaacctcta tttggtgcag gttctattag tagcggtgaa   1920
ctttatatag ataaaattga aattattcta gcagatgcaa caggaacgac aacctatgag   1980
tatgaagaga agcagaatct agaaaaagcg cagaaagcgt tgaacgcttt gtttacggat   2040
ggcacgaatg gctatctaca aatggatgcc actgattatg atatcaatca aactgcaaac   2100
ttaatagaat gtgtatcaga tgaattgtat gcaaagaaa agatagtttt attagatgaa    2160
gtcaaatatg cgaagcggct tagcatatca cgtaacctac ttttgaacga tgatttagaa   2220
ttttcagatg gatttggaga aaacggatgg acgacaagtg ataatatttc aatccaggcg   2280
gataatcccc ttttaagggg gaattattta aaaatgtttg gggcaagaga tattgatgga   2340
accctatttc caactatct ctatcaaaaa atagatgagt ccaggttaaa accatataca    2400
cgttatcgag taagagggtt tgtgggaagt agtaaaaatc taaaattagt ggtaacacgc   2460
tatgagaaag aaattgatgc cattatgaat gttccaaatg atttggcaca tatgcagctt   2520
aaccccttcat gtggagatta tcgctgtgaa tcatcgtccc agttttggt gaaccaagtg    2580
catcctacac caacagctgg atatgctctt gatatgtatg catgcccgtc aagttcagat   2640
aaaaaacata ttatgtgtca cgatcgtcat ccatttgatt ttcatattga caccggagaa   2700
ttaaatccaa acacaaacct gggtattgat gtcttgttta aaatttctaa tccaaatgga   2760
tacgctacat tagggaatct agaagtcatt gaagaaggac cactaacaga tgaagcattg   2820
gtacatgtaa aacaaaagga aaagaaatgg cgtcagcaca tggagaaaaa acgaatggaa   2880
acacaacaag cctatgatcc agcaaaacaa gctgtagatg cattatttac aaatgaacaa   2940
gagttagact atcatactac tttagatcat attcagaacg ccgatcagct ggtacaggcg   3000
attccctatg tacaccatgc ttggttaccg gatgctccag gtatgaacta tgatgtatat   3060
caagggttaa acgcacgtat catgcaggcg tacaattat atgatgcacg aaatgtcata    3120
```

-continued

```
ataaatggtg actttacaca aggactacaa ggatggcacg caacaggaaa agcagcggta      3180
caacaaatag atggagcttc agtattagtt ctatcaaact ggagtgccga ggtatctcag      3240
aatctgcatg cccaagatca tcatggatat atgttacgtg tgattgccaa aaaagaaggt      3300
cctggaaaag ggtatgtaat gatgatggat tttaatggaa agcaggaaac acttacgttc      3360
acttcttgtg aagaaggata tataacaaaa acaatagagg tattcccgga aagtgatcga      3420
atacgaattg aaatgggaga aacagagggt acgttttatg tagatagcat cgagttgctt      3480
tgtatgcaag gatatgctag cgataataac ccgcacacgg gtaatatgta tgagcaaagt      3540
tataatggaa attataatca aaatactagc gatgtgtatc accaaggata tataaacaac      3600
tataaccaaa attctagtag tatgtataat caaaattata ttaacaatga tgacctgcat      3660
tccggttgca catgtaaacca agggcataac tctggctgta catgtaatca aggatataac      3720
cgttag                                                                  3726
```

<210> SEQ ID NO 35
<211> LENGTH: 3726
<212> TYPE: DNA
<213> ORGANISM: Artificial
<220> FEATURE:
<223> OTHER INFORMATION: Synthetic nucleotide sequence designed for
      expression in a plant cell encoding TIC868_11.

<400> SEQUENCE: 35

```
atgacgagca accggaagaa cgagaacgag atcatcaacg ccctctcgat ccctgctgtt        60
tcaaaccact ccgcgcagat gaacctgtcc accgacgcgc gcatcgagga ctccctctgc       120
atagccgagg gcaacaacat cgacccattc gtgtcggcca gcacggttca gaccggcatc       180
aacatcgcgg gccgtatcct cggcgtcctc ggtgtcccat cgccggtca gatcgcgtcc        240 ttctactcgt tccttgtggg cgagctgtgg cctcgcggtc gtgacccgtg ggagatcttc       300
ctggagcatg tggagcagtt gatccggcag caagtcacgg agaacacccg cgatactgct       360
ctggccaggc tacagggcct gggaaaactcc tttcgggcat accagcagtc actggaggac      420
tggttggaga caggggatga cgcgcgaaca cgctcggtac tctacaccca gtacatcgct       480
ctcgaactcg acttcctgaa cgctatgccg ctgttcgcca tcaggaacca ggaagttcca       540
ctccttatgg tgtacgcccca ggccgccaac ttacatctgc tcctgctgcg ggacgccagc      600
ctgttcggct ccgagttcgg actcacatct caagaaatcc agcgttacta cgagcgccaa       660
gtggagaaga cccgtgagta cagtgactac tgcgctcgat ggtacaacac agggctcaac       720
aacctgcgcg gcaccaacgc tgagtcatgg ctccgttaca accagttccg ccgcgacttg       780
actttgggtg tcctagaccct ggtggcgcta ttcccgtctt acgacacacg ggtgtaccca       840
atgaacacta gcgcgcaact cacgcgggag atctacacag acccaatcgg ccggacgaac       900
gcacccctcc ggtttcgcatc cacgaattgg ttcaacaaca cgcaccctc cttctcggca       960 atcgaggccg ccgtcatccg ccctcctcac ctgctcgact ttcccgagca gctcacgatc      1020
ttctccgtgc tctcacgctg gtccaacaca cagtacatga actactgggt cgggcaccga      1080
ttggagagta ggacgatccg tggcagcttg agcaccagta cccacggcaa caccaacacc      1140
tccatcaacc cagttacgct acagttcacg agccgcgacg tttaccggac tgagtcgttc      1200
gcgggcatta acatccttct gacaacgccc gtcaacggcg tcccgtgggc ccggttcaac      1260
tggcgtaacc cgttgaactc cctgcgcggg tcattgctct acaccatcgg gtacacgggc      1320
gtcggcaccc agctcttcga cagtgaaact gagctgccgc ccgagaccac ggaacgcccg      1380
```

-continued

```
aactacgagt cctacagcca ccgcctgtcc aacatccggc tcatctctgg caacacgctg    1440
cgtgcgccgg tgtactcctg dacacaccgc agcgccgacc ggaccaacac gatctcttcc    1500
gactccatta accagatccc gctcgtgaag ggcttccgtg tgtggggtgg cacgagcgtc    1560
atcaccggtc cgggcttcac cggtggagac atactgcggc gcaacacttt cggcgacttc    1620
gtttcgttgc aagtgaacat caactcgccg atcacccagc gttaccgtct gaggttccgc    1680
tacgcttcaa gccgcgacgc gagggtcatt gtcctgaccg gagccgcgtc cacaggcgtg    1740
ggaggccaag tctcagtcaa catgcctctc cagaagacga tggagatagg cgagaacttg    1800
actagccgaa ccttccggta cactgatttc tcgaacccct tctcattcag agcgaaccct    1860
gacatcattg ggatctccga gcaaccgctg ttcggtgctg gctccatcag ctctggcgaa    1920
ctgtacatcg acaagattga gatcatcctg gcggatgcga cggggactac cacctacgag    1980
tacgaggaga agcagaatct cgagaaggct cagaaggctc tgaacgctct gttcactgac    2040
gggaccaacg gctacctcca gatggacgcc actgactacg acatcaacca gacagctaac    2100
ctgattgagt gtgtgagtga cgaactgtac gctaaggaga gatcgtact cctggacgag    2160 gtgaagtacg ctaagcgcct gagcattagc cgtaacctgc tgctgaacga cgatctggag    2220
ttcagcgacg gctttggcga gaacggctgg accaccagcg acaacatctc catccaggcc    2280
gacaatccac tcttcaaagg caactacctc aagatgttcg gagccaggga catcgacggc    2340
accctctttc cgacctacct ctaccagaag atcgacgagt cccgcctcaa accctacacc    2400
cgctacaggg tgcgcggctt cgtgggcagc agcaagaacc tcaagctcgt ggtcacacgg    2460
tatgagaagg agatcgacgc catcatgaac gtgcccaacg atctcgccca catgcagctc    2520
aatccatcct gcggcgacta ccggtgcgag tccagctccc agttcctcgt gaaccaggtg    2580
caccctactc cgaccgctgg ctatgccctg gacatgtacg cctgccctag ttcctccgac    2640
aagaagcaca tcatgtgcca cgaccgtcat ccgttcgact tccacatcga caccggcgaa    2700
ctgaacccga acaccaacct gggcatcgac gtactgttca agatttccaa cccgaacggg    2760
tacgccacct tgggcaacct ggaggtcatc gaagaaggcc cgctgaccga cgaggccctg    2820
gtccacgtca aacagaagga gaagaagtgg cggcagcaca tggagaagaa gcggatggag    2880
actcaacaag cctacgaccc ggccaagcaa gctgtggacg ctctgttcac caacgagcaa    2940
gagcttgact accacactac tcttgaccac atccagaatg ctgaccagct tgtccaggct    3000
attccgtacg tccaccacgc ttggctaccg gacgctccag ggatgaacta cgatgtgtac    3060
cagggtctga acgcgcggat catgcaagcg tacaacctgt acgacgcgcg taacgtcatc    3120
atcaacggtg acttcactca gggtcttcaa ggttggcacg cgactggcaa agcggcagtc    3180
cagcagattg atggtgcgtc tgttcttgtg ttgagcaact ggtctgcgga ggtttctcag    3240
aacctgcacg cacaggatca ccacggctac atgctgaggg tgattgctaa gaaggagggc    3300
cctggcaaag gctacgtcat gatgatggac ttcaacggaa agcaagaaac cctgaccttc    3360
actagctgtg aggagggcta catcactaag accattgagg tctttccgga gtctgaccgc    3420
atccggatcg agatgggcga gaccgaaggc acgttctacg tggactccat cgaactcctc    3480
tgcatgcaag gctacgcctc cgacaacaac ccacacacgg gcaacatgta cgagcagtcc    3540
tacaacggga actacaacca gaacacctcc gatgtgtacc atcagggcta catcaacaac    3600
tacaaccaga acagcagcag catgtacaac cagaactaca tcaacaacga tgacttgcac    3660
tcgggttgca cctgcaacca gggtcacaac agtgggtgca cgtgcaacca gggatacaac    3720
cgttga                                                              3726
```

<210> SEQ ID NO 36
<211> LENGTH: 1241
<212> TYPE: PRT
<213> ORGANISM: Artificial
<220> FEATURE:
<223> OTHER INFORMATION: Amino acid sequence of the chimeric protein variant TIC868_11.

<400> SEQUENCE: 36

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
```

-continued

```
            355                 360                 365
Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
                435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
                500                 505                 510

Arg Val Trp Gly Gly Thr Ser Val Ile Thr Gly Pro Gly Phe Thr Gly
                515                 520                 525

Gly Asp Ile Leu Arg Arg Asn Thr Phe Gly Asp Phe Val Ser Leu Gln
530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
                580                 585                 590

Thr Met Glu Ile Gly Glu Asn Leu Thr Ser Arg Thr Phe Arg Tyr Thr
                595                 600                 605

Asp Phe Ser Asn Pro Phe Ser Phe Arg Ala Asn Pro Asp Ile Ile Gly
                610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Gly Thr
                645                 650                 655

Thr Thr Tyr Glu Tyr Glu Glu Lys Gln Asn Leu Glu Lys Ala Gln Lys
                660                 665                 670

Ala Leu Asn Ala Leu Phe Thr Asp Gly Thr Asn Gly Tyr Leu Gln Met
                675                 680                 685

Asp Ala Thr Asp Tyr Asp Ile Asn Gln Thr Ala Asn Leu Ile Glu Cys
                690                 695                 700

Val Ser Asp Glu Leu Tyr Ala Lys Glu Lys Ile Val Leu Leu Asp Glu
705                 710                 715                 720

Val Lys Tyr Ala Lys Arg Leu Ser Ile Ser Arg Asn Leu Leu Leu Asn
                725                 730                 735

Asp Asp Leu Glu Phe Ser Asp Gly Phe Gly Glu Asn Gly Trp Thr Thr
                740                 745                 750

Ser Asp Asn Ile Ser Ile Gln Ala Asp Asn Pro Leu Phe Lys Gly Asn
                755                 760                 765

Tyr Leu Lys Met Phe Gly Ala Arg Asp Ile Asp Gly Thr Leu Phe Pro
                770                 775                 780
```

```
Thr Tyr Leu Tyr Gln Lys Ile Asp Glu Ser Arg Leu Lys Pro Tyr Thr
785                 790                 795                 800

Arg Tyr Arg Val Arg Gly Phe Val Gly Ser Lys Asn Leu Lys Leu
                805                 810                 815

Val Val Thr Arg Tyr Glu Lys Glu Ile Asp Ala Ile Met Asn Val Pro
            820                 825                 830

Asn Asp Leu Ala His Met Gln Leu Asn Pro Ser Cys Gly Asp Tyr Arg
                835                 840                 845

Cys Glu Ser Ser Ser Gln Phe Leu Val Asn Gln Val His Pro Thr Pro
850                 855                 860

Thr Ala Gly Tyr Ala Leu Asp Met Tyr Ala Cys Pro Ser Ser Ser Asp
865                 870                 875                 880

Lys Lys His Ile Met Cys His Asp Arg His Pro Phe Asp Phe His Ile
                885                 890                 895

Asp Thr Gly Glu Leu Asn Pro Asn Thr Asn Leu Gly Ile Asp Val Leu
            900                 905                 910

Phe Lys Ile Ser Asn Pro Asn Gly Tyr Ala Thr Leu Gly Asn Leu Glu
                915                 920                 925

Val Ile Glu Glu Gly Pro Leu Thr Asp Glu Ala Leu Val His Val Lys
            930                 935                 940

Gln Lys Glu Lys Lys Trp Arg Gln His Met Glu Lys Lys Arg Met Glu
945                 950                 955                 960

Thr Gln Gln Ala Tyr Asp Pro Ala Lys Gln Ala Val Asp Ala Leu Phe
                965                 970                 975

Thr Asn Glu Gln Glu Leu Asp Tyr His Thr Thr Leu Asp His Ile Gln
            980                 985                 990

Asn Ala Asp Gln Leu Val Gln Ala Ile Pro Tyr Val His His Ala Trp
        995                 1000                1005

Leu Pro Asp Ala Pro Gly Met Asn Tyr Asp Val Tyr Gln Gly Leu
    1010                1015                1020

Asn Ala Arg Ile Met Gln Ala Tyr Asn Leu Tyr Asp Ala Arg Asn
    1025                1030                1035

Val Ile Ile Asn Gly Asp Phe Thr Gln Gly Leu Gln Gly Trp His
    1040                1045                1050

Ala Thr Gly Lys Ala Ala Val Gln Gln Ile Asp Gly Ala Ser Val
    1055                1060                1065

Leu Val Leu Ser Asn Trp Ser Ala Glu Val Ser Gln Asn Leu His
    1070                1075                1080

Ala Gln Asp His His Gly Tyr Met Leu Arg Val Ile Ala Lys Lys
    1085                1090                1095

Glu Gly Pro Gly Lys Gly Tyr Val Met Met Met Asp Phe Asn Gly
    1100                1105                1110

Lys Gln Glu Thr Leu Thr Phe Thr Ser Cys Glu Glu Gly Tyr Ile
    1115                1120                1125

Thr Lys Thr Ile Glu Val Phe Pro Glu Ser Asp Arg Ile Arg Ile
    1130                1135                1140

Glu Met Gly Glu Thr Glu Gly Thr Phe Tyr Val Asp Ser Ile Glu
    1145                1150                1155

Leu Leu Cys Met Gln Gly Tyr Ala Ser Asp Asn Asn Pro His Thr
    1160                1165                1170

Gly Asn Met Tyr Glu Gln Ser Tyr Asn Gly Asn Tyr Asn Gln Asn
    1175                1180                1185
```

| Thr | Ser | Asp | Val | Tyr | His | Gln | Gly | Tyr | Ile | Asn | Asn | Tyr | Asn | Gln |
| | 1190 | | | | 1195 | | | | | 1200 | | | | |

| Asn | Ser | Ser | Ser | Met | Tyr | Gln | Asn | Tyr | Ile | Asn | Asn | Asp | Asp |
| | 1205 | | | | 1210 | | | | | 1215 | | | |

| Leu | His | Ser | Gly | Cys | Thr | Cys | Asn | Gln | Gly | His | Asn | Ser | Gly | Cys |
| | 1220 | | | | 1225 | | | | | 1230 | | | | |

| Thr | Cys | Asn | Gln | Gly | Tyr | Asn | Arg |
| | 1235 | | | | 1240 | | |

<210> SEQ ID NO 37
<211> LENGTH: 3468
<212> TYPE: DNA
<213> ORGANISM: Artificial
<220> FEATURE:
<223> OTHER INFORMATION: Recombinant nucleotide sequence used
for expression in a bacterial cell encoding TIC868_12.

<400> SEQUENCE: 37

| | | |
|---|---|---|
| atgacttcaa ataggaaaaa tgagaatgaa attataaatg ctttatcgat tccagctgta | 60 |
| tcgaatcatt ccgcacaaat gaatctatca accgatgctc gtattgagga tagcttgtgt | 120 |
| atagccgagg ggaacaatat cgatccattt gttagcgcat caacagtcca acgggtatt | 180 |
| aacatagctg gtagaatact aggtgtatta ggcgtaccgt ttgctggaca aatagctagt | 240 |
| tttatagtt tccttgttgg tgaattatgg ccccgcggca gagatccttg gaaattttc | 300 |
| ctagaacatg tcgaacaact tataagacaa caagtaacag aaaatactag ggatacggct | 360 |
| cttgctcgat tacaaggttt aggaaattcc tttagagcct atcaacagtc acttgaagat | 420 |
| tggctagaaa accgtgatga tgcaagaacg agaagtgttc tttataccca atatatagcc | 480 |
| ttagaacttg atttcttaa tgcgatgccg cttttcgcaa ttagaaacca gaagttcca | 540 |
| ttattaatgg tatatgctca agctgcaaat ttacacctat tattattgag agatgcctct | 600 |
| cttttttggta gtgaatttgg gcttacatcc caagaaattc aacgttatta tgagcgccaa | 660 |
| gtggaaaaaa cgagagaata ttctgattat tgcgcaagat ggtataatac gggtttaaat | 720 |
| aatttgagag gacaaatgc tgaaagttgg ttgcgatata atcaattccg tagagactta | 780 |
| acgctaggag tattagatct agtggcacta ttcccaagct atgacacgcg tgtttatcca | 840 |
| atgaatacca gtgctcaatt aacaagagaa atttatacag atccaattgg gagaacaaat | 900 |
| gcaccttcag gatttgcaag tacgaattgg tttaataata tgcaccatc gttttctgcc | 960 |
| atagaggctg ccgttattag gcctccgcat ctacttgatt ttccagaaca gcttacaatt | 1020 |
| ttcagcgtat taagtcgatg gagtaatact caatatatga attactgggt gggacataga | 1080 |
| cttgaatcgc gaacaataag ggggtcatta agtacctcga cacacggaaa taccaatact | 1140 |
| tctattaatc ctgtaacatt acagttcaca tctcgagacg tttatagaac agaatcattt | 1200 |
| gcagggataa atatacttct aactactcct gtgaatggag taccttgggc tagatttaat | 1260 |
| tggagaaatc ccctgaattc tcttagaggt agccttctct atactatagg gtatactgga | 1320 |
| gtggggacac aactatttga ttcagaaact gaattaccac cagaaacaac agaacgacca | 1380 |
| aattatgaat cttacagtca tagattatct aatataagac taatatcagg aaacactttg | 1440 |
| agagcaccag tatattcttg gacgcaccgt agtgcagatc gtacaaatac cattagttca | 1500 |
| gatagcatta tcaaatacc tttagtgaaa ggatttagag tttgggggg cacctctgtc | 1560 |
| attacaggac caggatttac aggaggggat atccttcgaa gaaataccttt tggtgatttt | 1620 |
| gtatctctac aagtcaatat taattcacca attacccaaa gataccgttt aagatttcgt | 1680 |

```
tacgcttcca gtagggatgc acgagttata gtattaacag gagcggcatc cacaggagtg   1740
ggaggccaag ttagtgtaaa tatgcctctt cagaaaacta tggaaatagg ggagaactta   1800
acatctagaa catttagata taccgatttt agtaatcctt tttcatttag agctaatcca   1860
gatataattg ggataagtga acaacctcta tttggtgcag gttctattag tagcggtgaa   1920
ctttatatag ataaaattga aattattcta gcagatgcaa caaatccgac gcgagaggcg   1980
gaagaggatc tagaagcagc gaagaaagcg gtggcgagct tgtttacacg tacaagggac   2040
ggattacaag taaatgtgac agattatcaa gtcgatcaag cggcaaattt agtgtcatgc   2100
ttatcagatg aacaatatgg gcatgacaaa aagatgttat tggaagcggt aagagcggca   2160
aaacgcctca gccgagaacg caacttactt caggatccag attttaatac aatcaatagt   2220
acagaagaaa atggatggaa agcaagtaac ggcgttacta ttagcgaggg cggtccattc   2280
tataaaggcc gtgcgcttca gctagcaagc gcaagagaaa attcccaac atacatttat    2340 caaaaagtaa atgcatcaga gttaaagccg tatacacgtt atagactgga tgggttcgtg   2400
aagagtagtc aagatttaga aattgatctc attcaccatc ataaagtcca tctcgtgaaa   2460
aatgtaccag ataatttagt atccgatact tactcggatg gttcttgcag tggaatgaat   2520
cgatgtgagg aacaacagat ggtaaatgcg caactggaaa cagaacatca tcatccgatg   2580
gattgctgtg aagcggctca aacacatgag ttttcttcct atattaatac aggcgatcta   2640
aattcaagtg tagatcaagg catttgggtt gtattgaaag ttcgaacaac cgatggttat   2700
gcgacgctag gaaatcttga attggtagag gtcggaccgt tatcgggtga atctctagaa   2760
cgtgaacaaa gggataatgc gaaatggagt gcagagctag gaagaaagcg tgcagaaaca   2820
gatcgcgtgt atcaagatgc caaacaatcc atcaatcatt tatttgtgga ttatcaagat   2880
caacaattaa atccagaaat agggatggca gatattattg acgctcaaaa tcttgtcgca   2940
tcaatttcag atgtgtatag cgatgcagta ctgcaaatcc ctggaattaa ctatgagatt   3000
tacacagagc tatccaatcg cttacaacaa gcatcgtatc tgtatacgtc tcgaaatgcg   3060
gtgcaaaatg gggactttaa cagcggtcta gatagttgga atgcaacagg gggggctacg   3120
gtacaacagg atggcaatac gcatttctta gttctttctc attgggatgc acaagtttct   3180
caacaattta gagtgcagcc gaattgtaaa tatgtattac gtgtaacagc agagaaagta   3240
ggcggcggag acggatacgt gacaatccgg gatggtgctc atcatacaga aaagcttaca   3300
tttaatgcat gtgattatga tataaatggc acgtacgtga ctgataatac gtatctaaca   3360
aaagaagtgg tattctattc acatacgaaa cacatgtggg tagaggtaag tgaaacagaa   3420
ggtgcatttc atatagatag tattgaattc gttgaaacag aaaagtag                3468
```

<210> SEQ ID NO 38
<211> LENGTH: 3468
<212> TYPE: DNA
<213> ORGANISM: Artificial
<220> FEATURE:
<223> OTHER INFORMATION: Synthetic nucleotide sequence designed for
      expression in a plant cell encoding TIC868_12.

<400> SEQUENCE: 38

```
atgacgagca accggaagaa cgagaacgag atcatcaacg ccctctcgat ccctgctgtt     60
tcaaaccact ccgcgcagat gaacctgtcc accgacgcgc gcatcgagga ctccctctgc   120
atagccgagg gcaacaacat cgacccattc gtgtcggcca gcacggttca gaccggcatc   180
aacatcgcgg gccgtatcct cggcgtcctc ggtgtcccat cgccggtca gatcgcgtcc   240
```

```
ttctactcgt tccttgtggg cgagctgtgg cctcgcggtc gtgacccgtg ggagatcttc    300
ctggagcatg tggagcagtt gatccggcag caagtcacgg agaacacccg cgatactgct    360
ctggccaggc tacagggcct gggaaactcc tttcgggcat accagcagtc actggaggac    420
tggttggaga acagggatga cgcgcgaaca cgctcggtac tctacaccca gtacatcgct    480
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag acccaatcgg ccggacgaac    900
gcaccctccg gtttcgcatc cacgaattgg ttcaacaaca cgcaccctc cttctcggca    960 atcgaggccg ccgtcatccg ccctcctcac ctgctcgact tccccgagca gctcacgatc   1020
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaacccctt tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cgaacccgac gcgggaagct   1980
gaggaagact tggaagccgc caagaaagcg gtcgccagcc tgtttactcg gacgcgggac   2040
gggctccaag tgaatgtgac ggactatcaa gtggatcagg ccgctaacct cgtgtcatgc   2100
ctgagcgacg agcagtacgg tcacgacaag aaaatgctgc tggaggccgt ccgggccgcc   2160
aagcggctgt ccagggagcg taacctgcta caagatcccg actttaacac gatcaacagc   2220
acagaggaga atggctggaa ggccagcaac ggagttacga taagcgaggg cggtccgttc   2280
tacaagggtc gtgccctcca gctcgcctct gcaagggaga actatccaac ctacatctat   2340
cagaaggtga acgcatccga gcttaagccc tacacacgct accgcctgga cgggttcgtt   2400
aagtccagtc aagacctaga gatagacctc atccaccacc acaaagtgca tctggtcaag   2460
aacgttcccg ataatctcgt gagcgatacc tactcagacg gctcatgctc tggcatgaac   2520
agatgtgagg agcaacagat ggttaatgct caactcgaaa ccgagcatca tcatcctatg   2580
gattgctgcg aggccgcgca gacccatgag ttcagctctt acatcaacac cggagacctc   2640
```

```
aacagtagcg tggatcaggg aatttgggtg gtgcttaaag tgcgtacaac cgacggctac    2700
gccaccctcg gcaaccttga gcttgtcgag gtcggaccac ttagcggcga gtccctggaa    2760
cgtgagcagc gggacaacgc caaatggagc gcagagctag ggcgcaaacg cgcggagacg    2820
gaccgggttt atcaggacgc gaagcagtcc atcaatcacc tcttcgtgga ttatcaggac    2880
cagcagctta atccagagat cggcatggcc gacatcatcg acgcccagaa cctagtagcg    2940
tcgatttccg atgtctattc cgacgccgtg cttcaaatac ctggcatcaa ctacgagatc    3000
tacacagagt tgtccaacag gctccagcaa gcgtcatacc tctacaccag ccgcaacgcc    3060
gtccagaatg gcgacttcaa ttccggacta gactcctgga acgccacggg cggagctacg    3120
gtgcaacaag acggcaacac ccacttcctc gtacttagcc actgggacgc tcaagtgagt    3180
cagcaattcc gggttcagcc gaactgcaag tacgtcctgc gcgtaacggc cgagaaggtt    3240
ggaggcggag acggctacgt taccatccgc gacggcgctc accacaccga gaaactgacg    3300
ttcaacgctt gtgactacga catcaacggc acttacgtga cggacaacac ctacctgacg    3360
aaggaggtgg tgttctattc tcacaccgag cacatgtggg ttgaggtcag cgagaccgag    3420
ggagccttcc acattgacag catcgagttc gtggagactg agaagtga                3468
```

<210> SEQ ID NO 39
<211> LENGTH: 1155
<212> TYPE: PRT
<213> ORGANISM: Artificial
<220> FEATURE:
<223> OTHER INFORMATION: Amino acid sequence of the chimeric protein variant TIC868_12.

<400> SEQUENCE: 39

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205
```

```
Thr Ser Gln Glu Ile Gln Arg Tyr Tyr Glu Arg Gln Val Glu Lys Thr
210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
610                 615                 620

Ile Ser Glu Gln Pro Leu Phe Gly Ala Gly Ser Ile Ser Ser Gly Glu
```

-continued

```
        625                 630                 635                 640
Leu Tyr Ile Asp Lys Ile Glu Ile Ile Leu Ala Asp Ala Thr Asn Pro
                    645                 650                 655
Thr Arg Glu Ala Glu Glu Asp Leu Glu Ala Ala Lys Lys Ala Val Ala
                    660                 665                 670
Ser Leu Phe Thr Arg Thr Arg Asp Gly Leu Gln Val Asn Val Thr Asp
                    675                 680                 685
Tyr Gln Val Asp Gln Ala Ala Asn Leu Val Ser Cys Leu Ser Asp Glu
                    690                 695                 700
Gln Tyr Gly His Asp Lys Lys Met Leu Leu Glu Ala Val Arg Ala Ala
705                 710                 715                 720
Lys Arg Leu Ser Arg Glu Arg Asn Leu Leu Gln Asp Pro Asp Phe Asn
                    725                 730                 735
Thr Ile Asn Ser Thr Glu Asn Gly Trp Lys Ala Ser Asn Gly Val
                    740                 745                 750
Thr Ile Ser Glu Gly Gly Pro Phe Tyr Lys Gly Arg Ala Leu Gln Leu
                    755                 760                 765
Ala Ser Ala Arg Glu Asn Tyr Pro Thr Tyr Ile Tyr Gln Lys Val Asn
                    770                 775                 780
Ala Ser Glu Leu Lys Pro Tyr Thr Arg Tyr Arg Leu Asp Gly Phe Val
785                 790                 795                 800
Lys Ser Ser Gln Asp Leu Glu Ile Asp Leu Ile His His Lys Val
                    805                 810                 815
His Leu Val Lys Asn Val Pro Asp Asn Leu Val Ser Asp Thr Tyr Ser
                    820                 825                 830
Asp Gly Ser Cys Ser Gly Met Asn Arg Cys Glu Glu Gln Met Val
                    835                 840                 845
Asn Ala Gln Leu Glu Thr Glu His His His Pro Met Asp Cys Cys Glu
                    850                 855                 860
Ala Ala Gln Thr His Glu Phe Ser Ser Tyr Ile Asn Thr Gly Asp Leu
865                 870                 875                 880
Asn Ser Ser Val Asp Gln Gly Ile Trp Val Val Leu Lys Val Arg Thr
                    885                 890                 895
Thr Asp Gly Tyr Ala Thr Leu Gly Asn Leu Glu Leu Val Glu Val Gly
                    900                 905                 910
Pro Leu Ser Gly Glu Ser Leu Glu Arg Glu Gln Arg Asp Asn Ala Lys
                    915                 920                 925
Trp Ser Ala Glu Leu Gly Arg Lys Arg Ala Glu Thr Asp Arg Val Tyr
930                 935                 940
Gln Asp Ala Lys Gln Ser Ile Asn His Leu Phe Val Asp Tyr Gln Asp
945                 950                 955                 960
Gln Gln Leu Asn Pro Glu Ile Gly Met Ala Asp Ile Ile Asp Ala Gln
                    965                 970                 975
Asn Leu Val Ala Ser Ile Ser Asp Val Tyr Ser Asp Ala Val Leu Gln
                    980                 985                 990
Ile Pro Gly Ile Asn Tyr Glu Ile Tyr Thr Glu Leu Ser Asn Arg Leu
                    995                 1000                1005
Gln Gln Ala Ser Tyr Leu Tyr Thr Ser Arg Asn Ala Val Gln Asn
        1010                1015                1020
Gly Asp Phe Asn Ser Gly Leu Asp Ser Trp Asn Ala Thr Gly Gly
        1025                1030                1035
Ala Thr Val Gln Gln Asp Gly Asn Thr His Phe Leu Val Leu Ser
        1040                1045                1050
```

His Trp Asp Ala Gln Val Ser Gln Gln Phe Arg Val Gln Pro Asn
1055             1060                 1065

Cys Lys Tyr Val Leu Arg Val Thr Ala Glu Lys Val Gly Gly Gly
    1070            1075                 1080

Asp Gly Tyr Val Thr Ile Arg Asp Gly Ala His His Thr Glu Lys
    1085             1090                1095

Leu Thr Phe Asn Ala Cys Asp Tyr Asp Ile Asn Gly Thr Tyr Val
    1100            1105                 1110

Thr Asp Asn Thr Tyr Leu Thr Lys Glu Val Val Phe Tyr Ser His
    1115            1120                 1125

Thr Glu His Met Trp Val Glu Val Ser Glu Thr Glu Gly Ala Phe
    1130            1135                 1140

His Ile Asp Ser Ile Glu Phe Val Glu Thr Glu Lys
    1145            1150                 1155

<210> SEQ ID NO 40
<211> LENGTH: 3732
<212> TYPE: DNA
<213> ORGANISM: Artificial
<220> FEATURE:
<223> OTHER INFORMATION: Synthetic nucleotide sequence designed for
      expression in a plant cell encoding TIC868_13.

<400> SEQUENCE: 40

```
atgacgagca accggaagaa cgagaacgag atcatcaacg ccctctcgat ccctgctgtt      60
tcaaaccact ccgcgcagat gaacctgtcc accgacgcgc gcatcgagga ctccctctgc     120
atagccgagg gcaacaacat cgacccattc gtgtcggcca gcacggttca gaccggcatc     180
aacatcgcgg gccgtatcct cggcgtcctc ggtgtcccat cgccggtca gatcgcgtcc      240 ttctactcgt tccttgtggg cgagctgtgg cctcgcggtc gtgaccgtg ggagatcttc      300 ctggagcatg tggagcagtt gatccggcag caagtcacgg agaacacccg cgatactgct     360
ctggccaggc tacagggcct gggaaactcc tttcgggcat accagcagtc actggaggac     420
tggttggaga cagggatga cgcgcgaaca cgctcggtac tctacaccca gtacatcgct      480
ctcgaactcg acttcctgaa cgctatgccg ctgttcgcca tcaggaacca ggaagttcca     540
ctccttatgg tgtacgccca ggccgccaac ttacatctgc cctgctgcg ggacgccagc      600 ctgttcggct ccgagttcgg actcacatct caagaaatcc agcgttacta cgagcgccaa     660
gtggagaaga cccgtgagta cagtgactac tgcgctcgat ggtacaacac agggctcaac     720
aacctgcgcg gcaccaacgc tgagtcatgg ctccgttaca accagttccg ccgcgacttg     780
actttgggtg tcctagacct ggtggcgcta ttcccgtctt acgacacacg ggtgtaccca     840
atgaacacta gcgcgcaact cacgcgggag atctacacag cccaatcgg ccggacgaac      900 gcaccctccg gtttcgcatc cacgaattgg ttcaacaaca cgcaccctc cttctcggca     960 atcgaggccg ccgtcatccg ccctcctcac ctgctcgact ttcccgagca gctcacgatc    1020
ttctccgtgc tctcacgctg gtccaacaca cagtacatga ctactgggt cgggcaccga    1080 ttggagagta ggacgatccg tggcagcttg agcaccagta cccacggcaa caccaacacc    1140
tccatcaacc cagttacgct acagttcacg agccgcgacg tttaccggac tgagtcgttc    1200
gcgggcatta acatccttct gacaacgccc gtcaacggcg tcccgtgggc ccggttcaac    1260
tggcgtaacc cgttgaactc cctgcgcggg tcattgctct acaccatcgg gtacacgggc    1320
gtcggcaccc agctcttcga cagtgaaact gagctgccgc ccgagaccac ggaacgcccg    1380
```

```
aactacgagt cctacagcca ccgcctgtcc aacatccggc tcatctctgg caacacgctg    1440
cgtgcgccgg tgtactcctg gacacaccgc agcgccgacc ggaccaacac gatctcttcc    1500
gactccatta accagatccc gctcgtgaag ggcttccgtg tgtggggtgg cacgagcgtc    1560
atcaccggtc cgggcttcac cggtggagac atactgcggc gcaacacttt cggcgacttc    1620
gtttcgttgc aagtgaacat caactcgccg atcacccagc gttaccgtct gaggttccgc    1680
tacgcttcaa gccgcgacgc gagggtcatt gtcctgaccg gagccgcgtc cacaggcgtg    1740
ggaggccaag tctcagtcaa catgcctctc cagaagacga tggagatagg cgagaacttg    1800
actagccgaa ccttccggta cactgatttc tcgaacccct tctcattcag agcgaaccct    1860
gacatcattg ggatctccga gcaaccgctg ttcggtgctg gctccatcag ctctggcgaa    1920
ctgtacatcg acaagattga gatcatcctg gcggatgcga cgacggcgac cttcgaggcg    1980
gagtatgact tggagcgggc tcaggaggcc gtcaacgcgc tgttcacaaa caccaatcct    2040
cgccgcctca agacgggtgt gactgattac cacattgacg aggtctccaa cttggtcgcg    2100
tgtctgtccg atgagttctg cctggacgag aagcggaaac tgctggagaa ggtcaagtac    2160
gccaagcgcc tctccgacga aaggaacctc ctccaagatc ccaactttac ttccattaac    2220
aagcagccga acttcatctc caccaacgag cagtccaact tcacctcaat ccacgagcag    2280
tcggagcacg ggtggtgggg cagcgagaac atcaccatcc aagagggcaa cgacgtcttc    2340
aaggagaact acgtgatcct gcccggcacc ttcaacgagt gttacccgac ctatctctac    2400
cagaagattg gcgaagcgga actcaaggct tacacccgtt accaactgag tggctacatt    2460
gaggactcac aagacctgga aatctacctg atccgctaca cgccaagca cgagaccctc    2520 gacgtgcctg gcacggagtc cgtctggccc ttgagcgtgg agtctcctat cggtcgttgc    2580
ggcgagccca atcgctgcgc tccgcacttt gagtggaatc ctgatttgga ttgctcctgc    2640
cgagacggtg agaaatgcgc ccaccactcg caccacttca gcctagacat cgacgtgggc    2700
tgcatcgacc tgcacgagaa cttgggcgtc tgggtcgtgt tcaagatcaa gacacaggag    2760
ggccatgctc ggcttgggaa cctggagttc atcgaggaga agccactgct gggtgaagcc    2820
ttgtcacggg tgaaacgcgc cgagaagaag tggcgggaca acgggagaa gctccagttg    2880 gagacaaagc gtgtgtacac agaggccaag gaggccgtgg atgccttgtt cgtggacagt    2940
cagtacgaca ggctgcaagc ggacaccaac atcgggatga tccacgcggc tgataagctt    3000
gttcacagaa tccgcgaggc gtacctgtca gagcttagcg tgatcccagg cgtcaacgcc    3060
gaaatcttcg aggaactgga gggccgcatt atcacggcaa tctcactta  tgacgcgagg    3120 aatgtggtca agaacggtga cttcaacaac ggcttggcgt gttggaacgt taagggcac    3180 gtggatgtac aacagtcaca ccacagaagt gtcttggtca tcccggagtg ggaggcggaa    3240
gtgagccagg ccgtccgggt ctgccctggg cgcggttaca tcctccgcgt gacagcgtac    3300
aaggagggct acggtgaggg ctgcgtgacg atccacgaga ttgagaacaa cacggacgag    3360
cttaagttca agaactgcga ggaggaggaa gtgtacccga cagacaccgg cacctgcaac    3420
gactacaccg cccaccaagg gaccgccgcc tgcaacagcc gcaacgcggg ctatgaagat    3480
gcgtacgagt tgataccac cgcctcagtg aactacaaac cgacttatga ggaggagaca    3540
tacacggacg tcaggcgcga caaccattgt gagtacgacc gtggctacgt gaactatccg    3600
ccggtgccag cgggctacat gacgaaggag ctagaatact ccctgagac ggacaaggtg    3660 tggattgaaa tcggcgagac cgagggcaag tttatcgtgg attctgtcga gctgctgcta    3720
atggaggagt ag                                                        3732
```

<210> SEQ ID NO 41
<211> LENGTH: 1243
<212> TYPE: PRT
<213> ORGANISM: Artificial
<220> FEATURE:
<223> OTHER INFORMATION: Amino acid sequence of the chimeric protein variant TIC868_13.

<400> SEQUENCE: 41

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
```

```
            355                 360                 365
Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Thr Ala
                645                 650                 655

Thr Phe Glu Ala Glu Tyr Asp Leu Glu Arg Ala Gln Glu Ala Val Asn
            660                 665                 670

Ala Leu Phe Thr Asn Thr Asn Pro Arg Arg Leu Lys Thr Gly Val Thr
        675                 680                 685

Asp Tyr His Ile Asp Glu Val Ser Asn Leu Val Ala Cys Leu Ser Asp
    690                 695                 700

Glu Phe Cys Leu Asp Glu Lys Arg Glu Leu Leu Glu Lys Val Lys Tyr
705                 710                 715                 720

Ala Lys Arg Leu Ser Asp Glu Arg Asn Leu Leu Gln Asp Pro Asn Phe
                725                 730                 735

Thr Ser Ile Asn Lys Gln Pro Asp Phe Ile Ser Thr Asn Glu Gln Ser
            740                 745                 750

Asn Phe Thr Ser Ile His Glu Gln Ser Glu His Gly Trp Trp Gly Ser
        755                 760                 765

Glu Asn Ile Thr Ile Gln Glu Gly Asn Asp Val Phe Lys Glu Asn Tyr
    770                 775                 780
```

```
Val Ile Leu Pro Gly Thr Phe Asn Glu Cys Tyr Pro Thr Tyr Leu Tyr
785                 790                 795                 800

Gln Lys Ile Gly Glu Ala Glu Leu Lys Ala Tyr Thr Arg Tyr Gln Leu
            805                 810                 815

Ser Gly Tyr Ile Glu Asp Ser Gln Asp Leu Glu Ile Tyr Leu Ile Arg
                820                 825                 830

Tyr Asn Ala Lys His Glu Thr Leu Asp Val Pro Gly Thr Glu Ser Val
            835                 840                 845

Trp Pro Leu Ser Val Glu Ser Pro Ile Gly Arg Cys Gly Glu Pro Asn
850                 855                 860

Arg Cys Ala Pro His Phe Glu Trp Asn Pro Asp Leu Asp Cys Ser Cys
865                 870                 875                 880

Arg Asp Gly Glu Lys Cys Ala His His Ser His His Phe Ser Leu Asp
                885                 890                 895

Ile Asp Val Gly Cys Ile Asp Leu His Glu Asn Leu Gly Val Trp Val
                900                 905                 910

Val Phe Lys Ile Lys Thr Gln Glu Gly His Ala Arg Leu Gly Asn Leu
            915                 920                 925

Glu Phe Ile Glu Lys Pro Leu Leu Gly Glu Ala Leu Ser Arg Val
930                 935                 940

Lys Arg Ala Glu Lys Lys Trp Arg Asp Lys Arg Glu Lys Leu Gln Leu
945                 950                 955                 960

Glu Thr Lys Arg Val Tyr Thr Glu Ala Lys Glu Ala Val Asp Ala Leu
                965                 970                 975

Phe Val Asp Ser Gln Tyr Asp Arg Leu Gln Ala Asp Thr Asn Ile Gly
                980                 985                 990

Met Ile His Ala Ala Asp Lys Leu Val His Arg Ile Arg Glu Ala Tyr
            995                 1000                1005

Leu Ser Glu Leu Ser Val Ile Pro Gly Val Asn Ala Glu Ile Phe
    1010                1015                1020

Glu Glu Leu Glu Gly Arg Ile Ile Thr Ala Ile Ser Leu Tyr Asp
    1025                1030                1035

Ala Arg Asn Val Val Lys Asn Gly Asp Phe Asn Asn Gly Leu Ala
    1040                1045                1050

Cys Trp Asn Val Lys Gly His Val Asp Val Gln Gln Ser His His
    1055                1060                1065

Arg Ser Val Leu Val Ile Pro Glu Trp Glu Ala Glu Val Ser Gln
    1070                1075                1080

Ala Val Arg Val Cys Pro Gly Arg Gly Tyr Ile Leu Arg Val Thr
    1085                1090                1095

Ala Tyr Lys Glu Gly Tyr Gly Glu Gly Cys Val Thr Ile His Glu
    1100                1105                1110

Ile Glu Asn Asn Thr Asp Glu Leu Lys Phe Lys Asn Cys Glu Glu
    1115                1120                1125

Glu Glu Val Tyr Pro Thr Asp Thr Gly Thr Cys Asn Asp Tyr Thr
    1130                1135                1140

Ala His Gln Gly Thr Ala Ala Cys Asn Ser Arg Asn Ala Gly Tyr
    1145                1150                1155

Glu Asp Ala Tyr Glu Val Asp Thr Thr Ala Ser Val Asn Tyr Lys
    1160                1165                1170

Pro Thr Tyr Glu Glu Glu Thr Tyr Thr Asp Val Arg Arg Asp Asn
    1175                1180                1185
```

| His | Cys | Glu | Tyr | Asp | Arg | Gly | Tyr | Val | Asn | Tyr | Pro | Pro | Val | Pro |
|---|---|---|---|---|---|---|---|---|---|---|---|---|---|---|
| 1190 | | | | | 1195 | | | | | 1200 | | | | |

| Ala | Gly | Tyr | Met | Thr | Lys | Glu | Leu | Glu | Tyr | Phe | Pro | Glu | Thr | Asp |
|---|---|---|---|---|---|---|---|---|---|---|---|---|---|---|
| 1205 | | | | | 1210 | | | | | 1215 | | | | |

| Lys | Val | Trp | Ile | Glu | Ile | Gly | Glu | Thr | Glu | Gly | Lys | Phe | Ile | Val |
|---|---|---|---|---|---|---|---|---|---|---|---|---|---|---|
| 1220 | | | | | 1225 | | | | | 1230 | | | | |

| Asp | Ser | Val | Glu | Leu | Leu | Leu | Met | Glu | Glu |
|---|---|---|---|---|---|---|---|---|---|
| 1235 | | | | | 1240 | | | | |

<210> SEQ ID NO 42
<211> LENGTH: 3702
<212> TYPE: DNA
<213> ORGANISM: Artificial
<220> FEATURE:
<223> OTHER INFORMATION: Synthetic nucleotide sequence designed for
      expression in a plant cell encoding TIC868_14.

<400> SEQUENCE: 42

```
atgacgagca accggaagaa cgagaacgag atcatcaacg ccctctcgat ccctgctgtt     60
tcaaaccact ccgcgcagat gaacctgtcc accgacgcgc gcatcgagga ctccctctgc    120
atagccgagg caacaacat cgacccattc gtgtcggcca gcacggttca gaccggcatc     180
aacatcgcgg gccgtatcct cggcgtcctc ggtgtcccat cgccggtca gatcgcgtcc     240
ttctactcgt tccttgtggg cgagctgtgg cctcgcggtc gtgacccgtg ggagatcttc    300
ctggagcatg tggagcagtt gatccggcag caagtcacgg agaacacccg cgatactgct    360
ctggccaggc tacagggcct gggaaactcc tttcgggcat accagcagtc actggaggac    420
tggttggaga cagggatga cgcgcgaaca cgctcggtac tctacaccca gtacatcgct    480
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag cccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc   1020
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
```

| | |
|---|---|
| tacgcttcaa gccgcgacgc gagggtcatt gtcctgaccg gagccgcgtc cacaggcgtg | 1740 |
| ggaggccaag tctcagtcaa catgcctctc cagaagacga tggagatagg cgagaacttg | 1800 |
| actagccgaa ccttccggta cactgatttc tcgaacccct tctcattcag agcgaaccct | 1860 |
| gacatcattg ggatctccga gcaaccgctg ttcggtgctg gctccatcag ctctggcgaa | 1920 |
| ctgtacatcg acaagattga gatcatcctg gcggatgcga cgaccgcgac gtttgaagct | 1980 |
| gaatccgacc tcgagcgtgc gcgcaaggcg gtgaacgctc tgttcacgag caccaaccct | 2040 |
| cgtggcttga agacggatgt gacggactac cacatcgacc aagtctcgaa cctcgtggag | 2100 |
| tgcctgagcg acgagttctg tcttgacaag aagcgcgagc tgctggagga ggtgaagtac | 2160 |
| gccaagcgcc tctccgatga gcgcaacctg ctccaagatc ctaccttcac gtcgatttcc | 2220 |
| ggccaaaccg accgtggatg gatcggctcg actggcatct ccatccaggg cggcgacgac | 2280 |
| atcttcaagg agaactatgt tcggctgccg ggcacggtgg acgagtgtta cccgacgtac | 2340 |
| ctctaccaga agatagacga gagtcaactc aagtcctaca cgcggtatca gttacgtggc | 2400 |
| tacattgaag actcccagga cttggaaatc tatctctatc ggtacaacgc caagcacgag | 2460 |
| accttaagcg tgccgggaac ggagtcgccc tggccaagct ctggcgtgta cccttccggt | 2520 |
| aggtgcggcg agcccaaccg ctgtgcacct cgaatcgaat ggaacccgga ccttgactgc | 2580 |
| tcttgccggt acggcgagaa gtgcgtccat cattctcacc acttcagctt ggacattgac | 2640 |
| gtcggctgca ccgacctcaa tgaagacctc ggagtgtggg tcatcttcaa gatcaagaca | 2700 |
| caggacgggc acgcgaaact aggaaacctg gagttcatcg aggagaagcc actcctcggc | 2760 |
| aaggcacttt ccagggtcaa gcgggccgag aagaaatgga gggacaagta cgagaaactc | 2820 |
| cagctcgaaa caaagcgggt gtacacggag gcaaggaat ccgtggacgc cctgttcgtg | 2880 |
| gactctcagt acgacaagct ccaggcgaac acaaacattg gcatcatcca cggtgcggac | 2940 |
| aagcaagtgc acaggatacg ggagccttac ctctcggagc tgccggtgat tccctcgatc | 3000 |
| aacgcggcga tcttcgagga actggagggc cacatcttca aggcgtattc tctgtacgac | 3060 |
| gcgcgtaacg tcatcaagaa cggcgacttc aacaatgggc tgtcctgctg gaacgttaaa | 3120 |
| ggccacgtcg atgtccagca gaaccaccat aggtcagtcc tggtgctgag cgagtgggag | 3180 |
| gcggaggtgt cccagaaggt gcgcgtgtgc ccggatcgcg gctacatctt gagggtgaca | 3240 |
| gcctacaagg agggctacgg cgagggctgt gtcacgatcc atgagttcga ggacaacacg | 3300 |
| gatgtcctga aattccgtaa cttcgtcgag gaggaggtct atcccaacaa caccgtgacc | 3360 |
| tgcaacgact acacgaccaa tcagtcggct gagggcagta ccgatgcctg caacagctac | 3420 |
| aaccgtggtt acgaagatgg atacgagaac cgctacgagc ccaatccttc ggctcccgtg | 3480 |
| aattacactc ccacgtacga ggagggcatg tacactgaca ctcagggcta caaccattgc | 3540 |
| gtcagcgacc gtggctaccg caaccacacg ccgctcccag cgggctacgt gacgctggag | 3600 |
| ctggaatact ttcccgagac agaacaagtg tggatagaga tcggcgagac cgagggcaca | 3660 |
| ttcatcgtgg gctctgtgga attgctcctc atggaggagt aa | 3702 |

<210> SEQ ID NO 43
<211> LENGTH: 1200
<212> TYPE: PRT
<213> ORGANISM: Artificial
<220> FEATURE:
<223> OTHER INFORMATION: Amino acid sequence of the chimeric protein variant TIC868_14.

<400> SEQUENCE: 43

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
            85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
            165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
    195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
            245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
    275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
            325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
```

```
            420              425              430
Leu Tyr Thr Ile Gly Tyr Thr Gly Val Gly Thr Gln Leu Phe Asp Ser
            435              440              445
Glu Thr Glu Leu Pro Pro Glu Thr Thr Glu Arg Pro Asn Tyr Glu Ser
            450              455              460
Tyr Ser His Arg Leu Ser Asn Ile Arg Leu Ile Ser Gly Asn Thr Leu
465              470              475              480
Arg Ala Pro Val Tyr Ser Trp Thr His Arg Ser Ala Asp Arg Thr Asn
            485              490              495
Thr Ile Ser Ser Asp Ser Ile Asn Gln Ile Pro Leu Val Lys Gly Phe
            500              505              510
Arg Val Trp Gly Gly Thr Ser Val Ile Thr Gly Pro Gly Phe Thr Gly
            515              520              525
Gly Asp Ile Leu Arg Arg Asn Thr Phe Gly Asp Phe Val Ser Leu Gln
            530              535              540
Val Asn Ile Asn Ser Pro Ile Thr Gln Arg Tyr Arg Leu Arg Phe Arg
545              550              555              560
Tyr Ala Ser Ser Arg Asp Ala Arg Val Ile Val Leu Thr Gly Ala Ala
            565              570              575
Ser Thr Gly Val Gly Gly Gln Val Ser Val Asn Met Pro Leu Gln Lys
            580              585              590
Thr Met Glu Ile Gly Glu Asn Leu Thr Ser Arg Thr Phe Arg Tyr Thr
            595              600              605
Asp Phe Ser Asn Pro Phe Ser Phe Arg Ala Asn Pro Asp Ile Ile Gly
            610              615              620
Ile Ser Glu Gln Pro Leu Phe Gly Ala Gly Ser Ile Ser Ser Gly Glu
625              630              635              640
Leu Tyr Ile Asp Lys Ile Glu Ile Ile Leu Ala Asp Ala Thr Thr Ala
            645              650              655
Thr Phe Glu Ala Glu Ser Asp Leu Glu Arg Ala Arg Lys Ala Val Asn
            660              665              670
Ala Leu Phe Thr Ser Thr Asn Pro Arg Gly Leu Lys Thr Asp Val Thr
            675              680              685
Asp Tyr His Ile Asp Gln Val Ser Asn Leu Val Glu Cys Leu Ser Asp
            690              695              700
Glu Phe Cys Leu Asp Lys Lys Arg Glu Leu Leu Glu Glu Val Lys Tyr
705              710              715              720
Ala Lys Arg Leu Ser Asp Glu Arg Asn Leu Leu Gln Asp Pro Thr Phe
            725              730              735
Thr Ser Ile Ser Gly Gln Thr Asp Arg Gly Trp Ile Gly Ser Thr Gly
            740              745              750
Ile Ser Ile Gln Gly Gly Asp Asp Ile Phe Lys Glu Asn Tyr Val Arg
            755              760              765
Leu Pro Gly Thr Val Asp Glu Cys Tyr Pro Thr Tyr Leu Tyr Gln Lys
            770              775              780
Ile Asp Glu Ser Gln Leu Lys Ser Tyr Thr Arg Tyr Gln Leu Arg Gly
785              790              795              800
Tyr Ile Glu Asp Ser Gln Asp Leu Glu Ile Tyr Leu Ile Arg Tyr Asn
            805              810              815
Ala Lys His Glu Thr Leu Ser Val Pro Gly Thr Glu Ser Pro Trp Pro
            820              825              830
Ser Ser Gly Val Tyr Pro Ser Gly Arg Cys Gly Glu Pro Asn Arg Cys
            835              840              845
```

Ala Pro Arg Ile Glu Trp Asn Pro Asp Leu Asp Cys Ser Cys Arg Tyr
850                 855                 860

Gly Glu Lys Cys Val His His Ser His His Phe Ser Leu Asp Ile Asp
865                 870                 875                 880

Val Gly Cys Thr Asp Leu Asn Glu Asp Leu Gly Val Trp Val Ile Phe
                885                 890                 895

Lys Ile Lys Thr Gln Asp Gly His Ala Lys Leu Gly Asn Leu Glu Phe
                900                 905                 910

Ile Glu Glu Lys Pro Leu Leu Gly Lys Ala Leu Ser Arg Val Lys Arg
            915                 920                 925

Ala Glu Lys Lys Trp Arg Asp Lys Tyr Glu Lys Leu Gln Leu Glu Thr
930                 935                 940

Lys Arg Val Tyr Thr Glu Ala Lys Glu Ser Val Asp Ala Leu Phe Val
945                 950                 955                 960

Asp Ser Gln Tyr Asp Lys Leu Gln Ala Asn Thr Asn Ile Gly Ile Ile
                965                 970                 975

His Gly Ala Asp Lys Gln Val His Arg Ile Arg Glu Pro Tyr Leu Ser
            980                 985                 990

Glu Leu Pro Val Ile Pro Ser Ile Asn Ala Ala Ile Phe Glu Glu Leu
        995                 1000                1005

Glu Gly His Ile Phe Lys Ala Tyr Ser Leu Tyr Asp Ala Arg Asn
        1010                1015                1020

Val Ile Lys Asn Gly Asp Phe Asn Asn Gly Leu Ser Cys Trp Asn
        1025                1030                1035

Val Lys Gly His Val Asp Val Gln Gln Asn His His Arg Ser Val
        1040                1045                1050

Leu Val Leu Ser Glu Trp Glu Ala Glu Val Ser Gln Lys Val Arg
        1055                1060                1065

Val Cys Pro Asp Arg Gly Tyr Ile Leu Arg Val Thr Ala Tyr Lys
        1070                1075                1080

Glu Gly Tyr Gly Glu Gly Cys Val Thr Ile His Glu Phe Glu Asp
        1085                1090                1095

Asn Thr Asp Val Leu Lys Phe Arg Asn Phe Val Glu Glu Val
        1100                1105                1110

Tyr Pro Asn Asn Thr Val Cys Asn Asp Tyr Thr Thr Asn Gln
        1115                1120                1125

Ser Ala Glu Gly Ser Thr Asp Ala Cys Asn Ser Tyr Asn Arg Gly
        1130                1135                1140

Tyr Glu Asp Gly Tyr Glu Asn Arg Tyr Glu Pro Asn Pro Ser Ala
        1145                1150                1155

Pro Val Asn Tyr Thr Pro Thr Tyr Glu Glu Gly Met Tyr Thr Asp
        1160                1165                1170

Thr Gln Gly Tyr Asn His Cys Val Ser Asp Arg Gly Tyr Arg Asn
        1175                1180                1185

His Thr Pro Leu Pro Ala Gly Tyr Val Thr Leu Glu
        1190                1195                1200

<210> SEQ ID NO 44
<211> LENGTH: 3687
<212> TYPE: DNA
<213> ORGANISM: Artificial
<220> FEATURE:
<223> OTHER INFORMATION: Synthetic nucleotide sequence designed for
    expression in a plant cell encoding TIC868_15.

```
<400> SEQUENCE: 44
atgacgagca accggaagaa cgagaacgag atcatcaacg ccctctcgat ccctgctgtt      60
tcaaaccact ccgcgcagat gaacctgtcc accgacgcgc gcatcgagga ctccctctgc     120
atagccgagg gcaacaacat cgacccattc gtgtcggcca gcacggttca gaccggcatc     180
aacatcgcgg gccgtatcct cggcgtcctc ggtgtcccat tcgccggtca gatcgcgtcc     240
ttctactcgt tccttgtggg cgagctgtgg cctcgcggtc gtgacccgtg ggagatcttc     300
ctggagcatg tggagcagtt gatccggcag caagtcacgg agaacacccg cgatactgct     360
ctggccaggc tacagggcct gggaaactcc tttcgggcat accagcagtc actggaggac     420
tggttggaga cagggatga cgcgcgaaca cgctcggtac tctacaccca gtacatcgct     480
ctcgaactcg acttcctgaa cgctatgccg ctgttcgcca tcaggaacca ggaagttcca     540
ctccttatgg tgtacgccca ggccgccaac ttacatctgc tcctgctgcg ggacgccagc     600
ctgttcggct ccgagttcgg actcacatct caagaaatcc agcgttacta cgagcgccaa     660
gtggagaaga cccgtgagta cagtgactac tgcgctcgat ggtacaacac agggctcaac     720
aacctgcgcg gcaccaacgc tgagtcatgg ctccgttaca accagttccg ccgcgacttg     780
actttgggtg tcctagacct ggtggcgcta ttcccgtctt acgacacacg ggtgtaccca     840
atgaacacta gcgcgcaact cacgcgggag atctacacag cccaatcgg ccggacgaac      900
gcaccctccg gtttcgcatc cacgaattgg ttcaacaaca acgcaccctc cttctcggca     960
atcgaggccg ccgtcatccg ccctcctcac ctgctcgact ttcccgagca gctcacgatc    1020
ttctccgtgc tctcacgctg gtccaacaca cagtacatga actactgggt cgggcaccga    1080
ttggagagta ggacgatccg tggcagcttg agcaccagta cccacggcaa caccaacacc    1140
tccatcaacc cagttacgct acagttcacg agccgcgacg tttaccggac tgagtcgttc    1200
gcgggcatta acatccttct gacaacgccc gtcaacggcg tcccgtgggc ccggttcaac    1260
tggcgtaacc cgttgaactc cctgcgcggg tcattgctct acaccatcgg gtacacgggc    1320
gtcggcaccc agctcttcga cagtgaaact gagctgccgc ccgagaccac ggaacgcccg    1380
aactacgagt cctacagcca ccgcctgtcc aacatccggc tcatctctgg caacacgctg    1440
cgtgcgccgg tgtactcctg gacacaccgc agcgccgacc ggaccaacac gatctcttcc    1500
gactccatta accagatccc gctcgtgaag ggcttccgtg tgtggggtgg cacgagcgtc    1560
atcaccggtc cgggcttcac cggtggagac atactgcggc gcaacacttt cggcgacttc    1620
gtttcgttgc aagtgaacat caactcgccg atcacccagc gttaccgtct gaggttccgc    1680
tacgcttcaa gccgcgacgc gagggtcatt gtcctgaccg gagccgcgtc cacaggcgtg    1740
ggaggccaag tctcagtcaa catgcctctc cagaagacga tggagatagg cgagaacttg    1800
actagccgaa ccttccggta cactgatttc tcgaacccct tctcattcag agcgaaccct    1860
gacatcattg ggatctccga gcaaccgctg ttcggtgctg gctccatcag ctctggcgaa    1920
ctgtacatcg acaagattga gatcatcctg gcggatgcga cggatgctac ctttgaagca    1980
gagtccgact ggaacgtgc acagaaggca gtgaacgcac tcttcacctc aagcaaccag    2040
atcggattga agacagatgt gacagattac cacatcgacc aagtgagcaa cttggtggat    2100
tgcttgtcag atgagttctg cttggatgag aagcgtgaac tctccgagaa ggtgaagcac    2160
gcaaagcgtc tctcagatga acgtaatctc cttcaagacc ctaactttcg tggtatcaat    2220
cgtcagccaa atcgtggatg gcgtggatca acagacatca ccatccaggg aggcgatgat    2280
gtgttcaagg agaactacgt gaccctccca ggaaccgtgg atgaatgcta cccaacctac    2340
```

```
ctctaccaga agatcgacga gtcaaagctc aaggcttaca cccgttatga actccgtggc    2400
tacatcgaag atagccagga tctcgaaatc tatctcatcc gttacaatgc taagcacgaa    2460
atcgtgaatg tgccaggaac cggctcactc tggccactct cagcacagtc accaatcggc    2520
aagtgcggcg aacccaatcg ctgcgctcct catctcgaat ggaatcccga tctcgactgc    2580
tcctgccgag acggcgagaa gtgtgcacat cactcacacc acttcaccct cgacatcgac    2640
gtgggctgca ccgacctcaa tgaagacctg ggcgtgtggg tgatcttcaa gatcaagacc    2700
caggacggcc acgcacgact gggcaatctg gagtttctgg aggagaagcc actgcttggc    2760
gaggcactgg cacgagtgaa acgagccgag aagaaatggc gagacaaacg tgagaagctg    2820
caactggaga ccaacatcgt gtacaaagag gccaagagt cagttgacgc cctgtttgtc    2880
aatagccagt atgaccgact gcaagttgac accaacatcg ccatgatcca cgctgcggac    2940
aagcgcgtcc accgcatccg cgaggcttat ctgcccgagc tgagcgtcat tcccggcgtc    3000
aatgccgcga tcttcgagga gttagagggc cgcatcttca ccgcctacag cctctatgac    3060
gcccgcaatg tcattaagaa tggcgacttc aacaatggct actatgctg aatgtcaaa     3120
gggcacgttg acgtcgagga gcagaacaat caccgcagcg tcttagtcat acccgagtgg    3180
gaggccgaag tcagccagga agtccgcgtc tgtccagggc gcgggtacat cctgcgggtc    3240
accgcctaca agagggata cggcgagggt tgtgtcacca tacacgagat agaggacaat    3300
accgacgaac tcaagttcag caattgtgtc gaggaggaag tctatcccaa caataccgta    3360
acctgcaaca actacaccgg aacccaggag gagtatgaag ggacgtacac ctcgcggaac    3420
cagggctatg acgaagccta tgggaacaac ccgtcggtgc ctgctgacta tgcgtcggtc    3480
tatgaggaga atcgtacac ggacgggcgg cgggagaatc cgtgtgagtc gaatcgcggg    3540
tatggtgact acacgccgct accggcgggc tatgtaacga aagacctgga atacttcccg    3600
gagacggaca agtatggat agagataggc gagacggagg gaacgttcat cgtggactcg    3660
gtagagctgc tgctcatgga ggagtga                                         3687
```

<210> SEQ ID NO 45
<211> LENGTH: 1228
<212> TYPE: PRT
<213> ORGANISM: Artificial
<220> FEATURE:
<223> OTHER INFORMATION: Amino acid sequence of the chimeric protein
      variant TIC868_15.

<400> SEQUENCE: 45

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

```
Thr Glu Asn Thr Arg Asp Thr Ala Leu Ala Arg Leu Gln Gly Leu Gly
            115                 120                 125
Asn Ser Phe Arg Ala Tyr Gln Gln Ser Leu Glu Asp Trp Leu Glu Asn
        130                 135                 140
Arg Asp Asp Ala Arg Thr Arg Ser Val Leu Tyr Thr Gln Tyr Ile Ala
145                 150                 155                 160
Leu Glu Leu Asp Phe Leu Asn Ala Met Pro Leu Phe Ala Ile Arg Asn
                165                 170                 175
Gln Glu Val Pro Leu Leu Met Val Tyr Ala Gln Ala Ala Asn Leu His
            180                 185                 190
Leu Leu Leu Leu Arg Asp Ala Ser Leu Phe Gly Ser Glu Phe Gly Leu
        195                 200                 205
Thr Ser Gln Glu Ile Gln Arg Tyr Tyr Glu Arg Gln Val Glu Lys Thr
    210                 215                 220
Arg Glu Tyr Ser Asp Tyr Cys Ala Arg Trp Tyr Asn Thr Gly Leu Asn
225                 230                 235                 240
Asn Leu Arg Gly Thr Asn Ala Glu Ser Trp Leu Arg Tyr Asn Gln Phe
                245                 250                 255
Arg Arg Asp Leu Thr Leu Gly Val Leu Asp Leu Val Ala Leu Phe Pro
            260                 265                 270
Ser Tyr Asp Thr Arg Val Tyr Pro Met Asn Thr Ser Ala Gln Leu Thr
        275                 280                 285
Arg Glu Ile Tyr Thr Asp Pro Ile Gly Arg Thr Asn Ala Pro Ser Gly
    290                 295                 300
Phe Ala Ser Thr Asn Trp Phe Asn Asn Asn Ala Pro Ser Phe Ser Ala
305                 310                 315                 320
Ile Glu Ala Ala Val Ile Arg Pro Pro His Leu Leu Asp Phe Pro Glu
                325                 330                 335
Gln Leu Thr Ile Phe Ser Val Leu Ser Arg Trp Ser Asn Thr Gln Tyr
            340                 345                 350
Met Asn Tyr Trp Val Gly His Arg Leu Glu Ser Arg Thr Ile Arg Gly
        355                 360                 365
Ser Leu Ser Thr Ser Thr His Gly Asn Thr Asn Thr Ser Ile Asn Pro
    370                 375                 380
Val Thr Leu Gln Phe Thr Ser Arg Asp Val Tyr Arg Thr Glu Ser Phe
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
            420                 425                 430
Leu Tyr Thr Ile Gly Tyr Thr Gly Val Gly Thr Gln Leu Phe Asp Ser
        435                 440                 445
Glu Thr Glu Leu Pro Pro Glu Thr Thr Glu Arg Pro Asn Tyr Glu Ser
    450                 455                 460
Tyr Ser His Arg Leu Ser Asn Ile Arg Leu Ile Ser Gly Asn Thr Leu
465                 470                 475                 480
Arg Ala Pro Val Tyr Ser Trp Thr His Arg Ser Ala Asp Arg Thr Asn
                485                 490                 495
Thr Ile Ser Ser Asp Ser Ile Asn Gln Ile Pro Leu Val Lys Gly Phe
            500                 505                 510
Arg Val Trp Gly Gly Thr Ser Val Ile Thr Gly Pro Gly Phe Thr Gly
        515                 520                 525
Gly Asp Ile Leu Arg Arg Asn Thr Phe Gly Asp Phe Val Ser Leu Gln
```

-continued

```
            530             535             540
Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                    565                 570                 575

Ser Thr Gly Val Gly Gly Gln Val Ser Val Asn Met Pro Leu Gln Lys
                580                 585                 590

Thr Met Glu Ile Gly Glu Asn Leu Thr Ser Arg Thr Phe Arg Tyr Thr
                595                 600                 605

Asp Phe Ser Asn Pro Phe Ser Phe Arg Ala Asn Pro Asp Ile Ile Gly
            610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Asp Ala
                645                 650                 655

Thr Phe Glu Ala Glu Ser Asp Leu Glu Arg Ala Gln Lys Ala Val Asn
                660                 665                 670

Ala Leu Phe Thr Ser Ser Asn Gln Ile Gly Leu Lys Thr Asp Val Thr
                675                 680                 685

Asp Tyr His Ile Asp Gln Val Ser Asn Leu Val Asp Cys Leu Ser Asp
                690                 695                 700

Glu Phe Cys Leu Asp Glu Lys Arg Glu Leu Ser Glu Lys Val Lys His
705                 710                 715                 720

Ala Lys Arg Leu Ser Asp Glu Arg Asn Leu Leu Gln Asp Pro Asn Phe
                725                 730                 735

Arg Gly Ile Asn Arg Gln Pro Asp Arg Gly Trp Arg Gly Ser Thr Asp
                740                 745                 750

Ile Thr Ile Gln Gly Gly Asp Asp Val Phe Lys Glu Asn Tyr Val Thr
                755                 760                 765

Leu Pro Gly Thr Val Asp Glu Cys Tyr Pro Thr Tyr Leu Tyr Gln Lys
                770                 775                 780

Ile Asp Glu Ser Lys Leu Lys Ala Tyr Thr Arg Tyr Glu Leu Arg Gly
785                 790                 795                 800

Tyr Ile Glu Asp Ser Gln Asp Leu Glu Ile Tyr Leu Ile Arg Tyr Asn
                805                 810                 815

Ala Lys His Glu Ile Val Asn Val Pro Gly Thr Gly Ser Leu Trp Pro
                820                 825                 830

Leu Ser Ala Gln Ser Pro Ile Gly Lys Cys Gly Glu Pro Asn Arg Cys
                835                 840                 845

Ala Pro His Leu Glu Trp Asn Pro Asp Leu Asp Cys Ser Cys Arg Asp
850                 855                 860

Gly Glu Lys Cys Ala His His Ser His His Phe Thr Leu Asp Ile Asp
865                 870                 875                 880

Val Gly Cys Thr Asp Leu Asn Glu Asp Leu Gly Val Trp Val Ile Phe
                885                 890                 895

Lys Ile Lys Thr Gln Asp Gly His Ala Arg Leu Gly Asn Leu Glu Phe
                900                 905                 910

Leu Glu Glu Lys Pro Leu Leu Gly Glu Ala Leu Ala Arg Val Lys Arg
                915                 920                 925

Ala Glu Lys Lys Trp Arg Asp Lys Arg Glu Lys Leu Gln Leu Glu Thr
                930                 935                 940

Asn Ile Val Tyr Lys Glu Ala Lys Glu Ser Val Asp Ala Leu Phe Val
945                 950                 955                 960
```

Asn Ser Gln Tyr Asp Arg Leu Gln Val Asp Thr Asn Ile Ala Met Ile
            965                 970                 975

His Ala Ala Asp Lys Arg Val His Arg Ile Arg Glu Ala Tyr Leu Pro
        980                 985                 990

Glu Leu Ser Val Ile Pro Gly Val Asn Ala Ala Ile Phe Glu Glu Leu
    995                 1000                1005

Glu Gly Arg Ile Phe Thr Ala Tyr Ser Leu Tyr Asp Ala Arg Asn
1010                1015                1020

Val Ile Lys Asn Gly Asp Phe Asn Asn Gly Leu Leu Cys Trp Asn
1025                1030                1035

Val Lys Gly His Val Asp Val Glu Glu Gln Asn Asn His Arg Ser
1040                1045                1050

Val Leu Val Ile Pro Glu Trp Glu Ala Glu Val Ser Gln Glu Val
1055                1060                1065

Arg Val Cys Pro Gly Arg Gly Tyr Ile Leu Arg Val Thr Ala Tyr
1070                1075                1080

Lys Glu Gly Tyr Gly Glu Gly Cys Val Thr Ile His Glu Ile Glu
1085                1090                1095

Asp Asn Thr Asp Glu Leu Lys Phe Ser Asn Cys Val Glu Glu Glu
1100                1105                1110

Val Tyr Pro Asn Asn Thr Val Thr Cys Asn Asn Tyr Thr Gly Thr
1115                1120                1125

Gln Glu Glu Tyr Glu Gly Thr Tyr Thr Ser Arg Asn Gln Gly Tyr
1130                1135                1140

Asp Glu Ala Tyr Gly Asn Asn Pro Ser Val Pro Ala Asp Tyr Ala
1145                1150                1155

Ser Val Tyr Glu Glu Lys Ser Tyr Thr Asp Gly Arg Arg Glu Asn
1160                1165                1170

Pro Cys Glu Ser Asn Arg Gly Tyr Gly Asp Tyr Thr Pro Leu Pro
1175                1180                1185

Ala Gly Tyr Val Thr Lys Asp Leu Glu Tyr Phe Pro Glu Thr Asp
1190                1195                1200

Lys Val Trp Ile Glu Ile Gly Glu Thr Glu Gly Thr Phe Ile Val
1205                1210                1215

Asp Ser Val Glu Leu Leu Leu Met Glu Glu
1220                1225

<210> SEQ ID NO 46
<211> LENGTH: 3600
<212> TYPE: DNA
<213> ORGANISM: Artificial
<220> FEATURE:
<223> OTHER INFORMATION: Synthetic nucleotide sequence designed for
      expression in a plant cell encoding TIC868_29.

<400> SEQUENCE: 46
atgacgagca accggaagaa cgagaacgag atcatcaacg ccctctcgat ccctgctgtt      60
tcaaaccact ccgcgcagat gaacctgtcc accgacgcgc gcatcgagga ctccctctgc     120
atagccgagg caacaacat cgacccattc gtgtcggcca gcacggttca gaccggcatc      180
aacatcgcgg gccgtatcct cggcgtcctc ggtgtcccat cgccggtca gatcgcgtcc      240 ttctactcgt tccttgtggg cgagctgtgg cctcgcggtc gtgaccgtg ggagatcttc      300 ctggagcatg tggagcagtt gatccggcag caagtcacgg agaacaccg cgatactgct      360 ctggccaggc tacagggcct gggaaactcc tttcgggcat accagtactc actggaggac      420

```
tggttggaga acagggatga cgcgcgaaca cgctcggtac tctacaccca gtacatcgct    480
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag acccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc    1020
ttctcccagc tctcacgctg gtcccacaca cagtacatga actactgggt cgggcaccga    1080
ttggagagta ggacgatccg tggcagcttg agcaccagta cccacggcaa caccaacacc    1140
tccatcaacc cagttacgct acagttcacg agccgcgacg tttaccggac tgagtcgttc    1200
gcgggcatta acatccttct gacaacgccc gtcaacggcg tcccgtgggc ccggttcaac    1260
tggcgtaacc cgttgaactc cctgcgcggg tcattgctct acaccatcgg gtacacgggc    1320
gtcggcaccc agctcttcga cagtgaaact gagctgccgc ccgagaccac ggaacgcccg    1380
aactacgagt cctacagcca ccgcctgtcc aacatccggc tcatctctgg caacacgctg    1440
cgtgcgccgg tgtactcctg gacacaccgc agcgccgacc ggaccaacac gatctcttcc    1500
gactccatta ccagatcccc gctcgtgaag ggcttccgtg tgtggggtgg cacgagcgtc    1560
atcaccggtc cgggcttcac cggtggagac atactgcggc gcaacacttt cggcgacttc    1620
gtttcgttgc aagtgaacat caactcgccg atcacccagc gttaccgtct gaggttccgc    1680
tacgcttcaa gccgcgacgc gagggtcatt gtcctgaccg agccgcgtc cacaggcgtg    1740 ggaggccaag tctcagtcaa catgcctctc cagaagacga tggagatagg cgagaacttg    1800
actagccgaa ccttccggta cactgatttc tcgaacccct tctcattcag agcgaaccct    1860
gacatcattg ggatctccga gcaaccgctg ttcggtgctg gctccatcag ctctggcgaa    1920
ctgtacatcg acaagattga gatcatcctg gcggatgcga cgttcgaggc cgagtctgac    1980
ctggagcggg ctcagaaggc tgtcaacgaa ctgttcacca gcagcaacca gattgggctc    2040
aagaccgacg tcacggacta tcacattgac caagtgtcca accttgtgga gtgcctgtcc    2100
gacgagttct gcctcgacga gaagaaggag ctgtccgaga aggtcaaaca cgcgaagcgt    2160
ctgagtgacg agcggaattt gctccaggac ccgaacttcc gtggcatcaa ccgccagctc    2220
gaccgtggtt ggcgcgggag tacagacatc accatccagg gaggcgacga tgtgttcaag    2280
gagaactatg tgacgctgct cgggactttc gacgaatgct acccgacgta tctctaccag    2340 aagatagacag agagtaaatt gaaggcgtac acccgctacc agcttcgcgg gtacatcgag    2400
gatagtcagg acctggaaat ctacctgatc cgatacaacg ccaagcacga gacagtgaac    2460
gtgccaggca cgggctcact ttggccattg agcgctccct ctccaatcgg aaagtgcgct    2520
caccactcgc accacttctc tctggacatc gacgtgggct gcaccgacct caacgaggac    2580
ctgggtgtct gggttatctt caagattaag acccaggacg gacatgcccg cctcggcaac    2640
ctggagttcc ttgaggagaa gcctctcgtg ggcgaggccc tcgctcgtgt gaagcgcgcc    2700
gagaagaaat ggcgagacaa gcgggagaag ctggagtggg agaccaacat cgtgtacaag    2760
```

```
gaggccaagg agtcagtgga cgcactcttc gtcaacagcc agtacgaccg cctccaggct   2820
gacaccaaca tcgccatgat ccacgcggct gacaagcggg tccacagcat ccgtgaggcg   2880
tacctgcccg agctgtcagt gatccctggt gtgaacgcgg cgatcttcga ggaactggag   2940
ggccgcatct tcacagcatt cagcctgtac gatgccagga atgttattaa aaccggtgac   3000
ttcaacaacg ggctgagttg ctggaacgtc aagggccatg tggacgtcga ggagcagaac   3060
aaccaccggt ccgtgctggt cgtgccggag tgggaggcag aggtgagcca ggaggtccgc   3120
gtctgccctg gtcgcggcta catcctccgt gtgactgcgt acaaggaagg ctacggtgaa   3180
ggctgcgtga ctatccacga gatcgagaac aacaccgacg agctcaagtt ctcgaactgt   3240
gtggaggagg aggtgtaccc gaacaacacc gttacttgca acgactacac tgccacgcaa   3300
gaggagtacg agggcactta cacttcccgg aatcgcggct atgatggcgc gtacgagtcc   3360
aacagcagcg tgcctgcgga ttatgcgtcc gcttacgagg agaaggcgta caccgacgga   3420
cggagggaca acccttgcga gtccaaccgt ggctacggtg actacactcc gctgcccgcc   3480
gggtacgtca ccaaggagct ggagtacttc ccggagaccg acaaagtctg gatcgagatc   3540
ggcgagacgg agggcacttt catcgtggac tcggtcgagc tgctactgat ggaggagtga   3600
```

<210> SEQ ID NO 47
<211> LENGTH: 1199
<212> TYPE: PRT
<213> ORGANISM: Artificial
<220> FEATURE:
<223> OTHER INFORMATION: Amino acid sequence of the chimeric protein variant TIC868_29.

<400> SEQUENCE: 47

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Tyr Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
```

```
            210                 215                 220
Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Val Tyr Pro Met Asn Thr Ser Ala Gln Leu Thr
            275                 280                 285

Arg Glu Ile Tyr Thr Asp Pro Ile Gly Arg Thr Asn Ala Pro Ser Gly
            290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Gln Leu Ser Arg Trp Ser His Thr Gln Tyr
                340                 345                 350

Met Asn Tyr Trp Val Gly His Arg Leu Glu Ser Arg Thr Ile Arg Gly
                355                 360                 365

Ser Leu Ser Thr Ser Thr His Gly Asn Thr Asn Thr Ser Ile Asn Pro
            370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
            450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
                500                 505                 510

Arg Val Trp Gly Gly Thr Ser Val Ile Thr Gly Pro Gly Phe Thr Gly
            515                 520                 525

Gly Asp Ile Leu Arg Arg Asn Thr Phe Gly Asp Phe Val Ser Leu Gln
            530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
                580                 585                 590

Thr Met Glu Ile Gly Glu Asn Leu Thr Ser Arg Thr Phe Arg Tyr Thr
            595                 600                 605

Asp Phe Ser Asn Pro Phe Ser Phe Arg Ala Asn Pro Asp Ile Ile Gly
            610                 615                 620

Ile Ser Glu Gln Pro Leu Phe Gly Ala Gly Ser Ile Ser Ser Gly Glu
625                 630                 635                 640
```

```
Leu Tyr Ile Asp Lys Ile Glu Ile Leu Ala Asp Ala Thr Phe Glu
            645                 650                 655

Ala Glu Ser Asp Leu Glu Arg Ala Gln Lys Ala Val Asn Glu Leu Phe
                660                 665                 670

Thr Ser Ser Asn Gln Ile Gly Leu Lys Thr Asp Val Thr Asp Tyr His
                675                 680                 685

Ile Asp Gln Val Ser Asn Leu Val Glu Cys Leu Ser Asp Glu Phe Cys
            690                 695                 700

Leu Asp Glu Lys Lys Glu Leu Ser Lys Val Lys His Ala Lys Arg
705                 710                 715                 720

Leu Ser Asp Glu Arg Asn Leu Leu Gln Asp Pro Asn Phe Arg Gly Ile
                725                 730                 735

Asn Arg Gln Leu Asp Arg Gly Trp Arg Gly Ser Thr Asp Ile Thr Ile
                740                 745                 750

Gln Gly Gly Asp Asp Val Phe Lys Glu Asn Tyr Val Thr Leu Leu Gly
            755                 760                 765

Thr Phe Asp Glu Cys Tyr Pro Thr Tyr Leu Tyr Gln Lys Ile Asp Glu
770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
                805                 810                 815

Glu Thr Val Asn Val Pro Gly Thr Gly Ser Leu Trp Pro Leu Ser Ala
            820                 825                 830

Pro Ser Pro Ile Gly Lys Cys Ala His His Ser His His Phe Ser Leu
            835                 840                 845

Asp Ile Asp Val Gly Cys Thr Asp Leu Asn Glu Asp Leu Gly Val Trp
850                 855                 860

Val Ile Phe Lys Ile Lys Thr Gln Asp Gly His Ala Arg Leu Gly Asn
865                 870                 875                 880

Leu Glu Phe Leu Glu Glu Lys Pro Leu Val Gly Glu Ala Leu Ala Arg
                885                 890                 895

Val Lys Arg Ala Glu Lys Lys Trp Arg Asp Lys Arg Glu Lys Leu Glu
                900                 905                 910

Trp Glu Thr Asn Ile Val Tyr Lys Glu Ala Lys Glu Ser Val Asp Ala
            915                 920                 925

Leu Phe Val Asn Ser Gln Tyr Asp Arg Leu Gln Ala Asp Thr Asn Ile
            930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
                965                 970                 975

Glu Glu Leu Glu Gly Arg Ile Phe Thr Ala Phe Ser Leu Tyr Asp Ala
            980                 985                 990

Arg Asn Val Ile Lys Asn Gly Asp Phe Asn Asn Gly Leu Ser Cys Trp
            995                 1000                1005

Asn Val Lys Gly His Val Asp Val Glu Glu Gln Asn Asn His Arg
        1010                1015                1020

Ser Val Leu Val Val Pro Glu Trp Glu Ala Glu Val Ser Gln Glu
        1025                1030                1035

Val Arg Val Cys Pro Gly Arg Gly Tyr Ile Leu Arg Val Thr Ala
        1040                1045                1050
```

| | | | | | | | | | | |
|---|---|---|---|---|---|---|---|---|---|---|
|Tyr|Lys|Glu|Gly|Tyr|Gly|Glu|Gly|Cys|Val|Thr|Ile|His|Glu|Ile|
| |1055| | | |1060| | | |1065| | | | | |

Tyr Lys Glu Gly Tyr Gly Glu Gly Cys Val Thr Ile His Glu Ile
    1055             1060              1065

Glu Asn Asn Thr Asp Glu Leu Lys Phe Ser Asn Cys Val Glu Glu
    1070             1075              1080

Glu Val Tyr Pro Asn Asn Thr Val Thr Cys Asn Asp Tyr Thr Ala
    1085             1090              1095

Thr Gln Glu Glu Tyr Glu Gly Thr Tyr Thr Ser Arg Asn Arg Gly
    1100             1105              1110

Tyr Asp Gly Ala Tyr Glu Ser Asn Ser Ser Val Pro Ala Asp Tyr
    1115             1120              1125

Ala Ser Ala Tyr Glu Glu Lys Ala Tyr Thr Asp Gly Arg Arg Asp
    1130             1135              1140

Asn Pro Cys Glu Ser Asn Arg Gly Tyr Gly Asp Tyr Thr Pro Leu
    1145             1150              1155

Pro Ala Gly Tyr Val Thr Lys Glu Leu Glu Tyr Phe Pro Glu Thr
    1160             1165              1170

Asp Lys Val Trp Ile Glu Ile Gly Glu Thr Glu Gly Thr Phe Ile
    1175             1180              1185

Val Asp Ser Val Glu Leu Leu Leu Met Glu Glu
    1190             1195

<210> SEQ ID NO 48
<211> LENGTH: 3432
<212> TYPE: DNA
<213> ORGANISM: Artificial
<220> FEATURE:
<223> OTHER INFORMATION: Recombinant nucleotide sequence used
      for expression in a bacterial cell encoding TIC869.

<400> SEQUENCE: 48

```
atggagataa ataatcagaa gcaatgcata ccatataatt gcttaagtaa tcctgaggaa      60
gtacttttgg atggggagag gatattacct gatatcgatc cactcgaagt ttctttgtcg     120
cttttgcaat ttcttttgaa taactttgtt ccagggggag gctttatttc aggattagtt     180
gataaaatat gggggctttg agaccatctg aatgggact tatttcttgc acagattgaa     240
cggttgattg atcaaagaat agaagcaaca gtaagagcaa agcaatcac tgaattagaa     300
ggattaggga gaaattatca atatacgct gaagcattta agaatggga atcagatcct     360
gataacgaag cggctaaaag tagagtaatt gatcgctttc gtatacttga tggtctaatt     420
gaagcaaata tcccttcatt tcggataatt ggatttgaag tgccactttt atcggtttat     480
gttcaagcag ctaatctaca tctcgctcta ttgagagatt ctgttatttt tggagagaga     540
tggggattga cgacaaaaaa tgtcaatgat atctataata gacaaattag agaaattcat     600
gaatatagca atcattgcgt agatacgtat aacacagaac tagaacgtct agggtttaga     660
tctatagcgc agtggagaat atataatcag tttagaagag aactaacact aactgtatta     720
gatattgtcg ctcttttccc gaactatgac agtagactgt atccgatcca aactttttct     780
caattgacaa gagaaattgt tacatcccca gtaagcgaat tttattatgg tgttattaat     840
agtggtaata taattggtac tcttactgaa cagcagataa ggcgaccaca tcttatggac     900
ttctttaact ccatgatcat gtatacatca gataatagag ggaacatta ttggtcagga     960
cttgaaatga cggcttattt tacaggattt gcaggagctc aagtgtcatt ccctttagtc    1020
gggactagag gggagtcagc tccaccatta actgttagaa gtgttaatga tggaattat     1080
agaatattat cggcaccgtt ttattcagcg ccttttctag gcaccattgt attgggaagt    1140
```

```
cgtggagaaa aatttgattt tgcgcttaat aatatttcac ctccgccatc tacaatatac   1200
agacatcctg gaacagtaga ttcactagtc agtataccgc cacaggataa tagcgtacca   1260
ccgcacaggg gatctagtca tcgattaagt catgttacaa tgcgcgcaag ttcccctata   1320
ttccattgga cgcatcgcag cgcaaccact acaaatacaa ttaatccaaa tgctattatc   1380
caaataccac tagtaaaagc atttaacctt cattcaggtg ccactgttgt tagaggacca   1440
gggtttacag gtggagatct cttacgaaga acgaatactg gtacatttgc agacataaga   1500
gtcaatgttc cttcatcact atttccccaa agatatcgcg taaggattcg ttatgcttct   1560
actaccgatt tacaattttt cacgagaatt aatggaactt ctgttaatca aggtaatttc   1620
tcaaaaacga tggatagagg ggataaactg aaatctgaaa actttagaac tgccggattt   1680
agtactcctt ttagattttc aaattttcaa agtacattca cgttgggtac tcaggctttt   1740
tcaaatcagg aagtttatat agatagaatt gaatttgtcc cggcagaagt aacattcgag   1800
gcagaatctg atttagaaag agcacaaaag gcggtgaatg agctgtttac ttcttccaat   1860
caaatcgggt taaaaacaga tgtgacggat tatcatattg atcaagtatc caatttagtt   1920
gagtgtttat ctgatgaatt ttgtctggat gaaaaaaaag aattgtccga gaaagtcaaa   1980
catgcgaagc gacttagtga tgagcggaat ttacttcaag atccaaactt tagagggatc   2040
aatagacaac tagaccgtgg ctggagagga agtacggata ttaccatcca aggaggcgat   2100
gacgtattca aagagaatta cgttacgcta ttgggtacct tgatgagtg ctatccaacg   2160 tatttatatc aaaaaataga tgagtcgaaa ttaaaagcct atacccgtta ccaattaaga   2220
gggtatatcg aagatagtca agacttagaa atctatttaa ttcgctacaa tgccaaacac   2280
gaaacagtaa atgtgccagg tacgggttcc ttatggccgc tttcagcccc aagtccaatc   2340
ggaaaatgtg cccatcattc ccatcatttc tccttggaca ttgatgttgg atgtacagac   2400
ttaaatgagg acttaggtgt atgggtgata ttcaagatta agacgcaaga tggccatgca   2460
agactaggaa atctagaatt tctcgaagag aaaccattag taggagaagc actagctcgt   2520
gtgaaaagag cggagaaaaa atggagagac aaacgtgaaa aattggaatg ggaaacaaat   2580
attgtttata aagaggcaaa agaatctgta gatgctttat ttgtaaactc tcaatatgat   2640
agattacaag cggataccaa catcgcgatg attcatgcgg cagataaacg cgttcatagc   2700
attcgagaag cttatctgcc tgagctgtct gtgattccgg gtgtcaatgc ggctattttt   2760
gaagaattag aagggcgtat tttcactgca ttctccctat atgatgcgag aaatgtcatt   2820
aaaaatggtg attttaataa tggcttatcc tgctggaacg tgaaagggca tgtagatgta   2880
gaagaacaaa acaaccaccg ttcggtcctt gttgttccgg aatgggaagc agaagtgtca   2940
caagaagttc gtgtctgtcc gggtcgtggc tatatccttc gtgtcacagc gtacaaggag   3000
ggatatggag aaggttgcgt aaccattcat gagatcgaga acaatacaga cgaactgaag   3060
tttagcaact gtgtagaaga ggaagtatat ccaaacaaca cggtaacgtg taatgattat   3120
actgcgactc aagaagaata tgagggtacg tacacttctc gtaatcgagg atatgacgga   3180
gcctatgaaa gcaattcttc tgtaccagct gattatgcat cagcctatga agaaaaagca   3240
tatacagatg gacgaagaga caatccttgt gaatctaaca gaggatatgg ggattacaca   3300
ccactaccag ctggctatgt gacaaaagaa ttagagtact ccccagaaac cgataaggta   3360
tggattgaga tcggagaaac ggaaggaaca ttcatcgtgg acagcgtgga attacttctt   3420
atggaggaat ag                                                       3432
```

<210> SEQ ID NO 49
<211> LENGTH: 3432
<212> TYPE: DNA
<213> ORGANISM: Artificial
<220> FEATURE:
<223> OTHER INFORMATION: Synthetic nucleotide sequence designed for
      expression in a plant cell encoding TIC869.

<400> SEQUENCE: 49

| | | | | | |
|---|---|---|---|---|---|
| atggagataa | acaaccagaa | gcagtgcatt | ccgtacaact | gcctcagcaa | cccggaggag | 60 |
| gtgctgctgg | acggcgagcg | tatcctccca | gacatcgacc | cactggaggt | cagcctgagc | 120 |
| ctcctccagt | tcctcctcaa | taacttcgtg | ccaggcggcg | gcttcatctc | cggcctggtg | 180 |
| gacaagatct | ggggcgcact | ccggccaagt | gagtgggatc | tgttcctggc | ccaaatcgag | 240 |
| cgcctgatcg | accagaggat | cgaggcgacg | gtccgcgcca | aggcgataac | cgagctggag | 300 |
| ggcctcggtc | gcaactacca | gatctacgca | gaggcgttca | aggagtggga | gagcgacccg | 360 |
| gacaacgagg | cggccaagtc | tcgggtgatt | gaccgcttcc | gcatcctcga | cggcctcatc | 420 |
| gaagccaaca | tcccttcctt | ccggatcata | ggcttcgaag | tcccgctcct | cagcgtgtac | 480 |
| gtgcaagcgg | ccaatctcca | cctcgcgttg | ctccgtgaca | cgtcatctt | tggcgagaga | 540 |
| tggggcctga | cgacgaagaa | cgtgaacgac | atctacaaca | ggcagatccg | agagattcac | 600 |
| gagtacagca | accactgcgt | ggacacatac | aacacggagc | tggagcggct | cggcttccgc | 660 |
| tcaatcgctc | agtggcggat | ctacaaccag | ttccgccgcg | agctgaccct | caccgtgctc | 720 |
| gacatcgtcg | cattgtttcc | caattacgac | tcacgcctct | acccaatcca | gactttcagc | 780 |
| cagctcacac | gcgagattgt | gaccagcccg | gtgtcagagt | tctactacgg | cgtcatcaac | 840 |
| tcaggcaaca | tcatcgggac | actgactgaa | cagcagatca | gacgtccgca | cttgatggac | 900 |
| ttcttcaact | ccatgattat | gtacacatca | gacaacagga | gagcacta | ctggtccggg | 960 |
| ttggagatga | ctgcttactt | caccggcttc | gccggtgccc | aagtgagctt | cccactggtc | 1020 |
| ggaactcgtg | gcgagtcagc | tcctccgcta | actgtgcgat | ctgtcaacga | cgggatctac | 1080 |
| agaatactgt | cggctcccctt | ctacagtgcg | ccgttcctcg | gcaccatcgt | cctcggctca | 1140 |
| cgtggtgaga | agttcgactt | cgcactgaac | aacattagcc | cgccgcctag | tacaatctac | 1200 |
| aggcaccctg | gcaccgtgga | ctcactggtt | tcgatcccgc | acaagacaa | cagtgtgccg | 1260 |
| ccacatcgtg | gttctagcca | caggctctcc | catgtgacca | tgcgcgcctc | ttcaccgatc | 1320 |
| tttcactgga | cccatcggtc | cgctacaacc | acaaacacca | tcaaccctaa | cgccatcatc | 1380 |
| caaatcccgc | tggtgaaggc | gtttaacctc | cacagcggcg | caactgtcgt | gcgcggccct | 1440 |
| ggattcaccg | gtggtgacct | gctccgtcgg | accaatactg | gcacgttcgc | agacatccga | 1500 |
| gtgaacgtcc | cgtcctcgct | gttcagtcag | cgctaccgtg | tccgcattcg | gtacgcttcc | 1560 |
| accacggatc | tccagttctt | tactcgcatc | aatgggacga | gcgtcaacca | gggcaacttc | 1620 |
| agcaagacga | tggaccgtgg | agataagctc | aagtccgaga | acttccgcac | ggctggcttc | 1680 |
| tcgacaccgt | tcagattcag | caacttccag | agcactttca | cgctgggcac | acaggcgttc | 1740 |
| tccaaccagg | aggtgtacat | cgaccgcatc | gagttcgtgc | ctgctgaggt | taccttcgag | 1800 |
| gcggaaagcg | acctcgaaag | ggcccagaag | gccgtcaacg | agctgttcac | ctccagcaac | 1860 |
| cagatcggtc | tcaagaccga | cgtcactgac | tatcacattg | accaagtcag | caacctggtg | 1920 |
| gagtgcctca | gtgatgagtt | ctgcctggat | gagaagaagg | agcttagcga | gaaggtcaag | 1980 |
| cacgcaaagc | gcttgagcga | cgagcgcaac | cttctccagg | acccgaattt | ccgtggtatc | 2040 |
| aatagacagc | ttgaccgtgg | gtggcgcggt | agtaccgaca | taaccatcca | gggtggcgac | 2100 |

-continued

```
gatgtgttca aggagaatta tgttacgctg ctcggtacgt tcgacgagtg ctatcccacg    2160
tacttgtacc agaagattga cgagagcaag ctcaaggcgt acacccgtta ccagctccgt    2220
ggctacatcg aggacagcca ggatctggaa atctacctta tccgatacaa tgctaagcac    2280
gagacagtca acgtgcccgg aacagggtcg ctctggccgc tcagtgctcc gtcgcccatt    2340
ggcaagtgcg cgcaccattc gcatcacttc tcacttgaca ttgacgtggg ctgcaccgac    2400
ctgaacgagg atctgggtgt ctgggtcatc ttcaagatca agacccaaga cggccacgcg    2460
cgcctcggga acctggagtt cctggaggag aagcctttgg taggtgaagc cctggcccgc    2520
gtcaagcgcg cggagaagaa gtggcgcgac aagagggaga agctggaatg ggagaccaac    2580
atcgtgtaca aggaggcgaa ggagtcggtg gacgcactat tcgtgaactc ccagtacgac    2640
cgtctccagg ccgacaccaa catcgccatg atccacgccg ctgacaaacg agttcattcc    2700
attcgtgaag cctatcttcc cgagctgtct gtcataccgg gcgtcaacgc ggccatcttc    2760
gaggagttag agggtcggat ctttacagct ttctcactgt acgatgcccg caacgtcatc    2820
aagaacggcg acttcaacaa cggtctctcc tgttggaacg tgaagggcca cgtggatgtc    2880
gaggagcaga caaccaccg ctctgtgctt gtggtgcccg agtgggaggc cgaggtgagc    2940
caggaggtcc gcgtctgtcc gggtcgcggc tacatcctgc gggtcaccgc ctacaaggag    3000
ggctacggcg aaggctgcgt tactattcac gagattgaga caataccga cgaactcaag    3060
ttctccaact gtgtcgagga ggaggtgtac ccgaacaaca ccgtgacgtg caacgactac    3120
accgcgacac aggaggaata cgagggcacc tacaccagcc gcaaccgagg ctacgacgga    3180
gcgtacgaga gcaactcgtc cgtgcccgct gattacgcga gtgcgtacga ggagaaggct    3240
tacaccgacg gacggcgcga caatccctgc gagagtaacc gtggatacgg agattacacg    3300
ccgctacccg ctggctacgt cactaaggaa ctggagtact cccagagac ggacaaggtg    3360
tggatcgaaa tcggcgagac agagggcacg ttcatcgtgg actccgtgga gctgctgctg    3420
atggaggagt ga                                                       3432
```

<210> SEQ ID NO 50
<211> LENGTH: 1143
<212> TYPE: PRT
<213> ORGANISM: Artificial
<220> FEATURE:
<223> OTHER INFORMATION: Amino acid sequence of the chimeric protein
    TIC869.

<400> SEQUENCE: 50

```
Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Thr Glu Leu Glu Gly Leu Gly Arg Asn Tyr Gln Ile Tyr Ala Glu Ala
            100                 105                 110
```

```
Phe Lys Glu Trp Glu Ser Asp Pro Asp Asn Glu Ala Ala Lys Ser Arg
            115                 120                 125

Val Ile Asp Arg Phe Arg Ile Leu Asp Gly Leu Ile Glu Ala Asn Ile
130                 135                 140

Pro Ser Phe Arg Ile Ile Gly Phe Glu Val Pro Leu Leu Ser Val Tyr
145                 150                 155                 160

Val Gln Ala Ala Asn Leu His Leu Ala Leu Leu Arg Asp Ser Val Ile
                165                 170                 175

Phe Gly Glu Arg Trp Gly Leu Thr Thr Lys Asn Val Asn Asp Ile Tyr
            180                 185                 190

Asn Arg Gln Ile Arg Glu Ile His Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Ile Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Leu Leu Arg Arg Thr Asn Thr Gly Thr Phe
                485                 490                 495

Ala Asp Ile Arg Val Asn Val Pro Ser Ser Leu Phe Ser Gln Arg Tyr
            500                 505                 510

Arg Val Arg Ile Arg Tyr Ala Ser Thr Thr Asp Leu Gln Phe Phe Thr
        515                 520                 525

Arg Ile Asn Gly Thr Ser Val Asn Gln Gly Asn Phe Ser Lys Thr Met
```

```
                530             535             540
Asp Arg Gly Asp Lys Leu Lys Ser Glu Asn Phe Arg Thr Ala Gly Phe
545                 550                 555                 560

Ser Thr Pro Phe Arg Phe Ser Asn Phe Gln Ser Thr Phe Thr Leu Gly
                565                 570                 575

Thr Gln Ala Phe Ser Asn Gln Glu Val Tyr Ile Asp Arg Ile Glu Phe
                580                 585                 590

Val Pro Ala Glu Val Thr Phe Glu Ala Glu Ser Asp Leu Glu Arg Ala
            595                 600                 605

Gln Lys Ala Val Asn Glu Leu Phe Thr Ser Ser Asn Gln Ile Gly Leu
        610                 615                 620

Lys Thr Asp Val Thr Asp Tyr His Ile Asp Gln Val Ser Asn Leu Val
625                 630                 635                 640

Glu Cys Leu Ser Asp Glu Phe Cys Leu Asp Lys Lys Glu Leu Ser
                645                 650                 655

Glu Lys Val Lys His Ala Lys Arg Leu Ser Asp Glu Arg Asn Leu Leu
            660                 665                 670

Gln Asp Pro Asn Phe Arg Gly Ile Asn Arg Gln Leu Asp Arg Gly Trp
        675                 680                 685

Arg Gly Ser Thr Asp Ile Thr Ile Gln Gly Gly Asp Asp Val Phe Lys
690                 695                 700

Glu Asn Tyr Val Thr Leu Leu Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Gln Leu Arg Gly Tyr Ile Glu Asp Ser Gln Asp Leu Glu Ile Tyr
            740                 745                 750

Leu Ile Arg Tyr Asn Ala Lys His Glu Thr Val Asn Val Pro Gly Thr
        755                 760                 765

Gly Ser Leu Trp Pro Leu Ser Ala Pro Ser Pro Ile Gly Lys Cys Ala
770                 775                 780

His His Ser His His Phe Ser Leu Asp Ile Asp Val Gly Cys Thr Asp
785                 790                 795                 800

Leu Asn Glu Asp Leu Gly Val Trp Val Ile Phe Lys Ile Lys Thr Gln
                805                 810                 815

Asp Gly His Ala Arg Leu Gly Asn Leu Glu Phe Leu Glu Glu Lys Pro
            820                 825                 830

Leu Val Gly Glu Ala Leu Ala Arg Val Lys Arg Ala Glu Lys Lys Trp
        835                 840                 845

Arg Asp Lys Arg Glu Lys Leu Glu Trp Glu Thr Asn Ile Val Tyr Lys
850                 855                 860

Glu Ala Lys Glu Ser Val Asp Ala Leu Phe Val Asn Ser Gln Tyr Asp
865                 870                 875                 880

Arg Leu Gln Ala Asp Thr Asn Ile Ala Met Ile His Ala Ala Asp Lys
                885                 890                 895

Arg Val His Ser Ile Arg Glu Ala Tyr Leu Pro Glu Leu Ser Val Ile
            900                 905                 910

Pro Gly Val Asn Ala Ala Ile Phe Glu Glu Leu Glu Gly Arg Ile Phe
        915                 920                 925

Thr Ala Phe Ser Leu Tyr Asp Ala Arg Asn Val Ile Lys Asn Gly Asp
930                 935                 940

Phe Asn Asn Gly Leu Ser Cys Trp Asn Val Lys Gly His Val Asp Val
945                 950                 955                 960
```

Glu Glu Gln Asn Asn His Arg Ser Val Leu Val Val Pro Glu Trp Glu
                965                 970                 975

Ala Glu Val Ser Gln Glu Val Arg Val Cys Pro Gly Arg Gly Tyr Ile
            980                 985                 990

Leu Arg Val Thr Ala Tyr Lys Glu Gly Tyr Gly Glu Gly Cys Val Thr
        995                1000                1005

Ile His Glu Ile Glu Asn Asn Thr Asp Glu Leu Lys Phe Ser Asn
    1010                1015                1020

Cys Val Glu Glu Glu Val Tyr Pro Asn Asn Thr Val Thr Cys Asn
    1025                1030                1035

Asp Tyr Thr Ala Thr Gln Glu Glu Tyr Glu Gly Thr Tyr Thr Ser
    1040                1045                1050

Arg Asn Arg Gly Tyr Asp Gly Ala Tyr Glu Ser Asn Ser Ser Val
    1055                1060                1065

Pro Ala Asp Tyr Ala Ser Ala Tyr Glu Glu Lys Ala Tyr Thr Asp
    1070                1075                1080

Gly Arg Arg Asp Asn Pro Cys Glu Ser Asn Arg Gly Tyr Gly Asp
    1085                1090                1095

Tyr Thr Pro Leu Pro Ala Gly Tyr Val Thr Lys Glu Leu Glu Tyr
    1100                1105                1110

Phe Pro Glu Thr Asp Lys Val Trp Ile Glu Ile Gly Glu Thr Glu
    1115                1120                1125

Gly Thr Phe Ile Val Asp Ser Val Glu Leu Leu Leu Met Glu Glu
    1130                1135                1140

<210> SEQ ID NO 51
<211> LENGTH: 3513
<212> TYPE: DNA
<213> ORGANISM: Artificial
<220> FEATURE:
<223> OTHER INFORMATION: Recombinant nucleotide sequence used
      for expression in a bacterial cell encoding TIC836.

<400> SEQUENCE: 51
atggagaata tattcaaaa tcaatgcgta ccttacaatt gtttaaataa tcctgaagta      60
gaaatattaa atgaagaaag aagtactggc agattaccgt tagatatatc cttatcgctt    120 acacgttttcc ttttgagtga atttgttcca ggtgtgggag ttgcgtttgg attatttgat   180
ttaatatggg gttttataac tccttctgat tggagcttat ttcttttaca gattgaacaa   240
ttgattgagc aaagaataga acattggaa aggaaccggg caattactac attacgaggg   300
ttagcagata gctatgaaat ttatattgaa gcactaagag agtgggaagc aaatcctaat   360
aatgcacaat taagggaaga tgtgcgtatt cgatttgcta atacagacga cgctttaata   420
acagcaataa ataatttttac acttacaagt tttgaaatcc ctcttttatc ggtctatgtt   480
caagcggcga atttacattt atcactatta agagacgctg tatcgtttgg gcagggttgg   540
ggactggata tagctactgt taataatcat tataatagat aataaatct tattcataga    600 tatacgaaac attgtttgga cacatacaat caaggattag aaaacttaag aggtactaat   660
actcgacaat gggcaagatt caatcagttt aggagagatt taacacttac tgtattagat   720
atcgttgctc tttttccgaa ctacgatgtt agaacatatc caattcaaac gtcatcccaa   780
ttaacaaggg aaatttatac aagttcagta attgaggatt ctccagtttc tgctaatata   840
cctaatggtt ttaatagggc ggaatttgga gttagaccgc ccatcttat ggactttatg    900 aattctttgt ttgtaactgc agagactgtt agaagtcaaa ctgtgtgggg aggacactta   960

```
gttagttcac gaaatacggc tggtaaccgt ataaatttcc ctagttacgg ggtcttcaat    1020
cctggtggcg ccatttggat tgcagatgag gatccacgtc cttttttatcg gacattatca    1080 gatcctgttt ttgtccgagg aggatttggg aatcctcatt atgtactggg gcttagggga    1140
gtagcatttc aacaaactgg tacgaaccac acccgaacat ttagaaatag tgggaccata    1200
gattctctag atgaaatccc acctcaggat aatagtgggg caccttggaa tgattatagt    1260
catgtattaa atcatgttac atttgtacga tggccaggtg agatttcagg aagtgattca    1320
tggagagctc caatgttttc ttggacgcac cgtagtgcaa cccctacaaa tacaattgat    1380
ccggagagga ttacacaaat acctttaaca aaatctacta atcttggctc tggaacttct    1440
gtcgttaaag gaccaggatt tacaggagga gatattcttc gaagaacttc acctggccag    1500
atttcaacct taagagtaaa tattactgca ccattatcac aaagatatcg ggtaagaatt    1560
cgctacgctt ctaccacaaa tttacaattc catacatcaa ttgacggaag acctattaat    1620
caggggaatt tttcagcaac tatgagtagt gggagtaatt tacagtccgg aagctttagg    1680
actgtaggtt ttactactcc gtttaacttt tcaaatggat caagtgtatt tacgttaagt    1740
gctcatgtct tcaattcagg caatgaagtt tatatagatc gaattgaatt tgttccggca    1800
gaagtaacct ttgaggcaga atatgattta gaaagagcgc agaaggcggt gaatgcgctg    1860
tttacgtcta caaaccaact agggctaaaa acaaatgtaa cggattatca tattgatcaa    1920
gtgtccaatt tagttacgta tttatcggat gaattttgtc tggatgaaaa gcgagaattg    1980
tccgagaaag tcaaacatgc gaagcgactc agtgatgaac gcaatttact ccaagattca    2040
aatttcaaag acattaatag gcaaccagaa cgtgggtggg gcggaagtac agggattacc    2100
atccaaggag gggatgacgt atttaaagaa aattacgtca cactatcagg tacctttgat    2160
gagtgctatc caacatattt gtatcaaaaa atcgatgaat caaaattaaa agcctttacc    2220
cgttatcaat taagagggta tatcgaagat agtcaagact tagaaatcta tttaattcgc    2280
tacaatgcaa aacatgaaac agtaaatgtg ccaggtacgg gttccttatg gccgctttca    2340
gcccaaagtc caatcggaaa gtgtggagag ccgaatcgat gcgcgccaca ccttgaatgg    2400
aatcctgact tagattgttc gtgtagggat ggagaaaagt gtgcccatca ttcgcatcat    2460
ttctccttag acattgatgt aggatgtaca gacttaaatg aggacctagg tgtatgggtg    2520
atctttaaga ttaagacgca agatgggcac gcaagactag ggaatctaga gtttctcgaa    2580
gaaaaaccat tagtaggaga agcgctagct cgtgtgaaaa gagcggagaa aaaatggaga    2640
gacaaacgtg aaaaattgga atgggaaaca aatatcgttt ataaagaggc aaaagaatct    2700
gtagatgctt tatttgtaaa ctctcaatat gatcaattac aagcggatac gaatattgcc    2760
atgattcatg cggcagataa acgtgttcat agcattcgag aagcttatct gcctgagctg    2820
tctgtgattc cgggtgtcaa tgcggctatt tttgaagaat tagaagggcg tattttcact    2880
gcattctccc tatatgatgc gagaaatgtc attaaaaatg gtgattttaa taatggctta    2940
tcctgctgga cgtgaaaggg gcatgtagat gtagaagaac aaaacaacca acgttcggtc    3000
cttgttgttc cggaatggga agcagaagtg tcacaagaag ttcgtgtctg tccgggtcgt    3060
ggctatatcc ttcgtgtcac agcgtacaag gagggatatg gagaaggttg cgtaaccatt    3120
catgagatcg agaacaatac agacgaactg aagtttagca actgcgtaga ggaggaaatc    3180
tatccaaata acacggtaac gtgtaatgat tatactgtaa atcaagaaga atacggaggt    3240
gcgtacactt ctcgtaatcg aggatataac gaagctcctt ccgtaccagc tgattatgcg    3300
```

```
tcagtctatg aagaaaaatc gtatacagat ggacgtagag agaatccttg tgaatttaac      3360
agagggtata gggattacac gccactacca gttggttatg tgacaaaaga attagaatac      3420
ttcccagaaa ccgataaggt atggattgag attggagaaa cggaaggaac atttatcgtg      3480
gacagcgtgg aattactcct tatggaggaa taa                                   3513
```

<210> SEQ ID NO 52
<211> LENGTH: 3513
<212> TYPE: DNA
<213> ORGANISM: Artificial
<220> FEATURE:
<223> OTHER INFORMATION: Synthetic nucleotide sequence designed for
      expression in a plant cell encoding TIC836.

<400> SEQUENCE: 52

```
atggagaaca acatccagaa ccagtgcgtg ccctacaact gcctgaacaa ccctgaggtt        60
gagatcctga cgaggagcg tagcaccggt aggctcccgc tagacatctc cctgagcctg       120
acccgcttcc tccttagtga gttcgtgccc ggcgtgggcg tggccttcgg cctcttcgac       180
ctcatctggg gcttcatcac tccttccgac tggtccctct tcctccttca gattgagcaa       240
ctgatcgagc agcgcatcga gacccttgag cgcaaccgcg ccatcaccac tctcagaggt       300
ctcgccgact cctacgaaat ctacatcgag gcactccgtg agtgggaggc caacccgaac       360
aatgcccagc tccgcgagga cgtgaggatc agattcgcca acaccgacga tgccctcatc       420
accgccatca acaatttcac cctcacctcc ttcgagatcc ctcttctgtc tgtgtacgtt       480
caagctgcta accttcacct ttccctcctg cgcgacgccg tgagcttcgg ccagggctgg       540
ggcctcgaca tcgccaccgt gaacaatcac tacaaccgcc tcatcaacct catccaccgc       600
tacaccaagc actgccttga cacctacaac cagggcttg agaacctccg tgcaccaac        660 acccgccagt gggcccgctt caaccagttc cgcagagacc tcaccctcac cgtgctcgac       720
atcgtggcac tcttcccaaa ctacgacgtg cgtacctacc ctatccagac ctccagccag       780
ctcaccaggg aaatctacac ctccagcgtg atcgaggact ctcctgtgtc cgccaacatc       840
cctaacggct caaccgcgc cgagttcggc gtgcgccctc ctcacctcat ggacttcatg       900
aactccctct tcgtcactgc cgagaccgtg cgctcccaga ccgtgtgggg cggtcacctc       960
gtgtccagcc gtaacaccgc tggcaacagg atcaacttcc cgtcctacgg cgtgttcaac      1020
ccaggcggtg ccatctggat cgccgatgaa gaccctcgtc ctttctaccg taccctgtcc      1080
gaccctgtgt tcgtgcgtgg cggtttcggc aaccctcact acgtgctggg cctgcgtggc      1140
gtggccttcc agcaaaccgg caccaaccac accaggacgt tccgtaactc cggcaccatc      1200
gacagtcttg acgagatccc tccgcaagac aactccggtg caccttggaa cgactactcc      1260
cacgtgctga ccacgtgac cttcgtgagg tggcctggcg aaatctccgg ctccgactcc      1320
tggagggctc ctatgttcag ttggacccac aggagcgcta cgcctaccaa caccatcgac      1380
cctgagcgta tcactcagat ccctctgact aagagcacta acctgggcag cggcactagc      1440
gtggtcaagg gccctggctt cactggcggt gacatcctga ggcggactag ccctggccag      1500
atcagcactc tgagggtgaa catcactgct ccgctgagcc agcgttacag ggtcagaatc      1560
cgttacgctt ctactactaa ccttcagttc cacactagca tcgacggccg tccgatcaac      1620
cagggcaact tctctgctac tatgagttct ggcagtaacc tccagtctgg tagtttccgg      1680
actgtcggtt tcactacgcc gttcaacttc tccaacggta gttctgtctt cactctgtct      1740
gctcacgtgt tcaactctgg caacgagtg tacatcgacc ggatcgagtt cgtccctgct      1800
```

```
gaggtgacgt tcgaggccga gtacgacctg agcgggctc agaaggctgt caacgctctg    1860
ttcacttcta ctaaccagct tggtttgaag actaacgtga ccgactacca cattgatcaa    1920
gtcagtaacc tggtcacgta cctgtctgac gagttctgtc ttgacgagaa gcgggagctg    1980
tctgagaagg tcaagcacgc taagcggctg tctgacgagc ggaacctgct tcaagacagt    2040
aacttcaagg acattaaccg ccagcctgag cgtggttggg gagggtccac gggtattacg    2100
attcaaggag gtgacgatgt ctttaaggag aactatgtga cgctttcggg tacgtttgat    2160
gagtgctatc caacgtacct ttaccagaag attgacgagt cgaagctgaa ggctttcact    2220
cgttaccagc ttcgtggtta cattgaggac tcgcaagacc tcgaaatcta cctcattcgt    2280
tacaacgcta agcacgagac tgtcaacgtc cctggtacgg gtagtctttg gccgctttct    2340
gctcagtcgc cgattggcaa gtgtggcgag ccgaaccgtt gcgctcctca cttggagtgg    2400
aacccggatc tcgattgctc gtgccgtgac ggtgagaagt gcgcgcacca tagtcatcac    2460
tttagccttg acattgatgt cggttgcacg gatcttaacg aggatcttgg agtctgggtg    2520
attttcaaga tcaaaactca ggatgggcac gcgcgtcttg ggaatcttga gttcctggag    2580
gagaagccac ttgtcggtga ggcgcttgcg cgtgtcaagc gtgcggagaa gaaatggcgt    2640
gataagcgtg agaagttgga gtgggagacg aacatcgtgt acaaggaggc gaaggagtcg    2700
gtcgatgcgt tgtttgtcaa tagtcaaatac gatcaattgc aagcggatac gaacatcgca    2760
atgattcatg cggcagataa gcgtgtccat tcgattcgtg aggcgtactt gccagagttg    2820
tcggtcatcc caggagttaa tgcggcaatc tttgaggaat tggagggcag aatcttcacg    2880
gcgttctcgt tgtacgatgc aagaaatgtt attaagaatg agatttcaa caatgggttg    2940 tcatgctgga atgttaaggg tcacgttgat gttgaagaac agaacaacca gagatcagtg    3000
ttggttgtac cagagtggga ggcagaggtt cacaagagg tgagagtttg cccaggcaga    3060
ggctacatct tgagagttac agcatacaaa gagggatacg gcgagggatg tgttacaatc    3120
cacgaaatcg agaacaatac cgatgagcta aagttctcaa attgtgttga ggaggagatc    3180 taccccgaaca acacggttac ttgtaatgat tacacagtga accaggagga gtatggtggt    3240
gcatacacat caagaaatag aggctacaat gaagcaccat cagttccagc agattatgcc    3300
tcagtttatg aggagaagtc atacacagat ggacgacgtg agaatccatg tgagttcaat    3360
cgaggatacc gagattacac accactacca gttggatacg ttacaaagga actagaaatac    3420 ttcccagaaa cagataaagt atggatagag atcggagaaa cagaaggaac attcatcgtt    3480
gattcagtag aactactact tatggaagaa tga                                 3513
```

<210> SEQ ID NO 53
<211> LENGTH: 1170
<212> TYPE: PRT
<213> ORGANISM: Artificial
<220> FEATURE:
<223> OTHER INFORMATION: Amino acid sequence of the chimeric protein
      TIC836.

<400> SEQUENCE: 53

Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly

-continued

```
            50                  55                  60
Phe Ile Thr Pro Ser Asp Trp Ser Leu Phe Leu Gln Ile Glu Gln
 65                  70                  75                  80
Leu Ile Glu Gln Arg Ile Glu Thr Leu Glu Arg Asn Arg Ala Ile Thr
                 85                  90                  95
Thr Leu Arg Gly Leu Ala Asp Ser Tyr Glu Ile Tyr Ile Glu Ala Leu
            100                 105                 110
Arg Glu Trp Glu Ala Asn Pro Asn Asn Ala Gln Leu Arg Glu Asp Val
            115                 120                 125
Arg Ile Arg Phe Ala Asn Thr Asp Asp Ala Leu Ile Thr Ala Ile Asn
            130                 135                 140
Asn Phe Thr Leu Thr Ser Phe Glu Ile Pro Leu Leu Ser Val Tyr Val
145                 150                 155                 160
Gln Ala Ala Asn Leu His Leu Ser Leu Leu Arg Asp Ala Val Ser Phe
                165                 170                 175
Gly Gln Gly Trp Gly Leu Asp Ile Ala Thr Val Asn Asn His Tyr Asn
                180                 185                 190
Arg Leu Ile Asn Leu Ile His Arg Tyr Thr Lys His Cys Leu Asp Thr
                195                 200                 205
Tyr Asn Gln Gly Leu Glu Asn Leu Arg Gly Thr Asn Thr Arg Gln Trp
210                 215                 220
Ala Arg Phe Asn Gln Phe Arg Arg Asp Leu Thr Leu Thr Val Leu Asp
225                 230                 235                 240
Ile Val Ala Leu Phe Pro Asn Tyr Asp Val Arg Thr Tyr Pro Ile Gln
                245                 250                 255
Thr Ser Ser Gln Leu Thr Arg Glu Ile Tyr Thr Ser Ser Val Ile Glu
                260                 265                 270
Asp Ser Pro Val Ser Ala Asn Ile Pro Asn Gly Phe Asn Arg Ala Glu
                275                 280                 285
Phe Gly Val Arg Pro Pro His Leu Met Asp Phe Met Asn Ser Leu Phe
                290                 295                 300
Val Thr Ala Glu Thr Val Arg Ser Gln Thr Val Trp Gly Gly His Leu
305                 310                 315                 320
Val Ser Ser Arg Asn Thr Ala Gly Asn Arg Ile Asn Phe Pro Ser Tyr
                325                 330                 335
Gly Val Phe Asn Pro Gly Gly Ala Ile Trp Ile Ala Asp Glu Asp Pro
                340                 345                 350
Arg Pro Phe Tyr Arg Thr Leu Ser Asp Pro Val Phe Val Arg Gly Gly
                355                 360                 365
Phe Gly Asn Pro His Tyr Val Leu Gly Leu Arg Gly Val Ala Phe Gln
                370                 375                 380
Gln Thr Gly Thr Asn His Thr Arg Thr Phe Arg Asn Ser Gly Thr Ile
385                 390                 395                 400
Asp Ser Leu Asp Glu Ile Pro Pro Gln Asp Asn Ser Gly Ala Pro Trp
                405                 410                 415
Asn Asp Tyr Ser His Val Leu Asn His Val Thr Phe Val Arg Trp Pro
                420                 425                 430
Gly Glu Ile Ser Gly Ser Asp Ser Trp Arg Ala Pro Met Phe Ser Trp
                435                 440                 445
Thr His Arg Ser Ala Thr Pro Thr Asn Thr Ile Asp Pro Glu Arg Ile
                450                 455                 460
Thr Gln Ile Pro Leu Thr Lys Ser Thr Asn Leu Gly Ser Gly Thr Ser
465                 470                 475                 480
```

```
Val Val Lys Gly Pro Gly Phe Thr Gly Gly Asp Ile Leu Arg Arg Thr
            485                 490                 495

Ser Pro Gly Gln Ile Ser Thr Leu Arg Val Asn Ile Thr Ala Pro Leu
            500                 505                 510

Ser Gln Arg Tyr Arg Val Arg Ile Arg Tyr Ala Ser Thr Thr Asn Leu
            515                 520                 525

Gln Phe His Thr Ser Ile Asp Gly Arg Pro Ile Asn Gln Gly Asn Phe
        530                 535                 540

Ser Ala Thr Met Ser Ser Gly Ser Asn Leu Gln Ser Gly Ser Phe Arg
545                 550                 555                 560

Thr Val Gly Phe Thr Thr Pro Phe Asn Phe Ser Asn Gly Ser Ser Val
                565                 570                 575

Phe Thr Leu Ser Ala His Val Phe Asn Ser Gly Asn Glu Val Tyr Ile
                580                 585                 590

Asp Arg Ile Glu Phe Val Pro Ala Glu Val Thr Phe Glu Ala Glu Tyr
        595                 600                 605

Asp Leu Glu Arg Ala Gln Lys Ala Val Asn Ala Leu Phe Thr Ser Thr
        610                 615                 620

Asn Gln Leu Gly Leu Lys Thr Asn Val Thr Asp Tyr His Ile Asp Gln
625                 630                 635                 640

Val Ser Asn Leu Val Thr Tyr Leu Ser Asp Glu Phe Cys Leu Asp Glu
                645                 650                 655

Lys Arg Glu Leu Ser Glu Lys Val Lys His Ala Lys Arg Leu Ser Asp
                660                 665                 670

Glu Arg Asn Leu Leu Gln Asp Ser Asn Phe Lys Asp Ile Asn Arg Gln
        675                 680                 685

Pro Glu Arg Gly Trp Gly Gly Ser Thr Gly Ile Thr Ile Gln Gly Gly
        690                 695                 700

Asp Asp Val Phe Lys Glu Asn Tyr Val Thr Leu Ser Gly Thr Phe Asp
705                 710                 715                 720

Glu Cys Tyr Pro Thr Tyr Leu Tyr Gln Lys Ile Asp Glu Ser Lys Leu
                725                 730                 735

Lys Ala Phe Thr Arg Tyr Gln Leu Arg Gly Tyr Ile Glu Asp Ser Gln
                740                 745                 750

Asp Leu Glu Ile Tyr Leu Ile Arg Tyr Asn Ala Lys His Glu Thr Val
        755                 760                 765

Asn Val Pro Gly Thr Gly Ser Leu Trp Pro Leu Ser Ala Gln Ser Pro
770                 775                 780

Ile Gly Lys Cys Gly Glu Pro Asn Arg Cys Ala Pro His Leu Glu Trp
785                 790                 795                 800

Asn Pro Asp Leu Asp Cys Ser Cys Arg Asp Gly Glu Lys Cys Ala His
                805                 810                 815

His Ser His His Phe Ser Leu Asp Ile Asp Val Gly Cys Thr Asp Leu
                820                 825                 830

Asn Glu Asp Leu Gly Val Trp Val Ile Phe Lys Ile Lys Thr Gln Asp
        835                 840                 845

Gly His Ala Arg Leu Gly Asn Leu Glu Phe Leu Glu Glu Lys Pro Leu
    850                 855                 860

Val Gly Glu Ala Leu Ala Arg Val Lys Arg Ala Glu Lys Lys Trp Arg
865                 870                 875                 880

Asp Lys Arg Glu Lys Leu Glu Trp Glu Thr Asn Ile Val Tyr Lys Glu
                885                 890                 895
```

-continued

```
Ala Lys Glu Ser Val Asp Ala Leu Phe Val Asn Ser Gln Tyr Asp Gln
            900                 905                 910

Leu Gln Ala Asp Thr Asn Ile Ala Met Ile His Ala Ala Asp Lys Arg
        915                 920                 925

Val His Ser Ile Arg Glu Ala Tyr Leu Pro Glu Leu Ser Val Ile Pro
    930                 935                 940

Gly Val Asn Ala Ala Ile Phe Glu Glu Leu Glu Gly Arg Ile Phe Thr
945                 950                 955                 960

Ala Phe Ser Leu Tyr Asp Ala Arg Asn Val Ile Lys Asn Gly Asp Phe
                965                 970                 975

Asn Asn Gly Leu Ser Cys Trp Asn Val Lys Gly His Val Asp Val Glu
            980                 985                 990

Glu Gln Asn Asn Gln Arg Ser Val Leu Val Val Pro Glu Trp Glu Ala
        995                 1000                1005

Glu Val Ser Gln Glu Val Arg Val Cys Pro Gly Arg Gly Tyr Ile
    1010                1015                1020

Leu Arg Val Thr Ala Tyr Lys Glu Gly Tyr Gly Glu Gly Cys Val
    1025                1030                1035

Thr Ile His Glu Ile Glu Asn Asn Thr Asp Glu Leu Lys Phe Ser
    1040                1045                1050

Asn Cys Val Glu Glu Glu Ile Tyr Pro Asn Asn Thr Val Thr Cys
    1055                1060                1065

Asn Asp Tyr Thr Val Asn Gln Glu Glu Tyr Gly Gly Ala Tyr Thr
    1070                1075                1080

Ser Arg Asn Arg Gly Tyr Asn Glu Ala Pro Ser Val Pro Ala Asp
    1085                1090                1095

Tyr Ala Ser Val Tyr Glu Glu Lys Ser Tyr Thr Asp Gly Arg Arg
    1100                1105                1110

Glu Asn Pro Cys Glu Phe Asn Arg Gly Tyr Arg Asp Tyr Thr Pro
    1115                1120                1125

Leu Pro Val Gly Tyr Val Thr Lys Glu Leu Glu Tyr Phe Pro Glu
    1130                1135                1140

Thr Asp Lys Val Trp Ile Glu Ile Gly Glu Thr Glu Gly Thr Phe
    1145                1150                1155

Ile Val Asp Ser Val Glu Leu Leu Leu Met Glu Glu
    1160                1165                1170
```

CHIMERIC INSECTICIDAL PROTEINS TOXIC OR INHIBITORY TO LEPIDOPTERAN PESTS

REFERENCE TO RELATED APPLICATION

This application is a continuation of U.S. patent application Ser. No. 14/884,469, filed Oct. 15, 2015, which claims the benefit of U.S. provisional application No. 62/064,989, filed Oct. 16, 2014, each of which are herein incorporated by reference in their entireties.

INCORPORATION OF SEQUENCE LISTING

A computer readable form of the Sequence Listing is filed with this application by electronic submission and is incorporated into this application by reference in its entirety. The Sequence Listing is contained in the file created on Dec. 11, 2017, having the file name P34230US02_SEQ.txt, and which is 371,792 bytes in size (as measured in the MS-Windows® operating system).

FIELD OF THE INVENTION

The invention generally relates to the field of insect inhibitory proteins. A novel class of chimeric insecticidal proteins exhibiting insect inhibitory activity against agriculturally-relevant pests of crop plants and seeds is disclosed in this application. In particular, the disclosed class of proteins exhibits insecticidal activity against the Lepidopteran order of insect pests. Plants, plant parts, and seeds containing a recombinant nucleic acid molecule encoding one or more of the disclosed toxin proteins are provided.

BACKGROUND OF THE INVENTION

Improving crop yield from agriculturally-significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts with respect to food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera, are considered a major cause of damage to field crops, thereby decreasing crop yields in infested areas. Lepidopteran pest species which negatively impact agriculture include, but are not limited to, fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Chrysodeixis includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*), European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*), codling moth (*Cydia pomonella*), grape berry moth (*Endopiza viteana*), oriental fruit moth (*Grapholita molesta*), sunflower bud moth (Suleima helianthana), diamondback moth (*Plutella xylostella*), pink bollworm (*Pectinophora gossypiella*), pink stem borer (*Sesamia inferens*), gypsy moth (*Lymantria dispar*), cotton leaf worm (*Alabama argillacea*), fruit tree leaf roller (*Archips argyrospila*), European leafroller (*Archips rosana*), Asiatic rice borer, or rice stem borer (*Chilo suppressalis*), rice leaf roller (*Cnaphalocrocis medinalis*), corn root webworm (*Crambus caliginosellus*), bluegrass webworm (*Crambus teterrellus*), southwestern corn borer (*Diatraea grandiosella*)), surgarcane borer (*Diatraea* saccharalis), spiny bollworm (*Earias insulana*), spotted bollworm (*Earias vittella*), Old World cotton bollworm (*Helicoverpa armigera*), corn earworm, soy podworm or cotton bollworm (*Helicoverpa zea*), sod webworm (*Herpetogramma licarsisalis*), European grape vine moth (*Lobesia botrana*), citrus leafminer (*Phyllocnistis citrella*), large white butterfly (*Pieris brassicae*), imported cabbageworm, or small white butterfly (*Pieris rapae*), tobacco cutworm, or cluster caterpillar (*Spodoptera litura*), and tomato leafminer (*Tuta absoluta*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for insecticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of other bacterial species, such as *Brevibacillus laterosporus, Lysinibacillus sphaericus* ("Ls" formerly known as *Bacillus sphaericus*) and *Paenibacillus popilliae.*

Crystalline and secreted soluble insecticidal protein toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal proteins has been globally adopted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal proteins used in these crops has created a selection pressure for existing insect alleles that impart resistance to the currently-utilized insecticidal proteins.

The development of resistance in target pests to insecticidal proteins creates the continuing need for discovery and development of new forms of insecticidal proteins that are useful for managing the increase in insect resistance to transgenic crops expressing insecticidal proteins. New insecticidal proteins with improved efficacy and which exhibit control over a broader spectrum of susceptible insect species will reduce the number of surviving insects which can develop resistance alleles. In addition, the use in one plant of two or more transgenic insecticidal proteins toxic to the same insect pest and displaying different modes of action reduces the probability of resistance in any single target insect species.

Consequently, there is a critical need to identify additional insecticidal proteins with improved insecticidal properties such as increased efficacy against a broader spectrum of target insect pests species and different modes of action compared to the toxins currently used in agricultural practices. To meet this need, the present invention discloses novel Cry1 chimeric insecticidal proteins that exhibit activity against significant target Lepidopteran pest species.

Members of the family of Cry1 crystal proteins are known in the art to exhibit bioactivity against Lepidopteran pests. The precursor form of Cry 1 crystal proteins consists of two approximately equal-sized segments. The carboxy-terminal portion of the precursor protein, known as the protoxin segment, stabilizes crystal formation and exhibits no insecticidal activity. The amino-terminal half of the precursor protein comprises the toxin segment of the Cry1 protein and, based on alignment of conserved or substantially conserved sequences within Cry1 family members, can be further sub-divided into three structural domains, domain I, domain II, and domain III. Domain I comprises about the first third of the active toxin segment and has been shown to be essential for channel formation. Domains II and III have both been implicated in receptor binding and insect species specificity, depending on the insect and insecticidal protein being examined.

The likelihood of arbitrarily creating a chimeric protein with enhanced properties from the assortment of the domain structures of the numerous native insecticidal proteins known in the art is remote. This is a result of the complex nature of protein structure, oligomerization, and activation (including correct proteolytic processing of the chimeric precursor, if expressed in such a form) required to release an insecticidal protein segment. Only by careful selection of protoxins and specific targets within each parental protein for the creation of a chimeric structure can functional chimeric insecticidal toxins be constructed that exhibit improved insecticidal activity in comparison to the parental proteins from which the chimeras are derived. It is known in the art that reassembly of the protoxin and toxin domains I, II and III of any two or more toxins that are different from each other often results in the construction of proteins that exhibit faulty crystal formation or the complete lack of any detectable insecticidal activity directed to a preferred target insect pest species. Only by trial and error are effective insecticidal chimeras designed, and even then, the skilled artisan is not certain to end up with a chimera that exhibits insecticidal activity that is equivalent to or improved in comparison to any single parental toxin protein from which the constituent protoxin or toxin domains of the chimera may have been derived. For example, the literature reports numerous examples of the construction or assembly of chimeric proteins from two or more crystal protein precursors. See, e.g. Jacqueline S. Knight, et al. "A Strategy for Shuffling Numerous *Bacillus thuringiensis* Crystal Protein Domains." *J. Economic Entomology*, 97 (6) (2004): 1805-1813; Bosch, et al. (U.S. Pat. No. 6,204,246); Malvar and Gilmer (U.S. Pat. No. 6,017,534). In each of these examples, many of the resultant chimeras failed to exhibit insecticidal or crystal forming properties that were equivalent to or improved in comparison to the precursor proteins from which the components of the chimeras were derived.

SUMMARY OF THE INVENTION

Recombinant nucleic acid molecules are provided that encode chimeric insecticidal proteins toxic to Lepidopteran species of plant pests. Each of the chimeric insecticidal proteins can be used alone or in combination with each other and with other insecticidal proteins and insect inhibitory agents in formulations and in planta; thus providing alternatives to insecticidal proteins and insecticidal chemistries currently in use in agricultural systems.

In certain embodiments disclosed herein is a chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53. This chimeric insecticidal protein exhibits inhibitory activity against an insect species of the order Lepidoptera such as, but not limited to, *Anticarsia gemmatalis, Diatraea saccharalis, Elasmopalpus lignosellus, Helicoverpa zea, Heliothis virescens, Chrysodeixis includens, Spodoptera cosmioides, Spodoptera eridania, Spodoptera frugiperda, Spodoptera exigua, Helicoverpa armigera, Spodoptera litura, Pectinophora gossypiella, Diatraea grandiosella, Earias vitella, Helicoverpa gelotopeon,* and *Rachiplusia* nu.

In another embodiment, a polynucleotide encoding a chimeric insecticidal protein, wherein the polynucleotide is operably linked to a heterologous promoter and the chimeric insecticidal protein comprises the amino acid sequence as set forth in any of SEQ ID NOs: 21, 10, 28, 7, 4, 13, 16, 19, 23, 25, 30, 33, 36, 39, 41, 43, 45, 47, 50 or 53 is disclosed. A polynucleotide encoding a chimeric insecticidal protein, wherein the polynucleotide comprises a nucleotide sequence that optionally: hybridizes under stringent conditions to the reverse complement of the polynucleotide sequence as set forth in any of SEQ ID NOs: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52; or encodes the chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53 is also contemplated.

In other embodiments disclosed herein is a host cell comprising the polynucleotide set forth in any of SEQ ID NO: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52, wherein the host cell is selected from the group consisting of a bacterial host cell or a plant host cell. Contemplated bacterial host include *Agrobacterium, Rhizobium, Bacillus, Brevibacillus, Escherichia, Pseudomonas, Klebsiella,* and *Erwinia*; and wherein the *Bacillus* species is a *Bacillus*

*cereus* or a *Bacillus thuringiensis*, said *Brevibacillus* is a *Brevibacillus laterosperous*, and said *Escherichia* is an *Escherichia coli*. Contemplated plant cells include monocots and dicots.

Other embodiments disclosed herein include insect inhibitory compositions comprising a chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53. In certain embodiments, the insect inhibitory composition further comprises at least one insect inhibitory agent different from the chimeric insecticidal protein. Contemplated insect inhibitory agents different from the chimeric insecticidal protein include an insect inhibitory protein, an insect inhibitory dsRNA molecule, and an insect inhibitory chemistry. These insect inhibitory agents different from the chimeric insecticidal protein can exhibit activity against one or more pest species of the orders Lepidoptera, Coleoptera, Hemiptera, Homoptera, or Thysanoptera.

In yet another embodiment, disclosed herein is a seed comprising an insect inhibitory effective amount of: a chimeric insecticidal protein comprising the amino acid sequence as set forth in any of SEQ ID NOs: 21, 10, 28, 7, 4, 13, 16, 19, 23, 25, 30, 33, 36, 39, 41, 43, 45, 47, 50 or 53; or a polynucleotide set forth in any of SEQ ID NOs: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52.

Methods of controlling a Lepidopteran pest comprising contacting the Lepidopteran pest with an inhibitory amount of a chimeric insecticidal protein of the invention are also contemplated.

In another embodiment, disclosed herein is a transgenic plant cell, plant or plant part comprising a chimeric insecticidal protein, wherein: the chimeric insecticidal protein comprises any amino acid sequence set forth in any of SEQ ID NO: 21, 10, 28, 7, 4, 13, 16, 19, 23, 25, 30, 33, 36, 39, 41, 43, 45, 47, 50 or 53; or the chimeric insecticidal protein comprises a protein having: at least 94% identical to SEQ ID NOs: 21, 10; at least 93% identical to SEQ ID NO:28 at least 87% identical to SEQ ID NO:7; at least 90% identity to SEQ ID NO:4; at least 91% identical to SEQ ID NO:13; at least 64% identical to SEQ ID NO:16; at least 66% identical to SEQ ID NO:19; at least 86% identical to SEQ ID NO:23; at least 91% identical to SEQ ID NO:25; at least 94% identical to SEQ ID NO:30; at least 91% identical to SEQ ID NO:33; at least 64% identical to SEQ ID NO:36; at least 66% identical to SEQ ID NO:39; at least 94% identical to SEQ ID NO:41; at least 84% identical to SEQ ID NO:43; at least 93% identical to SEQ ID NO:45; at least 94% identical to SEQ ID NO: 47; at least 91% identical to SEQ ID NO:50; or at least 93% identical to SEQ ID NO:53. Methods of controlling a Lepidopteran pest which comprise exposing the pest to this transgenic plant cell, plant or plant part, wherein said plant cell, plant or plant part expresses a Lepidopteran inhibitory amount of the chimeric insecticidal protein are also contemplated.

In other embodiments herein, commodity products derived from the plant cell, plant, or plant part wherein the product comprises a detectable amount of the chimeric insecticidal protein are provided. Contemplated commodity products include plant biomass, oil, meal, animal feed, flour, flakes, bran, lint, hulls, and processed seed.

Yet another method disclosed herein is a method of producing a seed comprising a chimeric insecticidal protein, the method comprising: planting at least one seed comprising a chimeric insecticidal protein; growing plants from said seed; and harvesting seed from said plants, wherein said harvested seed comprises the chimeric insecticidal protein.

Recombinant polynucleotide molecules encoding a chimeric insecticidal protein, comprising a nucleotide sequence selected from the group consisting of 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52; and optionally a polynucleotide sequence encoding an insect inhibitory agent different from the chimeric insecticidal protein are also contemplated herein.

Another recombinant nucleic acid molecule contemplated herein comprises a heterologous promoter operably linked to a polynucleotide segment encoding a chimeric insecticidal proteins, wherein: the chimeric insecticidal protein comprises any amino acid sequence set forth in any of SEQ ID NO: 21, 10, 28, 7, 4, 13, 16, 19, 23, 25, 30, 33, 36, 39, 41, 43, 45, 47, 50 or 53; or the chimeric insecticidal protein comprises a protein having: at least 94% identical to SEQ ID NOs: 21, 10; at least 93% identical to SEQ ID NO:28; at least 87% identical to SEQ ID NO:7; at least 90% identity to SEQ ID NO:4; at least 91% identical to SEQ ID NO:13; at least 64% identical to SEQ ID NO:16; at least 66% identical to SEQ ID NO:19; at least 86% identical to SEQ ID NO:23; at least 91% identical to SEQ ID NO:25; at least 94% identical to SEQ ID NO:30; at least 91% identical to SEQ ID NO:33; at least 64% identical to SEQ ID NO:36; at least 66% identical to SEQ ID NO:39; at least 94% identical to SEQ ID NO:41; at least 84% identical to SEQ ID NO:43; at least 93% identical to SEQ ID NO:45; at least 94% identical to SEQ ID NO: 47; at least 91% identical to SEQ ID NO:50; or at least 93% identical to SEQ ID NO:53; or the polynucleotide segment hybridizes to a polynucleotide having a nucleotide sequence as set forth in any of SEQ ID NO: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52.

Other embodiments, features, and advantages of the invention will be apparent from the following detailed description, examples, and claims.

BRIEF DESCRIPTION OF THE SEQUENCES

SEQ ID SEQ ID NO: 1 is a recombinant DNA sequence encoding TIC1100 used for expression in a bacterial cell.

SEQ ID NO: 2 is a synthetic DNA sequence encoding TIC1100 for expression in a plant cell.

SEQ ID NO: 3 is a synthetic DNA sequence encoding TIC1100 for expression in a plant cell.

SEQ ID NO: 4 is the amino acid sequence of TIC1100.

SEQ ID NO: 5 is a recombinant DNA sequence encoding TIC860 used for expression in a bacterial cell.

SEQ ID NO: 6 is a synthetic DNA sequence encoding TIC860 for expression in a plant cell.

SEQ ID NO: 7 is the amino acid sequence of TIC860.

SEQ ID NO: 8 is a recombinant DNA sequence encoding TIC867 used for expression in a bacterial cell.

SEQ ID NO: 9 is a synthetic DNA sequence encoding TIC867 for expression in a plant cell.

SEQ ID NO: 10 is the amino acid sequence of TIC867.

SEQ ID NO: 11 is a recombinant DNA sequence encoding TIC867_20 used for expression in a bacterial cell.

SEQ ID NO: 12 is a synthetic DNA sequence encoding TIC867_20 for expression in a plant cell.

SEQ ID NO: 13 is the amino acid sequence of TIC867_20.

SEQ ID NO: 14 is a recombinant DNA sequence encoding TIC867_21 used for expression in a bacterial cell.

SEQ ID NO: 15 is a synthetic DNA sequence encoding TIC867_21 for expression in a plant cell.

SEQ ID NO: 16 is the amino acid sequence of TIC867_21.

SEQ ID NO: 17 is a recombinant DNA sequence encoding TIC867_22 used for expression in a bacterial cell.

SEQ ID NO: 18 is a synthetic DNA sequence encoding TIC867_22 for expression in a plant cell.

SEQ ID NO: 19 is the amino acid sequence of TIC867_22.

SEQ ID NO: 20 is a synthetic DNA sequence encoding TIC867_23 for expression in the plant cell.

SEQ ID NO: 21 is the amino acid sequence of TIC867_23.

SEQ ID NO: 22 is a synthetic DNA sequence encoding TIC867_24 for expression in a plant cell.

SEQ ID NO: 23 is the amino acid sequence of TIC867_24.

SEQ ID NO: 24 is a synthetic DNA sequence encoding TIC867_24 for expression in a plant cell.

SEQ ID NO: 25 is the amino acid sequence of TIC867_25.

SEQ ID NO: 26 is a recombinant DNA sequence encoding TIC868 used for expression in a bacterial cell.

SEQ ID NO: 27 is a synthetic DNA sequence encoding TIC868 for expression in a plant cell.

SEQ ID NO: 28 is the amino acid sequence of TIC868.

SEQ ID NO: 29 is a synthetic DNA sequence encoding TIC868_9 for expression in a plant cell.

SEQ ID NO: 30 is the amino acid sequence of TIC868_9.

SEQ ID NO: 31 is a recombinant DNA sequence encoding TIC868_10 used for expression in a bacterial cell.

SEQ ID NO: 32 is a synthetic DNA sequence for expression in the plant cell encoding the TIC868 variant, TIC868_10.

SEQ ID NO: 33 is the amino acid sequence of TIC868_10.

SEQ ID NO: 34 is a recombinant DNA sequence encoding TIC868_11 used for expression in a bacterial cell.

SEQ ID NO: 35 is a synthetic DNA sequence encoding TIC868_11 for expression in a plant cell.

SEQ ID NO: 36 is the amino acid sequence of TIC868_11.

SEQ ID NO: 37 is a recombinant DNA sequence encoding TIC868_12 used for expression in a bacterial cell.

SEQ ID NO: 38 is a synthetic DNA sequence encoding TIC868_12 for expression in the plant cell.

SEQ ID NO: 39 is the amino acid sequence of TIC868_12.

SEQ ID NO: 40 is a synthetic DNA sequence encoding TIC868_13 for expression in the plant cell.

SEQ ID NO: 41 is the amino acid sequence of TIC868_13.

SEQ ID NO: 42 is a synthetic DNA sequence encoding TIC868_14 for expression in a plant cell.

SEQ ID NO: 43 is the amino acid sequence of TIC868_14.

SEQ ID NO: 44 is a synthetic DNA sequence encoding TIC868_15 for expression in a plant cell.

SEQ ID NO: 45 is the amino acid sequence of TIC868_15.

SEQ ID NO: 46 is a synthetic DNA sequence encoding TIC868_29 for expression in a plant cell.

SEQ ID NO: 47 is the amino acid sequence of TIC868_29.

SEQ ID NO: 48 is a recombinant DNA sequence encoding TIC869 used for expression in a bacterial cell.

SEQ ID NO: 49 is a synthetic DNA sequence encoding TIC869 for expression in a plant cell.

SEQ ID NO: 50 is the amino acid sequence of TIC869.

SEQ ID NO: 51 is a recombinant DNA sequence encoding TIC836 used for expression in a bacterial cell.

SEQ ID NO: 52 is a synthetic DNA sequence encoding TIC836 for expression in a plant cell.

SEQ ID NO: 53 is the amino acid sequence of TIC836.

DETAILED DESCRIPTION OF THE INVENTION

The problem in the art of agricultural pest control can be characterized as a need for new insecticidal proteins that are efficacious against target pests, exhibit broad spectrum toxicity against target pest species, are capable of being expressed in plants without causing undesirable agronomic issues, and provide an alternative mode of action compared to current toxins that are used commercially in plants. Novel chimeric insecticidal proteins are disclosed herein, and address each of these needs, particularly against a broad spectrum of Lepidopteran insect pests.

In order to avoid the development of, or circumvent insect resistance against currently used insecticidal proteins, new insecticidal proteins with different modes-of-action (MOA), as well as a broad spectrum and efficacy, are needed for Lepidoptera control. One way to address this need is to discover new insecticidal proteins from different biological sources, preferably from bacteria, fungi or plants. Another approach is to interchange segments between various Bt proteins that exhibit structural similarities to create new chimeric Bt proteins having insect inhibitory properties. The likelihood of creating a chimeric protein with enhanced properties from the re-assortment of the domain structures of numerous native insecticidal crystal proteins known in the art is known in the art to be remote. See, e.g. Jacqueline S. Knight, et al. "A Strategy for Shuffling Numerous *Bacillus thuringiensis* Crystal Protein Domains." *J. Economic Entomology*, 97 (6) (2004): 1805-1813.

Disclosed herein are recombinant nucleic acid molecule sequences that encode novel chimeric insecticidal proteins. These insecticidal proteins address the ongoing need in the art to engineer additional toxic insecticidal proteins with improved insecticidal properties such as increased efficacy against a broader spectrum of target insect pests species and different modes of action. Members of this group of proteins, including the exemplary proteins disclosed herein, exhibit insecticidal activity against Lepidopteran insect pest species.

The term "segment" or "fragment" is used in this application to describe consecutive amino acid or nucleic acid sequences that are shorter than the complete amino acid or nucleic acid sequence describing a disclosed chimeric insecticidal protein. A segment or fragment exhibiting insect inhibitory activity is also disclosed in this application if alignment of such segment or fragment, with the corresponding section of the chimeric insecticidal protein, results in amino acid sequence identity of any fraction percentage from about 65 to about 100 percent between the segment or fragment and the corresponding section of the chimeric insecticidal protein.

Reference in this application to the terms "active" or "activity", "pesticidal activity" or "pesticidal", or "insecticidal activity", "insect inhibitory" or "insecticidal" refer to efficacy of a toxic agent, such as an insecticidal protein, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the insecticidal protein) or killing (causing the morbidity, mortality, or reduced fecundity of) a pest. These terms are intended to include the result of providing a pesticidally effective amount of an insecticidal protein to a pest where the exposure of the pest to the insecticidal protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the insecticidal protein in or on the plant. In general, pesticidal activity refers to the ability of an insecticidal protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera. The insecticidal protein can be produced by the plant or can be applied to the plant or to the environment within the location where the plant is located. The terms "bioactivity", "effective", "efficacious" or variations thereof are also terms interchangeably utilized in this application to describe the effects of the chimeric insecticidal proteins of the present invention on target insect pests.

A pesticidally effective amount of a toxic agent, when provided in the diet of a target pest, exhibits pesticidal activity when the toxic agent contacts the pest. A toxic agent can be an insecticidal protein or one or more chemical agents known in the art. Insecticidal chemical agents and insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Insecticidal protein agents include the chimeric insecticidal proteins set forth in this application, as well as other proteinaceous toxic agents including those that target Lepidopteran pest species, as well as protein toxins that are used to control other plant pests such as Cry proteins available in the art for use in controlling Coleopteran, Thysanopteranm, Hemipteran and Homopteran species.

It is intended that reference to a pest, particularly a pest of a crop plant, means insect pests of crop plants, particularly those Lepidopteran insect pests that are controlled by the disclosed chimeric insecticidal proteins. However, reference to a pest can also include Coleopteran, Hemipteran and Homopteran insect pests of plants, as well as nematodes and fungi when toxic agents targeting these pests are co-localized or present together with the chimeric insecticidal protein, or a protein that is 65 to about 100 percent identical to the chimeric insecticidal protein.

The chimeric insecticidal proteins disclosed herein exhibit insecticidal activity towards insect pests from the Lepidopteran insect species, including adults, pupae, larvae, and neonates, as well as Hemipteran insect species, including adults and nymphs. The insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., *Alabama argillacea* (cotton leaf worm), *Archips argyrospila* (fruit tree leaf roller), *Archips rosana* (European leafroller) and other *Archips* species, *Chilo suppressalis* (Asiatic rice borer, or rice stem borer), *Cnaphalocrocis medinalis* (rice leaf roller), *Crambus caliginosellus* (corn root webworm), *Crambus teterrellus* (bluegrass webworm), *Diatraea grandiosella* (southwestern corn borer), *Diatraea saccharalis* (surgarcane borer), *Earias insulana* (spiny bollworm), *Earias vittella* (spotted bollworm), *Helicoverpa armigera* (American bollworm), *Helicoverpa zea* (corn earworm or cotton bollworm), *Heliothis virescens* (tobacco budworm), *Herpetogramma licarsisalis* (sod webworm), *Lobesia botrana* (European grape vine moth), *Phyllocnistis citrella* (citrus leafminer), *Pieris brassicae* (large white butterfly), *Pieris rapae* (imported cabbageworm, or small white butterfly), *Plutella xylostella* (diamondback moth), *Spodoptera exigua* (beet armyworm), *Spodoptera litura* (tobacco cutworm, cluster caterpillar), and *Tuta absoluta* (tomato leafminer).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in the Examples, through a chimeragenesis effort about eight hundred and forty four (844) nucleotide sequences that encode chimeric insecticidal proteins were constructed from the protoxin and toxin domains of known insecticidal toxins (referred to herein as the "parent proteins"), and expressed and tested in bioassay for Lepidopteran activity. A small number of the constructed chimeric insecticidal proteins exhibited improved Lepidopteran activity or an enhanced Lepidopteran spectrum compared to the parent proteins from which its toxin components were derived.

These novel chimeric insecticidal proteins with improved Lepidopteran activity or an enhanced Lepidopteran spectrum were constructed from the following insecticidal parent protein protoxin and toxin domains: Cry1Ah (Domain I), Cry1Bb1 (Domains I and II), Cry 1Be2 (Domains I and II), Cry1Ja1 (Domains I and II), Cry1Fa1 (Domains I and II), Cry1Ac (Domain II and protoxin), Cry1Ca (Domain III and protoxin), Cry1Ka (Domain III and protoxin), Cry1Jx (Domain III), Cry1Ab (Domain III), Cry1Ab3 (protoxin), Cry1Da1 (protoxin), Cry4 (protoxin), Cry9 (protoxin), Cry1Be (protoxin), and Cry1Ka (protoxin).

Specifically, the novel chimeric insecticidal proteins of this invention with improved Lepidopteran activity or an enhanced Lepidopteran spectrum comprise the following protoxin and domain combinations: TIC1100/SEQ ID NO:4 (Domain I-Cry1Ah, Domain II-Cry1Ac, Domain III-Cry1Ca, Protoxin-Cry1Ac), TIC860/SEQ ID NO:7 (Domain I-Cry1Bb1, Domain II-Cry1BB1, Domain III-Cry1Ca, Protoxin-Cry1Ac), TIC867/SEQ ID NO:10 (Domain I-Cry1Be2, Domain II-Cry1Be2, Domain III-Cry1Ka, Protoxin-Cry1Ab3), TIC868/SEQ ID NO:28 (Domain I-Cry1Be2, Domain II-Cry1Be2, and Domain III-Cry1Ca, Protoxin-Cry1Ab3), TIC869/SEQ ID NO:50 (Domain I-Cry1Ja1, Domain II-Cry1Ja1, Domain III-Cry1Jx, Protoxin-Cry1Ab3) and TIC836/SEQ ID NO:53 (Domain I-Cry1Fa1, Domain II-Cry 1Fa1, Domain III-Cry1Ab, Protoxin-Cry1Ac).

Variants in which amino acid substitutions or alternate protoxin domains were introduced were also constructed for the chimeric insecticidal proteins TIC867 and TIC868. Specifically, these variants of TIC867 and TIC868 comprise the following amino acid substitutions or alternate protoxin domains: TIC867_20/SEQ ID NO:13 (alternate protoxin domain Cry1Da1), TIC867_21/SEQ ID NO:16 (alternate protoxin domain Cry4), TIC867_22/SEQ ID NO:19 (alternate protoxin domain Cry9), TIC867_23/SEQ ID NO:21 (alternate protoxin domain Cry1Be), TIC867_24/SEQ ID NO:23 (alternate protoxin domain Cry1Ka), TIC867_25/SEQ ID NO: 25 (alternate protoxin domain Cry1Ka), TIC868_9/SEQ ID NO:30 (amino acid modification N240S_Y343QN349T), TIC868_10/SEQ ID NO:33 (alternate protoxin domain Cry1Da1), TIC868_11/SEQ ID NO:36 (alternate protoxin domain Cry4), TIC868_12/SEQ ID NO:39 (alternate protoxin domain Cry 9), TIC868_13/SEQ ID NO:41 (alternate protoxin domain Cry1Be), TIC868_14/SEQ ID NO:43 (alternate protoxin domain Cry1Ka), TIC868_15/SEQ ID NO:45 (alternate protoxin domain Cry1Ca), and TIC868_29/SEQ ID NO:47 (amino acid modification Q136Y_Y343Q_N349T).

As demonstrated in the Examples, each of these TIC867 and TIC868 variants altered the Lepidopteran activity and/or reduced the Lepidopteran activity spectrum of the parent chimeric insecticidal protein, thus indicating that the alternate protoxin domain and the amino acid substitutions had a direct consequence on the insecticidal activity and spectrum of the chimeric insecticidal proteins TIC867 and TIC868.

Many of the chimeric insecticidal proteins demonstrate insecticidal activity against multiple Lepidopteran insect pest species. Specifically, the novel chimeric insecticidal proteins disclosed in this application exhibited activity against one or more of the following Lepidopteran insect pests, Velvet bean caterpillar (VBC, *Anticarsia gemmatalis*), Sugarcane borer (SCB, *Diatraea saccharalis*), Lesser cornstalk borer (LSCB, *Elasmopalpus lignosellus*), Corn earworm (CEW, *Helicoverpa zea*), Soybean pod worm (SPW, *Helicoverpa zea*), Cotton bollworm (CBW, *Helicoverpa zea*), Tobacco budworm (TBW, *Heliothis virescens*), Soybean looper (SBL, *Chrysodeixis includens*), Black armyworm (BLAW, *Spodoptera cosmioides*), Southern armyworm (SAW, *Spodoptera eridania*), Fall armyworm (FAW, *Spodoptera frugiperda*), Beet armyworm (BAW, *Spodoptera exigua*), Old World bollworm (OBW, *Helicoverpa armigera*), Oriental leafworm (OLW, *Spodoptera litura*), Pink bollworm (PBW, *Pectinophora gossypiella*), Southwestern Corn Borer (SWCB, *Diatraea grandiosella*), Spotted bollworm (SBW, *Earias* vitella), American bollworm (SABW, *Helicoverpa* gelotopeon), and Sunflower looper (SFL, *Rachiplusia* nu). Thus, the exemplary proteins described in this application are related by common function and exhibit insecticidal activity towards insect pests from the Lepidoptera insect species including adults, larvae and pupae.

Proteins that resemble the chimeric insecticidal proteins can be identified by comparison to each other using various computer based algorithms known in the art. For example, amino acid sequence identities of proteins related to the chimeric insecticidal proteins can be analyzed using a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of the subject protein). Other alignment algorithms are also available in the art, provide results similar to those obtained using Clustal W alignment and are contemplated in this application.

It is intended that a query protein exhibiting insect inhibitory activity is disclosed in this application if alignment of such query protein with the subject chimeric insecticidal proteins set forth in SEQ ID NOs: 4, 7, 10, 13, 16, 19, 21, 23, 25, 28, 30, 33, 36, 39, 41, 43, 45, 47, 50 and 53 and results in at least about 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% amino acid sequence identity (or any fraction percentage in this range) between the query and subject protein.

As described further in the Examples of this application, synthetic or artificial sequences encoding the chimeric insecticidal proteins were designed for use in plants. Exemplary synthetic nucleotide sequences that were designed for use in plants are set forth in SEQ ID NOs: 2 and 3 (TIC1100), SEQ ID NO:6 (TIC860), SEQ ID NO:9 (TIC867), SEQ ID NO:12 (TIC867_20), SEQ ID NO:15 (TIC867_21), SEQ ID NO:18 (TIC867_22), SEQ ID NO:20 (TIC867_23), SEQ ID NO:22 (TIC867_24), SEQ ID NO: 24 (TIC867_25), SEQ ID NO:27

(TIC868), SEQ ID NO:29 (TIC868_9), SEQ ID NO:32 (TIC868_10), SEQ ID NO:35 (TIC868_11), SEQ ID NO:38 (TIC868_12), SEQ ID NO:40 (TIC868_13), SEQ ID NO:42 (TIC868_14), SEQ ID NO:44 (TIC868_15), SEQ ID NO:46 (TIC868_29), SEQ ID NO:49 (TIC869) and SEQ ID NO:52 (TIC836).

For expression in plant cells, the chimeric insecticidal proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the chimeric insecticidal proteins to the chloroplast, a sequence encoding a chloroplast transit peptide is placed 5' in operable linkage and in frame to a synthetic coding sequence encoding the chimeric insecticidal protein that has been designed for optimal expression in plant cells.

Expression cassettes and vectors containing these synthetic or artificial nucleotide sequences were constructed and introduced into corn, cotton, and soybean plant cells in accordance with transformation methods and techniques which are known in the art. Transformed cells were regenerated into transformed plants that were observed to be expressing the chimeric insecticidal protein. To test pesticidal activity, bioassays were performed in the presence of Lepidopteran pest larvae using plant leaf disks obtained from the transformed plants. Recombinant nucleic acid molecule compositions that encode the chimeric insecticidal proteins are contemplated. For example, the chimeric insecticidal proteins can be expressed with recombinant DNA constructs in which a polynucleotide molecule with an ORF encoding a chimeric insecticidal protein is operably linked to genetic expression elements such as a promoter and any other regulatory element necessary for expression in the system for which the construct is intended. Non-limiting examples include a plant-functional promoter operably linked to the synthetic chimeric insecticidal protein encoding sequences for expression of the chimeric insecticidal protein in plants or a Bt-functional promoter operably linked to a chimeric insecticidal protein encoding sequence for expression of the protein in a Bt bacterium or other *Bacillus* species. Other elements can be operably linked to the chimeric insecticidal proteins encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites.

Exemplary recombinant polynucleotide molecules provided herein include, but are not limited to, a heterologous promoter operably linked to a polynucleotide such as SEQ ID NOs: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51, and 52, that encodes the polypeptide or protein having the amino acid sequence as set forth in SEQ ID NOs: 4 (TIC1100), 7 (TIC860), 10 (TIC867), 13 (TIC867_20), 16 (TIC867_21), 19 (TIC867_22), 21 (TIC867_23), 23 (TIC867_24), 25 (TIC867_25), 28 (TIC868), 30 (TIC868_9), 33 (TIC868_10), 36 (TIC868_11), 39 (TIC867_12), 41 (TIC867_13), 43 (TIC867_14), 45 (TIC867_15), 47 (TIC867_29), 50 (TIC869) and 53 (TIC836). A heterologous promoter can also be operably linked to synthetic DNA coding sequences encoding a plastid targeted chimeric insecticidal protein and untargeted chimeric insecticidal protein. It is contemplated that the codons of a recombinant nucleic acid molecule encoding for a chimeric insecticidal protein disclosed herein can be substituted by synonymous codons (known in the art as a silent substitution).

A recombinant DNA molecule or construct comprising a chimeric insecticidal protein encoding sequence can further comprise a region of DNA that encodes for one or more toxic agents which can be configured to concomitantly express or co-express with a DNA sequence encoding a chimeric insecticidal protein, a protein different from a chimeric insecticidal protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA molecule or construct can be assembled so that all proteins or dsRNA molecules are expressed from one promoter or each protein or dsRNA molecule is under separate promoter control or some combination thereof. The proteins of this invention can be expressed from a multi-gene expression system in which a chimeric insecticidal protein is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes, each expressing a different protein or other toxic agent such as one or more dsRNA molecules.

Recombinant nucleic acid molecules or recombinant DNA constructs comprising chimeric insecticidal protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a chimeric insecticidal protein encoding sequence in a host cell, or subsequent expression of the encoded polypeptide. An exogenous recombinant polynucleotide or recombinant DNA construct that comprises chimeric insecticidal protein sequence encoding sequence and that is introduced into a host cell is referred herein as a "transgene".

Transgenic bacteria, transgenic plant cells, transgenic plants, and transgenic plant parts that contain a polynucleotide that encodes any one or more of the chimeric insecticidal proteins are provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided.

In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise Lepidoptera-inhibitory amounts of a chimeric insecticidal proteins are provided. Such plants can be made by introducing a polynucleotide that encodes the chimeric insecticidal proteins provided in this application into a plant cell, and selecting a plant derived from said plant cell that expresses an insect or Lepidoptera-inhibitory amount of the chimeric insecticidal protein. Plants can be derived from the plant cells by regeneration, seed, pollen, or meristem transformation techniques. Methods for transforming plants are known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), and 2008/0256667 (cotton).

Plants expressing the chimeric insecticidal proteins can be crossed by breeding with transgenic events expressing other insecticidal proteins and/or expressing other transgenic traits such as other insect control traits, herbicide tolerance genes, genes conferring yield or stress tolerance traits, and the like, or such traits can be combined in a single vector so that the traits are all linked.

Processed plant products, wherein the processed product comprises a detectable amount of a chimeric insecticidal protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a chimeric insecticidal protein.

Methods of controlling insects, in particular Lepidoptera infestations of crop plants, with the chimeric insecticidal proteins are also disclosed in this application. Such methods can comprise growing a plant comprising an insect- or Lepidoptera-inhibitory amount of the chimeric insecticidal protein. In certain embodiments, such methods can further comprise any one or more of: (i) applying any composition comprising or encoding a chimeric insecticidal protein to a plant or a seed that gives rise to a plant; and (ii) transforming a plant or a plant cell that gives rise to a plant with a polynucleotide encoding a chimeric insecticidal protein. In general, it is contemplated that chimeric insecticidal protein can be provided in a composition, provided in a microorganism, or provided in a transgenic plant to confer insect inhibitory activity against Lepidopteran insects.

In certain embodiments, the chimeric insecticidal protein is the insecticidally active ingredient of an insect inhibitory composition prepared by culturing recombinant *Bacillus* or any other recombinant bacterial cell transformed to express a chimeric insecticidal protein under conditions suitable for expression. Such a composition can be prepared by desiccation, lyophilization, homogenization, extraction, filtration, centrifugation, sedimentation, or concentration of a culture of such recombinant cells expressing/producing the chimeric insecticidal protein. Such a process can result in a *Bacillus* or other entomopathogenic bacterial cell extract, cell suspension, cell homogenate, cell lysate, cell supernatant, cell filtrate, or cell pellet. By obtaining the chimeric insecticidal protein so produced, a composition that includes the chimeric insecticidal protein can include bacterial cells, bacterial spores, and parasporal inclusion bodies and can be formulated for various uses, including as agricultural insect inhibitory spray products or as insect inhibitory formulations in diet bioassays.

The aforementioned compound or formulation can further comprise an agriculturally-acceptable carrier, such as a bait, a powder, dust, pellet, granule, spray, emulsion, a colloidal suspension, an aqueous solution, a *Bacillus* spore or crystal preparation or a seed treatment. The compound or formulation can also further comprise a recombinant plant cell, plant tissue, seed or plant transformed to express one or more of the proteins; or bacterium transformed to express one or more of the proteins. Depending on the level of insect inhibitory or insecticidal inhibition inherent in the recombinant polypeptide and the level of compound or formulation to be applied to a plant or diet assay, the compound or formulation can include various by weight amounts of the recombinant polypeptide, e.g. from 0.0001% to 0.001% to 0.01% to 1% to 99% by weight of the recombinant polypeptide.

In an embodiment, in order to reduce the likelihood of resistance development, an insect inhibitory composition or transgenic plant comprising a chimeric insecticidal protein can further comprise at least one additional toxic agent that exhibits insect inhibitory activity against the same Lepidopteran insect species, but which is different from the chimeric insecticidal protein. Possible additional toxic agents for such a composition include an insect inhibitory protein and an insect inhibitory dsRNA molecule. One example for the use of such ribonucleotide sequences to control insect pests is described in Baum, et al. (U.S. Patent Publication 2006/0021087 A1).

Such additional polypeptide(s) for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Ser. No. 10/525,318), Cry1C (U.S. Pat. No. 6,033,874), Cry1D, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like.

In other embodiments, an insect inhibitory composition or transgenic plant can further comprise at least one additional toxic agent that exhibits insect inhibitory activity to an insect pest that is not inhibited by the chimeric insecticidal proteins of the present invention (such as Coleopteran, Hemipteran and Homopteran pests), in order to expand the spectrum of insect inhibition obtained.

Such additional toxic agent for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), axmi207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), and ω-Hexatoxin-Hv1a (U.S. Patent Application Publication US2014-0366227 A1).

Such additional toxic agent for the control of Hemipteran pests may be selected from the group consisting of Hemipteran-active proteins such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

Chimeric insecticidal protein-encoding sequences and sequences having a substantial percentage identity to the chimeric insecticidal proteins can be identified using methods known to those of ordinary skill in the art such as polymerase chain reaction (PCR), thermal amplification and hybridization. For example, the chimeric insecticidal proteins can be used to produce antibodies that bind specifically to related proteins, and can be used to screen for and to find other proteins that are closely related.

Furthermore, nucleotide sequences encoding the chimeric insecticidal proteins can be used as probes and primers for screening to identify other members of the class using thermal-cycle or isothermal amplification and hybridization methods. For example, oligonucleotides derived from sequences as set forth in SEQ ID NO:2 can be used to determine the presence or absence of a chimeric insecticidal transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NO:2 can be used to detect the respective chimeric insecticidal protein in commodity products derived from pooled sources where only a fraction of the commodity product is derived from a transgenic plant containing any of SEQ ID NO:2.

EXAMPLES

In view of the foregoing, those of skill in the art will appreciate that the following disclosed embodiments are merely representative of the invention, which may be embodied in various forms. Thus, specific structural and functional details disclosed herein are not to be interpreted as limiting.

Example 1

Creation and Cloning of Lepidopteran-Active Novel Chimeric Insecticidal Protein Coding Sequences This Example illustrates the creation of the novel chimeric insecticidal proteins and the cloning and expressing of the chimeric insecticidal proteins.

Recombinant nucleic acid sequences were constructed from known Cry protein genes to produce polynucleotide sequences encoding novel chimeric insecticidal proteins. The resulting polynucleotide sequences were cloned into a *Bacillus thuringiensis* (Bt) expression plasmid vector. After confirmation of the polynucleotide sequence, the expression plasmid was transformed into Bt and expressed. Preparations of the expressed novel chimeric proteins were assayed for activity against various Lepidopteran pests.

Many polynucleotide sequences encoding chimeric insecticidal proteins were produced and tested in bioassay. Not all of the chimeric insecticidal proteins demonstrated activity. Only a few of the chimeric insecticidal proteins were selected based upon their activity to specific Lepidoptera demonstrated in bioassay. Amino acid variants in which amino acid substitutions, or alternate protoxin domains, were introduced were also produced based upon the original chimeric insecticidal proteins TIC867 and TIC868. The components of the chimeric insecticidal proteins (domains I, II and III and the protoxin) of the present invention are presented in Table 1. The amino acid substitutions in the TIC868 variants relative to the original TIC868 protein sequence are also presented.

TABLE 1

Novel chimeric pesticidal proteins and their components.

| Toxin | PRT SEQ ID NO: | Dom1 | Dom2 | Dom3 | Protox | Amino Acid Modifications* |
|---|---|---|---|---|---|---|
| TIC1100 | 4 | Cry1Ah | Cry1Ac | Cry1Ca | Cry1Ac | |
| TIC860 | 7 | Cry1Bb1 | Cry1Bb1 | Cry1Ca | Cry1Ac | |
| TIC867 | 10 | Cry1Be2 | Cry1Be2 | Cry1Ka | Cry1Ab3 | |
| TIC867_20 | 13 | Cry1Be2 | Cry1Be2 | Cry1Ka | Cry1Da1 | |
| TIC867_21 | 16 | Cry1Be2 | Cry1Be2 | Cry1Ka | Cry4 | |
| TIC867_22 | 19 | Cry1Be2 | Cry1Be2 | Cry1Ka | Cry9 | |
| TIC867_23 | 21 | Cry1Be2 | Cry1Be2 | Cry1Ka | Cry1Be | |
| TIC867_24 | 23 | Cry1Be2 | Cry1Be2 | Cry1Ka | Cry1Ka | |
| TIC867_25 | 25 | Cry1Be2 | Cry1Be2 | Cry1Ka | Cry1Ca | |
| TIC868 | 28 | Cry1Be2 | Cry1Be2 | Cry1Ca | Cry1Ab3 | |
| TIC868_9 | 30 | Cry1Be2 | Cry1Be2 | Cry1Ca | Cry1Ab3 | N240S_Y343Q_N349T |
| TIC868_10 | 33 | Cry1Be2 | Cry1Be2 | Cry1Ca | Cry1Da1 | |
| TIC868_11 | 36 | Cry1Be2 | Cry1Be2 | Cry1Ca | Cry4 | |
| TIC868_12 | 39 | Cry1Be2 | Cry1Be2 | Cry1Ca | Cry9 | |
| TIC868_13 | 41 | Cry1Be2 | Cry1Be2 | Cry1Ca | Cry1Be | |
| TIC868_14 | 43 | Cry1Be2 | Cry1Be2 | Cry1Ca | Cry1Ka | |
| TIC868_15 | 45 | Cry1Be2 | Cry1Be2 | Cry1Ca | Cry1Ca | |
| TIC868_29 | 47 | Cry1Be2 | Cry1Be2 | Cry1Ca | Cry1Ab3 | Q136Y_Y343Q_N349T |
| TIC869 | 50 | Cry1Ja1 | Cry1Ja1 | Cry1Jx | Cry1Ab3 | |
| TIC836 | 53 | Cry1Fa1 | Cry1Fa1 | Cry1Ab | Cry1Ac | |

*The amino acid mutations are identified using the standard IUPAC amino acid code. See IUPAC-IUB Joint Commission on Biochemical Nomenclature. Nomenclature and Symbolism for Amino Acids and Peptides. Eur. J. Biochem. 138: 9-37 (1984). The first amino acid sequence abbreviation indicates the original amino acid in the given scaffold protein, the number represents the position of the amino acid, and the second amino acid sequence abbreviation indicates the amino acid placed in that position in the improved variant protein.

Example 2

The Novel Chimeric Insecticidal Proteins Demonstrate Activity Against Lepidopteran Pests This Example illustrates the testing of the chimeric insecticidal proteins described in Example 1 and the Lepidopteran activity observed for the chimeric insecticidal proteins. Polynucleotide sequences encoding chimeric insecticidal proteins were expressed in Bt. The expressed chimeric insecticidal proteins were then assayed against a variety of Lepidoptera known to be pests of corn, sugarcane, soybean and cotton, as well as other crop plants. Specifically, the insecticidal proteins were assayed for activity against Velvetbean caterpillar (VBC, *Anticarsia gemmatalis*), Sugarcane borer (SCB, *Diatraea saccharalis*), Lesser cornstalk borer (LSCB, *Elasmopalpus lignosellus*), Corn earworm (CEW, *Helicoverpa zea*), Tobacco budworm (TBW, *Heliothis virescens*), Soybean looper (SBL, *Chrysodeixis includens*), Black armyworm (BLAW, *Spodoptera cosmioides*), Southern armyworm (SAW, *Spodoptera eridania*), Fall armyworm (FAW, *Spodoptera frugiperda*), Beet armyworm (BAW, *Spodoptera exigua*), Old World bollworm (OBW, *Helicoverpa armigera*), Oriental leafworm (OLW, *Spodoptera litura*), Pink bollworm (PBW, *Pectinophora gossypiella*), Black cutworm (BCW, *Agrotis ipsilon*), Southwestern Corn Borer (SWCB, *Diatraea grandiosella*), Spotted bollworm (SBW, *Earias vitella*), and European corn borer (ECB, *Ostrinia nubilalis*). Corn earworm (CEW, *Helicoverpa zea*) is also referred to as Soybean pod worm (SPW) and Cotton bollworm (CBW). Activity was determined through a combination of mortality and stunting scores as well as MIC50 scores. MIC50 refers to a molt inhibition concentration wherein both the dead larvae and L1 larvae (larvae that failed to molt to second instars) are factored into the score. Table 2 shows the activity of each chimeric insecticidal protein. A '+' sign indicates activity observed to the specific insect pest.

TABLE 3

Polynucleotide Sequences Encoding Chimeric Insecticidal Proteins Designed for Use in Plants.

| Insecticidal Protein | DNA SEQ ID NO: | PRT SEQ ID NO: |
|---|---|---|
| TIC1100 | 2 | 4 |
| TIC1100 | 3 | 4 |
| TIC860 | 6 | 7 |
| TIC867 | 9 | 10 |
| TIC867_20 | 12 | 13 |
| TIC867_21 | 15 | 16 |
| TIC867_22 | 18 | 19 |
| TIC867_23 | 20 | 21 |
| TIC867_24 | 22 | 23 |
| TIC867_25 | 24 | 25 |
| TIC868 | 27 | 28 |
| TIC868_9 | 29 | 30 |
| TIC868_10 | 32 | 33 |
| TIC868_11 | 35 | 36 |
| TIC868_12 | 38 | 39 |
| TIC868_13 | 40 | 41 |
| TIC868_14 | 42 | 43 |
| TIC868_15 | 44 | 45 |

TABLE 2

Bioassay activity against selected Lepidoptera.

| Toxin | PRT SEQ ID NO: | VBC | SCB | LSCB | CEW SPW CBW | BLAW | TBW | SBL | SAW | FAW | BAW | OBW | OLW | PBW | BCW | SWCB | ECB | SBW |
|---|---|---|---|---|---|---|---|---|---|---|---|---|---|---|---|---|---|---|
| TIC1100 | 4 | + | + | | | + | | + | | + | + | | + | + | | | | |
| TIC860 | 7 | + | + | + | | + | + | + | + | + | + | | + | + | | + | | + |
| TIC867 | 10 | + | + | | | + | | + | | + | + | + | + | | | + | | |
| TIC867_20 | 13 | | | | | | | | | | | | | | | | | |
| TIC867_21 | 16 | | | | + | | | | | | | | | | | | | |
| TIC867_22 | 19 | | | | + | | | | | + | | | | | | | | |
| TIC868 | 28 | + | + | | | + | | + | | + | + | | + | + | | + | | + |
| TIC868_10 | 33 | | | | | | | | | + | | | | | | | | |
| TIC868_11 | 36 | | | | | | | | | + | | | | | | | | |
| TIC868_12 | 39 | | | | | | | | | + | | | | | | | | |
| TIC869 | 50 | + | + | | | | | + | | + | | | | | | + | | |
| TIC836 | 53 | + | | | | + | | + | + | + | | | | | | | | |

As can be seen in Table 2 above, most of the chimeric insecticidal proteins exhibited activity against one or more Lepidopteran pest species.

Example 3

Synthesis of Genes Encoding Chimeric Insecticidal Proteins and for Expression in Plants This Example illustrates the synthesis of polynucleotides encoding the chimeric insecticidal proteins for expression in plants.

Synthetic coding sequences were constructed for use in expression of the chimeric insecticidal proteins in plants. The synthetic sequences were designed and synthesized according to methods generally described in U.S. Pat. No. 5,500,365, avoiding certain inimical problem sequences such as ATTTA and A/T rich plant polyadenylation sequences while preserving the amino acid sequence of the chimeric insecticidal protein. The nucleotide sequences for these genes encoding the chimeric insecticidal proteins for expression in plants are listed in Table 3.

TABLE 3-continued

Polynucleotide Sequences Encoding Chimeric Insecticidal Proteins Designed for Use in Plants.

| Insecticidal Protein | DNA SEQ ID NO: | PRT SEQ ID NO: |
|---|---|---|
| TIC868_29 | 46 | 47 |
| TIC869 | 49 | 50 |
| TIC836 | 52 | 53 |

Example 4

Expression Cassettes for the Expression of Chimeric Insecticidal Proteins in Plants This Example illustrates the construction of expression cassettes comprising polynucleotide sequences designed for use in plants which encode chimeric insecticidal proteins.

A variety of plant expression cassettes were constructed with the polynucleotide sequences encoding the chimeric insecticidal proteins designed for plant expression provided in Table 3. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated and remain in the cytosol. Another set of expression cassettes was designed to have a transit peptide contiguous with the toxin protein to allow targeting to an organelle of the cell such as the chloroplast or plastid. All expression cassettes were designed to begin at the 5' end with a promoter, which can be comprised of multiple promoter elements, enhancer elements, or other expression elements known to those of ordinary skill in the art operably linked to boost the expression of the transgene. The promoter sequence was usually followed contiguously with one or more leader sequences 3' to the promoter. An intron sequence was usually provided 3' to the leader sequence to improve expression of the transgene. A coding sequence for the toxin or transit peptide and coding sequence for the toxin was usually located 3' to the operably linked promoter, leader and intron configuration. A 3'UTR sequence was usually provided 3' of the coding sequence to facilitate termination of transcription and to provide sequences important for the polyadenylation of the resulting transcript. All of the elements described above were operably linked and arranged sequentially, often with additional sequences provided for the construction of the expression cassette.

used as a negative control. Multiple transformation events from each binary vector were assessed against Corn earworm (CEW, *Helicoverpa zea*), Fall armyworm (FAW, *Spodoptera frugiperda*), Black cutworm (BCW, *Agrotis ipsilon*) and Southwestern Corn Borer (SWCB, *Diatraea grandiosella*).

Leaf disc bioassay was performed on $R_0$ and $F_1$ generation transgenic plants. In addition, leaf damage ratings were assessed for whole transgenic $F_1$ plants expressing certain chimeric insecticidal proteins infested with the Lepidopteran insect pests. $F_1$ transgenic events expressing TIC860 and TIC868 were also assessed for activity in the field against FAW, CEW, and SWCB. The assay results are shown in Table 4. A '+' sign indicates activity observed to the specific insect pest. As can be seen in Table 4, most of the chimeric insecticidal proteins and many of the chimeric insecticidal protein variants demonstrated activity against one or more Lepidopteran pest species.

TABLE 4

Bioassay activity of chimeric insecticidal proteins from stably transformed corn leaf tissue.

| Toxin | PRT SEQ ID NO: | VBC | SCB | LSCB | CEW SPW CBW | BLAW | TBW | SBL | SAW | FAW | BAW | OBW | OLW | PBW | BCW | SWCB | ECB | SBW |
|---|---|---|---|---|---|---|---|---|---|---|---|---|---|---|---|---|---|---|
| TIC1100 | 4 | + | + |   |   | + |   |   | + |   | + |   | + | + |   |   |   |   |
| TIC860 | 7 | + | + |   |   | + | + | + | + | + | + |   | + | + |   | + |   | + |
| TIC867 | 10 | + | + |   |   | + |   | + |   | + | + | + | + |   |   | + |   |   |
| TIC867_20 | 13 | NT | NT | NT |   | NT | NT | NT | NT |   | NT | NT | NT | NT | NT | NT | NT | NT |
| TIC867_21 | 16 | NT | NT | NT | + | NT | NT | NT | NT |   | NT | NT | NT | NT | NT | NT | NT | NT |
| TIC867_22 | 19 | NT | NT | NT | + | NT | NT | NT | NT | + | NT | NT | NT | NT | NT | NT | NT | NT |
| TIC868 | 28 | + | + |   |   | + |   | + | + | + | + |   | + | + |   | + |   | + |
| TIC868_10 | 33 | NT | NT | NT | + | NT | NT | NT | NT | + | NT | NT | NT | NT | NT | NT | NT | NT |
| TIC868_11 | 36 | NT | NT | NT | + | NT | NT | NT | NT | + | NT | NT | NT | NT | NT | NT | NT | NT |
| TIC868_12 | 39 | NT | NT | NT | + | NT | NT | NT | NT | + | NT | NT | NT | NT | NT | NT | NT | NT |
| TIC869 | 50 | + | + |   |   |   |   | + | + | + |   |   |   |   |   | + |   |   |
| TIC836 | 53 | + |   |   |   | + |   | + | + | + |   |   |   |   |   |   |   |   |

Example 5

Lepidopteran Activity of the Chimeric Insecticidal Proteins in Stably Transformed Corn This Example illustrates the inhibitory activity exhibited by the chimeric insecticidal proteins against Lepidopteran pests when expressed in corn plants and provided as a diet to the respective corn insect pest.

Corn variety LH244 was transformed with the binary transformation vectors described in Example 4 using an *Agrobacterium*-mediated transformation method. The transformed cells were induced to form plants by methods known in the art. Bioassays using plant leaf disks were performed analogous to those described in U.S. Pat. No. 8,344,207. A non-transformed LH244 plant was used to obtain tissue to be Example 6

Lepidopteran Activity of the Chimeric Insecticidal Proteins in Stably Transformed Soybean This Example illustrates the inhibitory activity exhibited by the chimeric insecticidal proteins against Lepidopteran pests when expressed in soybean plants and provided as a diet to the respective insect pest.

The coding sequences for selected chimeric insecticidal proteins were redesigned for plant expression, cloned into a binary plant transformation vector, and used to transform soybean plant cells. The plant transformation vectors comprised a first transgene cassette for expression of the chimeric insecticidal protein as described in Example 4 and a second transgene cassette for the selection of transformed plant cells using spectinomycin selection. In some instances, such as in the case of TIC1100, TIC860 and TIC836, a chloroplast transit peptide coding sequence was operably linked to the chimeric insecticidal coding sequence. Assays were performed with plastid targeted and untargeted TIC1100, TIC860 and TIC836. Table 5 below shows the chimeric insecticidal and TIC867 variant chimeric insecticidal protein and associated coding sequences used for expression in stably transformed soybean.

Soybean plant cells were transformed using the binary transformation vectors described above by *Agrobacterium*-mediated transformation. The resulting transformed plant cells were induced to form whole soybean plants. Leaf tissue was harvested and used in bioassay as described in Example 5 or alternatively, lyophilized tissue was used in the insect diet for bioassay. Bioassay was performed against FAW, Southern armyworm (SAW, *Spodoptera eridania*), Soybean looper (SBL, *Chrysodeixis includens*), Soybean Pod Worm (SPW, *Helicoverpa zea*), Velvetbean caterpillar (VBC, *Anticarsia gemmatalis*), Tobacco budworm (TBW, *Heliothis virescens*), Black armyworm (BLAW, *Spodoptera cosmioides*), Lesser cornstalk borer (LSCB, *Elasmopalpus lignosellus*) and Old World bollworm (OBW, *Helicoverpa armigera*).

Table 5 shows the activity against selected species of Lepidoptera for each insecticidal protein in $R_0$ generation plants, wherein '+' indicates activity. As can be seen in Table 5, each of the chimeric insecticidal proteins expressed in stably transformed soybean demonstrated activity against multiple Lepidopteran species. Of particular note is that the TIC867 variant, TIC867_23 demonstrated activity against SPW.

TABLE 5

Bioassay activity of chimeric insecticidal proteins from stably transformed $R_0$ soybean leaf tissue.

| Insecticidal Protein | FAW | SAW | SBL | SPW | VBC | TBW | BLAW | LSCB | OBW |
|---|---|---|---|---|---|---|---|---|---|
| TIC1100 | + | + | + | | + | | + | + | + |
| TIC860 | + | + | + | | + | | | + | |
| TIC867 | + | + | + | | + | + | | + | |
| TIC867_20 | | + | + | | | | | | |
| TIC867_21 | | + | + | | | | | | |
| TIC867_22 | | + | + | | | | | | |
| TIC867_23 | + | + | + | + | | | | | |
| TIC867_24 | | + | + | | | | | | |
| TIC867_25 | | + | + | | | | | | |
| TIC868 | + | | + | | + | | + | + | |
| TIC869 | | | + | | + | + | | + | |
| TIC836 | + | + | + | | + | + | + | | + |

Selected transformed events were allowed to self-pollinate and the resulting seed was grown. Leaf tissue was harvested from the $R_1$ generation plants and used in a feeding bioassay. $R_1$ plants expressing TIC1100, TIC860, TIC867, TIC868, TIC869 and TIC836 were assayed for activity against SAW, SBL, SPW and VBC. Table 6 shows the activity observed in these tests. A '+' sign indicates activity observed to the specific insect pest. As demonstrated in Table 6, most of the expressed chimeric insecticidal proteins from $R_1$ generation plants demonstrated activity to one or more Lepidopteran species.

TABLE 6

Bioassay activity of chimeric insecticidal proteins from stably transformed $R_1$ soybean leaf tissue.

| Toxin | SAW | SBL | SPW | VBC |
|---|---|---|---|---|
| TIC1100 | + | + | | + |
| TIC860 | + | + | | + |
| TIC867 | + | | | |
| TIC868 | + | + | | + |
| TIC869 | + | + | | + |
| TIC836 | + | + | | + |

Table 7 demonstrates the results of field tests conducted in screen houses with stably transformed $R_1$ generation soybean plants expressing TIC1100, TIC860, and TIC836. Species used to infest plants in the screen houses include SAW, SBL and SPW. Resistance was defined as being less than or equal to fifteen percent defoliation in the soybean plants. The resistance observed in these cage trials is consistent with the resistance observed in the $R_1$ generation soybean leaf tissue assay presented in Table 6. A '+' sign indicates activity observed to the specific insect pest.

TABLE 7

Activity Profile of TIC1100, TIC860 and TIC836 Expressed in $R_1$ Generation Soybean Tested in Screen House Field Tests.

| Toxin | SAW | SBL | SPW |
|---|---|---|---|
| TIC1100 | + | + | |
| TIC860 | + | + | |
| TIC836 | + | + | |

Field tests in screen houses with stably transformed $R_1$ generation soybean plants expressing TIC867 and TIC869 were also conducted at two different locations in Argentina, Acevedo and Fontezuela. Species used to infest plants in the screen houses include South American bollworm (SABW, *Helicoverpa gelotopeon*), VBC, BLAW, and Sunflower looper (SFL, *Rachiplusia* nu). Resistance was defined as being less than or equal to fifteen percent defoliation in the soybean plants. Table 8 below shows the resistance observed. A '+' sign indicates activity observed to the specific insect pest. As demonstrated in Table 8, transgenic soybean plants expressing TIC867 demonstrated resistance to BLAW and VBC. Transgenic soybean plants expressing TIC869 demonstrated resistance to SABW, SFL, BLAW, and VBC.

TABLE 8

Activity Profile of TIC867 and TIC869 Expressed in $R_1$ Generation Soybean Tested in Screen House Field Tests.

| | Acevedo | | | Fontezuela | | |
|---|---|---|---|---|---|---|
| Toxin | SABW | SFL | VBC | SABW | BLAW | VBC |
| TIC867 | | | + | | + | + |
| TIC869 | | + | + | + | + | + |

Example 7

Lepidopteran Activity of the Chimeric Insecticidal Proteins in Stably Transformed Cotton This Example illustrates the inhibitory activity exhibited by the chimeric insecticidal proteins against Lepidopteran pests when expressed in cotton plants and provided as a diet to the respective insect pest.

The coding sequences for selected chimeric insecticidal proteins were redesigned for plant expression, cloned into a binary plant transformation vector, and used to transform cotton plant cells. The resulting binary vectors were similar to those described in Example 4 and were used to express plastid targeted and untargeted TIC860 (coding sequence: SEQ ID NO: 6; protein sequence: SEQ ID NO: 7), TIC867 (coding sequence: SEQ ID NO: 9; protein sequence: SEQ ID NO: 10), TIC868 (coding sequence: SEQ ID NO: 27; protein sequence: SEQ ID NO: 28) and TIC867_23 (coding sequence: SEQ ID NO: 20; protein sequence: SEQ ID NO: 23).

Cotton plant cells were transformed by an *Agrobacterium*-mediated transformation method. Transformed cotton cells were induced to form whole plants. Cotton leaf tissue was used in bioassay as described in Example 5 against Cotton Boll Worm (CBW, *Helicoverpa zea*), FAW, TBW and SBL. Table 9 shows the activity observed against these Lepidopteran species for TIC860, TIC867, and TIC868 in stably transformed $R_0$ generation cotton, wherein '+' indicate activity. As can be seen in Table 9, TIC860, TIC867, and TIC868 demonstrated activity against two or more Lepidopteran pest species in stably transformed $R_0$ generation cotton.

TABLE 9

Bioassay activity of TIC860, TIC867 and TIC868 from stably transformed $R_0$ cotton leaf tissue.

| Toxin | CBW | FAW | TBW | SBL |
|---|---|---|---|---|
| TIC860 |  | + |  | + |
| TIC867 | + | + | + | NT |
| TIC868 |  | + |  | + |

Selected transformation events were used to produce $R_1$ seed. $R_1$ Plants expressing TIC860, TIC867, and TIC868 were assayed for resistance to CBW, FAW, TBW, and SBL. Leaf, square and boll tissues were used in assay. Table 10 shows the activity observed in these tests. A '+' sign indicates activity observed to the specific insect pest. As demonstrated in Table 10, TIC860 demonstrated activity against FAW in the leaf tissue. Further, the chimeric insecticidal protein TIC867 demonstrated activity against CBW and FAW in the leaf, square and boll tissues, as well as TBW and SBL in the leaf. The chimeric insecticidal protein TIC868 demonstrated activity against FAW in the leaf, square and boll tissues, as well as TBW and SBL in the leaf.

TABLE 10

Bioassay activity of chimeric insecticidal proteins from stably transformed $R_1$ cotton leaf tissue.

| Toxin | CBW | | | FAW | | | TBW | SBL |
|---|---|---|---|---|---|---|---|---|
|  | Leaf | Square | Boll | Leaf | Square | Boll | Leaf | Leaf |
| TIC860 |  |  |  | + |  |  |  |  |
| TIC867 | + | + | + | + | + | + | + | + |
| TIC868 |  |  |  | + | + | + | + | + |

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A chimeric insecticidal protein comprising SEQ ID NO:4, wherein the chimeric insecticidal protein exhibits inhibitory activity against an insect species of the order Lepidoptera.

2. A polynucleotide encoding the chimeric insecticidal protein of claim 1, wherein the polynucleotide is operably linked to a heterologous promoter.

3. A polynucleotide encoding a chimeric insecticidal protein, wherein the polynucleotide:
   a) comprises SEQ ID NO:3; or
   b) encodes the chimeric insecticidal protein of claim 1.

4. A host cell comprising the polynucleotide of claim 3, wherein said polynucleotide comprises SEQ ID NO:3, wherein the host cell is selected from the group consisting of a bacterial host cell and a plant host cell.

5. The host cell of claim 4, wherein the bacterial host cell is selected from the group consisting of *Agrobacterium*, *Rhizobium*, *Bacillus*, *Brevibacillus*, *Escherichia*, *Pseudomonas*, *Klebsiella*, and *Erwinia*.

6. The host cell of claim 4, wherein said plant host cell is selected from the group of plants consisting of monocots and dicots.

7. An insect inhibitory composition comprising the chimeric insecticidal protein of claim 1.

8. The insect inhibitory composition of claim 7, further comprising at least one insect inhibitory agent different from the chimeric insecticidal protein.

9. The insect inhibitory composition of claim 8, wherein said at least one insect inhibitory agent is selected from the group consisting of an insect inhibitory protein and an insect inhibitory dsRNA molecule.

10. The insect inhibitory composition of claim 8, wherein said at least one other pesticidal agent exhibits activity against one or more pest species of the orders Lepidoptera, Coleoptera, Hemiptera, Homoptera, or Thysanoptera.

11. A seed comprising an insect inhibitory effective amount of:
   a) the chimeric insecticidal protein of claim 1; or
   b) the polynucleotide set forth in SEQ ID NO:3.

12. A method of controlling a Lepidopteran pest, the method comprising contacting the Lepidopteran pest with an inhibitory amount of the chimeric insecticidal protein of claim 1.

13. A transgenic plant cell, plant, or plant part comprising a chimeric insecticidal protein, wherein
the chimeric insecticidal protein comprises SEQ ID NO:4.

14. A method of controlling a Lepidopteran pest, comprising exposing the pest to the transgenic plant or plant part of claim 13, wherein said plant or plant part expresses a Lepidopteran inhibitory amount of the chimeric insecticidal protein.

15. A commodity product derived from the transgenic plant or plant part of claim 13, wherein the product comprises a detectable amount of the chimeric insecticidal protein.

16. The commodity product of claim 15, wherein the product is selected from the group consisting of plant biomass, oil, meal, animal feed, flour, flakes, bran, lint, hulls, and processed seed.

17. A method of producing a seed comprising the chimeric insecticidal protein of claim 1, the method comprising:
a) planting at least one seed comprising the chimeric insecticidal protein of claim 1;
b) growing at least one plant from said seed; and
c) harvesting seeds from said at least one plant, wherein the harvested seeds comprise the chimeric insecticidal protein of claim 1.

18. A recombinant polynucleotide molecule encoding the chimeric insecticidal protein of claim 1, said molecule comprising SEQ ID NO:3 and a polynucleotide sequence encoding an insect inhibitory agent different from the chimeric insecticidal protein.

19. A recombinant nucleic acid molecule comprising a heterologous promoter operably linked to a polynucleotide segment encoding a chimeric insecticidal protein, wherein:
a) the chimeric insecticidal protein comprises SEQ ID NO:4; or
b) the polynucleotide segment comprises SEQ ID NO:3;
wherein said chimeric insecticidal protein exhibits inhibitory activity against an insect species of the order Lepidoptera.

\* \* \* \* \*